(12) United States Patent
Alcazar Vaca et al.

(10) Patent No.: US 9,604,982 B2
(45) Date of Patent: *Mar. 28, 2017

(54) P2X7 MODULATORS

(71) Applicant: Janssen Pharmaceutica NV, Beerse (BE)

(72) Inventors: Manuel Jesus Alcazar Vaca, Toledo (ES); Jose Ignacio Andres Gil, Madrid (ES); Michael A. Letavic, San Diego, CA (US); Dale A. Rudolph, San Diego, CA (US); Brock T. Shireman, Poway, CA (US); Brice M. Stenne, San Diego, CA (US); Jeannie M. Ziff, San Diego, CA (US)

(73) Assignee: Janssen Pharmaceutica NV (BE)

( * ) Notice: Subject to any disclaimer, the term of this patent is extended or adjusted under 35 U.S.C. 154(b) by 0 days.

This patent is subject to a terminal disclaimer.

(21) Appl. No.: 14/775,424

(22) PCT Filed: Mar. 14, 2014

(86) PCT No.: PCT/US2014/027505
§ 371 (c)(1),
(2) Date: Sep. 11, 2015

(87) PCT Pub. No.: WO2014/152589
PCT Pub. Date: Sep. 25, 2014

(65) Prior Publication Data
US 2016/0024082 A1    Jan. 28, 2016

Related U.S. Application Data

(60) Provisional application No. 61/785,530, filed on Mar. 14, 2013.

(51) Int. Cl.
*A61K 31/519* (2006.01)
*C07D 471/04* (2006.01)

(52) U.S. Cl.
CPC .................................. *C07D 471/04* (2013.01)

(58) Field of Classification Search
CPC .................................................... C07D 471/04
See application file for complete search history.

(56) References Cited

U.S. PATENT DOCUMENTS

| | | | |
|---|---|---|---|
| 4,812,462 A | 3/1989 | Blankley et al. | |
| 4,816,463 A | 3/1989 | Blankley et al. | |
| 5,338,744 A | 8/1994 | Dudley et al. | |
| 8,431,704 B2 | 4/2013 | Love et al. | |
| 2005/0096345 A1 | 5/2005 | Thompson et al. | |
| 2006/0217448 A1 | 9/2006 | Kelly et al. | |
| 2006/0293337 A1 | 12/2006 | Evans et al. | |
| 2008/0275052 A1 | 11/2008 | Dhar et al. | |
| 2011/0294790 A1 | 12/2011 | Mantegani et al. | |
| 2012/0190680 A1 | 7/2012 | Bakthavatchalam et al. | |
| 2014/0275015 A1 | 9/2014 | Alcazar Vaca et al. | |
| 2014/0275056 A1 | 9/2014 | Letavic et al. | |
| 2014/0275096 A1 | 9/2014 | Ameriks et al. | |
| 2014/0275120 A1 | 9/2014 | Alcazar Vaca et al. | |
| 2015/0290190 A1 | 10/2015 | Ameriks et al. | |
| 2015/0322062 A1 | 11/2015 | Alcazar Vaca et al. | |
| 2016/0016962 A1 | 1/2016 | Ameriks et al. | |
| 2016/0024082 A1 | 1/2016 | Alcazar Vaca et al. | |
| 2016/0039809 A1 | 2/2016 | Alcazar Vaca et al. | |
| 2016/0039836 A1 | 2/2016 | Letavic et al. | |

FOREIGN PATENT DOCUMENTS

| | | |
|---|---|---|
| CN | 101778850 | 7/2010 |
| WO | WO2004/014374 | 2/2004 |
| WO | WO 2006/023750 A2 | 3/2006 |
| WO | WO 2006023750 | 3/2006 |
| WO | WO 2006/080884 | 8/2006 |
| WO | WO 2006/110516 | 10/2006 |
| WO | WO 2009/002423 | 12/2008 |
| WO | WO 2009/002423 A2 | 12/2008 |
| WO | WO 2009/023623 | 2/2009 |
| WO | WO 2009/023623 A1 | 2/2009 |
| WO | WO 2010/125101 | 11/2010 |
| WO | WO 2010/125101 A1 | 11/2010 |
| WO | WO 2010/125102 | 11/2010 |
| WO | WO 2010/125102 A1 | 11/2010 |

(Continued)

OTHER PUBLICATIONS

PCT International Search Report dated Aug. 12, 2014 for International Application No. PCT/US2014/027450.
PCT International Search Report dated Jul. 1, 2014 for International Application No. PCT/US2014/027505.
PCT International Search Report dated Jul. 1, 2014 for International Application No. PCT/US2014/027522.
PCT International Search Report dated Jun. 17, 2014 for International Application No. PCT/US2014/027540.
Arbeloa et al "P2X7 Receptor Blockade Prevents ATP Excitotoxicity in Neurons and Reduces Brain Damage After Ischemia" Neurobiology of Disease, 2012, vol. 45, pp. 954-961.
Avignone et al "Status Epilepticus Induces a Particular Microglial Activation State Characterized by Enhanced Purinergic Signalling" The Journal of Neuroscience, 2008, vol. 28(37), pp. 9133-9144.

(Continued)

*Primary Examiner* — Brian McDowell

(57) ABSTRACT

The present invention is directed to a compound of Formula (I) or (Ia)

Formula (I) or (Ia)

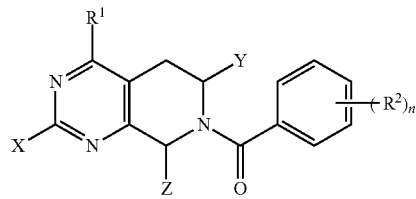

The invention also relates to pharmaceutical compositions comprising compounds of Formula (I) or (Ia). Methods of making and using the compounds of Formula (I) or (Ia) are also within the scope of the invention.

22 Claims, No Drawings

(56) References Cited

FOREIGN PATENT DOCUMENTS

| WO | WO2011/121137 | 10/2011 |
|----|---------------|---------|
| WO | WO 2012/040048 | 3/2012 |
| WO | WO 2012/040048 A2 | 3/2012 |
| WO | WO2014/152589 | 9/2014 |
| WO | WO2014/152621 | 9/2014 |
| WO | WO2014/154897 | 10/2014 |
| WO | WO2016/039977 | 3/2016 |
| WO | WO2016/039983 | 3/2016 |

OTHER PUBLICATIONS

Bagshawe et al "Antibody-Directed Enzyme Prodrug Therapy: A Review" Drug Development Research, 1995, vol. 34, pp. 220-230.
Basso et al "Behavioral Profile of P2X7 Receptor Knockout Mice in Animal Models of Depression and Anxiety: Relevance of Neuropsychiatric Disorders" Behavioral Brain Research, 2009, vol. 198, pp. 83-90.
Berge et al "Pharmaceutical Salts" Journal of Pharmaceutical Sciences, 1977, vol. 66(1), pp. 1-19.
Bertolini et al "A New Rational Hypothesis for the Pharmacophore of the Active Metabolite of Leflunomide, a Potent Immunosuppresive Drug" J Med Chem, 1997, vol. 40, pp. 2011-2016.
Bodor et al "Novel Approaches to the Design of Safer Drugs: Soft Drugs and Site-Specific Chemical Delivery Systems" Advances in Drug Research, 1984, vol. 13, pp. 255-331.
Bourzac et al "Glucose Transporter 2 Expression is Down Regulated Following P2X7 Activation in Enterocytes" J Cell Physiol, 2013, vol. 228, pp. 120-129.
Bundgaard "Design of Prodrugs—(Contents)", Elsevier Science Publishers B.V. (Biomedical Division), 1985, 4 Pgs.
Capouron et al "Immune System to Brain Signaling: Neuropsychopharmacological Implications" Pharmacology & Therapeutics, 2011, vol. 130, pp. 226-238.
Chessel et al "Disruption of the P2X7 Purinoreceptor Gene Abolishes Chronic Inflammatory and Neuropathic Pain", Pain, 2005, vol. 114, pp. 386-396.
Chu et al "Inhibition of P2XY Receptor Ameliorates Transient Global Cerebral Ischemia/Reperfusion Injury Via Modulating Inflammatory Responses in the Rat Hippocampus" Journal of Neuroinflammation, 2012 9:69, pp. 1-10.
Van Nostrand'S Encyclopedia of Chemistry, 2005, $5^{th}$ Ed. p. 261 Considine G D. Ed.
Dantzer et al "Cytokine, Sickness Behavior, and Depression" Immunol Allergy Clin N Am, 2009, vol. 29, pp. 247-264.
Delarasse et al "The Purinergic Receptor P2X7 Triggers α-Secretase-dependent Processing of the Amyloid Precursor Protein" Journal of Biological Chemistry 2011 vol. 286(4) pp. 2596-2606.
Diaz-Hernandez et al "Altered P2X7-Receptor Level and Function in Mouse Models of Huntington'S Disease and Therapeutic Efficacy of Antagonist Administration" FASEB J. 2009 vol. 23(6) pp. 1893-1906.
Diaz-Hernandez et al "In Vivo P2X7 Inhibition Reduces Amyloid Plaques in Alzheimer'S Disease Through GXK3β and Secretases" Neurobiology of Aging 2012 vol. 33 pp. 1816-1828.
Donnelly-Roberts et al "[$^3$H]A-804598 ([$^3$H]2-Cyano-1- [(1S)-1-Phenylethyl]-3-Quinolin-5-Ylguanidine) Is a Novel, Potent, and Selective Antagonist Radioligand for P2X7 Receptors" Neuropharmacology 2009 vol. 56 pp. 223-229.
Duan et al "P2X7 Receptors: Properties and Relevance to CNX Function" Glia 2006 vol. 54 pp. 738-746.
Engel et al "Seizure Suppression and Neuroprotection by Targeting the Purinergic P2X7 Receptor During Status Epilepticus in Mice" FASEB J 2012 vol. 26 pp. 1616-1628.
Ferrari et al "The P2X7 Receptor: A Key Player in IL-1 Processing and Release" J Immunol 2006 vol. 176 pp. 3877-3883.
Fleisher et al "Improved Oreal Drug Delivery: Solubility Limitations Overcome by the Use of Prodrugs" Advanced Drug Delivery Reviews 1996 vol. 19 pp. 115-130.

Friedle et al "Recent Patents on Novel P2X7 Receptor Antagonists and Their Potential for Reducing Central Nervous System Inflammation" Recent Patents on CNS Drug Discovery 2010 vol. 5 pp. 35-45.
Furlan-Freguia et al "P2X7 Receptor Signaling Contributes to Tissue Factor-Dependent Thrombosis in Mice" J Clin Invest 2011 vol. 121(7) pp. 2932-2944.
Grygorowicz et al "Temporal Expression of P2X7 Purinergic Receptor During the Course of Experimental Autoimmune Encephalomyelitis" Neurochemistry International 2010 vol. 57 pp. 823-829.
Guile et al., "Antagonists of the $P2X_7$, Receptor. From Lead Identification to Drug Development", Journal of Medicinal Chemistry, May 28, 2009, vol. 52, No. 10, pp. 3123-3141.
Gunosewoyo and Kassiou, "PX2 Purinergic Receptor Ligands: Recently Patented Compounds", Brain and Mind Research Institute, 2010, pp. 625-646.
Hackam and Redelmeier, "Translation of Research Evidence From Animals to Humans", JAMA, 2006, vol. 296, No. 14, 1731-1732.
Ji et al "P2X7 Deficiency Attenuates Hypertension and Renal Injury in Deoxycorticosterone Acetate-Salt Hypertension" Am J Physiol Renal Physiol 2012 vol. 303 pp. F1207-F1215.
Jordan, Craig, "Tamoxifen: A Most Unlikely Pioneering Medicine", Nature Reviews, 2003, vol. 2, 205-213.
Keating et al "P2X7 Receptor-Dependent Intestinal Afferent Hypersensitivity in a Mouse Model of Postinfectious Irritable Bowel Syndrome" The Journal of Immunology 2011 vol. 187 pp. 1467-1474.
Kim et al "Blockade of P2X7 Receptor Prevents Astroglial Death in the Dentate Gyrus Following Pilocarpine-Induced Status Epilepticus" Neurol Res 2009 vol. 31 pp. 982-988.
Larsen and Bundgaard "A Textbook of Drug Design and Development—(Index)", 1992, 18 Pgs., Harwood Academic Publishers.
Marcellino et al "On the Role of P2X7 Receptors in Dopamine Nerve Cell Degeneration in a Rat Model of Parkinson'S Disease: Studies With the P2X7 Receptor Antagonist A-438079" J Neural Transm 2010 vol. 117 pp. 681-687.
Martins et al "The Role of P2X7 Purinergic Receptors in Inflammatory and Nociceptive Changes Accompanying Cyclophosphamde-Induced Haemorrhagic Cystitis in Mice" BR J Pharmacol 2012 vol. 165 pp. 183-196.
Muller et al "A Potential Role for P2X7R in Allergic Airway Inflammation in Mice and Humans" Am J Respir Cell Mol Biol 2011 vol. 44 pp. 456-464.
Oyanguren-Desez et al "Gain-of-Function of P2X7 Receptor Gene Variants in Multiple Sclerosis" Cell Calcium 2011 vol. 50 pp. 468-472.
Parvathenani et al "P2X7 Mediates Superoxide Production in Primary Microglia and is Up-Regulated in a Transgenic Mouse Model of Alzheimer'S Disease" J Biol Chem 2003 vol. 278(15) pp. 13309-13317.
Paulekuhn et al "Trends in Active Pharmaceutical Ingredient Salt Selection Based on Analysis of Athe Orange Book Database" J Med Chem 2007 vol. 30 pp. 6665-6672.
Robinson et al "Discovery of the Hemifumarate and ($_{αL}$ Alanyloxy)Methyl Ether as Prodrugs of an Antirheumatic Oxindole: Prodrugs for the Enolic OH Group" J Med Chem 1996 vol. 39 pp. 10-18.
Romagnoli et al "The P2X7 Receptor as a Therapeutic Agent" Expert Opin Ther Targets 2008 vol. 12(5) pp. 647-661.
Sanz et al "Activation of Microglia by Amyloid β Requires P2X7 Receptor Expression" J Immunol 2009 vol. 182 pp. 4378-4385.
Shan et al "Prodrug Strategies Based on Intramolecular Cyclization Reactions" J Pharm Sci 1997 vol. 86(7) pp. 765-767.
Sharp et al "P2X7 Deficiency Suppresses Development of Experimental Autoimmune Encephalomyelitis" J Neuroinflammation 2008 vol. 5 :33.
Skaper et al "The P2X7 Purinergic Receptor: From Physiology to Neurological Disorders" FASEB J 2009 vol. 24 pp. 337-345.
Solini et al "Enhanced P2X7 Activity in Human Fibroblasts From Diabetic Patients—a Possible Pathogenic Mechanism for Vascular Damage in Diabetes" Artherioscler Thromb Vasc Biol 2004 vol. 24 pp. 1240-1245.

(56) References Cited

OTHER PUBLICATIONS

Stahl and Wermuth, "Handbook of Pharmaceutical Salts—(Index)", International Union of Pure and Applied Chemistry (IUPAC), 2002, 3 Pgs.
Surprenant et al "Signaling at Purinergic P2X Receptors" Annu Rev Physiol 2009 vol. 71 pp. 333-359.
Dyatkin et al "Determination of the Absolute Configuration of a Key Tricyclic Component of a Novel Vasopressing Receptor Antagonist by Use of Vibrational Circular Dichroism" Chirality 2002 vol. 14 pp. 215-219.
Rudolph et al., "Novel Methyl Substituted 1-(5,6-Dihydro-[1,2,4]Triazolo[4,3-A]Pyrazine-7(8H)-YL)Methanones are P2X7 Antagonists", Bioorganic & Medicinal Chemistry Letters, vol. 25, No. 16, Aug. 1, 2015 (Aug. 1, 2015), pp. 3157-3162.
Database Chemcats Enamine Screening Library Database Accession 2035772210 Jan. 17, 2008.
Database Chemcats Ukrorgsynthesis Screeing Collection Accession 2033253463 Mar. 6, 2007.
Database Chemcats Ryan Scientific Screening Library Database Accession 2042676574 Jan. 25, 2008.
Database Chemcats Ambinter Stock Screeing Collection Database Accession 2046454718 Feb. 13, 2008.
Database Chemcats Ryan Scientific Screening Library Database Accession 2043876860 Jan. 25, 2008.
Database Chemcats Ryan Scientific Screening Library Database Accession 2042637020 Jan. 25, 2008.
Database Chemcats Ryan Scientific Screening Library Database Accession 2042634059 Jan. 25, 2008.
Database Chemcats Ambinter Stock Screening Collection Database Accession 2040548370 Feb. 13, 2008.
Database Chemcats Ambinter Stock Screening Collection Database Accession 2040381923 Feb. 13, 2008.
Database Chemcats Ambinter Stock Screening Collection Database Accession 2040033692 Feb. 13, 2008.
Database Chemcats Aurora Screening Library Database Accession 2037938546 Sep. 6, 2007.
PCT ISR dated Jul. 31, 2009 for International Application No. PCT/US2009/041249.
PCT ISR dated Oct. 15, 2015 for International Application No. PCT/US2015/046710.
U.S. Appl. No. 14/714,714, Non-Final Rejection Office Action, Dated Nov. 23, 2015.
U.S. Appl. No. 14/714,714, Notice of Allowance, Dated Mar. 30, 2016.
U.S. Appl. No. 14/714,714, Notice of Allowance, Dated Jul. 18, 2016.
U.S. Appl. No. 14/775,436, Non-Final Rejection Office Action, Dated Jul. 27, 2016.
U.S. Appl. No. 14/775,436, Restriction Requirement Office Action, Dated Apr. 27, 2016.
Arulkumaran, N., et al. "A Potential Therapeutic Role for P2X7 Receptor (P2X7R) Antagonists in the Treatment of Inflammatory Diseases", Expert Opinion on Investigative Drugs, vol. 20(7), pp. 897-915 (2011).
Hudson, Derek, "Methodological Implications of Simultaneous Solid-Phase Peptide Synthesis. 1. Comparison of Different Coupling Procedures", J. Organic Chemistry, vol. 53, pp. 617-624 (1988).
Killeen, M. E., et al., "Signaling Through Purinergic Receptors for ATP Induces Human Cutaneous Innate and Adaptive Th17 Responses: Implications in the Pathogenesis of Psoriasis", J. Immunology, vol. 190(8), pp. 4324-4336 (2013).
Skaper, S., et al., "The $P2X_7$ Purinergic Receptor: From Physiology to Neurological Disorders", FASEB Journal, vol. 24, pp. 337-345 (2010).
Thiboutot, D., J. "Inflammasome Activation by *Propionibacterium acnes*: The Study of IL-1 in Acne Continues to Unfold", Investigative Dermatology, vol. 134, pp. 595-597 (2014).
Vergani, A., et al., "Long-Term Heart Transplant Survival by Targeting the Ionotropic Purinergic Receptor P2X7", Circulation, vol. 127, pp. 463-475 (2013).
Vergani, A., et al., "Effect of the Purinergic Inhibitor Oxidized ATP in a Model of Islet Allograft Rejection", Diabetes, vol. 62, pp. 1665-1675 (2013).
U.S. Appl. No. 15/258,320, filed Sep. 7, 2016, Janssen Pharmaceutica NV.
U.S. Appl. No. 62/049,727, filed Sep. 12, 2014, Janssen Pharmaceutica NV.
U.S. Appl. No. 62/049,687, filed Sep. 12, 2014, Janssen Pharmaceutica NV.
European Search Report for corresponding EP Application 08154909.9 mailed on Jun. 20, 2008.
European Search Report for corresponding EP 16176059.0/1462 mailed Sep. 21, 2016.
PCT ISR Dated Oct. 15, 2015 for International Application No. PCT/US2015/046852.
Government of Pakistan Intellectual Property Organization the Patent Office Karachi, Mailed Apr. 28, 2016.
U.S. Appl. No. 14/714,714, Notice of Allowance, Dated Aug. 15, 2016.
U.S. Appl. No. 14/775,432, Restriction Requirement, Office Action Dated Aug. 25, 2016.
Singapore Search Report corresponding to Application No. 11201507259U Dated May 5, 2016.
China Application No. 201480027363.2 First Office Action Dated May 5, 2016.
U.S. Appl. No. 14/775,436, Notice of Allowance, Dated Oct. 14, 2016.
U.S. Appl. No. 14/775,436, Notice of Allowance, Dated Nov. 8, 2016.

P2X7 MODULATORS

CROSS REFERENCE TO RELATED APPLICATIONS

This application is a national phase of International Application No. PCT/US2014/027505 filed on Mar. 14, 2014, which claims the benefit of U.S. Provisional Application No. 61/785,530 filed on Mar. 14, 2013, each of which are incorporated herein by reference in its entirety.

FIELD OF THE INVENTION

The present invention is related compounds having P1X7 modulating properties, pharmaceutical compositions comprising these compounds, chemical processes for preparing these compounds and their use in the treatment of diseases associated with P2X7 receptor activity in animals, in particular humans.

BACKGROUND OF THE INVENTION

The P2X7 receptor is a ligand-gated ion channel and is present on a variety of cell types, largely those known to be involved in the inflammatory and/or immune process, specifically, macrophages and monocytes in the periphery and predominantly in glial cells (microglia and astrocytes) of the CNS. (Duan and Neary, *Glia* 2006, 54, 738-746; Skaper et al., *FASEB J* 2009, 24, 337-345; Surprenant and North, *Annu. Rev. Physiol.* 2009, 71, 333-359). Activation of the P2X7 receptor by extracellular nucleotides, in particular adenosine triphosphate, leads to the release of proinflammatory cytokines IL-1β and IL-18 (Muller, et. al. *Am. J. Respir. Cell Mol. Biol.* 2011, 44, 456-464), giant cell formation (macrophages/microglial cells), degranulation (mast cells) and L-selectin shedding (lymphocytes) (Ferrari et al., *J. Immunol.* 2006, 176, 3877-3883; Surprenant and North, *Annu. Rev. Physiol.* 2009, 71, 333-359). P2X7 receptors are also located on antigen-presenting cells (keratinocytes, salivary acinar cells (parotid cells)), hepatocytes, erythrocytes, erythroleukaemic cells, monocytes, fibroblasts, bone marrow cells, neurones, and renal mesangial cells.

The importance of P2X7 in the nervous system arises primarily from experiments using P2X7 knock out mice. These mice demonstrate the role of P2X7 in the development and maintenance of pain as these mice were protected from the development of both adjuvant-induced inflammatory pain and partial nerve ligation induced neuropathic pain (Chessell et al., *Pain* 2005, 114, 386-396). In addition P2X7 knock out mice also exhibit an anti-depressant phenotype based on reduced immobility in forced swim and tail suspension tests (Basso et al., *Behav. Brain Res.* 2009, 198, 83-90.). Moreover, the P2X7 pathway is linked to the release of the pro-inflammatory cytokine, IL-1β, which has been linked to precipitation of mood disorders in humans (Dantzer, *Immunol. Allergy Clin. North Am.* 2009, 29, 247-264; Capuron and Miller, *Pharmacol. Ther.* 2011, 130, 226-238). In addition, in murine models of Alzheimer's disease, P2X7 was upregulated around amyloid plaques indicating a role of this target in such pathology as well (Parvathenani et al., *J. Biol. Chem.* 2003, 278, 13309-13317).

In view of the clinical importance of P2X7, the identification of compounds that modulate P2X7 receptor function represents an attractive avenue into the development of new therapeutic agents. Such compounds are provided herein.

SUMMARY OF THE INVENTION

The invention is directed to the general and preferred embodiments defined, respectively, by the independent and dependent claims appended hereto, which are incorporated by reference herein. One aspect of this invention concerns compounds of Formula (I):

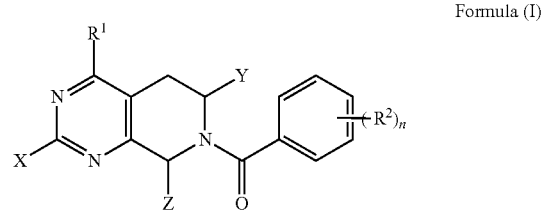

Formula (I)

wherein:
each $R^2$ is independently selected from the group consisting of H, halo, CN, $C_1$-$C_3$ alkyl, perhaloalkyl, $C_1$-$C_3$ alkoxy and perhaloalkoxy;
n is an integer from 0-3;
X is independently selected from the group consisting of H, $C_1$-$C_3$ alkyl, $C_3$ cycloalkyl, perfluoroalkyl, —$NH_2$, and —$N(CH_3)_2$;
Y and Z are independently H or $CH_3$;
$R^1$ is independently selected from the group consisting of:

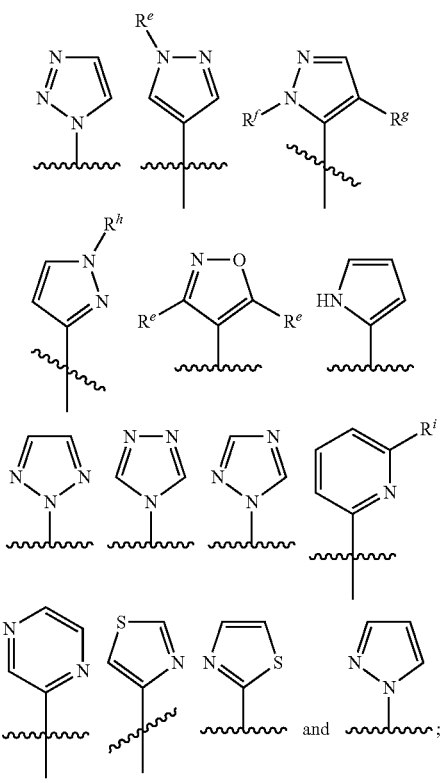

$R^e$ and $R^f$ are H or $C_1$-$C_3$ alkyl;
$R^g$ is H, F, or perfluoroalkyl;
$R^h$ is H, $C_1$-$C_3$ alkyl, —$CH_2CH_2OCH_3$ or perfluoroalkyl; and
$R^i$ is H or halo; or pharmaceutically acceptable salts of compounds of Formula (I).

Another aspect of this invention concerns compounds of Formula (Ia):

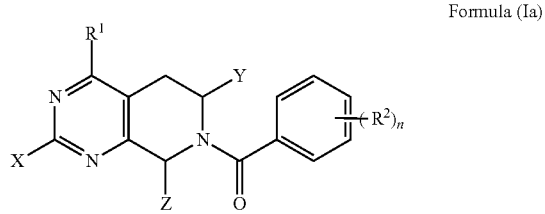

Formula (Ia)

wherein:
$R^2$ is H, halo, $C_{1-3}$ alkyl, or perhaloalkyl;
n is an integer from 0-4;
X is H, $C_1$-$C_4$ alkyl, $C_3$-$C_4$ cycloalkyl, perfluoroalkyl, —$NH_2$, or —$N(C_{1-3}alkyl)_2$;
Y and Z are independently H or $C_{1-3}$alkyl;
$R^1$ is selected from the group consisting of:

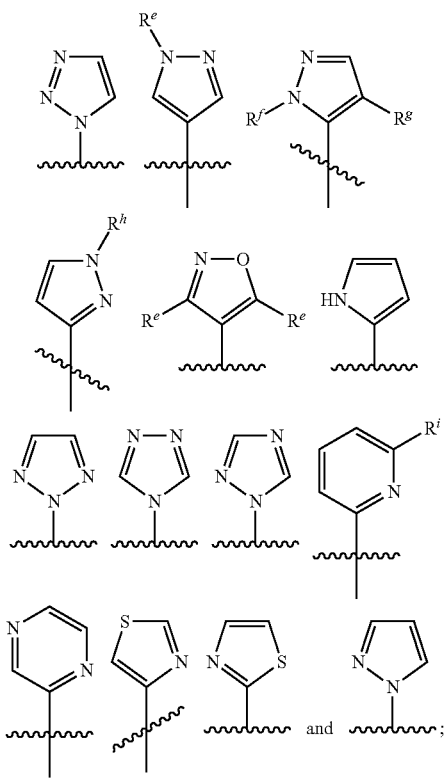

$R^e$ and $R^f$ are H or $C_{1-3}$alkyl;
$R^g$ is H, F, or perfluoroalkyl;
$R^h$ is H, $C_{1-3}$alkyl, $CH_2CH_2OCH_3$ or perfluoroalkyl; and
$R^i$ is H or halo; or
pharmaceutically acceptable salts of compounds of Formula (Ia).

Further embodiments are provided by pharmaceutically acceptable salts of compounds of Formula (I) or (Ia), pharmaceutically acceptable prodrugs of compounds of Formula (I) or (Ia), and pharmaceutically active metabolites of compounds of Formula (I) or (Ia).

In certain embodiments, the compound of Formula (I) or (Ia) is a compound selected from those species described or exemplified in the detailed description below.

In a further aspect, the invention relates to pharmaceutical compositions for treating a disease, disorder, or medical condition mediated by P2X7 receptor activity, comprising a therapeutically effective amount of at least one compound selected from compounds of Formula (I) or (Ia), pharmaceutically acceptable salts of compounds of Formula (I) or (Ia), pharmaceutically acceptable prodrugs of compounds of Formula (I) or (Ia), and pharmaceutically active metabolites of Formula (I) or (Ia).

Pharmaceutical compositions according to the invention may further comprise one or more pharmaceutically acceptable excipients.

In another aspect, the chemical embodiments of the present invention are useful as P2X7 receptor modulators. Thus, the invention is directed to a method for modulating P2X7 receptor activity, including when such receptor is in a subject, comprising exposing P2X7 receptor to a therapeutically effective amount of at least one compound selected from compounds of Formula (I) or (Ia), pharmaceutically acceptable salts of compounds of Formula (I) or (Ia), pharmaceutically acceptable prodrugs of compounds of Formula (I) or (Ia), and pharmaceutically active metabolites of compounds of Formula (I) or (Ia).

In another aspect, the invention is directed to a method of treating a subject suffering from or diagnosed with a disease, disorder, or medical condition mediated by P2X7 receptor activity, comprising administering to the subject in need of such treatment a therapeutically effective amount of at least one compound selected from compounds of Formula (I) or (Ia), pharmaceutically acceptable salts of compounds of Formula (I) or (Ia), pharmaceutically acceptable prodrugs of compounds of Formula (I) or (Ia), and pharmaceutically active metabolites of compounds of Formula (I) or (Ia). Additional embodiments of methods of treatment are set forth in the detailed description.

In another aspect, a method of studying isotopically labeled compounds in metabolic studies (preferably with $^{14}C$), reaction kinetic studies (with, for example $^2H$ or $^3H$), detection or imaging techniques [such as positron emission tomography (PET) or single-photon emission computed tomography (SPECT)] including drug or substrate tissue distribution assays, or in radioactive treatment of patients. For example, an $^{18}F$ or $^{11}C$ labeled compound may be particularly preferred for PET or SPECT studies.

An object of the present invention is to overcome or ameliorate at least one of the disadvantages of the conventional methodologies and/or prior art, or to provide a useful alternative thereto.

Additional embodiments, features, and advantages of the invention will be apparent from the following detailed description and through practice of the invention.

Additional embodiments of this invention include methods of making compounds of Formula (I) or (Ia), pharmaceutically acceptable salts of compounds of Formula (I) or (Ia), pharmaceutically acceptable prodrugs of compounds of Formula (I) or (Ia), and pharmaceutically active metabolites of Formula (I) or (Ia).

DETAILED DESCRIPTION OF THE INVENTION

This invention concerns compounds of Formula (I):

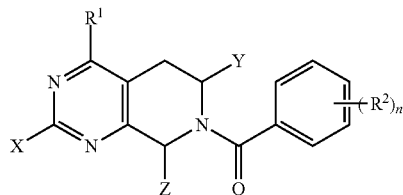

Formula (I)

wherein:

each $R^2$ is independently selected from the group consisting of H, halo, CN, $C_1$-$C_3$ alkyl, perhaloalkyl, $C_1$-$C_3$ alkoxy and perhaloalkoxy;

n is an integer from 0-3;

X is independently selected from the group consisting of H, $C_1$-$C_3$ alkyl, $C_3$ cycloalkyl, perfluoroalkyl, —$NH_2$, and —$N(CH_3)_2$;

Y and Z are independently H or $CH_3$;

$R^1$ is independently selected from the group consisting of:

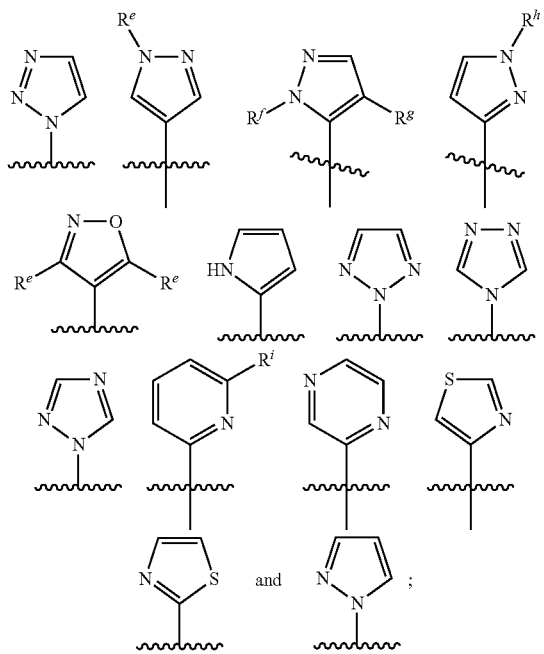

$R^e$ and $R^f$ are H or $C_1$-$C_3$ alkyl;

$R^g$ is H, F, or perfluoroalkyl;

$R^h$ is H, $C_1$-$C_3$ alkyl, —$CH_2CH_2OCH_3$ or perfluoroalkyl; and $R^i$ is H or halo; or pharmaceutically acceptable salts of compounds of Formula (I).

Another aspect of this invention concerns compounds of Formula (Ia):

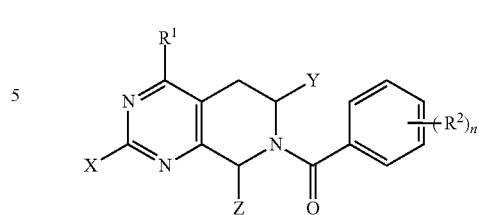

Formula (Ia)

wherein:
$R^2$ is H, halo, $C_{1-3}$ alkyl, or perhaloalkyl;
n is an integer from 0-4;
X is H, $C_1$-$C_4$ alkyl, $C_3$-$C_4$ cycloalkyl, perfluoroalkyl, —$NH_2$, or —$N(C_{1-3}alkyl)_2$;
Y and Z are independently H or $C_{1-3}$alkyl;
$R^1$ is selected from the group consisting of:

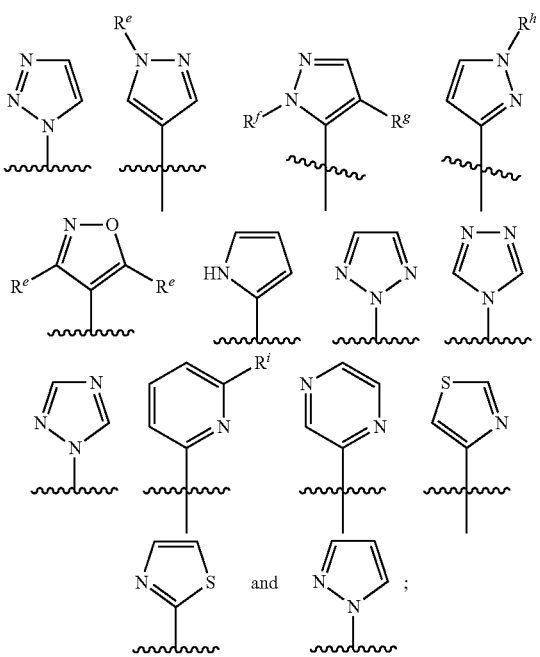

$R^e$ and $R^f$ are H or $C_{1-3}$alkyl;
$R^g$ is H, F, or perfluoroalkyl;
$R^h$ is H, $C_{1-3}$alkyl, $CH_2CH_2OCH_3$ or perfluoroalkyl; and
$R^i$ is H or halo; or
pharmaceutically acceptable salts of compounds of Formula (Ia).

An additional embodiment of the invention is a compound of Formula (I) or Formula (Ia), wherein $R^2$ is halo.

An additional embodiment of the invention is a compound of Formula (I) or Formula (Ia), wherein $R^2$ is halo and perfluoroalkyl.

An additional embodiment of the invention is a compound of Formula (I) or Formula (Ia), wherein n is 0-3 and 0-4, respectively.

An additional embodiment of the invention is a compound of Formula (I) or Formula (Ia), wherein n is 2-3.

An additional embodiment of the invention is a compound of Formula (I) or Formula (Ia), wherein n is 2.

An additional embodiment of the invention is a compound of Formula (I) or Formula (Ia), wherein n is 3.

An additional embodiment of the invention is a compound of Formula (I) or Formula (Ia), wherein at least one $R^2$ substituent is in the ortho position.

An additional embodiment of the invention is a compound of Formula (I) or Formula (Ia), wherein at least one $R^2$ substituent is in the para position.

An additional embodiment of the invention is a compound of Formula (I) or Formula (Ia), wherein at least one $R^2$ substituent is in the ortho position and at least one $R^2$ substituent is in the meta position.

An additional embodiment of the invention is a compound of Formula (I) or Formula (Ia), wherein at least one $R^2$ substituent is in the ortho position and at least one $R^2$ substituent is in the para position.

An additional embodiment of the invention is a compound of Formula (I) or Formula (Ia), wherein $R^2$ is Cl or F.

An additional embodiment of the invention is a compound of Formula (I) or Formula (Ia), wherein $R^2$ is $CF_3$.

An additional embodiment of the invention is a compound of Formula (I) or Formula (Ia), wherein n is 2, $R^2$ is $CF_3$ and $R^2$ is Cl.

An additional embodiment of the invention is a compound of Formula (I) or Formula (Ia), wherein n is 2, $R^2$ is F and $R^2$ is Cl.

An additional embodiment of the invention is a compound of Formula (I) or Formula (Ia), wherein n is 2, $R^2$ is Cl and $R^2$ is Cl or F.

An additional embodiment of the invention is a compound of Formula (I) or Formula (Ia), wherein n is 2, $R^2$ is Cl and is in the ortho position and $R^2$ is $CF_3$ and is in the meta position.

An additional embodiment of the invention is a compound of Formula (I) or Formula (Ia), wherein n is 2, $R^2$ is Cl and is in the ortho position and $R^2$ is Cl and is in the meta position.

An additional embodiment of the invention is a compound of Formula (I) or Formula (Ia), wherein n is 2, $R^2$ is Cl and is in the ortho position and $R^2$ is Cl and is in the para position.

An additional embodiment of the invention is a compound of Formula (I) or Formula (Ia), wherein n is 2, $R^2$ is F and is in the ortho position and $R^2$ is Cl and is in the para position.

An additional embodiment of the invention is a compound of Formula (I) or Formula (Ia), wherein Y is H.

An additional embodiment of the invention is a compound of Formula (I) or Formula (Ia), wherein Y is $CH_3$ or $C_1$-$C_3$ alkyl, respectively.

An additional embodiment of the invention is a compound of Formula (I) or Formula (Ia), wherein Y is $CH_3$.

An additional embodiment of the invention is a compound of Formula (I) or Formula (Ia), wherein Y is H or $CH_3$.

An additional embodiment of the invention is a compound of Formula (I) or Formula (Ia), wherein Z is H.

An additional embodiment of the invention is a compound of Formula (I) or Formula (Ia), wherein Z is $CH_3$ or $C_1$-$C_3$ alkyl, respectively.

An additional embodiment of the invention is a compound of Formula (I) or Formula (Ia), wherein Z is $CH_3$.

An additional embodiment of the invention is a compound of Formula (I) or Formula (Ia), wherein Y and Z are H.

An additional embodiment of the invention is a compound of Formula (I) or Formula (Ia), wherein Y is H and Z is $CH_3$.

An additional embodiment of the invention is a compound of Formula (I) or Formula (Ia), wherein Y is $CH_3$ and Z is H.

An additional embodiment of the invention is a compound of Formula (I) or Formula (Ia), wherein Y and Z are $CH_3$.

An additional embodiment of the invention is a compound of Formula (I), wherein X is H, $C_1$-$C_3$ alkyl, $C_3$ cycloalkyl, or perfluoroalkyl.

An additional embodiment of the invention is a compound of Formula (Ia), wherein X is H, $C_1$-$C_4$ alkyl, $C_3$-$C_4$ cycloalkyl, or perfluoroalkyl.

An additional embodiment of the invention is a compound of Formula (I), wherein X is H, $C_1$-$C_3$ alkyl or $C_3$ cycloalkyl.

An additional embodiment of the invention is a compound of Formula (Ia), wherein X is H, $C_1$-$C_4$ alkyl or $C_3$-$C_4$ cycloalkyl.

An additional embodiment of the invention is a compound of Formula (I), wherein X is H or $C_1$-$C_3$ alkyl.

An additional embodiment of the invention is a compound of Formula (Ia), wherein X is H or $C_1$-$C_4$ alkyl.

An additional embodiment of the invention is a compound of Formula (I) or Formula (Ia), wherein X is H.

An additional embodiment of the invention is a compound of Formula (I), wherein X is $C_1$-$C_3$ alkyl.

An additional embodiment of the invention is a compound of Formula (Ia), wherein X is $C_1$-$C_4$ alkyl.

An additional embodiment of the invention is a compound of Formula (I) or Formula (Ia), wherein X is $CH_3$.

An additional embodiment of the invention is a compound of Formula (I) or Formula (Ia), wherein X is H or $CH_3$.

An additional embodiment of the invention is a compound of Formula (I) or Formula (Ia), wherein $R^1$ is selected from the group consisting of:

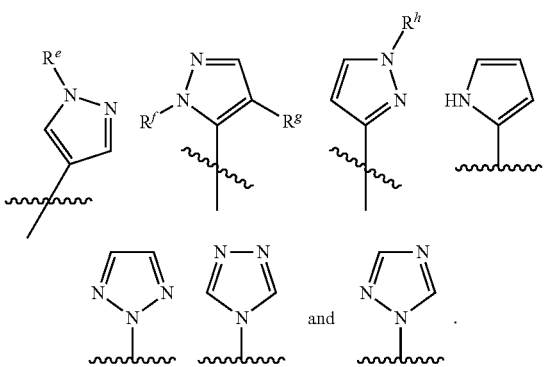

An additional embodiment of the invention is a compound of Formula (I) or Formula (Ia), wherein $R^1$ is selected from the group consisting of:

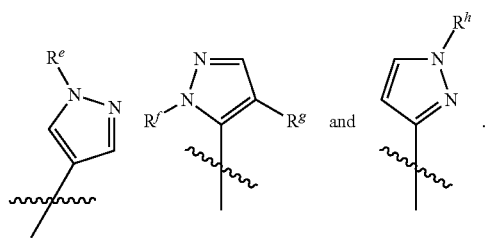

An additional embodiment of the invention is a compound of Formula (I) or Formula (Ia), wherein $R^1$ is selected from the group consisting of:

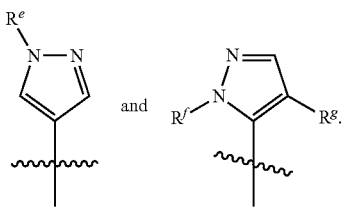

An additional embodiment of the invention is a compound of Formula (I) or Formula (Ia), wherein $R^1$ is selected from the group consisting of:

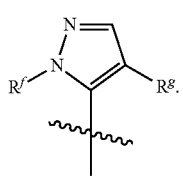

An additional embodiment of the invention is a compound of Formula (I) or Formula (Ia), wherein $R^f$ and $R^g$ are H and $R^1$ is

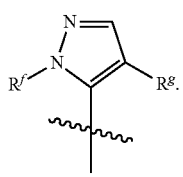

An additional embodiment of the invention is a compound of Formula (I) or Formula (Ia), wherein X, Y, Z, $R^f$ and $R^g$ are H, n is 2, $R^2$ is in the ortho position and is Cl, $R^2$ is in the meta position and is Cl and $R^1$ is

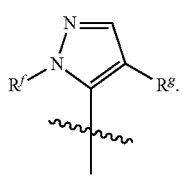

An additional embodiment of the invention is a compound of Formula (I) or Formula (Ia), wherein Y, Z, $R^f$ and $R^g$ are H, X is $CH_3$, n is 2, $R^2$ is in the ortho position and is Cl, $R^2$ is in the meta position and is $CF_3$ and $R^1$ is

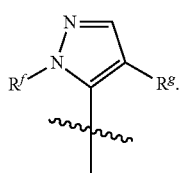

An additional embodiment of the invention is a compound of Formula (I) or Formula (Ia), wherein Z, $R^f$ and $R^g$ are H, X and Y are $CH_3$, n is 2, $R^2$ is in the ortho position and is Cl, $R^2$ is in the meta position and is $CF_3$ and $R^1$ is

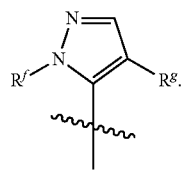

An additional embodiment of the invention is a compound of Formula (I) or Formula (Ia), wherein Z, $R^f$ and $R^g$ are H, X and Y are $CH_3$, n is 2, $R^2$ is in the ortho position and is Cl, $R^2$ is in the para position and is Cl and $R^1$ is

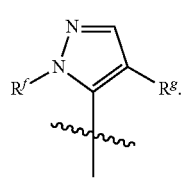

An additional embodiment of the invention is a compound of Formula (I) or Formula (Ia), wherein Z, $R^f$ and $R^g$ are H, X and Y are $CH_3$, n is 2, $R^2$ is in the ortho position and is F, $R^2$ is in the para position and is Cl and $R^1$ is

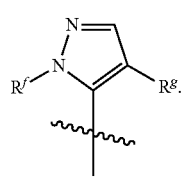

An additional embodiment of the invention is a compound selected from the group consisting of those presented in Table 1:

TABLE 1

| Compounds of Formula (I) or (Ia) |
|---|
| 7-{[2-Chloro-3-(trifluoromethyl)phenyl]carbonyl}-4-phenyl-5,6,7,8-tetrahydropyrido[3,4-d]pyrimidine; |
| 7-[(2,3-Dichlorophenyl)carbonyl]-4-phenyl-5,6,7,8-tetrahydropyrido[3,4-d]pyrimidine; |
| 4-(2,6-dimethyl-4-(1H-pyrazol-5-yl)-5,6,7,8-tetrahydropyrido[3,4-d]pyrimidine-7-carbonyl)-3-methylbenzonitrile; |
| 7-[(2,3-Dichlorophenyl)carbonyl]-4-(1H-pyrazol-4-yl)-5,6,7,8-tetrahydropyrido[3,4-d]pyrimidine; |
| 7-[(2,3-Dichlorophenyl)carbonyl]-4-(1-methyl-1H-pyrazol-4-yl)-5,6,7,8-tetrahydropyrido[3,4-d]pyrimidine; |
| 7-[(2-Chloro-3-methylphenyl)carbonyl]-4-(1-methyl-1H-pyrazol-4-yl)-5,6,7,8-tetrahydropyrido[3,4-d]pyrimidine; |
| 7-[(2,3-Dichlorophenyl)carbonyl]-4-(1H-pyrazol-5-yl)-5,6,7,8-tetrahydropyrido[3,4-d]pyrimidine; |
| 7-[(2-Chloro-3-methylphenyl)carbonyl]-4-(1H-pyrazol-5-yl)-5,6,7,8-tetrahydropyrido[3,4-d]pyrimidine; |
| 7-[(2,3-Dimethylphenyl)carbonyl]-4-(1H-pyrazol-5-yl)-5,6,7,8-tetrahydropyrido[3,4-d]pyrimidine; |
| 7-{[2-Methyl-3-(trifluoromethyl)phenyl]carbonyl}-4-(1H-pyrazol-5-yl)-5,6,7,8-tetrahydropyrido[3,4-d]pyrimidine; |
| 7-[(2,3-Dichlorophenyl)carbonyl]-4-pyridin-2-yl-5,6,7,8-tetrahydropyrido[3,4-d]pyrimidine; |
| 7-{[2-Chloro-3-(trifluoromethyl)phenyl]carbonyl}-4-pyridin-2-yl-5,6,7,8-tetrahydropyrido[3,4-d]pyrimidine; |
| 7-[(2-Chloro-3-methylphenyl)carbonyl]-4-pyridin-2-yl-5,6,7,8-tetrahydropyrido[3,4-d]pyrimidine; |
| 7-[(2,3-Dichlorophenyl)carbonyl]-4-pyrazin-2-yl-5,6,7,8-tetrahydropyrido[3,4-d]pyrimidine; |

TABLE 1-continued

Compounds of Formula (I) or (Ia)

7-{[2-Methyl-3-(trifluoromethyl)phenyl]carbonyl}-4-pyrazin-2-yl-5,6,7,8-tetrahydropyrido[3,4-d]pyrimidine;
7-[(2-Chloro-4,5-difluorophenyl)carbonyl]-4-pyrazin-2-yl-5,6,7,8-tetrahydropyrido[3,4-d]pyrimidine;
7-{[2-Chloro-3-(trifluoromethyl)phenyl]carbonyl}-4-[1-(tetrahydro-2H-pyran-2-yl)-1H-pyrazol-5-yl]-5,6,7,8-tetrahydropyrido[3,4-d]pyrimidine;
(4-(1H-pyrazol-5-yl)-5,6-dihydropyrido[3,4-d]pyrimidin-7(8H)-yl)(2-chloro-3-(trifluoromethyl)phenyl)methanone;
7-{[2-Chloro-3-(trifluoromethyl)phenyl]carbonyl}-4-(1-methyl-1H-pyrazol-3-yl)-5,6,7,8-tetrahydropyrido[3,4-d]pyrimidine;
7-[(2,4-Dichloro-3-fluorophenyl)carbonyl]-4-(1H-pyrazol-5-yl)-5,6,7,8-tetrahydropyrido[3,4-d]pyrimidine;
7-[(2-chloro-4-fluorophenyl)carbonyl]-4-(1H-pyrazol-5-yl)-5,6,7,8-tetrahydropyrido[3,4-d]pyrimidine;
7-[(2,3-Dichlorophenyl)carbonyl]-4-(1H-pyrazol-1-yl)-5,6,7,8-tetrahydropyrido[3,4-d]pyrimidine;
7-[(2,3-Dichlorophenyl)carbonyl]-4-(2H-1,2,3-triazol-2-yl)-5,6,7,8-tetrahydropyrido[3,4-d]pyrimidine;
7-{[2-Chloro-3-(trifluoromethyl)phenyl]carbonyl}-4-(2H-1,2,3-triazol-2-yl)-5,6,7,8-tetrahydropyrido[3,4-d]pyrimidine;
7-[(2,3-Dichlorophenyl)carbonyl]-N,N-dimethyl-4-phenyl-5,6,7,8-tetrahydropyrido[3,4-d]pyrimidin-2-amine;
7-{[2-Chloro-3-(trifluoromethyl)phenyl]carbonyl}-N,N-dimethyl-4-phenyl-5,6,7,8-tetrahydropyrido[3,4-d]pyrimidin-2-amine;
7-[(2,3-Dichlorophenyl)carbonyl]-2-methyl-4-phenyl-5,6,7,8-tetrahydropyrido[3,4-d]pyrimidine;
7-[(2,3-Dichlorophenyl)carbonyl]-4-(4-fluorophenyl)-2-methyl-5,6,7,8-tetrahydropyrido[3,4-d]pyrimidine;
7-[(2,3-Dichlorophenyl)carbonyl]-4-phenyl-5,6,7,8-tetrahydropyrido[3,4-d]pyrimidin-2-amine;
7-{[2-Chloro-3-(trifluoromethyl)phenyl]carbonyl}-2-methyl-4-pyridin-2-yl-5,6,7,8-tetrahydropyrido[3,4-d]pyrimidine;
7-[(2,3-Dichlorophenyl)carbonyl]-2-methyl-4-pyridin-2-yl-5,6,7,8-tetrahydropyrido[3,4-d]pyrimidine;
7-{[2-Chloro-3-(trifluoromethyl)phenyl]carbonyl}-2-methyl-4-phenyl-5,6,7,8-tetrahydropyrido[3,4-d]pyrimidine;
7-{[2-Chloro-3-(trifluoromethyl)phenyl]carbonyl}-2-methyl-4-(1H-pyrazol-5-yl)-5,6,7,8-tetrahydropyrido[3,4-d]pyrimidine;
7-[(2,3-Dichlorophenyl)carbonyl]-2-methyl-4-(1H-pyrazol-5-yl)-5,6,7,8-tetrahydropyrido[3,4-d]pyrimidine;
7-{[2-Chloro-3-(trifluoromethyl)phenyl]carbonyl}-4-(4-fluoro-1H-pyrazol-5-yl)-2-methyl-5,6,7,8-tetrahydropyrido[3,4-d]pyrimidine;
7-[(2,3-Dichlorophenyl)carbonyl]-4-(4-fluoro-1H-pyrazol-5-yl)-2-methyl-5,6,7,8-tetrahydropyrido[3,4-d]pyrimidine;
7-{[2-Chloro-3-(trifluoromethyl)phenyl]carbonyl}-4-(1,3-thiazol-2-yl)-5,6,7,8-tetrahydropyrido[3,4-d]pyrimidine;
7-[(2,3-Dichlorophenyl)carbonyl]-4-(1,3-thiazol-2-yl)-5,6,7,8-tetrahydropyrido[3,4-d]pyrimidine;
7-{[2-Chloro-3-(trifluoromethyl)phenyl]carbonyl}-2-methyl-4-[4-(trifluoromethyl)-1H-pyrazol-5-yl]-5,6,7,8-tetrahydropyrido[3,4-d]pyrimidine;
7-[(2,3-Dichlorophenyl)carbonyl]-2-methyl-4-[4-(trifluoromethyl)-1H-pyrazol-5-yl]-5,6,7,8-tetrahydropyrido[3,4-d]pyrimidine;
7-[(2,3-Dichlorophenyl)carbonyl]-4-(1H-pyrrol-2-yl)-5,6,7,8-tetrahydropyrido[3,4-d]pyrimidine;
7-{[2-Chloro-3-(trifluoromethyl)phenyl]carbonyl}-4-(1H-pyrrol-2-yl)-5,6,7,8-tetrahydropyrido[3,4-d]pyrimidine;
7-{[2-Chloro-3-(trifluoromethyl)phenyl]carbonyl}-4-(1,3-thiazol-4-yl)-5,6,7,8-tetrahydropyrido[3,4-d]pyrimidine;
7-{[2-Chloro-3-(trifluoromethyl)phenyl]carbonyl}-2-methyl-4-(1,3-thiazol-4-yl)-5,6,7,8-tetrahydropyrido[3,4-d]pyrimidine;
7-{[2-Chloro-3-(trifluoromethyl)phenyl]carbonyl}-2-methyl-4-(1H-pyrrol-2-yl)-5,6,7,8-tetrahydropyrido[3,4-d]pyrimidine;
7-{[2-Chloro-3-(trifluoromethyl)phenyl]carbonyl}-4-(3,5-dimethylisoxazol-4-yl)-2-methyl-5,6,7,8-tetrahydropyrido[3,4-d]pyrimidine;
7-{[2-Chloro-3-(trifluoromethyl)phenyl]carbonyl}-2-methyl-4-(2H-1,2,3-triazol-2-yl)-5,6,7,8-tetrahydropyrido[3,4-d]pyrimidine;
7-{[2-Chloro-3-(trifluoromethyl)phenyl]carbonyl}-2-methyl-4-(1H-1,2,3-triazol-1-yl)-5,6,7,8-tetrahydropyrido[3,4-d]pyrimidine;
7-{[2-Chloro-3-(trifluoromethyl)phenyl]carbonyl}-isoxazol-4-yl-2-methyl-5,6,7,8-tetrahydropyrido[3,4-d]pyrimidine;
7-{[2-Chloro-3-(trifluoromethyl)phenyl]carbonyl}-4-(3,5-dimethylisoxazol-4-yl)-5,6,7,8-tetrahydropyrido[3,4-d]pyrimidine;
7-{[2-Fluoro-3-(trifluoromethyl)phenyl]carbonyl}-2-methyl-4-(1H-pyrazol-5-yl)-5,6,7,8-tetrahydropyrido[3,4-d]pyrimidine;
2-Methyl-7-{[2-methyl-3-(trifluoromethyl)phenyl]carbonyl}-4-(1H-pyrazol-5-yl)-5,6,7,8-tetrahydropyrido[3,4-d]pyrimidine;
7-[(2,4-Dichloro-3-fluorophenyl)carbonyl]-2-methyl-4-(1H-pyrazol-5-yl)-5,6,7,8-tetrahydropyrido[3,4-d]pyrimidine;
7-{[2-Chloro-3-(trifluoromethyl)phenyl]carbonyl}-N,N-dimethyl-4-(1H-pyrazol-5-yl)-5,6,7,8-tetrahydropyrido[3,4-d]pyrimidin-2-amine;
7-{[2-Chloro-3-(trifluoromethyl)phenyl]carbonyl}-4-(1H-pyrazol-5-yl)-5,6,7,8-tetrahydropyrido[3,4-d]pyrimidin-2-amine;
7-{[2-Chloro-3-(trifluoromethyl)phenyl]carbonyl}-2,6-dimethyl-4-(1H-pyrazol-5-yl)-5,6,7,8-tetrahydropyrido[3,4-d]pyrimidine;
7-{[2-Chloro-3-(trifluoromethyl)phenyl]carbonyl}-2-cyclopropyl-4-(1H-pyrazol-5-yl)-5,6,7,8-tetrahydropyrido[3,4-d]pyrimidine;
(6R)-7-{[2-Chloro-3-(trifluoromethyl)phenyl]carbonyl}-2,6-dimethyl-4-(1H-pyrazol-5-yl)-5,6,7,8-tetrahydropyrido[3,4-d]pyrimidine;
(6S)-7-{[2-Chloro-3-(trifluoromethyl)phenyl]carbonyl}-2,6-dimethyl-4-(1H-pyrazol-5-yl)-5,6,7,8-tetrahydropyrido[3,4-d]pyrimidine;
(4-(1H-pyrazol-5-yl)-2-(trifluoromethyl)-5,6-dihydropyrido[3,4-d]pyrimidin-7(8H)-yl)(2-chloro-3-(trifluoromethyl)phenyl)methanone;
3-(2,6-dimethyl-4-(1H-pyrazol-5-yl)-5,6,7,8-tetrahydropyrido[3,4-d]pyrimidine-7-carbonyl)-2-methylbenzonitrile;
(2-chloro-3-(trifluoromethyl)phenyl)(6-methyl-4-(1H-pyrazol-5-yl)-5,6-dihydropyrido[3,4-d]pyrimidin-7(8H)-yl)methanone
(2-amino-6-methyl-4-(1H-pyrazol-5-yl)-5,6-dihydropyrido[3,4-d]pyrimidin-7(8H)-yl)(2-chloro-3-(trifluoromethyl)phenyl)methanone;
(2-chloro-4-fluoro-3-(trifluoromethyl)phenyl)(2,6-dimethyl-4-(1H-pyrazol-5-yl)-5,6-dihydropyrido[3,4-d]pyrimidin-7(8H)-yl)methanone;
(S)-(2-chloro-4-fluoro-3-(trifluoromethyl)phenyl)(2,6-dimethyl-4-(1H-pyrazol-5-yl)-5,6-dihydropyrido[3,4-d]pyrimidin-7(8H)-yl)methanone;
(R)-(2-chloro-4-fluoro-3-(trifluoromethyl)phenyl)(2,6-dimethyl-4-(1H-pyrazol-5-yl)-5,6-dihydropyrido[3,4-d]pyrimidin-7(8H)-yl)methanone;
(2,3-dichlorophenyl)(2,6-dimethyl-4-(1H-pyrazol-5-yl)-5,6-dihydropyrido[3,4-d]pyrimidin-7(8H)-yl)methanone;
(R)-(2,3-dichlorophenyl)(2,6-dimethyl-4-(1H-pyrazol-5-yl)-5,6-dihydropyrido[3,4-d]pyrimidin-7(8H)-yl)methanone;
(S)-(2,3-dichlorophenyl)(2,6-dimethyl-4-(1H-pyrazol-5-yl)-5,6-dihydropyrido[3,4-d]pyrimidin-7(8H)-yl)methanone;
(2,4-dichloro-3-fluorophenyl)(2,6-dimethyl-4-(1H-pyrazol-5-yl)-5,6-dihydropyrido[3,4-d]pyrimidin-7(8H)-yl)methanone;
(R)-(2,4-dichloro-3-fluorophenyl)(2,6-dimethyl-4-(1H-pyrazol-5-yl)-5,6-dihydropyrido[3,4-d]pyrimidin-7(8H)-yl)methanone;
(S)-(2,4-dichloro-3-fluorophenyl)(2,6-dimethyl-4-(1H-pyrazol-5-yl)-5,6-dihydropyrido[3,4-d]pyrimidin-7(8H)-yl)methanone;
(2-chloro-3-(trifluoromethyl)phenyl)(2,6-dimethyl-4-(1-methyl-1H-pyrazol-5-yl)-5,6-dihydropyrido[3,4-d]pyrimidin-7(8H)-yl)methanone;
(2,6-dimethyl-4-(1H-pyrazol-5-yl)-5,6-dihydropyrido[3,4-d]pyrimidin-7(8H)-yl)(2-fluoro-3-(trifluoromethyl)phenyl)methanone;
(R)-(2,6-dimethyl-4-(1H-pyrazol-5-yl)-5,6-dihydropyrido[3,4-d]pyrimidin-7(8H)-yl)(2-fluoro-3-(trifluoromethyl)phenyl)methanone;
(S)-(2,6-dimethyl-4-(1H-pyrazol-5-yl)-5,6-dihydropyrido[3,4-d]pyrimidin-7(8H)-yl)(2-fluoro-3-(trifluoromethyl)phenyl)methanone;
(2,6-dimethyl-4-(1H-pyrazol-5-yl)-5,6-dihydropyrido[3,4-d]pyrimidin-7(8H)-yl)(2-methyl-3-(trifluoromethyl)phenyl)methanone
(R)-(2,6-dimethyl-4-(1H-pyrazol-5-yl)-5,6-dihydropyrido[3,4-d]pyrimidin-7(8H)-yl)(2-methyl-3-(trifluoromethyl)phenyl)methanone
(S)-(2,6-dimethyl-4-(1H-pyrazol-5-yl)-5,6-dihydropyrido[3,4-d]pyrimidin-7(8H)-yl)(2-methyl-3-(trifluoromethyl)phenyl)methanone
(2,3-dichloro-4-fluorophenyl)(2,6-dimethyl-4-(1H-pyrazol-5-yl)-5,6-dihydropyrido[3,4-d]pyrimidin-7(8H)-yl)methanone
(R)-(2,3-dichloro-4-fluorophenyl)(2,6-dimethyl-4-(1H-pyrazol-5-yl)-5,6-dihydropyrido[3,4-d]pyrimidin-7(8H)-yl)methanone;
(S)-(2,3-dichloro-4-fluorophenyl)(2,6-dimethyl-4-(1H-pyrazol-5-yl)-5,6-dihydropyrido[3,4-d]pyrimidin-7(8H)-yl)methanone;
(2,4-dichlorophenyl)(2,6-dimethyl-4-(1H-pyrazol-5-yl)-5,6-dihydropyrido[3,4-d]pyrimidin-7(8H)-yl)methanone;
(R)-(2,4-dichlorophenyl)(2,6-dimethyl-4-(1H-pyrazol-5-yl)-5,6-dihydropyrido[3,4-d]pyrimidin-7(8H)-yl)methanone;
(S)-(2,4-dichlorophenyl)(2,6-dimethyl-4-(1H-pyrazol-5-yl)-5,6-dihydropyrido[3,4-d]pyrimidin-7(8H)-yl)methanone;
(2,5-dichlorophenyl)(2,6-dimethyl-4-(1H-pyrazol-5-yl)-5,6-dihydropyrido[3,4-d]pyrimidin-7(8H)-yl)methanone;
(4-chloro-2-fluorophenyl)(2,6-dimethyl-4-(1H-pyrazol-5-yl)-5,6-dihydropyrido[3,4-d]pyrimidin-7(8H)-yl)methanone;
(R)-(4-chloro-2-fluorophenyl)(2,6-dimethyl-4-(1H-pyrazol-5-yl)-5,6-dihydropyrido[3,4-d]pyrimidin-7(8H)-yl)methanone;
(S)-(4-chloro-2-fluorophenyl)(2,6-dimethyl-4-(1H-pyrazol-5-yl)-5,6-dihydropyrido[3,4-d]pyrimidin-7(8H)-yl)methanone;
(2-chloro-4-fluorophenyl)(2,6-dimethyl-4-(1H-pyrazol-5-yl)-5,6-dihydropyrido[3,4-d]pyrimidin-7(8H)-yl)methanone;
(R)-(2-chloro-4-fluorophenyl)(2,6-dimethyl-4-(1H-pyrazol-5-yl)-5,6-dihydropyrido[3,4-d]pyrimidin-7(8H)-yl)methanone;

TABLE 1-continued

Compounds of Formula (I) or (Ia)

(S)-(2-chloro-4-fluorophenyl)(2,6-dimethyl-4-(1H-pyrazol-5-yl)-5,6-dihydropyrido[3,4-d]pyrimidin-7(8H)-yl)methanone;
(2,4-difluorophenyl)(2,6-dimethyl-4-(1H-pyrazol-5-yl)-5,6-dihydropyrido[3,4-d]pyrimidin-7(8H)-yl)methanone;
(R)-(2,4-difluorophenyl)(2,6-dimethyl-4-(1H-pyrazol-5-yl)-5,6-dihydropyrido[3,4-d]pyrimidin-7(8H)-yl)methanone;
(S)-(2,4-difluorophenyl)(2,6-dimethyl-4-(1H-pyrazol-5-yl)-5,6-dihydropyrido[3,4-d]pyrimidin-7(8H)-yl)methanone;
(4-chlorophenyl)(2,6-dimethyl-4-(1H-pyrazol-5-yl)-5,6-dihydropyrido[3,4-d]pyrimidin-7(8H)-yl)methanone;
(2-chlorophenyl)(2,6-dimethyl-4-(1H-pyrazol-5-yl)-5,6-dihydropyrido[3,4-d]pyrimidin-7(8H)-yl)methanone;
(2-chloro-3-(trifluoromethyl)phenyl)(2-ethyl-6-methyl-4-(1H-pyrazol-5-yl)-5,6-dihydropyrido[3,4-d]pyrimidin-7(8H)-yl)methanone;
((R)-(2-chloro-3-(trifluoromethyl)phenyl)(2-ethyl-6-methyl-4-(1H-pyrazol-5-yl)-5,6-dihydropyrido[3,4-d]pyrimidin-7(8H)-yl)methanone;
(S)-(2-chloro-3-(trifluoromethyl)phenyl)(2-ethyl-6-methyl-4-(1H-pyrazol-5-yl)-5,6-dihydropyrido[3,4-d]pyrimidin-7(8H)-yl)methanone
(2-chloro-3-(trifluoromethyl)phenyl)(2-isopropyl-6-methyl-4-(1H-pyrazol-5-yl)-5,6-dihydropyrido[3,4-d]pyrimidin-7(8H)-yl)methanone;
(R)-(2-chloro-3-(trifluoromethyl)phenyl)(2-isopropyl-6-methyl-4-(1H-pyrazol-5-yl)-5,6-dihydropyrido[3,4-d]pyrimidin-7(8H)-yl)methanone;
(S)-(2-chloro-3-(trifluoromethyl)phenyl)(2-isopropyl-6-methyl-4-(1H-pyrazol-5-yl)-5,6-dihydropyrido[3,4-d]pyrimidin-7(8H)-yl)methanone;
(2,4-dichloro-3-fluorophenyl)(2-ethyl-6-methyl-4-(1H-pyrazol-5-yl)-5,6-dihydropyrido[3,4-d]pyrimidin-7(8H)-yl)methanone;
(4-(1H-pyrazol-1-yl)-5,6-dihydropyrido[3,4-d]pyrimidin-7(8H)-yl)(2,3-dimethylphenyl)methanone;
(4-(1H-1,2,3-triazol-1-yl)-5,6-dihydropyrido[3,4-d]pyrimidin-7(8H)-yl)(2-chloro-3-(trifluoromethyl)phenyl)methanone;
7-[(2,3-Dichlorophenyl)carbonyl]-4-(2H-1,2,3-triazol-2-yl)-5,6,7,8-tetrahydropyrido[3,4-d]pyrimidine;
7-{[2-Chloro-3-(trifluoromethyl)phenyl]carbonyl}-4-(2H-1,2,3-triazol-2-yl)-5,6,7,8-tetrahydropyrido[3,4-d]pyrimidine;
(4-(4H-1,2,4-triazol-4-yl)-5,6-dihydropyrido[3,4-d]pyrimidin-7(8H)-yl)(2-chloro-3-(trifluoromethyl)phenyl)methanone;
(4-(1H-1,2,4-triazol-1-yl)-5,6-dihydropyrido[3,4-d]pyrimidin-7(8H)-yl)(2-chloro-3-(trifluoromethyl)phenyl)methanone;
(4-(1H-pyrazol-5-yl)-5,6-dihydropyrido[3,4-d]pyrimidin-7(8H)-yl)(2-fluoro-3-(trifluoromethyl)phenyl)methanone;
(2-chloro-3-(trifluoromethyl)phenyl)(8-methyl-4-(1H-pyrazol-5-yl)-5,6-dihydropyrido[3,4-d]pyrimidin-7(8H)-yl)methanone;
(R)-(2-chloro-3-(trifluoromethyl)phenyl)(8-methyl-4-(1H-pyrazol-5-yl)-5,6-dihydropyrido[3,4-d]pyrimidin-7(8H)-yl)methanone;
(S)-(2-chloro-3-(trifluoromethyl)phenyl)(8-methyl-4-(1H-pyrazol-5-yl)-5,6-dihydropyrido[3,4-d]pyrimidin-7(8H)-yl)methanone;
(2-chloro-4-fluoro-3-(trifluoromethyl)phenyl)(8-methyl-4-(1H-pyrazol-5-yl)-5,6-dihydropyrido[3,4-d]pyrimidin-7(8H)-yl)methanone;
(R)-(2-chloro-4-fluoro-3-(trifluoromethyl)phenyl)(8-methyl-4-(1H-pyrazol-5-yl)-5,6-dihydropyrido[3,4-d]pyrimidin-7(8H)-yl)methanone;
(2-chloro-4-fluoro-3-(trifluoromethyl)phenyl)(8-methyl-4-(1H-pyrazol-5-yl)-5,6-dihydropyrido[3,4-d]pyrimidin-7(8H)-yl)methanone;
(2,3-dichloro-4-fluorophenyl)(8-methyl-4-(1H-pyrazol-5-yl)-5,6-dihydropyrido[3,4-d]pyrimidin-7(8H)-yl)methanone;
(R)-(2,3-dichloro-4-fluorophenyl)(8-methyl-4-(1H-pyrazol-5-yl)-5,6-dihydropyrido[3,4-d]pyrimidin-7(8H)-yl)methanone;
(S)-(2,3-dichloro-4-fluorophenyl)(8-methyl-4-(1H-pyrazol-5-yl)-5,6-dihydropyrido[3,4-d]pyrimidin-7(8H)-yl)methanone;
((2,4-dichloro-3-fluorophenyl)(8-methyl-4-(1H-pyrazol-5-yl)-5,6-dihydropyrido[3,4-d]pyrimidin-7(8H)-yl)methanone;
(R)-(2,4-dichloro-3-fluorophenyl)(8-methyl-4-(1H-pyrazol-5-yl)-5,6-dihydropyrido[3,4-d]pyrimidin-7(8H)-yl)methanone;
(S)-(2,4-dichloro-3-fluorophenyl)(8-methyl-4-(1H-pyrazol-5-yl)-5,6-dihydropyrido[3,4-d]pyrimidin-7(8H)-yl)methanone;
(R)-(2-chloro-3-(trifluoromethyl)phenyl)(4-(1-(2-fluoroethyl)-1H-pyrazol-3-yl)-2,6-dimethyl-5,6-dihydropyrido[3,4-d]pyrimidin-7(8H)-yl)methanone;
(S)-(2-chloro-3-(trifluoromethyl)phenyl)(4-(1-(2-fluoroethyl)-1H-pyrazol-3-yl)-2,6-dimethyl-5,6-dihydropyrido[3,4-d]pyrimidin-7(8H)-yl)methanone;
(2-chloro-3-(trifluoromethyl)phenyl)(4-(1-(2-methoxyethyl)-1H-pyrazol-3-yl)-2,6-dimethyl-5,6-dihydropyrido[3,4-d]pyrimidin-7(8H)-yl)methanone
(S)-(2-chloro-3-(trifluoromethyl)phenyl)(4-(1-(2-methoxyethyl)-1H-pyrazol-3-yl)-2,6-dimethyl-5,6-dihydropyrido[3,4-d]pyrimidin-7(8H)-yl)methanone;
(R)-(2-chloro-3-(trifluoromethyl)phenyl)(4-(1-(2-methoxyethyl)-1H-pyrazol-3-yl)-2,6-dimethyl-5,6-dihydropyrido[3,4-d]pyrimidin-7(8H)-yl)methanone;
(2,3-dichloro-4-fluorophenyl)(4-(6-fluoropyridin-2-yl)-5,6-dihydropyrido[3,4-d]pyrimidin-7(8H)-yl)methanone;
(2-chloro-3-(trifluoromethyl)phenyl)(4-(6-fluoropyridin-2-yl)-5,6-dihydropyrido[3,4-d]pyrimidin-7(8H)-yl)methanone;
(2,6-dimethyl-4-(1H-pyrazol-5-yl)-5,6-dihydropyrido[3,4-d]pyrimidin-7(8H)-yl)(2,4-dimethylphenyl)methanone;
(2,6-dimethyl-4-(1H-pyrazol-5-yl)-5,6-dihydropyrido[3,4-d]pyrimidin-7(8H)-yl)(2,3-dimethylphenyl)methanone;
(2,6-dimethyl-4-(1H-pyrazol-5-yl)-5,6-dihydropyrido[3,4-d]pyrimidin-7(8H)-yl)(4-fluoro-2-methylphenyl)methanone;
(2,6-dimethyl-4-(1H-pyrazol-5-yl)-5,6-dihydropyrido[3,4-d]pyrimidin-7(8H)-yl)(3-fluoro-2-methylphenyl)methanone;
(2,6-dimethyl-4-(1H-pyrazol-5-yl)-5,6-dihydropyrido[3,4-d]pyrimidin-7(8H)-yl)(2-fluoro-3-methylphenyl)methanone;
(R)-(2,4-dichloro-3-fluorophenyl)(2,6-dimethyl-4-(1H-pyrazol-5-yl)-5,6-dihydropyrido[3,4-d]pyrimidin-7(8H)-yl)methanone;
(R)-(2,6-dimethyl-4-(1H-pyrazol-5-yl)-5,6-dihydropyrido[3,4-d]pyrimidin-7(8H)-yl)(phenyl)methanone and
(2,4-dichlorophenyl)((6R,8S)-2,6,8-trimethyl-4-(1H-pyrazol-5-yl)-5,6-dihydropyrido[3,4-d]pyrimidin-7(8H)-yl)methanone.
(2,6-dimethyl-4-(1H-pyrazol-5-yl)-5,6-dihydropyrido[3,4-d]pyrimidin-7(8H)-yl)(2-fluoro-3-(trifluoromethoxy)phenyl)methanone
(2,6-dimethyl-4-(1H-pyrazol-5-yl)-5,6-dihydropyrido[3,4-d]pyrimidin-7(8H)-yl)(3-(trifluoromethoxy)phenyl)methanone
(R*)-(2,6-dimethyl-4-(1H-pyrazol-5-yl)-5,6-dihydropyrido[3,4-d]pyrimidin-7(8H)-yl)(3-(trifluoromethoxy)phenyl)methanone
(S*)-(2,6-dimethyl-4-(1H-pyrazol-5-yl)-5,6-dihydropyrido[3,4-d]pyrimidin-7(8H)-yl)(3-(trifluoromethoxy)phenyl)methanone
(2-chloro-3-fluorophenyl)(2,6-dimethyl-4-(1H-pyrazol-5-yl)-5,6-dihydropyrido[3,4-d]pyrimidin-7(8H)-yl)methanone
(R*)-(2-chloro-3-fluorophenyl)(2,6-dimethyl-4-(1H-pyrazol-5-yl)-5,6-dihydropyrido[3,4-d]pyrimidin-7(8H)-yl)methanone
(S*)-(2-chloro-3-fluorophenyl)(2,6-dimethyl-4-(1H-pyrazol-5-yl)-5,6-dihydropyrido[3,4-d]pyrimidin-7(8H)-yl)methanone
(2,6-dimethyl-4-(1H-pyrazol-5-yl)-5,6-dihydropyrido[3,4-d]pyrimidin-7(8H)-yl)(3-methoxy-2-methylphenyl)methanone
(2,6-dimethyl-4-(1H-pyrazol-5-yl)-5,6-dihydropyrido[3,4-d]pyrimidin-7(8H)-yl)(5-methoxypyridin-3-yl)methanone An additional embodiment of the invention is a compound selected from the group consisting of those presented in Table 1A:

TABLE 1A

Compounds of Formula (I) or (Ia)

7-{[2-Chloro-3-(trifluoromethyl)phenyl]carbonyl}-4-phenyl-5,6,7,8-tetrahydropyrido[3,4-d]pyrimidine;
7-[(2,3-Dichlorophenyl)carbonyl]-4-phenyl-5,6,7,8-tetrahydropyrido[3,4-d]pyrimidine;
4-(2,6-dimethyl-4-(1H-pyrazol-5-yl)-5,6,7,8-tetrahydropyrido[3,4-d]pyrimidine-7-carbonyl)-3-methylbenzonitrile;
7-[(2,3-Dichlorophenyl)carbonyl]-4-(1H-pyrazol-4-yl)-5,6,7,8-tetrahydropyrido[3,4-d]pyrimidine;
7-[(2,3-Dichlorophenyl)carbonyl]-4-(1-methyl-1H-pyrazol-4-yl)-5,6,7,8-tetrahydropyrido[3,4-d]pyrimidine;
7-[(2-Chloro-3-methylphenyl)carbonyl]-4-(1-methyl-1H-pyrazol-4-yl)-5,6,7,8-tetrahydropyrido[3,4-d]pyrimidine;
7-[(2,3-Dichlorophenyl)carbonyl]-4-(1H-pyrazol-5-yl)-5,6,7,8-tetrahydropyrido[3,4-d]pyrimidine;
7-[(2-Chloro-3-methylphenyl)carbonyl]-4-(1H-pyrazol-5-yl)-5,6,7,8-tetrahydropyrido[3,4-d]pyrimidine;
7-[(2,3-Dimethylphenyl)carbonyl]-4-(1H-pyrazol-5-yl)-5,6,7,8-tetrahydropyrido[3,4-d]pyrimidine;
7-{[2-Methyl-3-(trifluoromethyl)phenyl]carbonyl}-4-(1H-pyrazol-5-yl)-5,6,7,8-tetrahydropyrido[3,4-d]pyrimidine;
7-[(2,3-Dichlorophenyl)carbonyl]-4-pyridin-2-yl-5,6,7,8-tetrahydropyrido[3,4-d]pyrimidine;
7-{[2-Chloro-3-(trifluoromethyl)phenyl]carbonyl}-4-pyridin-2-yl-5,6,7,8-tetrahydropyrido[3,4-d]pyrimidine;
7-[(2-Chloro-3-methylphenyl)carbonyl]-4-pyridin-2-yl-5,6,7,8-tetrahydropyrido[3,4-d]pyrimidine;

TABLE 1A-continued

Compounds of Formula (I) or (Ia)

7-[(2,3-Dichlorophenyl)carbonyl]-4-pyrazin-2-yl-5,6,7,8-tetrahydropyrido[3,4-d]pyrimidine;
7-{2-Methyl-3-(trifluoromethyl)phenyl]carbonyl}-4-pyrazin-2-yl-5,6,7,8-tetrahydropyrido[3,4-d]pyrimidine;
7-[(2-Chloro-4,5-difluorophenyl)carbonyl]-4-pyrazin-2-yl-5,6,7,8-tetrahydropyrido[3,4-d]pyrimidine;
7-{[2-Chloro-3-(trifluoromethyl)phenyl]carbonyl}-4-[1-(tetrahydro-2H-pyran-2-yl)-1H-pyrazol-5-yl]-5,6,7,8-tetrahydropyrido[3,4-d]pyrimidine;
(4-(1H-pyrazol-5-yl)-5,6-dihydropyrido[3,4-d]pyrimidin-7(8H)-yl)(2-chloro-3-(trifluoromethyl)phenyl)methanone;
7-{[2-Chloro-3-(trifluoromethyl)phenyl]carbonyl}-4-(1-methyl-1H-pyrazol-3-yl)-5,6,7,8-tetrahydropyrido[3,4-d]pyrimidine;
7-[(2,4-Dichloro-3-fluorophenyl)carbonyl]-4-(1H-pyrazol-5-yl)-5,6,7,8-tetrahydropyrido[3,4-d]pyrimidine;
7-[(2-chloro-4-fluorophenyl)carbonyl]-4-(1H-pyrazol-5-yl)-5,6,7,8-tetrahydropyrido[3,4-d]pyrimidine;
7-[(2,3-Dichlorophenyl)carbonyl]-4-(1H-pyrazol-1-yl)-5,6,7,8-tetrahydropyrido[3,4-d]pyrimidine;
7-[(2,3-Dichlorophenyl)carbonyl]-4-(2H-1,2,3-triazol-2-yl)-5,6,7,8-tetrahydropyrido[3,4-d]pyrimidine;
7-{[2-Chloro-3-(trifluoromethyl)phenyl]carbonyl}-4-(2H-1,2,3-triazol-2-yl)-5,6,7,8-tetrahydropyrido[3,4-d]pyrimidine;
7-[(2,3-Dichlorophenyl)carbonyl]-N,N-dimethyl-4-phenyl-5,6,7,8-tetrahydropyrido[3,4-d]pyrimidin-2-amine;
7-{[2-Chloro-3-(trifluoromethyl)phenyl]carbonyl}-N,N-dimethyl-4-phenyl-5,6,7,8-tetrahydropyrido[3,4-d]pyrimidin-2-amine;
7-[(2,3-Dichlorophenyl)carbonyl]-2-methyl-4-phenyl-5,6,7,8-tetrahydropyrido[3,4-d]pyrimidine;
7-[(2,3-Dichlorophenyl)carbonyl]-4-(4-fluorophenyl)-2-methyl-5,6,7,8-tetrahydropyrido[3,4-d]pyrimidine;
7-[(2,3-Dichlorophenyl)carbonyl]-4-phenyl-5,6,7,8-tetrahydropyrido[3,4-d]pyrimidin-2-amine;
7-{[2-Chloro-3-(trifluoromethyl)phenyl]carbonyl}-2-methyl-4-pyridin-2-yl-5,6,7,8-tetrahydropyrido[3,4-d]pyrimidine;
7-[(2,3-Dichlorophenyl)carbonyl]-2-methyl-4-pyridin-2-yl-5,6,7,8-tetrahydropyrido[3,4-d]pyrimidine;
7-{[2-Chloro-3-(trifluoromethyl)phenyl]carbonyl}-2-methyl-4-phenyl-5,6,7,8-tetrahydropyrido[3,4-d]pyrimidine;
7-{[2-Chloro-3-(trifluoromethyl)phenyl]carbonyl}-2-methyl-4-(1H-pyrazol-5-yl)-5,6,7,8-tetrahydropyrido[3,4-d]pyrimidine;
7-[(2,3-Dichlorophenyl)carbonyl]-2-methyl-4-(1H-pyrazol-5-yl)-5,6,7,8-tetrahydropyrido[3,4-d]pyrimidine;
7-{[2-Chloro-3-(trifluoromethyl)phenyl]carbonyl}-4-(4-fluoro-1H-pyrazol-5-yl)-2-methyl-5,6,7,8-tetrahydropyrido[3,4-d]pyrimidine;
7-[(2,3-Dichlorophenyl)carbonyl]-4-(4-fluoro-1H-pyrazol-5-yl)-2-methyl-5,6,7,8-tetrahydropyrido[3,4-d]pyrimidine;
7-{[2-Chloro-3-(trifluoromethyl)phenyl]carbonyl}-4-(1,3-thiazol-2-yl)-5,6,7,8-tetrahydropyrido[3,4-d]pyrimidine;
7-[(2,3-Dichlorophenyl)carbonyl]-4-(1,3-thiazol-2-yl)-5,6,7,8-tetrahydropyrido[3,4-d]pyrimidine;
7-{[2-Chloro-3-(trifluoromethyl)phenyl]carbonyl}-2-methyl-4-[4-(trifluoromethyl)-1H-pyrazol-5-yl]-5,6,7,8-tetrahydropyrido[3,4-d]pyrimidine;
7-[(2,3-Dichlorophenyl)carbonyl]-2-methyl-4-[4-(trifluoromethyl)-1H-pyrazol-5-yl]-5,6,7,8-tetrahydropyrido[3,4-d]pyrimidine;
7-[(2,3-Dichlorophenyl)carbonyl]-4-(1H-pyrrol-2-yl)-5,6,7,8-tetrahydropyrido[3,4-d]pyrimidine;
7-{[2-Chloro-3-(trifluoromethyl)phenyl]carbonyl}-4-(1H-pyrrol-2-yl)-5,6,7,8-tetrahydropyrido[3,4-d]pyrimidine;
7-{[2-Chloro-3-(trifluoromethyl)phenyl]carbonyl}-4-(1,3-thiazol-4-yl)-5,6,7,8-tetrahydropyrido[3,4-d]pyrimidine;
7-{[2-Chloro-3-(trifluoromethyl)phenyl]carbonyl}-2-methyl-4-(1,3-thiazol-4-yl)-5,6,7,8-tetrahydropyrido[3,4-d]pyrimidine;
7-{[2-Chloro-3-(trifluoromethyl)phenyl]carbonyl}-2-methyl-4-(1H-pyrrol-2-yl)-5,6,7,8-tetrahydropyrido[3,4-d]pyrimidine;
7-{[2-Chloro-3-(trifluoromethyl)phenyl]carbonyl}-4-(3,5-dimethylisoxazol-4-yl)-2-methyl-5,6,7,8-tetrahydropyrido[3,4-d]pyrimidine;
7-{[2-Chloro-3-(trifluoromethyl)phenyl]carbonyl}-2-methyl-4-(2H-1,2,3-triazol-2-yl)-5,6,7,8-tetrahydropyrido[3,4-d]pyrimidine;
7-{[2-Chloro-3-(trifluoromethyl)phenyl]carbonyl}-2-methyl-4-(1H-1,2,3-triazol-1-yl)-5,6,7,8-tetrahydropyrido[3,4-d]pyrimidine;
7-{[2-Chloro-3-(trifluoromethyl)phenyl]carbonyl}-4-isoxazol-4-yl-2-methyl-5,6,7,8-tetrahydropyrido[3,4-d]pyrimidine;
7-{[2-Chloro-3-(trifluoromethyl)phenyl]carbonyl}-4-(3,5-dimethylisoxazol-4-yl)-5,6,7,8-tetrahydropyrido[3,4-d]pyrimidine;
7-{[2-Fluoro-3-(trifluoromethyl)phenyl]carbonyl}-2-methyl-4-(1H-pyrazol-5-yl)-5,6,7,8-tetrahydropyrido[3,4-d]pyrimidine;
2-Methyl-7-{[2-methyl-3-(trifluoromethyl)phenyl]carbonyl}-4-(1H-pyrazol-5-yl)-5,6,7,8-tetrahydropyrido[3,4-d]pyrimidine;
7-[(2,4-Dichloro-3-fluorophenyl)carbonyl]-2-methyl-4-(1H-pyrazol-5-yl)-5,6,7,8-tetrahydropyrido[3,4-d]pyrimidine;
7-{[2-Chloro-3-(trifluoromethyl)phenyl]carbonyl}-N,N-dimethyl-4-(1H-pyrazol-5-yl)-5,6,7,8-tetrahydropyrido[3,4-d]pyrimidin-2-amine;
7-{[2-Chloro-3-(trifluoromethyl)phenyl]carbonyl}-4-(1H-pyrazol-5-yl)-5,6,7,8-tetrahydropyrido[3,4-d]pyrimidin-2-amine;
7-{[2-Chloro-3-(trifluoromethyl)phenyl]carbonyl}-2,6-dimethyl-4-(1H-pyrazol-5-yl)-5,6,7,8-tetrahydropyrido[3,4-d]pyrimidine;
7-{[2-Chloro-3-(trifluoromethyl)phenyl]carbonyl}-2-cyclopropyl-4-(1H-pyrazol-5-yl)-5,6,7,8-tetrahydropyrido[3,4-d]pyrimidine;
(6R)-7-{[2-Chloro-3-(trifluoromethyl)phenyl]carbonyl}-2,6-dimethyl-4-(1H-pyrazol-5-yl)-5,6,7,8-tetrahydropyrido[3,4-d]pyrimidine;
(6S)-7-{[2-Chloro-3-(trifluoromethyl)phenyl]carbonyl}-2,6-dimethyl-4-(1H-pyrazol-5-yl)-5,6,7,8-tetrahydropyrido[3,4-d]pyrimidine;
(4-(1H-pyrazol-5-yl)-2-(trifluoromethyl)-5,6-dihydropyrido[3,4-d]pyrimidin-7(8H)-yl)(2-chloro-3-(trifluoromethyl)phenyl)methanone;
3-(2,6-dimethyl-4-(1H-pyrazol-5-yl)-5,6,7,8-tetrahydropyrido[3,4-d]pyrimidine-7-carbonyl)-2-methylbenzonitrile;
(2-chloro-3-(trifluoromethyl)phenyl)(6-methyl-4-(1H-pyrazol-5-yl)-5,6-dihydropyrido[3,4-d]pyrimidin-7(8H)-yl)methanone
(2-amino-6-methyl-4-(1H-pyrazol-5-yl)-5,6-dihydropyrido[3,4-d]pyrimidin-7(8H)-yl)(2-chloro-3-(trifluoromethyl)phenyl)methanone;
(2-chloro-4-fluoro-3-(trifluoromethyl)phenyl)(2,6-dimethyl-4-(1H-pyrazol-5-yl)-5,6-dihydropyrido[3,4-d]pyrimidin-7(8H)-yl)methanone;
(S)-(2-chloro-4-fluoro-3-(trifluoromethyl)phenyl)(2,6-dimethyl-4-(1H-pyrazol-5-yl)-5,6-dihydropyrido[3,4-d]pyrimidin-7(8H)-yl)methanone;
(R)-(2-chloro-4-fluoro-3-(trifluoromethyl)phenyl)(2,6-dimethyl-4-(1H-pyrazol-5-yl)-5,6-dihydropyrido[3,4-d]pyrimidin-7(8H)-yl)methanone;
(2,3-dichlorophenyl)(2,6-dimethyl-4-(1H-pyrazol-5-yl)-5,6-dihydropyrido[3,4-d]pyrimidin-7(8H)-yl)methanone;
(R)-(2,3-dichlorophenyl)(2,6-dimethyl-4-(1H-pyrazol-5-yl)-5,6-dihydropyrido[3,4-d]pyrimidin-7(8H)-yl)methanone;
(S)-(2,3-dichlorophenyl)(2,6-dimethyl-4-(1H-pyrazol-5-yl)-5,6-dihydropyrido[3,4-d]pyrimidin-7(8H)-yl)methanone;
(2,4-dichloro-3-fluorophenyl)(2,6-dimethyl-4-(1H-pyrazol-5-yl)-5,6-dihydropyrido[3,4-d]pyrimidin-7(8H)-yl)methanone;
(R)-(2,4-dichloro-3-fluorophenyl)(2,6-dimethyl-4-(1H-pyrazol-5-yl)-5,6-dihydropyrido[3,4-d]pyrimidin-7(8H)-yl)methanone;
(S)-(2,4-dichloro-3-fluorophenyl)(2,6-dimethyl-4-(1H-pyrazol-5-yl)-5,6-dihydropyrido[3,4-d]pyrimidin-7(8H)-yl)methanone;
(2-chloro-3-(trifluoromethyl)phenyl)(2,6-dimethyl-4-(1-methyl-1H-pyrazol-5-yl)-5,6-dihydropyrido[3,4-d]pyrimidin-7(8H)-yl)methanone;
(2,6-dimethyl-4-(1H-pyrazol-5-yl)-5,6-dihydropyrido[3,4-d]pyrimidin-7(8H)-yl)(2-fluoro-3-(trifluoromethyl)phenyl)methanone;
(R)-(2,6-dimethyl-4-(1H-pyrazol-5-yl)-5,6-dihydropyrido[3,4-d]pyrimidin-7(8H)-yl)(2-fluoro-3-(trifluoromethyl)phenyl)methanone;
(S)-(2,6-dimethyl-4-(1H-pyrazol-5-yl)-5,6-dihydropyrido[3,4-d]pyrimidin-7(8H)-yl)(2-fluoro-3-(trifluoromethyl)phenyl)methanone;
(2,6-dimethyl-4-(1H-pyrazol-5-yl)-5,6-dihydropyrido[3,4-d]pyrimidin-7(8H)-yl)(2-methyl-3-(trifluoromethyl)phenyl)methanone
(R)-(2,6-dimethyl-4-(1H-pyrazol-5-yl)-5,6-dihydropyrido[3,4-d]pyrimidin-7(8H)-yl)(2-methyl-3-(trifluoromethyl)phenyl)methanone
(S)-(2,6-dimethyl-4-(1H-pyrazol-5-yl)-5,6-dihydropyrido[3,4-d]pyrimidin-7(8H)-yl)(2-methyl-3-(trifluoromethyl)phenyl)methanone
(2,3-dichloro-4-fluorophenyl)(2,6-dimethyl-4-(1H-pyrazol-5-yl)-5,6-dihydropyrido[3,4-d]pyrimidin-7(8H)-yl)methanone
(R)-(2,3-dichloro-4-fluorophenyl)(2,6-dimethyl-4-(1H-pyrazol-5-yl)-5,6-dihydropyrido[3,4-d]pyrimidin-7(8H)-yl)methanone;
(S)-(2,3-dichloro-4-fluorophenyl)(2,6-dimethyl-4-(1H-pyrazol-5-yl)-5,6-dihydropyrido[3,4-d]pyrimidin-7(8H)-yl)methanone;
(2,4-dichlorophenyl)(2,6-dimethyl-4-(1H-pyrazol-5-yl)-5,6-dihydropyrido[3,4-d]pyrimidin-7(8H)-yl)methanone;
(R)-(2,4-dichlorophenyl)(2,6-dimethyl-4-(1H-pyrazol-5-yl)-5,6-dihydropyrido[3,4-d]pyrimidin-7(8H)-yl)methanone;
(S)-(2,4-dichlorophenyl)(2,6-dimethyl-4-(1H-pyrazol-5-yl)-5,6-dihydropyrido[3,4-d]pyrimidin-7(8H)-yl)methanone;
(2,5-dichlorophenyl)(2,6-dimethyl-4-(1H-pyrazol-5-yl)-5,6-dihydropyrido[3,4-d]pyrimidin-7(8H)-yl)methanone;
(4-chloro-2-fluorophenyl)(2,6-dimethyl-4-(1H-pyrazol-5-yl)-5,6-dihydropyrido[3,4-d]pyrimidin-7(8H)-yl)methanone;
(R)-(4-chloro-2-fluorophenyl)(2,6-dimethyl-4-(1H-pyrazol-5-yl)-5,6-dihydropyrido[3,4-d]pyrimidin-7(8H)-yl)methanone;
(S)-(4-chloro-2-fluorophenyl)(2,6-dimethyl-4-(1H-pyrazol-5-yl)-5,6-dihydropyrido[3,4-d]pyrimidin-7(8H)-yl)methanone;

TABLE 1A-continued

Compounds of Formula (I) or (Ia)

(2-chloro-4-fluorophenyl)(2,6-dimethyl-4-(1H-pyrazol-5-yl)-5,6-dihydropyrido[3,4-d]pyrimidin-7(8H)-yl)methanone;
(R)-(2-chloro-4-fluorophenyl)(2,6-dimethyl-4-(1H-pyrazol-5-yl)-5,6-dihydropyrido[3,4-d]pyrimidin-7(8H)-yl)methanone;
(S)-(2-chloro-4-fluorophenyl)(2,6-dimethyl-4-(1H-pyrazol-5-yl)-5,6-dihydropyrido[3,4-d]pyrimidin-7(8H)-yl)methanone;
(2,4-difluorophenyl)(2,6-dimethyl-4-(1H-pyrazol-5-yl)-5,6-dihydropyrido[3,4-d]pyrimidin-7(8H)-yl)methanone;
(R)-(2,4-difluorophenyl)(2,6-dimethyl-4-(1H-pyrazol-5-yl)-5,6-dihydropyrido[3,4-d]pyrimidin-7(8H)-yl)methanone;
(S)-(2,4-difluorophenyl)(2,6-dimethyl-4-(1H-pyrazol-5-yl)-5,6-dihydropyrido[3,4-d]pyrimidin-7(8H)-yl)methanone;
(4-chlorophenyl)(2,6-dimethyl-4-(1H-pyrazol-5-yl)-5,6-dihydropyrido[3,4-d]pyrimidin-7(8H)-yl)methanone;
(2-chlorophenyl)(2,6-dimethyl-4-(1H-pyrazol-5-yl)-5,6-dihydropyrido[3,4-d]pyrimidin-7(8H)-yl)methanone;
(2-chloro-3-(trifluoromethyl)phenyl)(2-ethyl-6-methyl-4-(1H-pyrazol-5-yl)-5,6-dihydropyrido[3,4-d]pyrimidin-7(8H)-yl)methanone;
((R)-(2-chloro-3-(trifluoromethyl)phenyl)(2-ethyl-6-methyl-4-(1H-pyrazol-5-yl)-5,6-dihydropyrido[3,4-d]pyrimidin-7(8H)-yl)methanone;
(S)-(2-chloro-3-(trifluoromethyl)phenyl)(2-ethyl-6-methyl-4-(1H-pyrazol-5-yl)-5,6-dihydropyrido[3,4-d]pyrimidin-7(8H)-yl)methanone
(2-chloro-3-(trifluoromethyl)phenyl)(2-isopropyl-6-methyl-4-(1H-pyrazol-5-yl)-5,6-dihydropyrido[3,4-d]pyrimidin-7(8H)-yl)methanone;
(R)-(2-chloro-3-(trifluoromethyl)phenyl)(2-isopropyl-6-methyl-4-(1H-pyrazol-5-yl)-5,6-dihydropyrido[3,4-d]pyrimidin-7(8H)-yl)methanone;
(S)-(2-chloro-3-(trifluoromethyl)phenyl)(2-isopropyl-6-methyl-4-(1H-pyrazol-5-yl)-5,6-dihydropyrido[3,4-d]pyrimidin-7(8H)-yl)methanone;
(2,4-dichloro-3-fluorophenyl)(2-ethyl-6-methyl-4-(1H-pyrazol-5-yl)-5,6-dihydropyrido[3,4-d]pyrimidin-7(8H)-yl)methanone;
(4-(1H-pyrazol-1-yl)-5,6-dihydropyrido[3,4-d]pyrimidin-7(8H)-yl)(2,3-dimethylphenyl)methanone;
(4-(1H-1,2,3-triazol-1-yl)-5,6-dihydropyrido[3,4-d]pyrimidin-7(8H)-yl)(2-chloro-3-(trifluoromethyl)phenyl)methanone;
7-[(2,3-Dichlorophenyl)carbonyl]-4-(2H-1,2,3-triazol-2-yl)-5,6,7,8-tetrahydropyrido[3,4-d]pyrimidine;
7-{[2-Chloro-3-(trifluoromethyl)phenyl]carbonyl}-4-(2H-1,2,3-triazol-2-yl)-5,6,7,8-tetrahydropyrido[3,4-d]pyrimidine;
(4-(4H-1,2,4-triazol-4-yl)-5,6-dihydropyrido[3,4-d]pyrimidin-7(8H)-yl)(2-chloro-3-(trifluoromethyl)phenyl)methanone;
(4-(1H-1,2,4-triazol-1-yl)-5,6-dihydropyrido[3,4-d]pyrimidin-7(8H)-yl)(2-chloro-3-(trifluoromethyl)phenyl)methanone;
(4-(1H-pyrazol-5-yl)-5,6-dihydropyrido[3,4-d]pyrimidin-7(8H)-yl)(2-fluoro-3-(trifluoromethyl)phenyl)methanone;
(2-chloro-3-(trifluoromethyl)phenyl)(8-methyl-4-(1H-pyrazol-5-yl)-5,6-dihydropyrido[3,4-d]pyrimidin-7(8H)-yl)methanone;
(R)-(2-chloro-3-(trifluoromethyl)phenyl)(8-methyl-4-(1H-pyrazol-5-yl)-5,6-dihydropyrido[3,4-d]pyrimidin-7(8H)-yl)methanone;
(S)-(2-chloro-3-(trifluoromethyl)phenyl)(8-methyl-4-(1H-pyrazol-5-yl)-5,6-dihydropyrido[3,4-d]pyrimidin-7(8H)-yl)methanone;
(2-chloro-4-fluoro-3-(trifluoromethyl)phenyl)(8-methyl-4-(1H-pyrazol-5-yl)-5,6-dihydropyrido[3,4-d]pyrimidin-7(8H)-yl)methanone;
(R)-(2-chloro-4-fluoro-3-(trifluoromethyl)phenyl)(8-methyl-4-(1H-pyrazol-5-yl)-5,6-dihydropyrido[3,4-d]pyrimidin-7(8H)-yl)methanone;
(2-chloro-4-fluoro-3-(trifluoromethyl)phenyl)(8-methyl-4-(1H-pyrazol-5-yl)-5,6-dihydropyrido[3,4-d]pyrimidin-7(8H)-yl)methanone;
(2,3-dichloro-4-fluorophenyl)(8-methyl-4-(1H-pyrazol-5-yl)-5,6-dihydropyrido[3,4-d]pyrimidin-7(8H)-yl)methanone;
(R)-(2,3-dichloro-4-fluorophenyl)(8-methyl-4-(1H-pyrazol-5-yl)-5,6-dihydropyrido[3,4-d]pyrimidin-7(8H)-yl)methanone;
(S)-(2,3-dichloro-4-fluorophenyl)(8-methyl-4-(1H-pyrazol-5-yl)-5,6-dihydropyrido[3,4-d]pyrimidin-7(8H)-yl)methanone;
((2,4-dichloro-3-fluorophenyl)(8-methyl-4-(1H-pyrazol-5-yl)-5,6-dihydropyrido[3,4-d]pyrimidin-7(8H)-yl)methanone;
(R)-(2,4-dichloro-3-fluorophenyl)(8-methyl-4-(1H-pyrazol-5-yl)-5,6-dihydropyrido[3,4-d]pyrimidin-7(8H)-yl)methanone;
(S)-(2,4-dichloro-3-fluorophenyl)(8-methyl-4-(1H-pyrazol-5-yl)-5,6-dihydropyrido[3,4-d]pyrimidin-7(8H)-yl)methanone;
(R)-(2-chloro-3-(trifluoromethyl)phenyl)(4-(1-(2-fluoroethyl)-1H-pyrazol-3-yl)-2,6-dimethyl-5,6-dihydropyrido[3,4-d]pyrimidin-7(8H)-yl)methanone;
(S)-(2-chloro-3-(trifluoromethyl)phenyl)(4-(1-(2-fluoroethyl)-1H-pyrazol-3-yl)-2,6-dimethyl-5,6-dihydropyrido[3,4-d]pyrimidin-7(8H)-yl)methanone;
(2-chloro-3-(trifluoromethyl)phenyl)(4-(1-(2-methoxyethyl)-1H-pyrazol-3-yl)-2,6-dimethyl-5,6-dihydropyrido[3,4-d]pyrimidin-7(8H)-yl)methanone
(S)-(2-chloro-3-(trifluoromethyl)phenyl)(4-(1-(2-methoxyethyl)-1H-pyrazol-3-yl)-2,6-dimethyl-5,6-dihydropyrido[3,4-d]pyrimidin-7(8H)-yl)methanone;
(R)-(2-chloro-3-(trifluoromethyl)phenyl)(4-(1-(2-methoxyethyl)-1H-pyrazol-3-yl)-2,6-dimethyl-5,6-dihydropyrido[3,4-d]pyrimidin-7(8H)-yl)methanone;
(2,3-dichloro-4-fluorophenyl)(4-(6-fluoropyridin-2-yl)-5,6-dihydropyrido[3,4-d]pyrimidin-7(8H)-yl)methanone;
(2-chloro-3-(trifluoromethyl)phenyl)(4-(6-fluoropyridin-2-yl)-5,6-dihydropyrido[3,4-d]pyrimidin-7(8H)-yl)methanone;
(2,6-dimethyl-4-(1H-pyrazol-5-yl)-5,6-dihydropyrido[3,4-d]pyrimidin-7(8H)-yl)(2,4-dimethylphenyl)methanone;
(2,6-dimethyl-4-(1H-pyrazol-5-yl)-5,6-dihydropyrido[3,4-d]pyrimidin-7(8H)-yl)(2,3-dimethylphenyl)methanone;
(2,6-dimethyl-4-(1H-pyrazol-5-yl)-5,6-dihydropyrido[3,4-d]pyrimidin-7(8H)-yl)(4-fluoro-2-methylphenyl)methanone;
(2,6-dimethyl-4-(1H-pyrazol-5-yl)-5,6-dihydropyrido[3,4-d]pyrimidin-7(8H)-yl)(3-fluoro-2-methylphenyl)methanone;
(2,6-dimethyl-4-(1H-pyrazol-5-yl)-5,6-dihydropyrido[3,4-d]pyrimidin-7(8H)-yl)(2-fluoro-3-methylphenyl)methanone;
(R)-(2,4-dichloro-3-fluorophenyl)(2,6-dimethyl-4-(1H-pyrazol-5-yl)-5,6-dihydropyrido[3,4-d]pyrimidin-7(8H)-yl)methanone;
(R)-(2,6-dimethyl-4-(1H-pyrazol-5-yl)-5,6-dihydropyrido[3,4-d]pyrimidin-7(8H)-yl)(phenyl)methanone and
(2,4-dichlorophenyl)((6R,8S)-2,6,8-trimethyl-4-(1H-pyrazol-5-yl)-5,6-dihydropyrido[3,4-d]pyrimidin-7(8H)-yl)methanone.

An additional embodiment of the invention is a compound selected from the group consisting of those presented in Table 1B:

TABLE 1B

Selected Compounds (2,6-dimethyl-4-(1H-pyrazol-5-yl)-5,6-dihydropyrido[3,4-d]pyrimidin-7(8H)-yl)(2-fluoro-3-(trifluoromethoxy)phenyl)methanone
(2,6-dimethyl-4-(1H-pyrazol-5-yl)-5,6-dihydropyrido[3,4-d]pyrimidin-7(8H)-yl)(3-(trifluoromethoxy)phenyl)methanone
(R*)-(2,6-dimethyl-4-(1H-pyrazol-5-yl)-5,6-dihydropyrido[3,4-d]pyrimidin-7(8H)-yl)(3-(trifluoromethoxy)phenyl)methanone
(S*)-(2,6-dimethyl-4-(1H-pyrazol-5-yl)-5,6-dihydropyrido[3,4-d]pyrimidin-7(8H)-yl)(3-(trifluoromethoxy)phenyl)methanone
(2-chloro-3-fluorophenyl)(2,6-dimethyl-4-(1H-pyrazol-5-yl)-5,6-dihydropyrido[3,4-d]pyrimidin-7(8H)-yl)methanone
(R*)-(2-chloro-3-fluorophenyl)(2,6-dimethyl-4-(1H-pyrazol-5-yl)-5,6-dihydropyrido[3,4-d]pyrimidin-7(8H)-yl)methanone
(S*)-(2-chloro-3-fluorophenyl)(2,6-dimethyl-4-(1H-pyrazol-5-yl)-5,6-dihydropyrido[3,4-d]pyrimidin-7(8H)-yl)methanone
(2,6-dimethyl-4-(1H-pyrazol-5-yl)-5,6-dihydropyrido[3,4-d]pyrimidin-7(8H)-yl)(3-methoxy-2-methylphenyl)methanone and
(2,6-dimethyl-4-(1H-pyrazol-5-yl)-5,6-dihydropyrido[3,4-d]pyrimidin-7(8H)-yl)(5-methoxypyridin-3-yl)methanone An additional embodiment of the invention is a pharmaceutical composition for treating a disease, disorder or medical condition mediated by P2X7 activity comprising:

(a) a therapeutically effective amount of a compound of Formula (I):

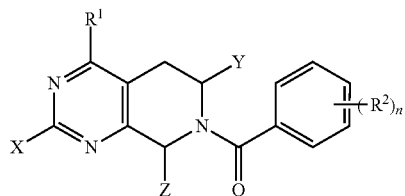

Formula (I)

wherein:

each $R^2$ is independently selected from the group consisting of H, halo, CN, $C_1$-$C_3$ alkyl, perhaloalkyl, $C_1$-$C_3$ alkoxy and perhaloalkoxy;

n is an integer from 0-3;

X is independently selected from the group consisting of H, $C_1$-$C_3$ alkyl, $C_3$ cycloalkyl, perfluoroalkyl, —$NH_2$, and —$N(CH_3)_2$;

Y and Z are independently H or $CH_3$;

$R^1$ is independently selected from the group consisting of:

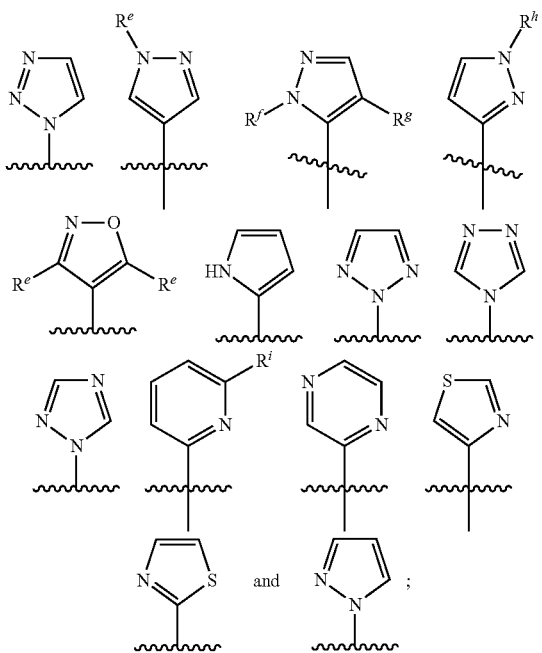

$R^e$ and $R^f$ are H or $C_1$-$C_3$ alkyl;

$R^g$ is H, F, or perfluoroalkyl;

$R^h$ is H, $C_1$-$C_3$ alkyl, —$CH_2CH_2OCH_3$ or perfluoroalkyl; and $R^i$ is H or halo; or pharmaceutically acceptable salts of compounds of Formula (I); and (b) at least one pharmaceutically acceptable excipient.

An additional embodiment of the invention is a pharmaceutical composition for treating a disease, disorder or medical condition mediated by P2X7 activity comprising:

(a) a therapeutically effective amount of a compound of Formula (Ia):

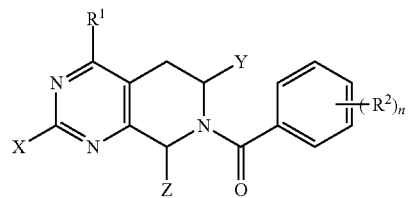

Formula (Ia)

wherein:

$R^2$ is H, halo, $C_{1-3}$ alkyl, or perhaloalkyl;

n is an integer from 0-4;

X is H, $C_1$-$C_4$ alkyl, $C_3$-$C_4$ cycloalkyl, perfluoroalkyl, —$NH_2$, or —$N(C_{1-3}alkyl)_2$;

Y and Z are independently H or $C_{1-3}$alkyl;

$R^1$ is selected from the group consisting of:

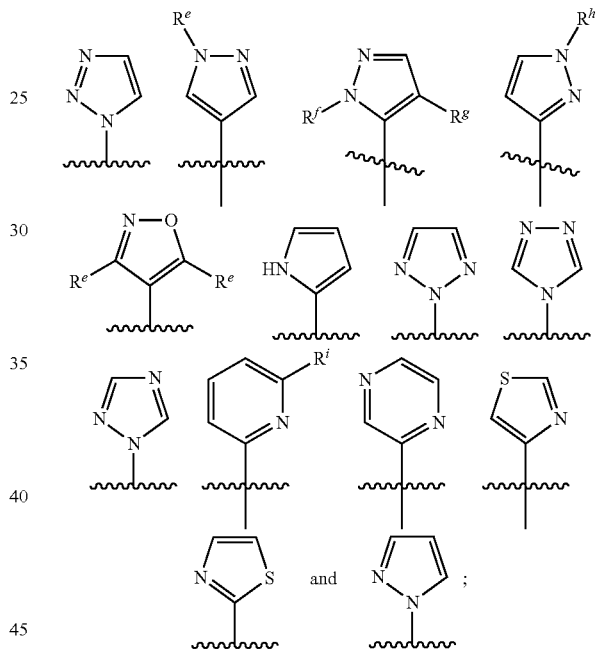

$R^e$ and $R^f$ are H or $C_{1-3}$alkyl;

$R^g$ is H, F, or perfluoroalkyl;

$R^h$ is H, $C_{1-3}$alkyl, $CH_2CH_2OCH_3$ or perfluoroalkyl; and $R^i$ is H or halo; or pharmaceutically acceptable salts of compounds of Formula (Ia) and (b) at least one pharmaceutically acceptable excipient.

An additional embodiment of the invention is a pharmaceutical composition comprising and a therapeutically effective amount of at least one compound listed in Tables 1, 1A or 1B and at least one pharmaceutically acceptable excipient.

An additional embodiment of the invention is a method of treating a subject suffering from or diagnosed with a disease, disorder, or medical condition mediated by P2X7 receptor activity, comprising administering to a subject in need of such treatment a therapeutically effective amount of at least one compound selected from compounds of Formula (I):

Formula (I)

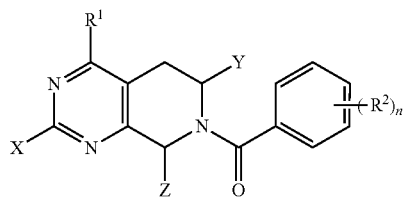

wherein:

each $R^2$ is independently selected from the group consisting of H, halo, CN, $C_{1-3}$ alkyl, perhaloalkyl, $C_1$-$C_3$ alkoxy and perhaloalkoxy;

n is an integer from 0-3;

X is independently selected from the group consisting of H, $C_1$-$C_3$ alkyl, $C_3$ cycloalkyl, perfluoroalkyl, —$NH_2$, and —$N(CH_3)_2$;

Y and Z are independently H or $CH_3$;

$R^1$ is independently selected from the group consisting of:

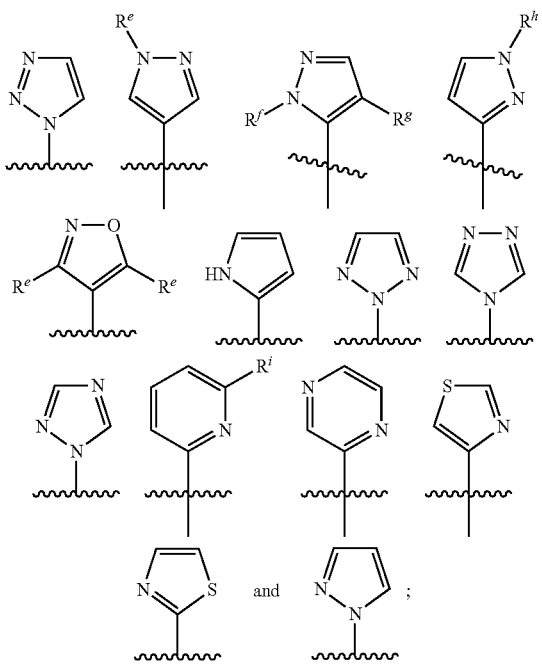

$R^e$ and $R^f$ are H or $C_1$-$C_3$ alkyl;

$R^g$ is H, F, or perfluoroalkyl;

$R^h$ is H, $C_1$-$C_3$ alkyl, —$CH_2CH_2OCH_3$ or perfluoroalkyl; and $R^i$ is H or halo; or pharmaceutically acceptable salts of compounds of Formula (I).

An additional embodiment of the invention is a method of treating a subject suffering from or diagnosed with a disease, disorder, or medical condition mediated by P2X7 receptor activity, comprising administering to a subject in need of such treatment a therapeutically effective amount of at least one compound selected from compounds of Formula (Ia):

Formula (Ia)

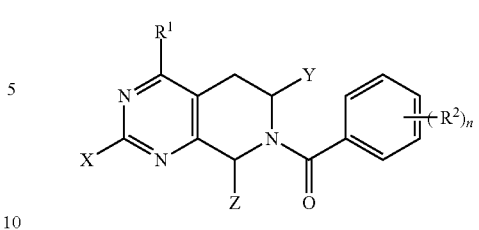

wherein:
$R^2$ is H, halo, $C_{1-3}$ alkyl, or perhaloalkyl;
n is an integer from 0-4;
X is H, $C_1$-$C_4$ alkyl, $C_3$-$C_4$ cycloalkyl, perfluoroalkyl, —$NH_2$, or —$N(C_{1-3}alkyl)_2$;
Y and Z are independently H or $C_{1-3}$alkyl;
$R^1$ is selected from the group consisting of:

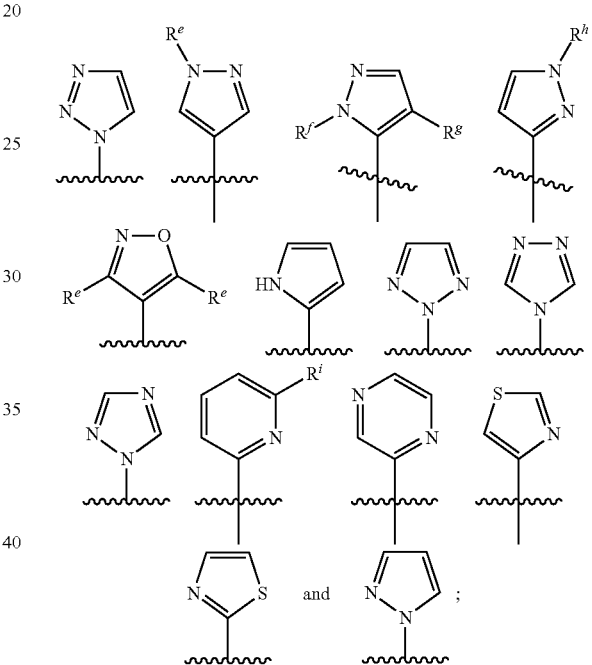

$R^e$ and $R^f$ are H or $C_{1-3}$alkyl;
$R^g$ is H, F, or perfluoroalkyl;
$R^h$ is H, $C_{1-3}$alkyl, $CH_2CH_2OCH_3$ or perfluoroalkyl; and
$R^i$ is H or halo; or
pharmaceutically acceptable salts of compounds of Formula (Ia).

In preferred embodiments of the inventive method, the disease, disorder, or medical condition is selected from: diseases of the autoimmune and inflammatory system such as: rheumatoid arthritis, osteoarthritis, psoriasis, septic shock, allergic dermatitis, asthma, allergic asthma, mild to severe asthma, steroid resistant asthma, idiopathic pulmonary fibrosis, allergic rhinitis, chronic obstructive pulmonary disease and airway hyper-responsiveness; diseases of the nervous and neuro-immune system such as acute and chronic pain states of neuropathic pain, inflammatory pain, spontaneous pain (opioid induced pain, diabetic neuropathy, postherpetic neuralgia, low back pain, chemotherapy-induced neuropathic pain, fibromyalgia) (Romagnoli, R, et. al., *Expert Opin. Ther. Targets*, 2008, 12(5), 647-661), and diseases involved with and without neuroinflammation of the CNS such as mood disorders (major depression, major depressive disorder, treatment resistant depression, bipolar disorder, anxious depression, anxiety) (Friedle, S A, et. al., *Recent Patents on CNS Drug Discovery*, 2010, 5, 35-45, Romagnoli, R, et. al., *Expert Opin. Ther. Targets*, 2008, 12(5), 647-661), cognition, sleep disorders, multiple sclerosis (Sharp A J, et. al., *J Neuroinflammation*. 2008 Aug. 8; 5:33, Oyanguren-Desez O, et. al., *Cell Calcium*. 2011 November; 50(5):468-72, Grygorowicz T, et. al., *Neurochem Int*. 2010 December; 57(7):823-9), epileptic seizures (Engel T, et. al., *FASEB J*. 2012 April; 26(4):1616-28, Kim J E, et. al. *Neurol Res*. 2009 November; 31(9):982-8, Avignone E, et. al., *J Neurosci*. 2008 Sep. 10; 28(37):9133-44), Parkinson's disease (Marcellino D, et. al., *J Neural Transm*. 2010 June; 117(6):681-7), schizophrenia, Alzheimer's disease (Diaz-Hernandez J I, et. al., *Neurobiol Aging*. 2012 August; 33(8):1816-28, Delarasse C, *J Biol Chem*. 2011 Jan. 28; 286(4):2596-606, Sanz J M, et. al., *J Immunol*. 2009 Apr. 1; 182(7):4378-85), Huntington's disease (Díaz-Hernández M, et. Al., *FASEB J*. 2009 June; 23(6):1893-906), autism, spinal cord injury and cerebral ischemia/traumatic brain injury (Chu K, et. al., *J Neuroinflammation*. 2012 Apr. 18; 9:69, Arbeloa J, et. al, *Neurobiol Dis*. 2012 March; 45(3): 954-61).

P2X7 antagonism may also be beneficial in several stress-related disorders. In addition, P2X7 intervention may be beneficial in diseases of the cardiovascular, metabolic, gastrointestinal and urogenital systems such as diabetes (*Arterioscler Thromb Vasc Biol*. 2004 July; 24(7):1240-5, *J Cell Physiol*. 2013 January; 228(1):120-9), thrombosis (Furlan-Freguia C, et. al., *J Clin Invest*. 2011 July; 121(7):2932-44), irritable bowel syndrome, Crohn's disease, ischemic heart disease, hypertension (Ji X, et. al., *Am J Physiol Renal Physiol*. 2012 October; 303(8):F1207-15), myocardial infarction, and lower urinary tract dysfunction such as incontinence. P2X7 antagonism may also present a novel therapeutic strategy for skeletal disorders, namely osteoporosis/osteopetrosis and may also modulate secretory function of exocrine glands. It is also hypothesized that blocking P2X7 may also be beneficial in glaucoma, interstitial cystitis (Martins J P, et. al., *Br J Pharmacol*. 2012 January; 165(1): 183-96) and lower urinary tract syndrome (*Br J Pharmacol*. 2012 January; 165(1):183-96), IBD/IBS (*J Immunol*. 2011 Aug. 1; 187(3):1467-74. Epub 2011 Jun. 22), Sleep, RA/OA, Cough/COPD/asthma, cardiovascular disease, GN, ureteric obstruction, diabetes mellitus, hypertension, sepsis, ischaemia, Amyotrophic Lateral Sclerosis, Chaga's Disease, *Chlamydia*, Neuroblastoma, Tuberculosis, Polycystic Kidney Disease, and migraine.

An additional embodiment of the invention is a method of treating a subject suffering from or diagnosed with a disease, disorder, or medical condition mediated by P2X7 receptor activity, wherein the disease, disorder, or medical condition is selected from the group consisting of: rheumatoid arthritis, osteoarthritis, psoriasis, septic shock, allergic dermatitis, asthma, allergic asthma, mild to severe asthma, steroid resistant asthma, idiopathic pulmonary fibrosis, allergic rhinitis, chronic obstructive pulmonary disease (COPD) and airway hyper-responsiveness; diseases of the nervous and neuro-immune system such as acute and chronic pain states of neuropathic pain, inflammatory pain, spontaneous pain (opioid induced pain, diabetic neuropathy, postherpetic neuralgia, low back pain, chemotherapy-induced neuropathic pain, fibromyalgia); diseases involved with and without neuroinflammation of the CNS such as mood disorders (major depression, major depressive disorder, treatment resistant depression, bipolar disorder, anxious depression, anxiety), cognition, sleep disorders, multiple sclerosis, epileptic seizures, Parkinson's disease, schizophrenia, Alzheimer's disease, Huntington's disease, autism, spinal cord injury and cerebral ischemia/traumatic brain injury, stress-related disorders; diseases of the cardiovascular, metabolic, gastrointestinal and urogenital systems such as diabetes, diabetes mellitus, thrombosis, irritable bowel syndrome, IBD, Crohn's disease, ischemic heart disease, ischaemia, hypertension, cardiovascular disease, myocardial infarction, and lower urinary tract dysfunction such as incontinence, lower urinary tract syndrome, Polycystic Kidney Disease, Glomerulonephritis, (GN); skeletal disorders, namely osteoporosis/osteopetrosis: and glaucoma, interstitial cystitis, cough, ureteric obstruction, sepsis, Amyotrophic Lateral Sclerosis, Chaga's Disease, *chlamydia*, neuroblastoma, Tuberculosis, and migraine.

An additional embodiment of the invention is a method of treating a subject suffering from or diagnosed with a disease, disorder, or medical condition mediated by P2X7 receptor activity wherein the disease, disorder or medical condition is treatment resistant depression.

Additional embodiments, features, and advantages of the invention will be apparent from the following detailed description and through practice of the invention.

The invention may be more fully appreciated by reference to the following description, including the following glossary of terms and the concluding examples. For the sake of brevity, the disclosures of the publications, including patents, cited in this specification are herein incorporated by reference.

As used herein, the terms "including", "containing" and "comprising" are used herein in their open, non-limiting sense.

The term "alkyl" refers to a straight- or branched-chain alkyl group having from 1 to 12 carbon atoms in the chain. Examples of alkyl groups include methyl (Me, which also may be structurally depicted by the symbol, "/"), ethyl (Et), n-propyl, isopropyl, butyl, isobutyl, sec-butyl, tert-butyl (tBu), pentyl, isopentyl, tert-pentyl, hexyl, isohexyl, and groups that in light of the ordinary skill in the art and the teachings provided herein would be considered equivalent to any one of the foregoing examples. The term $C_1$-$C_3$ alkyl as used here refers to a straight- or branched-chain alkyl group having from 1 to 3 carbon atoms in the chain. The term $C_1$-$C_4$ alkyl as used here refers to a straight- or branched-chain alkyl group having from 1 to 4 carbon atoms in the chain.

The term "alkoxy" includes a straight chain or branched alkyl group having from 1 to 6 carbon atoms in the chain with a terminal oxygen linking the alkyl group to the rest of the molecule. Alkoxy includes methoxy, ethoxy, propoxy, isopropoxy, butoxy, t-butoxy and pentoxy. The term $C_1$-$C_3$ alkoxy as used here refers to a straight- or branched-chain alkyl group having from 1 to 3 carbon atoms in the chain with a terminal oxygen linking the alkyl group to the rest of the molecule. Examples of a $C_1$-$C_3$ alkoxy substituent include for example: methoxy, ethoxy and isopropoxy.

The term "cycloalkyl" refers to a saturated carbocycle having from 3 to 6 ring atoms per carbocycle. Illustrative examples of cycloalkyl groups include the following entities, in the form of properly bonded moieties:

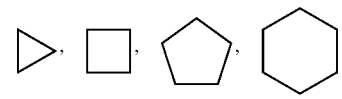

The term "C₃-C₄ cycloalkyl" as used here refers to a saturated carbocycle having from 3 to 4 ring atoms.

A "heterocycloalkyl" refers to a monocyclic ring structure that is saturated and has from 4 to 6 ring atoms per ring structure selected from carbon atoms and one nitrogen atom. Illustrative entities, in the form of properly bonded moieties, include:

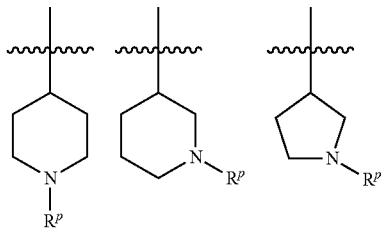

The term "aryl" refers to a monocyclic, aromatic carbocycle (ring structure having ring atoms that are all carbon) having 6 atoms per ring. (Carbon atoms in the aryl groups are $sp^2$ hybridized.)

The term "phenyl" represents the following moiety:

The term "heteroaryl" refers to a monocyclic or fused bicyclic heterocycle (ring structure having ring atoms selected from carbon atoms and up to four heteroatoms selected from nitrogen, oxygen, and sulfur) having from 3 to 9 ring atoms per heterocycle. Illustrative examples of heteroaryl groups include the following entities, in the form of properly bonded moieties:

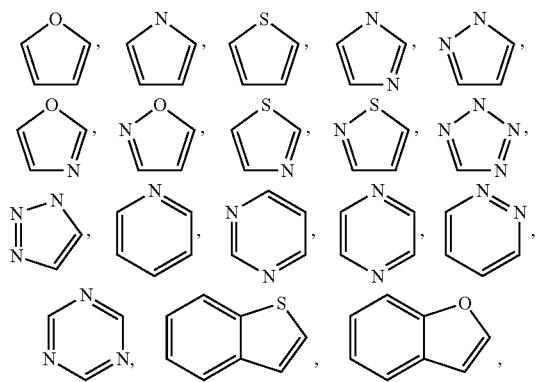

Those skilled in the art will recognize that the species of heteroaryl, cycloalkyl, aryl and heterocycloalkyl groups listed or illustrated above are not exhaustive, and that additional species within the scope of these defined terms may also be selected.

The term "cyano" refers to the group —CN.

The term "halo" represents chloro, fluoro, bromo or iodo.

The term "perhaloalkyl" refers to a straight- or branched-chain alkyl group having from 1 to 4 carbon atoms in the chain optionally substituting hydrogens with halogens. Examples of perhaloalkyl groups include trifluoromethyl (CF₃), difluoromethyl (CF₂H), monofluoromethyl (CH₂F), pentafluoroethyl (CF₂CF₃), tetrafluoroethyl (CHFCF₃), monofluoroethyl (CH₂CH₂F), trifluoroethyl (CH₂CF₃), tetrafluorotrifluoromethylethyl (—CF(CF₃)₂), and groups that in light of the ordinary skill in the art and the teachings provided herein would be considered equivalent to any one of the foregoing examples.

The term "perhaloalkoxy" refers to a straight- or branched-chain alkoxy group having from 1 to 4 carbon atoms in the chain optionally substituting hydrogens with halogens. Examples of perhaloalkoxy groups include trifluoromethoxy (OCF₃), difluoromethoxy (OCF₂H), monofluoromethoxy (OCH₂F), momofluoroethoxy (OCH₂CH₂F), pentafluoroethoxy (OCF₂CF₃), tetrafluoroethoxy (OCHFCF₃), trifluoroethoxy (OCH₂CF₃), tetrafluorotrifluoromethylethoxy (—OCF(CF₃)₂), and groups that in light of the ordinary skill in the art and the teachings provided herein would be considered equivalent to any one of the foregoing examples.

The term "substituted" means that the specified group or moiety bears one or more substituents. The term "unsubstituted" means that the specified group bears no substituents. The term "optionally substituted" means that the specified group is unsubstituted or substituted by one or more substituents. Where the term "substituted" is used to describe a structural system, the substitution is meant to occur at any valency-allowed position on the system. In cases where a specified moiety or group is not expressly noted as being optionally substituted or substituted with any specified substituent, it is understood that such a moiety or group is intended to be unsubstituted.

The terms "para", "meta", and "ortho" have the meanings as understood in the art. Thus, for example, a fully substituted phenyl group has substituents at both "ortho" (o) positions adjacent to the point of attachment of the phenyl ring, both "meta" (m) positions, and the one "para" (p) position across from the point of attachment. To further clarify the position of substituents on the phenyl ring, the 2 different ortho positions will be designated as ortho and ortho' and the 2 different meta positions as meta and meta' as illustrated below.

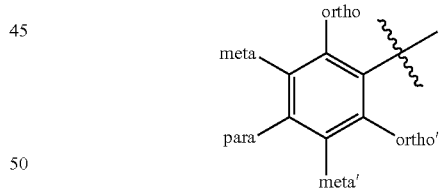

To provide a more concise description, some of the quantitative expressions given herein are not qualified with the term "about". It is understood that, whether the term "about" is used explicitly or not, every quantity given herein is meant to refer to the actual given value, and it is also meant to refer to the approximation to such given value that would reasonably be inferred based on the ordinary skill in the art, including equivalents and approximations due to the experimental and/or measurement conditions for such given value. Whenever a yield is given as a percentage, such yield refers to a mass of the entity for which the yield is given with respect to the maximum amount of the same entity that could be obtained under the particular stoichiometric conditions. Concentrations that are given as percentages refer to mass ratios, unless indicated differently.

The terms "buffered" solution or "buffer" solution are used herein interchangeably according to their standard meaning. Buffered solutions are used to control the pH of a medium, and their choice, use, and function is known to those of ordinary skill in the art. See, for example, G. D. Considine, ed., Van Nostrand's Encyclopedia of Chemistry, p. 261, 5$^{th}$ ed. (2005), describing, inter alia, buffer solutions and how the concentrations of the buffer constituents relate to the pH of the buffer. For example, a buffered solution is obtained by adding $MgSO_4$ and $NaHCO_3$ to a solution in a 10:1 w/w ratio to maintain the pH of the solution at about 7.5.

Any formula given herein is intended to represent compounds having structures depicted by the structural formula as well as certain variations or forms. In particular, compounds of any formula given herein may have asymmetric centers and therefore exist in different enantiomeric forms. All optical isomers of the compounds of the general formula, and mixtures thereof, are considered within the scope of the formula. Thus, any formula given herein is intended to represent a racemate, one or more enantiomeric forms, one or more diastereomeric forms, one or more atropisomeric forms, and mixtures thereof. Furthermore, certain structures may exist as geometric isomers (i.e., cis and trans isomers), as tautomers, or as atropisomers.

It is also to be understood that compounds that have the same molecular formula but differ in the nature or sequence of bonding of their atoms or the arrangement of their atoms in space are termed "isomers." Isomers that differ in the arrangement of their atoms in space are termed "stereoisomers."

Stereoisomers that are not mirror images of one another are termed "diastereomers" and those that are non-superimposable mirror images of each other are termed "enantiomers." When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture."

"Tautomers" refer to compounds that are interchangeable forms of a particular compound structure, and that vary in the displacement of hydrogen atoms and electrons. Thus, two structures may be in equilibrium through the movement of π electrons and an atom (usually H). For example, enols and ketones are tautomers because they are rapidly interconverted by treatment with either acid or base. Another example of tautomerism is the aci- and nitro-forms of phenyl nitromethane, that are likewise formed by treatment with acid or base.

Tautomeric forms may be relevant to the attainment of the optimal chemical reactivity and biological activity of a compound of interest.

Compounds of the invention may also exist as "rotamers," that is, conformational isomers that occur when the rotation leading to different conformations is hindered, resulting a rotational energy barrier to be overcome to convert from one conformational isomer to another.

The compounds of this invention may possess one or more asymmetric centers; such compounds can therefore be produced as individual (R)- or (S)-stereoisomers or as mixtures thereof.

Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art.

Certain examples contain chemical structures that are depicted as an absolute enantiomer but are intended to indicate enantiopure material that is of unknown configuration. In these cases (R*) or (S*) is used in the name to indicate that the absolute stereochemistry of the corresponding stereocenter is unknown. Thus, a compound designated as (R*) refers to an enantiopure compound with an absolute configuration of either (R) or (S). In cases where the absolute stereochemistry has been confirmed, the structures are named using (R) and (S).

The symbols ▬ and ▬ are used as meaning the same spatial arrangement in chemical structures shown herein. Analogously, the symbols ⦀⦀⦀ and ⁃⁃⁃ are used as meaning the same spatial arrangement in chemical structures shown herein.

Additionally, any formula given herein is intended to refer also to hydrates, solvates, and polymorphs of such compounds, and mixtures thereof, even if such forms are not listed explicitly. Certain compounds of Formula (I) or (Ia) or pharmaceutically acceptable salts of compounds of Formula (I) or (Ia) may be obtained as solvates. Solvates include those formed from the interaction or complexation of compounds of the invention with one or more solvents, either in solution or as a solid or crystalline form. In some embodiments, the solvent is water and then the solvates are hydrates. In addition, certain crystalline forms of compounds of Formula (I) or (Ia) or pharmaceutically acceptable salts of compounds of Formula (I) or (Ia) may be obtained as co-crystals. In certain embodiments of the invention, compounds of Formula (I) or (Ia) were obtained in a crystalline form. In other embodiments, crystalline forms of compounds of Formula (I) or (Ia) were cubic in nature. In other embodiments, pharmaceutically acceptable salts of compounds of Formula (I) or (Ia) were obtained in a crystalline form. In still other embodiments, compounds of Formula (I) or (Ia) were obtained in one of several polymorphic forms, as a mixture of crystalline forms, as a polymorphic form, or as an amorphous form. In other embodiments, compounds of Formula (I) or (Ia) convert in solution between one or more crystalline forms and/or polymorphic forms.

Reference to a compound herein stands for a reference to any one of: (a) the actually recited form of such compound, and (b) any of the forms of such compound in the medium in which the compound is being considered when named. For example, reference herein to a compound such as R—COOH, encompasses reference to any one of, for example, R—COOH$_{(s)}$, R—COOH$_{(sol)}$, and R—COO$^-_{(sol)}$. In this example, R—COOH$_{(s)}$ refers to the solid compound, as it could be for example in a tablet or some other solid pharmaceutical composition or preparation; R—COOH$_{(sol)}$ refers to the undissociated form of the compound in a solvent; and R—COO$^-_{(sol)}$ refers to the dissociated form of the compound in a solvent, such as the dissociated form of the compound in an aqueous environment, whether such dissociated form derives from R—COOH, from a salt thereof, or from any other entity that yields R—COO$^-$ upon dissociation in the medium being considered. In another example, an expression such as "exposing an entity to compound of formula R—COOH" refers to the exposure of such entity to the form, or forms, of the compound R—COOH that exists, or exist, in the medium in which such exposure takes place. In still another example, an expression such as "reacting an entity with a compound of formula R—COOH" refers to the reacting of (a) such entity in the chemically relevant form, or forms, of such entity that exists, or exist, in the medium in which such reacting takes place, with (b) the chemically relevant form, or forms, of the compound R—COOH that exists, or exist, in the medium in which such reacting takes place. In this regard, if such entity is for example in an aqueous environment, it is understood that the compound R—COOH is in such same medium, and therefore the entity is being exposed to species such as R—COOH$_{(aq)}$ and/or R—COO$^-_{(aq)}$, where the subscript "(aq)" stands for "aqueous" according to its conventional meaning in chemistry and biochemistry. A carboxylic acid functional group has been chosen in these nomenclature examples; this choice is not intended, however, as a limitation but it is merely an illustration. It is understood that analogous examples can be provided in terms of other functional groups, including but not limited to hydroxyl, basic nitrogen members, such as those in amines, and any other group that interacts or transforms according to known manners in the medium that contains the compound. Such interactions and transformations include, but are not limited to, dissociation, association, tautomerism, solvolysis, including hydrolysis, solvation, including hydration, protonation, and deprotonation. No further examples in this regard are provided herein because these interactions and transformations in a given medium are known by any one of ordinary skill in the art.

In another example, a zwitterionic compound is encompassed herein by referring to a compound that is known to form a zwitterion, even if it is not explicitly named in its zwitterionic form. Terms such as zwitterion, zwitterions, and their synonyms zwitterionic compound(s) are standard IUPAC-endorsed names that are well known and part of standard sets of defined scientific names. In this regard, the name zwitterion is assigned the name identification CHEBI: 27369 by the Chemical Entities of Biological Interest (ChEBI) dictionary of molecular entities. As generally well known, a zwitterion or zwitterionic compound is a neutral compound that has formal unit charges of opposite sign. Sometimes these compounds are referred to by the term "inner salts". Other sources refer to these compounds as "dipolar ions", although the latter term is regarded by still other sources as a misnomer. As a specific example, aminoethanoic acid (the amino acid glycine) has the formula H$_2$NCH$_2$COOH, and it exists in some media (in this case in neutral media) in the form of the zwitterion $^+$H$_3$NCH$_2$COO$^-$. Zwitterions, zwitterionic compounds, inner salts and dipolar ions in the known and well established meanings of these terms are within the scope of this invention, as would in any case be so appreciated by those of ordinary skill in the art. Because there is no need to name each and every embodiment that would be recognized by those of ordinary skill in the art, no structures of the zwitterionic compounds that are associated with the compounds of this invention are given explicitly herein. They are, however, part of the embodiments of this invention. No further examples in this regard are provided herein because the interactions and transformations in a given medium that lead to the various forms of a given compound are known by any one of ordinary skill in the art.

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorus, fluorine, and chlorine, such as $^2$H, $^3$H, $^{11}$C, $^{13}$C, $^{14}$C, $^{15}$N, $^{18}$O, $^{17}$O, $^{31}$P, $^{32}$P, $^{35}$S, $^{18}$F, $^{36}$Cl, $^{125}$I respectively. Such isotopically labeled compounds are useful in metabolic studies (preferably with $^{14}$C), reaction kinetic studies (with, for example $^2$H or $^3$H), detection or imaging techniques [such as positron emission tomography (PET) or single-photon emission computed tomography (SPECT)] including drug or substrate tissue distribution assays, or in radioactive treatment of patients. In particular, an $^{18}$F or $^{11}$C labeled compound may be particularly preferred for PET or SPECT studies. Further, substitution with heavier isotopes such as deuterium (i.e., $^2$H) may afford certain therapeutic advantages resulting from greater metabolic stability, for example increased in vivo half-life or reduced dosage requirements. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent.

When referring to any formula given herein, the selection of a particular moiety from a list of possible species for a specified variable is not intended to define the same choice of the species for the variable appearing elsewhere. In other words, where a variable appears more than once, the choice of the species from a specified list is independent of the choice of the species for the same variable elsewhere in the formula, unless stated otherwise.

According to the foregoing interpretive considerations on assignments and nomenclature, it is understood that explicit reference herein to a set implies, where chemically meaningful and unless indicated otherwise, independent reference to embodiments of such set, and reference to each and every one of the possible embodiments of subsets of the set referred to explicitly.

The invention includes also pharmaceutically acceptable salts of the compounds of Formula (I) or (Ia), preferably of those described above and of the specific compounds exemplified herein, and methods of treatment using such salts.

Pharmaceutically acceptable means approved or approvable by a regulatory agency of Federal or a state government or the corresponding agency in countries other than the United States, or that is listed in the U. S. Pharmacopoeia or other generally recognized pharmacopoeia for use in animals, and more particularly, in humans.

A "pharmaceutically acceptable salt" is intended to mean a salt of a free acid or base of a compound represented by Formula (I) or (Ia) that is non-toxic, biologically tolerable, or otherwise biologically suitable for administration to the subject. It should possess the desired pharmacological activity of the parent compound. See, generally, G. S. Paulekuhn, et al., "Trends in Active Pharmaceutical Ingredient Salt Selection based on Analysis of the Orange Book Database", *J. Med. Chem.*, 2007, 50:6665-72, S. M. Berge, et al., "Pharmaceutical Salts", *J Pharm Sci.*, 1977, 66:1-19, and *Handbook of Pharmaceutical Salts, Properties, Selection, and Use*, Stahl and Wermuth, Eds., Wiley-VCH and VHCA, Zurich, 2002. Examples of pharmaceutically acceptable salts are those that are pharmacologically effective and suitable for contact with the tissues of patients without undue toxicity, irritation, or allergic response. A compound of Formula (I) or (Ia) may possess a sufficiently acidic group, a sufficiently basic group, or both types of functional groups, and accordingly react with a number of inorganic or organic bases, and inorganic and organic acids, to form a pharmaceutically acceptable salt.

Examples of pharmaceutically acceptable salts include sulfates, pyrosulfates, bisulfates, sulfites, bisulfites, phosphates, monohydrogen-phosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, xylenesulfonates, phenylacetates, phenylpropionates, phenylbutyrates, citrates, lactates, γ-hydroxybutyrates, glycolates, tartrates, methane-sulfonates, propanesulfonates, naphthalene-1-sulfonates, naphthalene-2-sulfonates, and mandelates.

When the compound of Formula (I) or (Ia) contains a basic nitrogen, the desired pharmaceutically acceptable salt may be prepared by any suitable method available in the art, for example, treatment of the free base with an inorganic acid, such as hydrochloric acid, hydrobromic acid, sulfuric acid, sulfamic acid, nitric acid, boric acid, phosphoric acid, and the like, or with an organic acid, such as acetic acid, phenylacetic acid, propionic acid, stearic acid, lactic acid, ascorbic acid, maleic acid, hydroxymaleic acid, isethionic acid, succinic acid, valeric acid, fumaric acid, malonic acid, pyruvic acid, oxalic acid, glycolic acid, salicylic acid, oleic acid, palmitic acid, lauric acid, a pyranosidyl acid, such as glucuronic acid or galacturonic acid, an alpha-hydroxy acid, such as mandelic acid, citric acid, or tartaric acid, an amino acid, such as aspartic acid, glutaric acid or glutamic acid, an aromatic acid, such as benzoic acid, 2-acetoxybenzoic acid, naphthoic acid, or cinnamic acid, a sulfonic acid, such as laurylsulfonic acid, p-toluenesulfonic acid, methanesulfonic acid, ethanesulfonic acid, any compatible mixture of acids such as those given as examples herein, and any other acid and mixture thereof that are regarded as equivalents or acceptable substitutes in light of the ordinary level of skill in this technology.

When the compound of Formula (I) or (Ia) is an acid, such as a carboxylic acid or sulfonic acid, the desired pharmaceutically acceptable salt may be prepared by any suitable method, for example, treatment of the free acid with an inorganic or organic base, such as an amine (primary, secondary or tertiary), an alkali metal hydroxide, alkaline earth metal hydroxide, any compatible mixture of bases such as those given as examples herein, and any other base and mixture thereof that are regarded as equivalents or acceptable substitutes in light of the ordinary level of skill in this technology. Illustrative examples of suitable salts include organic salts derived from amino acids, such as N-methyl-D-glucamine, lysine, choline, glycine and arginine, ammonia, carbonates, bicarbonates, primary, secondary, and tertiary amines, and cyclic amines, such as tromethamine, benzylamines, pyrrolidines, piperidine, morpholine, and piperazine, and inorganic salts derived from sodium, calcium, potassium, magnesium, manganese, iron, copper, zinc, aluminum, and lithium.

The invention also relates to pharmaceutically acceptable prodrugs of the compounds of Formula (I) or (Ia), and treatment methods employing such pharmaceutically acceptable prodrugs. The term "prodrug" means a precursor of a designated compound that, following administration to a subject, yields the compound in vivo via a chemical or physiological process such as solvolysis or enzymatic cleavage, or under physiological conditions (e.g., a prodrug on being brought to physiological pH is converted to the compound of Formula (I) or (Ia)). A "pharmaceutically acceptable prodrug" is a prodrug that is non-toxic, biologically tolerable, and otherwise biologically suitable for administration to the subject. Illustrative procedures for the selection and preparation of suitable prodrug derivatives are described, for example, in "*Design of Prodrugs*", ed. H. Bundgaard, Elsevier, 1985.

Exemplary prodrugs include compounds having an amino acid residue, or a polypeptide chain of two or more (e.g., two, three or four) amino acid residues, covalently joined through an amide or ester bond to a free amino, hydroxy, or carboxylic acid group of a compound of Formula (I) or (Ia). Examples of amino acid residues include the twenty naturally occurring amino acids, commonly designated by three letter symbols, as well as 4-hydroxyproline, hydroxylysine, demosine, isodemosine, 3-methylhistidine, norvalin, beta-alanine, gamma-aminobutyric acid, citrulline homocysteine, homoserine, ornithine and methionine sulfone.

Additional types of prodrugs may be produced, for instance, by derivatizing free carboxyl groups of structures of Formula (I) or (Ia) as amides or alkyl esters. Examples of amides include those derived from ammonia, primary $C_{1-6}$alkyl amines and secondary di($C_{1-6}$alkyl) amines Secondary amines include 5- or 6-membered heterocycloalkyl or heteroaryl ring moieties. Examples of amides include those that are derived from ammonia, $C_{1-3}$alkyl primary amines, and di($C_{1-2}$alkyl)amines Examples of esters of the invention include $C_{1-7}$alkyl, $C_{5-7}$cycloalkyl, phenyl, and phenyl($C_{1-6}$alkyl) esters. Preferred esters include methyl esters. Prodrugs may also be prepared by derivatizing free hydroxy groups using groups including hemisuccinates, phosphate esters, dimethylaminoacetates, and phosphoryloxymethyloxycarbonyls, following procedures such as those outlined in Fleisher et al., *Adv. Drug Delivery Rev.* 1996, 19, 115-130. Carbamate derivatives of hydroxy and amino groups may also yield prodrugs. Carbonate derivatives, sulfonate esters, and sulfate esters of hydroxy groups may also provide prodrugs. Derivatization of hydroxy groups as (acyloxy)methyl and (acyloxy)ethyl ethers, wherein the acyl group may be an alkyl ester, optionally substituted with one or more ether, amine, or carboxylic acid functionalities, or where the acyl group is an amino acid ester as described above, is also useful to yield prodrugs. Prodrugs of this type may be prepared as described in Robinson et al., *J Med Chem.* 1996, 39 (1), 10-18. Free amines can also be derivatized as amides, sulfonamides or phosphonamides. All of these prodrug moieties may incorporate groups including ether, amine, and carboxylic acid functionalities.

The present invention also relates to pharmaceutically active metabolites of the compounds of Formula (I) or (Ia), which may also be used in the methods of the invention. A "pharmaceutically active metabolite" means a pharmacologically active product of metabolism in the body of a compound of Formula (I) or (Ia) or salt thereof. Prodrugs and active metabolites of a compound may be determined using routine techniques known or available in the art. See, e.g., Bertolini, et al., *J Med Chem.* 1997, 40, 2011-2016; Shan, et al., *J Pharm Sci.* 1997, 86 (7), 765-767; Bagshawe, *Drug Dev Res.* 1995, 34, 220-230; Bodor, *Adv Drug Res.* 1984, 13, 224-331; Bundgaard, *Design of Prodrugs* (Elsevier Press, 1985); and Larsen, *Design and Application of Prodrugs, Drug Design and Development* (Krogsgaard-Larsen, et al., eds., Harwood Academic Publishers, 1991).

The compounds of Formula (I) or (Ia) and their pharmaceutically acceptable salts, pharmaceutically acceptable prodrugs, and pharmaceutically active metabolites of the present invention are useful as modulators of the P2X7 receptor in the methods of the invention. As such modulators, the compounds may act as antagonists, agonists, or inverse agonists. The term "modulators" include both inhibitors and activators, where "inhibitors" refer to compounds that decrease, prevent, inactivate, desensitize or down-regulate the P2X7 receptor expression or activity, and "activators" are compounds that increase, activate, facilitate, sensitize, or up-regulate P2X7 receptor expression or activity.

The term "treat", "treatment" or "treating" as used herein is intended to refer to administration of an active agent or composition of the invention to a subject for the purpose of affecting a therapeutic or prophylactic benefit through modulation of P2X7 receptor activity. Treating includes reversing, ameliorating, alleviating, inhibiting the progress of, lessening the severity of, or preventing a disease, disorder, or condition, or one or more symptoms of such disease, disorder or condition mediated through modulation of P2X7 receptor activity. The term "subject" refers to a mammalian patient in need of such treatment, such as a human.

Accordingly, the invention relates to methods of using the compounds described herein to treat subjects diagnosed with or suffering from a disease, disorder, or condition mediated by P2X7 receptor activity, such as: rheumatoid arthritis, osteoarthritis, psoriasis, septic shock, allergic dermatitis, asthma, allergic asthma, mild to severe asthma, steroid resistant asthma, idiopathic pulmonary fibrosis, allergic rhinitis, chronic obstructive pulmonary disease (COPD) and airway hyper-responsiveness; diseases of the nervous and neuro-immune system such as acute and chronic pain states of neuropathic pain, inflammatory pain, spontaneous pain (opioid induced pain, diabetic neuropathy, postherpetic neuralgia, low back pain, chemotherapy-induced neuropathic pain, fibromyalgia); diseases involved with and without neuroinflammation of the CNS such as mood disorders (major depression, major depressive disorder, treatment resistant depression, bipolar disorder, anxious depression, anxiety), cognition, sleep disorders, multiple sclerosis, epileptic seizures, Parkinson's disease, schizophrenia, Alzheimer's disease, Huntington's disease, autism, spinal cord injury and cerebral ischemia/traumatic brain injury, stress-related disorders; diseases of the cardiovascular, metabolic, gastrointestinal and urogenital systems such as diabetes, diabetes mellitus, thrombosis, irritable bowel syndrome, IBD, Crohn's disease, ischemic heart disease, ischaemia, hypertension, cardiovascular disease, myocardial infarction, and lower urinary tract dysfunction such as incontinence, lower urinary tract syndrome, Polycystic Kidney Disease, Glomerulonephritis, (GN); skeletal disorders, namely osteoporosis/osteopetrosis: and glaucoma, interstitial cystitis, cough, ureteric obstruction, sepsis, Amyotrophic Lateral Sclerosis, Chaga's Disease, chlamydia, neuroblastoma, Tuberculosis, and migraine.

In treatment methods according to the invention, a therapeutically effective amount of a pharmaceutical agent according to the invention is administered to a subject suffering from or diagnosed as having such a disease, disorder, or condition. An "effective amount" or "therapeutically effective amount" means an amount or dose sufficient to generally bring about the desired therapeutic or prophylactic benefit in patients in need of such treatment for the designated disease, disorder, or condition. Therapeutically effective amounts or doses of the compounds of the present invention may be ascertained by routine methods such as modeling, dose escalation studies or clinical trials, and by taking into consideration routine factors, e.g., the mode or route of administration or drug delivery, the pharmacokinetics of the compound, the severity and course of the disease, disorder, or condition, the subject's previous or ongoing therapy, the subject's health status and response to drugs, and the judgment of the treating physician. An example of a dose is in the range of from about 0.001 to about 200 mg of compound per kg of subject's body weight per day, preferably about 0.05 to 100 mg/kg/day, or about 1 to 35 mg/kg/day, in single or divided dosage units (e.g., BID, TID, QID). For a 70-kg human, an illustrative range for a suitable dosage amount is from about 0.05 to about 7 g/day, or about 0.2 to about 2.5 g/day.

Once improvement of the patient's disease, disorder, or condition has occurred, the dose may be adjusted for preventative or maintenance treatment. For example, the dosage or the frequency of administration, or both, may be reduced as a function of the symptoms, to a level at which the desired therapeutic or prophylactic effect is maintained. Of course, if symptoms have been alleviated to an appropriate level, treatment may cease. Patients may, however, require intermittent treatment on a long-term basis upon any recurrence of symptoms.

In addition, the active agents of the invention may be used in combination with additional active ingredients in the treatment of the above conditions. The additional active ingredients may be coadministered separately with an active agent of compounds of Table 1 or included with such an agent in a pharmaceutical composition according to the invention. In an exemplary embodiment, additional active ingredients are those that are known or discovered to be therapeutically effective in the treatment of conditions, disorders, or diseases mediated by P2X7 activity, such as another P2X7 modulator or a compound active against another target associated with the particular condition, disorder, or disease. The combination may serve to increase efficacy (e.g., by including in the combination a compound potentiating the potency or effectiveness of an active agent according to the invention), decrease one or more side effects, or decrease the required dose of the active agent according to the invention.

The active agents of the invention are used, alone or in combination with one or more additional active ingredients, to formulate pharmaceutical compositions of the invention. A pharmaceutical composition of the invention comprises: (a) a therapeutically effective amount of at least one active agent in accordance with the invention; and (b) a pharmaceutically acceptable excipient.

A "pharmaceutically acceptable excipient" refers to a substance that is non-toxic, biologically tolerable, and otherwise biologically suitable for administration to a subject, such as an inert substance, added to a pharmacological composition or otherwise used as a vehicle, carrier, or diluent to facilitate administration of an agent and that is compatible therewith. Examples of excipients include calcium carbonate, calcium phosphate, various sugars and types of starch, cellulose derivatives, gelatin, vegetable oils, and polyethylene glycols.

Delivery forms of the pharmaceutical compositions containing one or more dosage units of the active agents may be prepared using suitable pharmaceutical excipients and compounding techniques known or that become available to those skilled in the art. The compositions may be administered in the inventive methods by a suitable route of delivery, e.g., oral, parenteral, rectal, topical, or ocular routes, or by inhalation.

The preparation may be in the form of tablets, capsules, sachets, dragees, powders, granules, lozenges, powders for reconstitution, liquid preparations, or suppositories. Preferably, the compositions are formulated for intravenous infusion, topical administration, or oral administration.

For oral administration, the compounds of the invention can be provided in the form of tablets or capsules, or as a solution, emulsion, or suspension. To prepare the oral compositions, the compounds may be formulated to yield a dosage of, e.g., from about 0.05 to about 100 mg/kg daily, or from about 0.05 to about 35 mg/kg daily, or from about 0.1 to about 10 mg/kg daily. For example, a total daily dosage of about 5 mg to 5 g daily may be accomplished by dosing once, twice, three, or four times per day.

Oral tablets may include a compound according to the invention mixed with pharmaceutically acceptable excipients such as inert diluents, disintegrating agents, binding agents, lubricating agents, sweetening agents, flavoring agents, coloring agents and preservative agents. Suitable inert fillers include sodium and calcium carbonate, sodium and calcium phosphate, lactose, starch, sugar, glucose, methyl cellulose, magnesium stearate, mannitol, sorbitol, and the like. Exemplary liquid oral excipients include ethanol, glycerol, water, and the like. Starch, polyvinyl-pyrrolidone (PVP), sodium starch glycolate, microcrystalline cellulose, and alginic acid are suitable disintegrating agents. Binding agents may include starch and gelatin. The lubricating agent, if present, may be magnesium stearate, stearic acid or talc. If desired, the tablets may be coated with a material such as glyceryl monostearate or glyceryl distearate to delay absorption in the gastrointestinal tract, or may be coated with an enteric coating.

Capsules for oral administration include hard and soft gelatin capsules. To prepare hard gelatin capsules, compounds of the invention may be mixed with a solid, semi-solid, or liquid diluent. Soft gelatin capsules may be prepared by mixing the compound of the invention with water, an oil such as peanut oil or olive oil, liquid paraffin, a mixture of mono and di-glycerides of short chain fatty acids, polyethylene glycol 400, or propylene glycol.

Liquids for oral administration may be in the form of suspensions, solutions, emulsions or syrups or may be lyophilized or presented as a dry product for reconstitution with water or other suitable vehicle before use. Such liquid compositions may optionally contain: pharmaceutically-acceptable excipients such as suspending agents (for example, sorbitol, methyl cellulose, sodium alginate, gelatin, hydroxyethylcellulose, carboxymethylcellulose, aluminum stearate gel and the like); non-aqueous vehicles, e.g., oil (for example, almond oil or fractionated coconut oil), propylene glycol, ethyl alcohol, or water; preservatives (for example, methyl or propyl p-hydroxybenzoate or sorbic acid); wetting agents such as lecithin; and, if desired, flavoring or coloring agents.

The active agents of this invention may also be administered by non-oral routes. For example, the compositions may be formulated for rectal administration as a suppository. For parenteral use, including intravenous, intramuscular, intraperitoneal, or subcutaneous routes, the compounds of the invention may be provided in sterile aqueous solutions or suspensions, buffered to an appropriate pH and isotonicity or in parenterally acceptable oil. Suitable aqueous vehicles include Ringer's solution and isotonic sodium chloride. Such forms will be presented in unit-dose form such as ampules or disposable injection devices, in multi-dose forms such as vials from which the appropriate dose may be withdrawn, or in a solid form or pre-concentrate that can be used to prepare an injectable formulation. Illustrative infusion doses may range from about 1 to 1000 µg/kg/minute of compound, admixed with a pharmaceutical carrier over a period ranging from several minutes to several days.

For topical administration, the compounds may be mixed with a pharmaceutical carrier at a concentration of about 0.1% to about 10% of drug to vehicle. Another mode of administering the compounds of the invention may utilize a patch formulation to affect transdermal delivery.

Compounds of the invention may alternatively be administered in methods of this invention by inhalation, via the nasal or oral routes, e.g., in a spray formulation also containing a suitable carrier.

Exemplary compounds useful in methods of the invention will now be described by reference to the illustrative synthetic schemes for their general preparation below and the specific examples that follow. Artisans will recognize that, to obtain the various compounds herein, starting materials may be suitably selected so that the ultimately desired substituents will be carried through the reaction scheme with or without protection as appropriate to yield the desired product. Alternatively, it may be necessary or desirable to employ, in the place of the ultimately desired substituent, a suitable group that may be carried through the reaction scheme and replaced as appropriate with the desired substituent. Unless otherwise specified, the variables are as defined above in reference to Formula (I) and/or (Ia). Reactions may be performed between the melting point and the reflux temperature of the solvent, and preferably between 0° C. and the reflux temperature of the solvent. Reactions may be heated employing conventional heating or microwave heating. Reactions may also be conducted in sealed pressure vessels above the normal reflux temperature of the solvent.

Synthetic procedures described in the Schemes below are meant to describe the synthesis of intermediates and general procedures to prepare embodiments of the invention. Variables presented in the schemes are intended to refer to the synthesis described in that scheme.

Scheme I

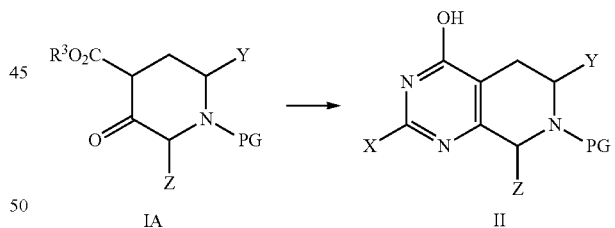

The group PG represents a protecting group. One skilled in the art will select the appropriate protecting group compatible with the desired reactions. The protecting groups may be removed at a convenient subsequent stage using methods known from the art. Alternatively, it may be necessary to employ, in the place of the ultimately desired substituent, a suitable group that may be carried through the reaction scheme and replaced as appropriate with the desired substituent. Such compounds, precursors, or prodrugs are also within the scope of the invention. Examples of preferred protecting groups include; carbamates, benzyl and substituted benzyl groups. Especially preferred protecting groups are; tert-butyloxycarbonyl, 2,2,2-trichloroethoxycarbonyl, alpha-chloroethoxycarbonyl, benzyl, 4-nitrobenzyl and diphenylmethyl.

Compound IA is converted to Compound II upon treatment for approximately 12 hours with the appropriately substituted formamidine hydrochloride, with a base such as NaOEt or NaOMe in a solvent such as EtOH or MeOH at a temperature such as the reflux temperature of said solvent. Alternative conditions which can be used are: an appropriately substituted formamidine hydrochloride, a base such as $K_2CO_3$ in a solvent such as MeOH and water; an appropriately substituted guanidine salt, such as the sulfate or carbonate salts, a base such as $K_2CO_3$ in a solvent such as MeOH and water; an appropriately substituted guanidine salt, such as the sulfate or carbonate salts, a base such as TEA in a solvent such as tBuOH.

or DIPEA in a solvent such as DCM or DMF. Chloride VI is converted to compound VII using the conditions just described. Compound VIII (where W is OH) is converted to compound VIII (where W is Cl) through chlorinating conditions for example treating compound VIII (where W is OH) with $(COCl)_2$ and DMF in a solvent such as DCM.

Hydroxy compound II is converted into chloride VI by heating a combination of the following reagents to a temperature such as the reflux temperature of the solvent: a chlorinating agent such as $POCl_3$, along with a base such as dimethyl aniline in a solvent such as DCE. Alternatively

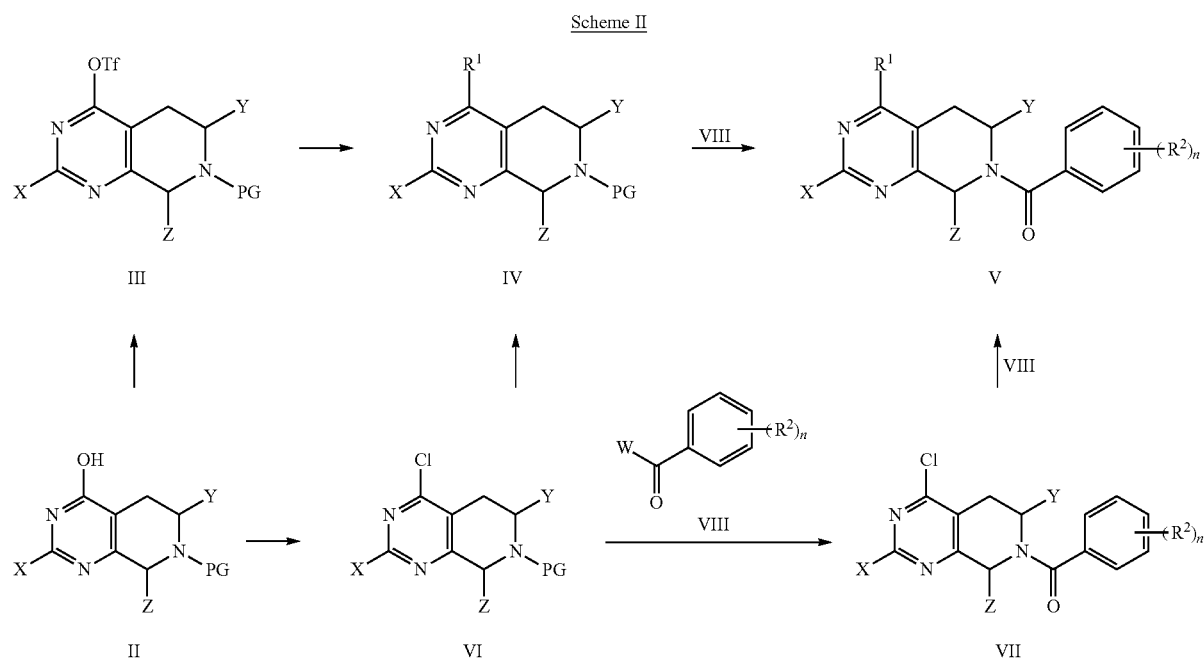

Scheme II

Hydroxy compound II is converted to triflate III through treatment with triflic anhydride in a solvent such as DCM or DMF at a temperature of approximately 0° C. Triflate III is converted to tricycle IV using coupling conditions, sometimes known as Suzuki coupling conditions, wherein the following elements are heated for approximately 12 hours to a temperature around 100° C.: triflate III, an aromatic or heteroaromatic boronic ester or an aromatic or heteroaromatic boronic acid, a palladium catalyst such as $PdCl_2dppf$, a ligand such as dppf and a salt such as $K_3PO_4$ in a solvent such as dioxane.

Tricycle IV is transformed to final compound V. Initial deprotection of the piperdine protecting group is performed using standard conditions such as: when PG=Boc, TFA in DCM. The resulting compound (not shown) can then be coupled to (a) carboxylic acids using VIII (where W is OH) or (b) carboxylic acid chlorides (where W is Cl). The couplings using carboxylic acids (VIII, W is OH) are performed using any number of amide bond coupling conditions such as: VIII (W is OH), EDC, HOBt, a base such as TEA or DIPEA in a solvent such as DCM or DMF; VIII (W is OH), HATU, HOBt, in a base such as TEA or DIPEA in a solvent such as DCM or DMF. The couplings using carboxylic acid chlorides (VIII, W is Cl) are accomplished using VIII (W is Cl) in the presence of a base such as TEA chloride VI is prepared by treatment of hydroxy compound II with $PPh_3$ and $CCl_4$ at a temperature of about 70° C. for approximately 2.5 h.

Chloride VI is converted to compound IV by treatment with a heteroaryl or aryldioxaborolane, heteroaryl or aryl boronic ester or a heteroaryl or aryl boronic acid with a catalyst such as $(Ph_3P)_4Pd$, with a base such as $Na_2CO_3$ in a solvent such as dioxane with heating for about one hour in a microwave reactor at a temperature of about 150° C. An alternative method, designated Method 3-B, for the conversion of VI to IV may be used when $R^1$ in a N-linked 5-membered ring heterocycle, for example a pyrazole or triazole. This method involves the treatment of the NH-heterocycle with a base such as NaH in a solvent such as DMF followed by addition of chloride VI, providing compound IV. Another method, designated Method 3-C, to affect this conversion also uses the N-linked 5-membered heterocycle, for example pyrazole or triazole and involves heating chloride VI, said 5-membered heterocycle, a base such as Hunig's base in a solvent such as ACN. An additional method, designated Method 3-D, is sometimes known as a Stille coupling method. This involves the reaction of chloride VI, with the appropriate stannane $R^1SnBu_3$, $(Ph_3P)_4Pd$ in a solvent such as dioxane with heating to a temperature of about 140° C. C for approximately 90 minutes in a microwave reactor. Chloride VII may also be converted to compound V using the same conditions described above for the conversion of compound VI to compound IV.

pound XI is converted to XII using the same conditions as described in Scheme I for the conversion of compound IA to compound II.

Scheme 3

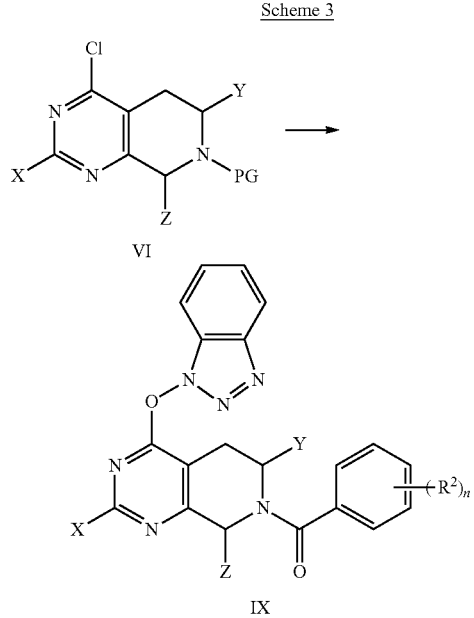

Compound VI is converted to compound IX through treatment with compound VIII (where W is OH), EDCI, HOBt, a base such as TEA or DIPEA in a solvent such as DCM or DMF for approximately 12 hours at approximately room temperature. Intermediate IX is then converted to final compound V using the same conditions as described above using Method 3-B.

Scheme 4

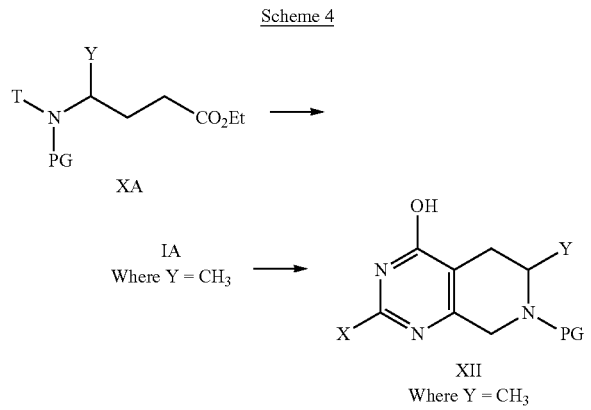

Compound XA, where T is H, PG is CH(CH$_3$)Ph and Y is CH$_3$, is prepared through the reaction of ethyl levulinate and DL-alpha-methylbenzylamine with a reducing agent such as Na(OAc)$_3$BH in a solvent such as DCE or DCM. This compound is converted to compound XA, where T is CH$_2$CO$_2$Et, PG is CH(CH$_3$)Ph and Y is CH$_3$, and upon treatment with glyoxylic acid ethyl ester and Na(OAc)$_3$BH in a solvent such as DCE or DCM. Compound XA, where T is CH$_2$CO$_2$Et, PG is CH(CH$_3$)Ph and Y is CH$_3$, is converted to compound IA upon treatment with a base such as KOtBu in a solvent such as toluene or benzene. Com- Scheme 5

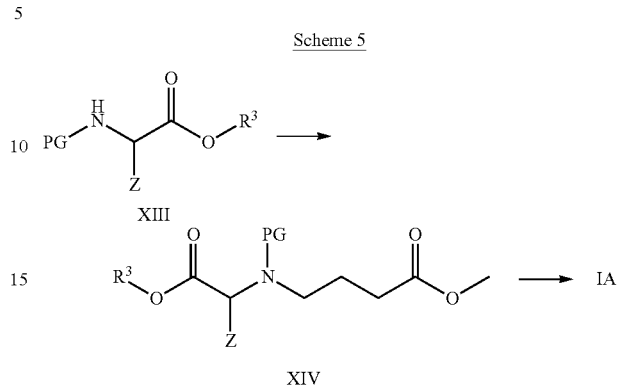

Compound XIII is prepared by the addition of a nitrogen protecting group to the appropriate amino acid ester. In the case of compound XIII (where Z is CH$_3$), DL-alanine ethyl ester hydrochloride is used. Compound XIII (where Z is CH$_3$) is converted to compound XIV upon treatment of compound XIII (where Z is CH$_3$), methyl-4-oxo-butanoate with a reducing agent such as Na(OAc)$_3$BH in a solvent such as DCE or DCM. Compound XIV can be converted to compound 1 upon treatment of compound XIV with a base such as K$_3$CO$_3$ in a solvent such as toluene.

Scheme 6

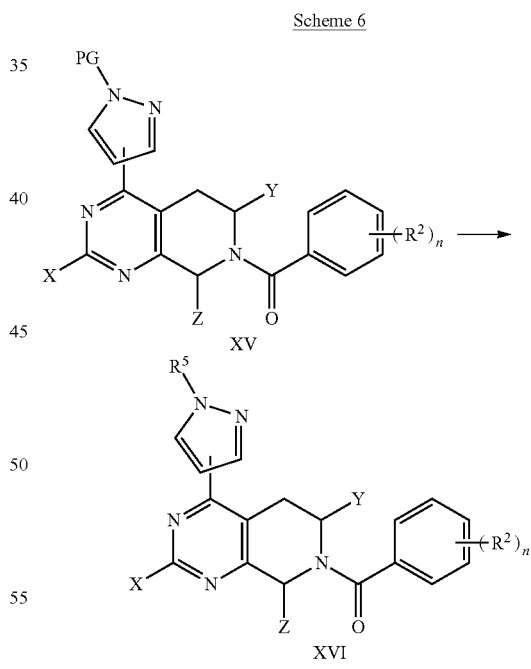

R$^5$ is R$^e$, R$^f$ or R$^g$

Compound XV is converted to compound XVI (where R$^5$ is R$^e$, R$^f$ or R$^g$) and where R$^5$ is H through deprotection of the protecting group (PG). This compound XVI (where R$^5$ is H) is converted to compound XVI (where R$^5$ is CH$_2$CH$_2$F) upon treatment with 1-bromo-2-fluoroethane in a solvent such as DMF heated to a temperature of about 120° C. for approximately 10 minutes under microwave irradiation.

Compound XVI (where $R^5$ is H) is converted to compound XVI (where $R^5$ is $CH_2CH_2OCH_3$) using the same procedure but employing 2-bromoethyl methyl ether Compound XVI (where $R^5$ is $CH_3$) is made from compound XVI (where $R^5$ is H) by treatment of said compound with NaH in DMF followed by addition of MeI.

An intermediate compound, 2-fluoro-6-(4,4,5,5-tetramethyl-1,3,2-dioxaborolan-2-yl)pyridine (Compound XVII, structure not shown) is prepared through the reaction of $Pd(dppf)_2Cl_2\cdot HCl$, 2-bromo-6-fluoropyridine, bis(pinacolato)diboron, and KOAc in a solvent such as dioxane with heating to a temperature of approximately 115° C. for approximately 1 h.

EXAMPLES

In obtaining the compounds described in the examples below and the corresponding analytical data, the following experimental and analytical protocols were followed unless otherwise indicated.

Unless otherwise stated, reaction mixtures were magnetically stirred at room temperature (rt) under a nitrogen atmosphere. Where solutions were "dried," they were generally dried over a drying agent such as $Na_2SO_4$ or $MgSO_4$. Where mixtures, solutions, and extracts were "concentrated", they were typically concentrated on a rotary evaporator under reduced pressure. Reactions under microwave irradiation conditions were carried out in a Biotage Initiator or CEM Discover instrument.

The term $R^1Sn\ Bu_3$ is intended to encompass similar stannane reagents such as $R^1SnMe_3$, $R^1Sn\ Ph_3$ and the like.

Normal-phase silica gel column chromatography (sgc) was performed on silica gel ($SiO_2$) using prepackaged cartridges, eluting with 2 M $NH_3$/MeOH in $CH_2Cl_2$ unless otherwise indicated.

Preparative reverse-phase high performance liquid chromatography (HPLC) was performed on a Gilson HPLC with an Xterra Prep $RP_{18}$ (5 μm, 30×100 mm) column, and a gradient of 10 to 99% acetonitrile/water (20 mM $NH_4OH$) over 12 to 18 min, and a flow rate of 30 mL/min.

Compounds obtained as HCl salts were prepared by the addition of 1 M HCl in diethyl ether to a $CH_2Cl_2$ solution of the free base, followed by concentration, unless specified otherwise.

Mass spectra (MS) were obtained on an Agilent series 1100 MSD using electrospray ionization (ESI) in positive mode unless otherwise indicated. Calculated (calcd.) mass corresponds to the exact mass.

Nuclear magnetic resonance (NMR) spectra were obtained on Bruker model DRX spectrometers. The format of the $^1H$ NMR data below is: chemical shift in ppm downfield of the tetramethylsilane reference (multiplicity, coupling constant J in Hz, integration).

Chemical names were generated using ChemDraw Ultra 6.0.2 (CambridgeSoft Corp., Cambridge, Mass.) or ACD/Name Version 9 (Advanced Chemistry Development, Toronto, Ontario, Canada).

Abbreviations and acronyms used herein include the following:

| Term | Acronym |
|---|---|
| Acetonitrile | ACN |
| tert-Butylcarbamoyl | Boc or BOC |
| t-butanol | t-buOH |
| Dichloroethane | DCE |
| Dichloromethane | DCM |
| Diisopropylether | DIPE |
| Diisopropylethylamine | DIPEA or Hunig's base |
| N,N-Dimethylformamide | DMF |
| Dimethylsulfoxide | DMSO |
| 1,1'-Bis(diphenylphosphino)ferrocene | Dppf or dppf |
| N-(3-Dimethylaminopropyl)-N'-ethylcarbodiimide | ECD or EDCI |
| Ethyl Acetate | EtOAc, or EA |
| Ethanol | EtOH |
| 2-(1H-9-Azobenzotriazole-1-yl)-1,1,3,3-tetramethylaminium hexafluorophosphate | HATU |
| High-pressure liquid chromatography | HPLC |
| 1-Hydroxybenzotriazole | HOBt |
| Isopropyl alcohol | IPA or iPrOH |
| Isopropyl amine | $iPrNH_2$ |
| Methyl Iodide | MeI |
| Methanol-$d_1$ | MeOD |
| Methanol | MeOH |
| 1,1'-Bis(diphenylphosphino)ferrocene-palladium(II)dichloride | $Pd(dppf)_2Cl_2$ |
| Potassium Acetate | KOAc |
| Sodium Ethoxide | NaOEt |
| Triphenylphosphine | $Ph_3P$ |
| Tetrakis(triphenylphosphine)palladium(0) | $(Ph_3P)_4Pd$ |
| Supercritical fluid HPLC | SFC |
| Silica gel chromatography | sgc |
| Triethylamine | TEA, $Et_3N$ |
| Tetrahydrofuran | THF |
| Tetrahydropyran | THP |
| Trifluoroacetic acid | TFA |
| Thin Layer Chromatography | TLC |
| Phenyl | Ph |

Intermediate 1:
4-Phenyl-5,6,7,8-tetrahydropyrido[3,4-d]pyrimidine

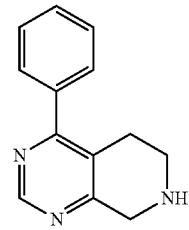

Intermediate 1, Step a: tert-Butyl 4-hydroxy-5,6-dihydropyrido[3,4-d]pyrimidine-7(8H)-carboxylate To a solution of 1-tert-butyl 4-ethyl 3-oxopiperidine-1,4-dicarboxylate (2.00 g, 7.39 mmol) in EtOH (37 mL) was added formamidine hydrochloride (910 mg, 11.08 mmol) followed by NaOEt (6.89 mL, 2.68 M in EtOH) dropwise. The mixture was then heated to reflux overnight. The mixture was concentrated in vacuo and then dissolved in a minimum amount of water. The pH was adjusted to pH 7 with 1 N HCl. The aqueous layer was then saturated with solid NaCl and extracted with a combination of EtOAc and DCM. The combined organic extracts were dried over $Na_2SO_4$, filtered and concentrated in vacuo. Chromatography on $SiO_2$ eluting with IPA/EtOAc afforded the desired product as a white solid (993 mg, 53%). MS (ESI) mass calcd. $C_{12}H_{17}N_3O_3$, 251.13; m/z found 252.1 $[M+H]^+$. $^1H$ NMR (500 MHz, $CDCl_3$): 8.05 (s, 1H), 4.42 (s, 2H), 3.69-3.61 (m, 2H), 2.63 (s, 2H), 1.49 (s, 9H).

Intermediate 1, Step b: tert-butyl 4-(((trifluoromethyl)sulfonyl)oxy)-5,6-dihydropyrido[3,4-d]pyrimidine-7(8H)-carboxylate To a solution of the product of Intermediate 1, step a (966 mg, 3.84 mmol) in DCM (19 mL) was added Et$_3$N (0.64 mL, 4.61 mmol) followed by triflic anhydride (0.72 mL, 4.23 mmol) dropwise at 0° C. The mixture was quenched with the addition of saturated aqueous NH$_4$Cl solution. The combined organic layers were dried over sodium sulfate, filtered and concentrated in vacuo. Chromatography on SiO$_2$ eluting with EtOAc/hexanes afforded the desired product as a viscous colorless oil (427 mg, 29%). MS (ESI) mass calcd. C$_{13}$H$_{16}$F$_3$N$_3$O$_5$S, 383.08; m/z found 328.0 [M+H-$^t$Bu]$^+$. $^1$H NMR (500 MHz, CDCl$_3$): 8.83 (s, 1H), 4.71 (s, 2H), 3.75 (t, J=5.7 Hz, 2H), 2.85 (t, J=5.5 Hz, 2H), 1.50 (s, 9H).

Intermediate 1, Step c: tert-butyl 4-phenyl-5,6-dihydropyrido[3,4-d]pyrimidine-7(8H)-carboxylate To a 25 mL round bottom flask was added the following reagents: phenylboronic acid (210 mg, 1.67 mmol), PdCl$_2$dppf (33 mg, 0.04 mmol), dppf (13 mg, 0.02 mmol) and K$_3$PO$_4$ (366 mg, 1.67 mmol). The product of Intermediate 1, step B (427 mg, 1.11 mmol) was dissolved in dioxane (11 mL) and added. The mixture was heated to 100° C. overnight. The mixture was concentrated in vacuo and then dissolved in toluene and filtered through Celite. The toluene was then concentrated in vacuo and chromatography on SiO$_2$ eluting EtOAc/hexane afforded the desired product as a viscous orange oil (272 mg, 78%). MS (ESI) mass calcd. C$_{18}$H$_{21}$N$_3$O$_2$, 311.16; m/z found 312.2 [M+H]$^+$. $^1$H NMR (500 MHz, CDCl$_3$): 9.08 (s, 1H), 7.63-7.58 (m, 2H), 7.53-7.46 (m, 3H), 4.72 (s, 2H), 3.62 (t, J=5.6 Hz, 2H), 2.91 (s, 2H), 1.51 (s, 9H).

Intermediate 1, step d: 4-Phenyl-5,6,7,8-tetrahydropyrido[3,4-d]pyrimidine

To the product of Intermediate 1, step c (265 mg, 0.85 mmol) in DCM (4 mL) was added TFA (0.85 mL). After stirring 3 h, the mixture was concentrated in vacuo. The residue was dissolved in DCM and treated with saturated aqueous NaHCO$_3$ solution. The aqueous layer was then extracted with DCM and EtOAc. The combined organic layers were dried over Na$_2$SO$_4$, filtered and concentrated in vacuo. Chromatography on SiO$_2$ eluting with 2 M NH$_3$ in MeOH/DCM afforded the desired product as a dark orange oil (172 mg, 96%). MS (ESI) mass calcd. C$_{13}$H$_{13}$N$_3$, 211.11; m/z found 212.1 [M+H]$^+$. $^1$H NMR (500 MHz, CDCl$_3$): 9.03 (s, 1H), 7.62-7.56 (m, 2H), 7.52-7.43 (m, 3H), 4.16 (s, 2H), 3.09 (t, J=5.7 Hz, 2H), 2.85 (t, J=5.6 Hz, 2H).

Intermediate 2: tert-Butyl 4-chloro-5,6-dihydropyrido[3,4-d]pyrimidine-7(8H)-carboxylate

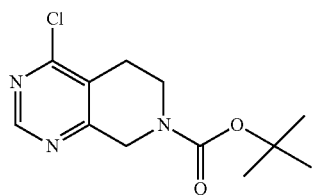 [SMILES: CC(C)(C)OC(=O)N1CCc2c(Cl)ncnc2C1]

To a solution of the product of Intermediate 1, step a (1.26 g, 5.02 mmol) in DCE (36 mL) was added PPh$_3$ (2.69 g, 10.05 mmol) followed by CCl$_4$ (1.46 mL, 15.07 mmol) and the mixture was heated to 70° C. for 2.5 h. The mixture was concentrated in vacuo and chromatographed on SiO$_2$ eluting with EtOAc/hexane to afford the desired compound as a pale yellow solid (1.20 g, 88%). MS (ESI) mass calcd. C$_{12}$H$_{16}$ClN$_3$O$_2$, 269.09; m/z found 270.1 [M+H]$^+$. $^1$H NMR (400 MHz, CDCl$_3$): 8.79 (s, 1H), 4.65 (br s, 2H), 3.80-3.68 (m, 2H), 2.93-2.82 (m, 2H), 1.49 (s, 9H).

Intermediate 3: 4-Chloro-7-{[2-chloro-3-(trifluoromethyl)phenyl]carbonyl}-5,6,7,8-tetrahydropyrido[3,4-d]pyrimidine

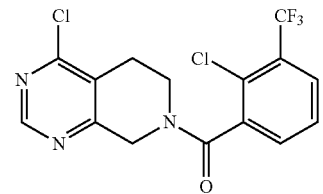 [SMILES: O=C(c1cccc(C(F)(F)F)c1Cl)N1CCc2c(Cl)ncnc2C1]

Intermediate 3, step a: 4-Chloro-5,6,7,8-tetrahydropyrido[3,4-d]pyrimidine

To Intermediate 2 (521 mg, 1.93 mmol) in DCM (10 mL) was added TFA (4 mL). After stirring 3 h, the mixture was concentrated in vacuo and the residue was redissolved in DCM, cooled to 0° C. in an ice bath and treated with saturated aqueous NaHCO$_3$ solution. After stirring for 30 min, the layers were separated and the aqueous layer extracted with 5% IPA in DCM. The combined organic layers were dried over Na$_2$SO$_4$, filtered and concentrated in vacuo to a very pale yellow solid (304, 93%). This material was used as is without further purification. MS (ESI) mass calcd. C$_7$H$_8$ClN$_3$, 169.04; m/z found 170.1 [M+H]$^+$.

Intermediate 3, step b: 4-Chloro-7-{[2-chloro-3-(trifluoromethyl)phenyl]carbonyl}-5,6,7,8-tetrahydropyrido[3,4-d]pyrimidine To a solution of the product of Intermediate 3 step a (305 mg, 1.80 mmol) in DCM (9 mL) was added 2-chloro-3-(trifluoromethyl)benzoic acid (404 mg, 1.80 mmol) followed by EDCI (517 mg, 2.70 mmol), HOBt (170 mg, 1.26 mmol) and TEA (0.50 mL, 3.60 mmol). The mixture was stirred overnight and then loaded directly on a column. Chromatography on SiO$_2$ eluting with EtOAc/hexane afforded the desired product (267 mg, 39%) and 4-(1H-benzotriazol-1-yloxy)-7-{[2-chloro-3-(trifluoromethyl)phenyl]carbonyl}-5,6,7,8-tetrahydropyrido[3,4-d]pyrimidine (203 mg, 24%) as a side product. MS (ESI) mass calcd. C$_{15}$H$_{10}$Cl$_2$F$_3$N$_3$O, 375.02; m/z found 376.0 [M+H]$^+$. $^1$H NMR (500 MHz, CDCl$_3$): 8.89-8.74 (m, 1H), 7.84-7.76 (m, 1H), 7.55-7.45 (m, 2H), 5.13-4.94 (m, 1H), 4.54-4.35 (m, 1H), 4.23-4.06 (m, 1H), 3.64-3.52 (m, 1H), 3.10-2.78 (m, 2H).

Intermediate 4: 4-(1H-Benzotriazol-1-yloxy)-7-{[2-chloro-3-(trifluoromethyl)phenyl]carbonyl}-5,6,7,8-tetrahydropyrido[3,4-d]pyrimidine

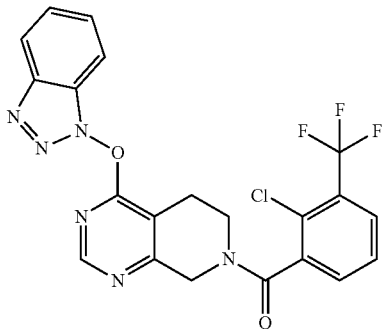 [SMILES: O=C(c1cccc(C(F)(F)F)c1Cl)N1CCc2c(ncnc2On2nnc3ccccc32)C1]

Intermediate 4 was formed as a side product during the synthesis of Intermediate 3 in step b. MS (ESI) mass calcd. $C_{21}H_{14}ClF_3N_6O_2$, 474.08; m/z found 475.1 $[M+H]^+$. $^1$H NMR (500 MHz, CDCl$_3$): 8.55-8.40 (m, 1H), 8.16-8.11 (m, 1H), 7.86-7.78 (m, 1H), 7.60-7.42 (m, 5H), 5.18-5.03 (m, 1H), 4.62-4.42 (m, 1H), 4.32-4.18 (m, 1H), 3.75-3.62 (m, 1H), 3.30-3.01 (m, 2H).

Intermediate 5: 4-Chloro-7-[(2,4-dichlorophenyl)carbonyl]-5,6,7,8-tetrahydropyrido[3,4-d]pyrimidine

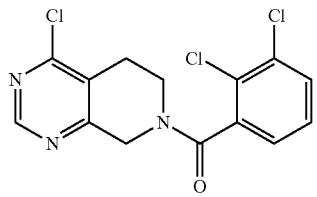 [SMILES: O=C(c1cccc(Cl)c1Cl)N1CCc2c(Cl)ncnc2C1]

Intermediate 5, step a:
4-Chloro-5,6,7,8-tetrahydropyrido[3,4-d]pyrimidine

To Intermediate 2 (1.23 g, 4.54 mmol) in DCM (23 mL) was added TFA (9 mL). After stirring 3 h, the mixture was concentrated in vacuo and used without further purification. MS (ESI) mass calcd. $C_7H_8ClN_3$, 169.04; m/z found 170.1 $[M+H]^+$.

Intermediate 5, step b: 4-Chloro-7-[(2,4-dichlorophenyl)carbonyl]-5,6,7,8-tetrahydropyrido[3,4-d]pyrimidine To a heterogeneous mixture of 2,3-dichlorobenzoic acid (894 mg, 4.68 mmol) in DCM (23 mL) was added 2 M oxalyl chloride in DCM (2.73 mL) followed by 3 drops of DMF. Gentle bubbling proceeded and after bubbling was complete, the mixture was concentrated in vacuo and then recharged with fresh DCM (12 mL). Then the product of Intermediate 5, step a (771 mg, 4.54 mmol) was added as a solution in DCM (12 mL) followed by Et$_3$N (2.97 mL, 21.36 mmol) at 0° C. The reaction was allowed to warm to room temperature over several hours and then was partially concentrated in vacuo and filter loaded on SiO$_2$ eluting with EtOAc/hexane to afford the title compound (585 mg, 38%) MS (ESI) mass calcd. $C_{14}H_{10}Cl_3N_3O$, 340.99; m/z found 342.0 $[M+H]^+$ and 1-(4-chloro-5,6-dihydropyrido[3,4-d]pyrimidin-7(8H)-yl)-2,2,2-trifluoroethanone as a side product (262 mg, 22%).

Intermediate 6: 1-(4-Chloro-5,6-dihydropyrido[3,4-d]pyrimidin-7(8H)-yl)-2,2,2-trifluoroethanone

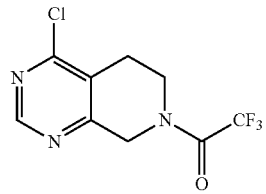 [SMILES: O=C(N1CCc2c(Cl)ncnc2C1)C(F)(F)F]

Intermediate 6 was formed as a side product during the synthesis of Intermediate 4 in step b. MS (ESI) mass calcd. $C_9H_7ClF_3N_3O$, 265.02; m/z found 266.0 $[M+H]^+$.

Example 1

7-{[2-Chloro-3-(trifluoromethyl)phenyl]carbonyl}-4-phenyl-5,6,7,8-tetrahydropyrido[3,4-d]pyrimidine

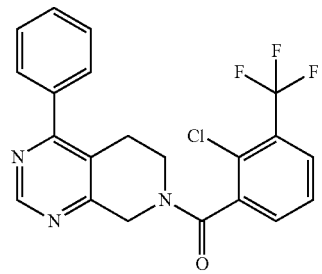 [SMILES: O=C(c1cccc(C(F)(F)F)c1Cl)N1CCc2c(ncnc2-c2ccccc2)C1]

To a solution of Intermediate 1 (55 mg, 0.26 mmol) in DCM (3 mL) was added 2-chloro-3-(trifluoromethyl)benzoic acid (60 mg, 0.26 mmol) followed by EDCI (75 mg, 0.39 mmol), HOBt (28 mg, 0.21 mmol) and TEA (0.72 mL, 0.52 mmol). The mixture was stirred overnight and then loaded directly on a column. Chromatography on SiO$_2$ eluting with EtOAc/hexane afforded the desired product as a colorless foam (80 mg, 73%). MS (ESI) mass calcd. $C_{21}H_{15}ClF_3N_3O$, 417.09; m/z found 418.2 $[M+H]^+$. $^1$H NMR (500 MHz, CDCl$_3$): 9.16-9.03 (m, 1H), 7.82-7.77 (m, 1H), 7.65-7.46 (m, 7H), 5.16-5.02 (m, 1H), 4.61-4.42 (m, 1H), 4.09-3.97 (m, 1H), 3.52-3.38 (m, 1H), 3.11-2.83 (m, 2H).

Example 2

7-[(2,3-Dichlorophenyl)carbonyl]-4-phenyl-5,6,7,8-tetrahydropyrido[3,4-d]pyrimidine

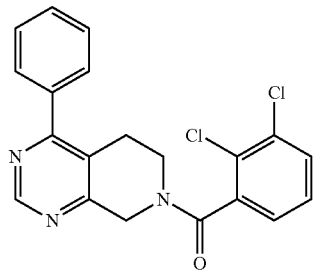 [SMILES: O=C(c1cccc(Cl)c1Cl)N1CCc2c(ncnc2-c2ccccc2)C1]

The title compound was prepared in a manner analogous to Example 1 substituting 2,3-dichlorobenzoic acid for 2-chloro-3-(trifluoromethyl)benzoic acid. MS (ESI) mass calcd. $C_{20}H_{15}Cl_2N_3O$, 383.06; m/z found 384.1 [M+H]$^+$. $^1$H NMR (500 MHz, CDCl$_3$): 9.16-9.02 (m, 1H), 7.65-7.46 (m, 6H), 7.34-7.29 (m, 1H), 7.28-7.26 (m, 1H), 5.07 (s, 1H), 4.61-4.43 (m, 1H), 4.03-3.98 (m, 1H), 3.52-3.38 (m, 1H), 3.13-2.82 (m, 2H).

Example 3

4-(2,6-dimethyl-4-(1H-pyrazol-5-yl)-5,6,7,8-tetrahydropyrido[3,4-d]pyrimidine-7-carbonyl)-3-methylbenzonitrile

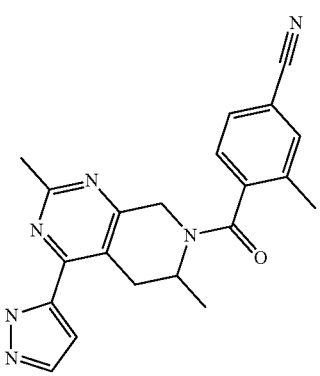 [SMILES: Cc1nc2c(c(-c3ccn[nH]3)n1)CC(C)N(C(=O)c1ccc(C#N)cc1C)C2]

The title compound was prepared in a manner analogous to Example 74 substituting 4-cyano-2-methylbenzoic acid for 2-fluoro-3-(trifluoromethyl)benzoic acid in the synthesis of Intermediate 44. MS (ESI) mass calcd. $C_{21}H_{20}N_6O$, 372.2; m/z found 373.2 [M+H]$^+$. $^1$H NMR (500 MHz, CDCl$_3$) δ 11.65-10.82 (s, 1H), 7.83-7.29 (m, 4H), 7.04-6.73 (m, 1H), 5.88-5.27 (m, 1H), 4.81-3.91 (m, 2H), 3.61-2.95 (m, 2H), 2.90-2.06 (m, 6H), 1.42-1.08 (m, 3H).

Example 4

7-[(2,3-Dichlorophenyl)carbonyl]-4-(1H-pyrazol-4-yl)-5,6,7,8-tetrahydropyrido[3,4-d]pyrimidine

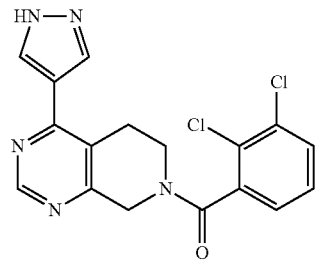 [SMILES: O=C(c1cccc(Cl)c1Cl)N1CCc2c(ncnc2-c2cn[nH]c2)C1]

Example 4, Step a: tert-butyl 4-(1H-pyrazol-4-yl)-5,6-dihydropyrido[3,4-d]pyrimidine-7(8H)-carboxylate To a microwave vial was added Intermediate 2 (113 mg, 0.42 mmol) and 4-(4,4,5,5-tetramethyl-1,3,2-dioxaborolan-2-yl)-1H-pyrazole (138 mg, 0.71 mmol) followed by dioxane (4 mL) and 2M Na$_2$CO$_3$ (0.52 mL). To this mixture was added Pd(PPh$_3$)$_4$ (24 mg, 0.02 mmol) and the reaction heated in the microwave for 1 h at 150° C. The reaction was diluted with water and extracted with DCM and EtOAc. The combined organic extracts were dried over Na$_2$SO$_4$, filtered and concentrated in vacuo. Chromatography on SiO$_2$ eluting with EtOAc/hexane afforded the desired product as a slowly crystallizing white solid (97 mg, 77%). MS (ESI) mass calcd. $C_{15}H_{19}N_5O_2$, 301.15; m/z found 302.1 [M+H]$^+$. $^1$H NMR (500 MHz, CDCl$_3$): 8.96 (s, 1H), 8.21 (s, 2H), 4.68 (s, 2H), 3.82-3.70 (m, 2H), 3.07-2.93 (m, 2H), 1.51 (s, 9H).

Example 4, step b: 4-(1H-pyrazol-4-yl)-5,6,7,8-tetrahydropyrido[3,4-d]pyrimidine To the product of Example 4, step a (81 mg, 0.27 mmol) in DCM (3 mL) was added TFA (0.27 mL). After stirring 3 h the mixture was concentrated in vacuo and loaded directly on a column. Chromatography on SiO$_2$ eluting with 2 M NH$_3$ in MeOH/DCM afforded the desired product as a white solid (22 mg, 41%). MS (ESI) mass calcd. 201.10; m/z found 202.0 [M+H]$^+$.

Example 4, step c: 7-[(2,3-Dichlorophenyl)carbonyl]-4-(1H-pyrazol-4-yl)-5,6,7,8-tetrahydropyrido[3,4-d]pyrimidine The title compound was prepared in a manner analogous to Example 1 substituting the product of Example 4, step b for Intermediate 1 and 2,3-dichlorobenzoic acid for 2-chloro-3-(trifluoromethyl)benzoic acid. MS (ESI) mass calcd. $C_{17}H_{13}Cl_2N_5O$, 373.05; m/z found 373.9 [M+H]$^+$. $^1$H NMR (500 MHz, CDCl$_3$): 9.04-8.88 (m, 1H), 8.27-8.13 (m, 2H), 7.59-7.51 (m, 1H), 7.38-7.27 (m, 2H), 5.09-4.99 (m, 1H), 4.58-4.39 (m, 1H), 4.19-4.09 (m, 1H), 3.66-3.52 (m, 1H), 3.21-2.89 (m, 2H).

Example 5

7-[(2,3-Dichlorophenyl)carbonyl]-4-(1-methyl-1H-pyrazol-4-yl)-5,6,7,8-tetrahydropyrido[3,4-d]pyrimidine

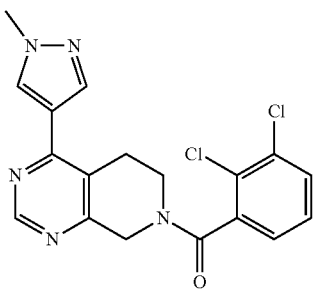 [SMILES: Cn1cc(-c2ncnc3c2CCN(C(=O)c2cccc(Cl)c2Cl)C3)cn1]

The title compound was prepared in a manner analogous to Example 4 substituting 1-methyl-4-(4,4,5,5-tetramethyl-1,3,2-dioxaborolan-2-yl)-1H-pyrazole for 4-(4,4,5,5-tetramethyl-1,3,2-dioxaborolan-2-yl)-1H-pyrazole in Example 4, step a. MS (ESI) mass calcd. $C_{18}H_{15}C_{12}N_5O$, 387.07; m/z found 387.9 [M+H]$^+$. $^1$H NMR (600 MHz, CDCl$_3$): 8.99-8.84 (m, 1H), 8.07-7.94 (m, 2H), 7.58-7.50 (m, 1H), 7.36-7.27 (m, 1H), 7.24-7.21 (m, 1H), 5.06-4.96 (m, 1H), 4.54-4.37 (m, 1H), 4.16-4.09 (m, 1H), 4.02-3.96 (m, 3H), 3.64-3.51 (m, 1H), 3.16-2.86 (m, 2H).

Example 6

7-[(2-Chloro-3-methylphenyl)carbonyl]-4-(1-methyl-1H-pyrazol-4-yl)-5,6,7,8-tetrahydropyrido[3,4-d]pyrimidine

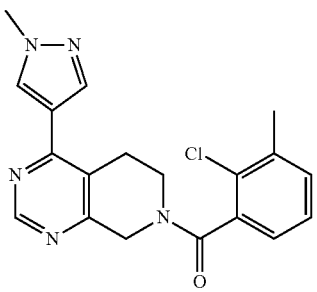 [SMILES: Cc1cccc(C(=O)N2CCc3c(ncnc3-c3cnn(C)c3)C2)c1Cl]

The title compound was prepared in a manner analogous to Example 4 substituting 1-methyl-4-(4,4,5,5-tetramethyl-1,3,2-dioxaborolan-2-yl)-1H-pyrazole for 4-(4,4,5,5-tetramethyl-1,3,2-dioxaborolan-2-yl)-1H-pyrazole in Example 4, step a and 2-chloro-3-methylbenzoic acid for 2,3-dichlorobenzoic acid in Example 4, step c. MS (ESI) mass calcd. $C_{19}H_{18}ClN_5O$, 367.12; m/z found 367.9 [M+H]$^+$. $^1$H NMR (500 MHz, CDCl$_3$): 9.00-8.84 (m, 1H), 8.09-7.93 (m, 2H), 7.35-7.27 (m, 1H), 7.25-7.13 (m, 2H), 5.10-4.95 (m, 1H), 4.58-4.38 (m, 1H), 4.19-4.07 (m, 1H), 4.04-3.96 (m, 3H), 3.65-3.53 (m, 1H), 3.18-2.85 (m, 2H), 2.48-2.37 (m, 3H).

Example 7

7-[(2,3-Dichlorophenyl)carbonyl]-4-(1H-pyrazol-5-yl)-5,6,7,8-tetrahydropyrido[3,4-d]pyrimidine

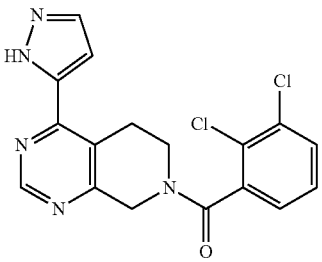 [SMILES: O=C(c1cccc(Cl)c1Cl)N1CCc2c(ncnc2-c2ccn[nH]2)C1]

Method I

Example 7, Step I-a: tert-Butyl 4-[1-(tetrahydro-2H-pyran-2-yl)-1H-pyrazol-5-yl]-5,8-dihydropyrido[3,4-d]pyrimidine-7(6H)-carboxylate The title compound was prepared in a manner analogous to Example 4, step a, substituting 1-(tetrahydropyran-2-yl)-1H-pyrazole-5-boronic acid pinacol ester for 4-(4,4,5,5-tetramethyl-1,3,2-dioxaborolan-2-yl)-1H-pyrazole. MS (ESI) mass calcd. $C_{20}H_{27}N_5O_3$, 385.21; m/z found 386.0 [M+H]$^+$. $^1$H NMR (500 MHz, CDCl$_3$): 9.10 (s, 1H), 7.66 (d, J=1.8 Hz, 1H), 6.52 (d, J=1.8 Hz, 1H), 5.88-5.79 (m, 1H), 5.30 (s, 1H), 4.93-4.81 (m, 1H), 4.61-4.53 (m, 1H), 4.04-3.86 (m, 2H), 3.48-3.29 (m, 2H), 2.96-2.77 (m, 2H), 2.53-2.42 (m, 1H), 2.14-2.06 (m, 2H), 1.73-1.61 (m, 2H), 1.51 (s, 9H).

Example 7, step I-b: 4-(1H-pyrazol-5-yl)-5,6,7,8-tetrahydropyrido[3,4-d]pyrimidine To the product of Example 7, step I-a (191 mg, 0.50 mmol) in DCM (2 mL) was added 4 M HCl in dioxane (1.24 mL). After 2 h the reaction was complete and concentrated in vacuo to a red solid. This material was used without further purification. MS (ESI) mass calcd. $C_{10}H_{11}N_5$, 201.10; m/z found 202.1 [M+H]$^+$.

Example 7, step I-c: 7-[(2,3-Dichlorophenyl)carbonyl]-4-(1H-pyrazol-5-yl)-5,6,7,8-tetrahydropyrido[3,4-d]pyrimidine To a solution of the product of Example 7, step I-b (41 mg, 0.17 mmol) in DCM (2 mL) was added 2,3-dichlorobenzoic acid (33 mg, 0.17 mmol) followed by EDCI (33 mg, 0.17 mmol), HOBt (16 mg, 0.12 mmol) and TEA (0.60 mL, 0.44 mmol). The mixture was stirred overnight and then loaded directly on a Prep Agilent system with a XBridge C18 OBD 50×100 mm column eluting with 5 to 99% 0.05% NH$_4$OH in H$_2$O/ACN over 17 min to afford the desired product as a colorless solid (8 mg, 12%). MS (ESI) mass calcd. $C_{17}H_{13}Cl_2N_5O$, 373.05; m/z found 374.1 [M+H]$^+$. $^1$H NMR (600 MHz, CDCl$_3$): 11.19 (br s, 1H), 9.10-8.93 (m, 1H), 7.75-7.68 (m, 1H), 7.58-7.51 (m, 1H), 7.36-7.22 (m, 2H), 7.00-6.93 (m, 1H), 5.16-4.99 (m, 1H), 4.60-4.42 (m, 1H), 4.18-4.11 (m, 1H), 3.64-3.50 (m, 1H), 3.39-3.09 (m, 2H).

Method II

Example 7, Step II-a: 7-[(2,3-dichlorophenyl)carbonyl]-4-[1-(tetrahydro-2H-pyran-2-yl)-1H-pyrazol-5-yl]-5,6,7,8-tetrahydropyrido[3,4-d]pyrimidine The title compound was prepared in a manner analogous to Example 4, step a, substituting Intermediate 5 for Intermediate 2 and 1-(tetrahydropyran-2-yl)-1H-pyrazole-5-boronic acid pinacol ester for 4-(4,4,5,5-tetramethyl-1,3,2-dioxaborolan-2-yl)-1H-pyrazole. MS (ESI) mass calcd. $C_{22}H_{21}Cl_2N_5O_2$, 457.11; m/z found 458.1 [M+H]+.

Example 7, step II-b: 7-[(2,3-Dichlorophenyl)carbonyl]-4-(1H-pyrazol-5-yl)-5,6,7,8-tetrahydropyrido[3,4-d]pyrimidine To a solution of the product of, Example 7, step I-a (749 mg, 1.63 mmol) in MeOH (8 mL) was added 6 M HCl (1.09 mL). The mixture was aged for 3 h and then neutralized with solid NaOH (74 mg, 1.84 mmol) dissolved in a minimum amount of water. The mixture was then concentrated in vacuo. The material was dissolved in DCM and stirred overnight. Filtration removed the inorganic solids and the filtrate was concentrated in vacuo. Chromatography on a Prep Agilent system with a XBridge C18 OBD 50×100 mm column eluting with 5 to 99% 0.05% $NH_4OH$ in $H_2O$/ACN over 17 min afforded the desired product as a colorless solid (301 mg, 49%). MS (ESI) mass calcd. $C_{17}H_{13}Cl_2N_5O$, 373.05; m/z found 374.1 [M+H]+. 1H NMR (500 MHz, $CDCl_3$): 9.10-8.93 (m, 1H), 7.76-7.67 (m, 1H), 7.58-7.51 (m, 1H), 7.36-7.21 (m, 2H), 7.07-6.83 (m, 1H), 5.15-4.98 (m, 1H), 4.61-4.42 (m, 1H), 4.19-4.12 (m, 1H), 3.65-3.52 (m, 1H), 3.44-3.06 (m, 2H).

Example 8

7-[(2-Chloro-3-methylphenyl)carbonyl]-4-(1H-pyrazol-5-yl)-5,6,7,8-tetrahydropyrido[3,4-d]pyrimidine

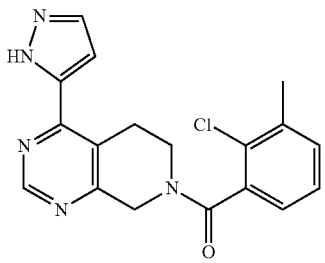 [SMILES: Cc1cccc(C(=O)N2CCc3c(ncnc3-c3ccn[nH]3)C2)c1Cl]

The title compound was prepared in a manner analogous to Example 7-Method I substituting 2-chloro-3-methylbenzoic acid for 2,3-dichlorobenzoic acid in Example 7, step I-c. MS (ESI) mass calcd. $C_{18}H_{16}ClN_5O$, 353.10; m/z found 354.1 [M+H]+. 1H NMR (500 MHz, $CDCl_3$): 9.11-8.92 (m, 1H), 7.78-7.66 (m, 1H), 7.35-7.13 (m, 3H), 6.99-6.89 (m, 1H), 5.17-4.98 (m, 1H), 4.62-4.42 (m, 1H), 4.21-4.08 (m, 1H), 3.66-3.50 (m, 1H), 3.42-3.05 (m, 2H), 2.47-2.38 (m, 3H).

Example 9

7-[(2,3-Dimethylphenyl)carbonyl]-4-(1H-pyrazol-5-yl)-5,6,7,8-tetrahydropyrido[3,4-d]pyrimidine

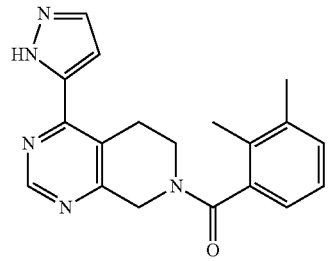 [SMILES: Cc1cccc(C(=O)N2CCc3c(ncnc3-c3ccn[nH]3)C2)c1C]

The title compound was prepared in a manner analogous to Example 7-Method I substituting 2,3-dimethylbenzoic acid for 2,3-dichlorobenzoic acid in Example 7, step I-c. MS (ESI) mass calcd. $C_{19}H_{19}N_5O$, 333.16; m/z found 334.2 [M+H]+. 1H NMR (500 MHz, $CDCl_3$): 9.10-8.90 (m, 1H), 7.74-7.65 (m, 1H), 7.25-6.90 (m, 4H), 5.28-4.88 (m, 1H), 4.55-4.44 (m, 1H), 4.31-4.01 (m, 1H), 3.67-3.49 (m, 1H), 3.35 (s, 1H), 3.14-3.04 (m, 1H), 2.35-2.11 (m, 6H).

Example 10

7-{[2-Methyl-3-(trifluoromethyl)phenyl]carbonyl}-4-(1H-pyrazol-5-yl)-5,6,7,8-tetrahydropyrido[3,4-d]pyrimidine

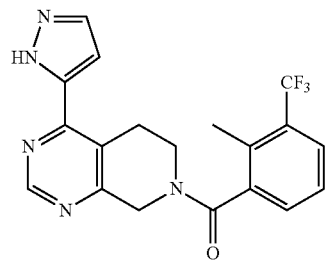 [SMILES: Cc1c(C(=O)N2CCc3c(ncnc3-c3ccn[nH]3)C2)cccc1C(F)(F)F]

The title compound was prepared in a manner analogous to Example 7-Method I substituting 2-methyl-3-(trifluoromethyl)benzoic acid for 2,3-dichlorobenzoic acid in Example 7, step I-c. MS (ESI) mass calcd. $C_{19}H_{16}F_3N_5O$, 387.13; m/z found 388.2 [M+H]+. 1H NMR (600 MHz, $CDCl_3$): 9.10-8.93 (m, 1H), 7.75-7.67 (m, 2H), 7.45-7.34 (m, 2H), 7.01-6.93 (m, 1H), 5.28-4.88 (m, 1H), 4.52-4.39 (m, 1H), 4.27-4.05 (m, 1H), 3.63-3.47 (m, 1H), 3.41-3.28 (m, 1H), 3.17-3.11 (m, 1H), 2.49-2.35 (m, 3H).

Example 11

7-[(2,3-Dichlorophenyl)carbonyl]-4-pyridin-2-yl-5,6,7,8-tetrahydropyrido[3,4-d]pyrimidine

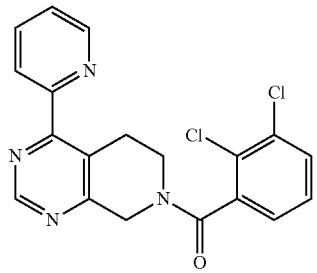 [SMILES: O=C(c1cccc(Cl)c1Cl)N1CCc2c(ncnc2-c2ccccn2)C1]

Example 11, Step a: tert-Butyl 4-(pyridin-2-yl)-5,6-dihydropyrido[3,4-d]pyrimidine-7(8H)-carboxylate To a microwave vial was added Intermediate 2 (136 mg, 0.50 mmol) and Pd(Ph$_3$)$_4$ (29 mg, 0.03 mmol). To these solid reagents were quickly added degassed dioxane (3 mL) and 2-tri-n-butylstannylpyridine (327 mg, 0.75 mmol). The microwave tube was sealed and the reaction heated at 140° C. for 90 min. The mixture was diluted with saturated aqueous KF and stirred for 30 min. EtOAc was added and the layers separated. The combined organic layers were dried over Na$_2$SO$_4$, filtered and concentrated in vacuo. Chromatography on SiO$_2$ eluting with EtOAc/hexane afforded the desired product (157 mg, 99%). MS (ESI) mass calcd. C$_{17}$H$_{20}$N$_4$O$_2$, 312.16; m/z found 313.2 [M+H]$^+$.

Example 11, Step b: 4-Pyridin-2-yl-5,6,7,8-tetrahydropyrido[3,4-d]pyrimidine To the product of Example 11, step a (157 mg, 0.50 mmol) in DCM (3 mL) was added TFA (1.00 mL). After stirring for 3 h, the mixture was concentrated in vacuo and loaded directly on a Prep Agilent system with a XBridge C18 OBD 50×100 mm column eluting with 5 to 99% 0.05% NH$_4$OH in H$_2$O/ACN over 17 min to afford the desired product as a tan solid (89 mg, 83%). MS (ESI) mass calcd. C$_{12}$H$_{12}$N$_4$, 212.11; m/z found 213.2 [M+H]$^+$. $^1$H NMR (400 MHz, CDCl$_3$): 9.05 (s, 1H), 8.71 (s, 1H), 8.06-7.94 (m, 1H), 7.93-7.81 (m, 1H), 7.45-7.32 (m, 1H), 4.17 (s, 2H), 3.16 (s, 4H).

Example 11, step c: 7-[(2,3-Dichlorophenyl)carbonyl]-4-pyridin-2-yl-5,6,7,8-tetrahydropyrido[3,4-d]pyrimidine The title compound was prepared in a manner analogous to Example 7, step 1-c (26 mg, 48%). MS (ESI) mass calcd. C$_{19}$H$_{14}$Cl$_2$N$_4$O, 384.05; m/z found 385.1 [M+H]$^+$. $^1$H NMR (500 MHz, CDCl$_3$): 9.19-9.01 (m, 1H), 8.77-8.62 (m, 1H), 8.17-8.06 (m, 1H), 7.93-7.84 (m, 1H), 7.57-7.50 (m, 1H), 7.44-7.36 (m, 1H), 7.34-7.22 (m, 2H), 5.23-4.95 (m, 1H), 4.63-4.44 (m, 1H), 4.15-3.94 (m, 1H), 3.53-3.27 (m, 3H).

Example 12

7-{[2-Chloro-3-(trifluoromethyl)phenyl]carbonyl}-4-pyridin-2-yl-5,6,7,8-tetrahydropyrido[3,4-d]pyrimidine

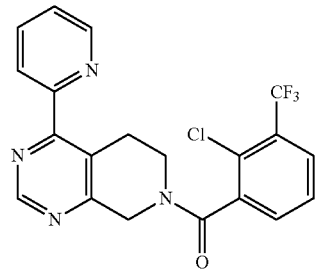 [SMILES: O=C(c1cccc(C(F)(F)F)c1Cl)N1CCc2c(ncnc2-c2ccccn2)C1]

The title compound was prepared in a manner analogous to Example 11 substituting 2-chloro-3-(trifluoromethyl)benzoic acid for 2,3-dichlorobenzoic acid in Example 11, step c. MS (ESI) mass calcd. C$_{20}$H$_{14}$ClF$_3$N$_4$O, 418.08; m/z found 419.1 [M+H]$^+$. $^1$H NMR (500 MHz, CDCl$_3$): 9.18-9.02 (m, 1H), 8.76-8.63 (m, 1H), 8.17-8.08 (m, 1H), 7.92-7.86 (m, 1H), 7.81-7.77 (m, 1H), 7.58-7.36 (m, 3H), 5.26-4.94 (m, 1H), 4.63-4.44 (m, 1H), 4.21-3.91 (m, 1H), 3.53-3.27 (m, 3H).

Example 13

7-[(2-Chloro-3-methylphenyl)carbonyl]-4-pyridin-2-yl-5,6,7,8-tetrahydropyrido[3,4-d]pyrimidine

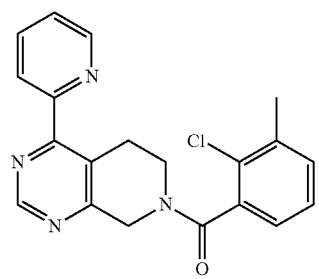 [SMILES: Cc1cccc(C(=O)N2CCc3c(ncnc3-c3ccccn3)C2)c1Cl]

The title compound was prepared in a manner analogous to Example 11 substituting 2-chloro-3-methylbenzoic acid for 2,3-dichlorobenzoic acid in Example 11, step c. MS (ESI) mass calcd. C$_{20}$H$_{17}$ClN$_4$O, 364.11; m/z found 365.1 [M+H]$^+$. $^1$H NMR (500 MHz, CDCl$_3$): 9.16-9.02 (m, 1H), 8.75-8.64 (m, 1H), 8.13-8.06 (m, 1H), 7.91-7.85 (m, 1H), 7.43-7.35 (m, 1H), 7.32-7.14 (m, 3H), 5.24-4.95 (m, 1H), 4.64-4.46 (m, 1H), 4.13-3.96 (m, 1H), 3.52-3.35 (m, 2H), 3.30-3.25 (m, 1H), 2.46-2.39 (m, 3H).

Example 14

7-[(2,3-Dichlorophenyl)carbonyl]-4-pyrazin-2-yl-5,6,7,8-tetrahydropyrido[3,4-d]pyrimidine

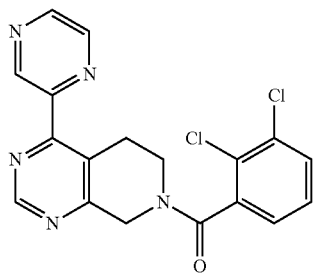 [SMILES: O=C(c1cccc(Cl)c1Cl)N1CCc2c(ncnc2-c2cnccn2)C1]

The title compound was prepared in a manner analogous to Example 11 substituting 2-tributylstannylpyrazine for 2-tri-n-butylstannylpyridine in Example 11, step a. MS (ESI) mass calcd. $C_{18}H_{13}Cl_2N_5O$, 385.05; m/z found 386.1 [M+H]$^+$. $^1$H NMR (500 MHz, CDCl$_3$): 9.48-9.42 (m, 1H), 9.21-9.06 (m, 1H), 8.71-8.60 (m, 2H), 7.56-7.52 (m, 1H), 7.35-7.22 (m, 2H), 5.19-5.01 (m, 1H), 4.64-4.46 (m, 1H), 4.09-4.04 (m, 1H), 3.57-3.43 (m, 2H), 3.37-3.23 (m, 1H).

Example 15

7-{[2-Methyl-3-(trifluoromethyl)phenyl]carbonyl}-4-pyrazin-2-yl-5,6,7,8-tetrahydropyrido[3,4-d]pyrimidine

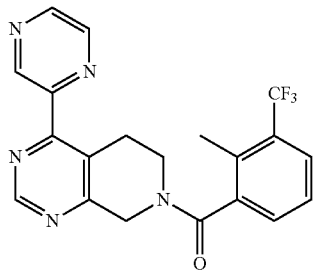 [SMILES: Cc1c(C(=O)N2CCc3c(ncnc3-c3cnccn3)C2)cccc1C(F)(F)F]

The title compound was prepared in a manner analogous to Example 11 substituting 2-tributylstannylpyrazine for 2-tri-n-butylstannylpyridine in Example 11, step a and 2-methyl-3-(trifluoromethyl)benzoic acid for 2,3-dichlorobenzoic acid in Example 11, step c. MS (ESI) mass calcd. $C_{20}H_{16}F_3N_5O$, 399.13; m/z found 400.1 [M+H]$^+$. $^1$H NMR (600 MHz, CDCl$_3$): 9.48-9.43 (m, 1H), 9.21-9.06 (m, 1H), 8.72-8.59 (m, 2H), 7.73-7.68 (m, 1H), 7.45-7.35 (m, 2H), 5.29-4.96 (m, 1H), 4.55-4.45 (m, 1H), 4.18-3.99 (m, 1H), 3.55-3.42 (m, 2H), 3.32-3.17 (m, 1H), 2.49-2.38 (m, 3H).

Example 16

7-[(2-Chloro-4,5-difluorophenyl)carbonyl]-4-pyrazin-2-yl-5,6,7,8-tetrahydropyrido[3,4-d]pyrimidine

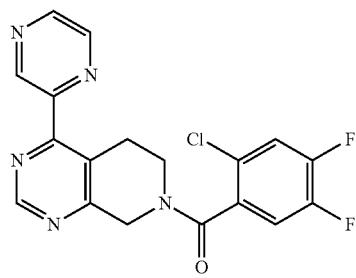 [SMILES: O=C(c1cc(F)c(F)cc1Cl)N1CCc2c(ncnc2-c2cnccn2)C1]

The title compound was prepared in a manner analogous to Example 11 substituting 2-tributylstannylpyrazine for 2-tri-n-butylstannylpyridine in Example 11, step a and 2-chloro-4,5-difluorobenzoic acid for 2,3-dichlorobenzoic acid in Example 11, step c. MS (ESI) mass calcd. $C_{18}H_{12}ClF_2N_5O$, 387.07; m/z found 388.1 [M+H]$^+$. $^1$H NMR (500 MHz, CDCl$_3$): 9.49-9.42 (m, 1H), 9.22-9.07 (m, 1H), 8.72-8.59 (m, 2H), 7.34-7.27 (m, 1H), 7.25-7.19 (m, 1H), 5.22-4.94 (m, 1H), 4.67-4.46 (m, 1H), 4.08-4.01 (m, 1H), 3.57-3.51 (m, 1H), 3.47-3.42 (m, 1H), 3.39-3.24 (m, 1H).

Example 17

7-{[2-Chloro-3-(trifluoromethyl)phenyl]carbonyl}-4-[1-(tetrahydro-2H-pyran-2-yl)-1H-pyrazol-5-yl]-5,6,7,8-tetrahydropyrido[3,4-d]pyrimidine

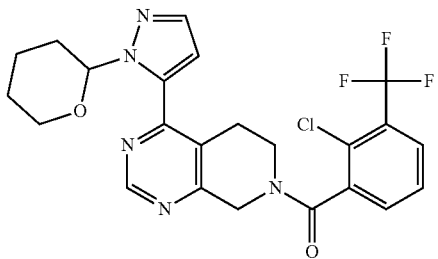 [SMILES: O=C(c1cccc(C(F)(F)F)c1Cl)N1CCc2c(ncnc2-c2ccnn2C2CCCCO2)C1]

The title compound was prepared in a manner analogous to Example 4, step a, substituting Intermediate 3 for Intermediate 2 and 1-(tetrahydropyran-2-yl)-1H-pyrazole-5-boronic acid pinacol ester for 4-(4,4,5,5-tetramethyl-1,3,2-dioxaborolan-2-yl)-1H-pyrazole. MS (ESI) mass calcd. $C_{23}H_{21}ClF_3N_5O_2$, 491.13; m/z found 492.1 [M+H]$^+$ 1H NMR (500 MHz, CDCl$_3$): 9.19-9.03 (m, 1H), 7.82-7.77 (m, 1H), 7.71-7.61 (m, 1H), 7.57-7.46 (m, 2H), 6.59-6.45 (m, 1H), 5.92-5.79 (m, 1H), 5.37-4.82 (m, 1H), 4.65-4.42 (m, 2H), 3.92-3.83 (m, 1H), 3.68-3.32 (m, 2H), 3.14-2.75 (m, 2H), 2.53-2.40 (m, 1H), 2.16-2.05 (m, 2H), 1.73-1.58 (m, 2H), 1.54-1.49 (m, 1H).

Example 18

(4-(1H-pyrazol-5-yl)-5,6-dihydropyrido[3,4-d]pyrimidin-7(8H)-yl)(2-chloro-3-(trifluoromethyl)phenyl)methanone

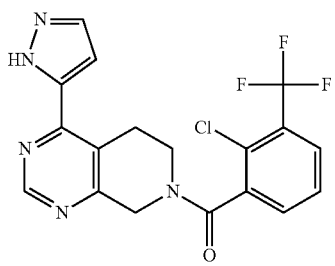 [SMILES: O=C(c1cccc(C(F)(F)F)c1Cl)N1CCc2c(ncnc2-c2ccn[nH]2)C1]

To a solution of Example 17 (224 mg, 0.46 mmol) in MeOH (2 mL) was added 6 M HCl (0.30 mL). The mixture was aged for 3 h and then neutralized with solid NaOH (74 mg, 1.84 mmol) dissolved in a minimum amount of water. The mixture was then concentrated in vacuo. The material was dissolved in DCM and stirred overnight. Filtration removed the inorganic solids and the filtrate was concentrated in vacuo. Chromatography on $SiO_2$ EtOAc/hexane afforded the desired compound as a colorless foam (151 mg, 81%). MS (ESI) mass calcd. $C_{18}H_{13}ClF_3N_5O$, 407.08; m/z found 408.1 $[M+H]^+$. $^1H$ NMR (500 MHz, $CDCl_3$): 9.10-8.95 (m, 1H), 7.83-7.77 (m, 1H), 7.76-7.69 (m, 1H), 7.58-7.45 (m, 2H), 7.05-6.89 (m, 1H), 5.18-4.98 (m, 1H), 4.60-4.41 (m, 1H), 4.25-4.04 (m, 1H), 3.64-3.51 (m, 1H), 3.43-3.09 (m, 2H).

Example 19

7-{[2-Chloro-3-(trifluoromethyl)phenyl]carbonyl}-4-(1-methyl-1H-pyrazol-3-yl)-5,6,7,8-tetrahydropyrido[3,4-d]pyrimidine

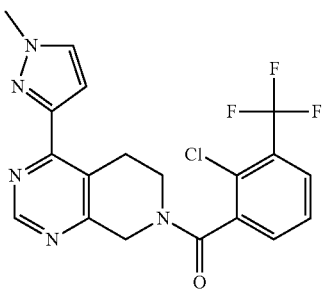 [SMILES: Cn1ccc(-c2ncnc3c2CCN(C(=O)c2cccc(C(F)(F)F)c2Cl)C3)n1]

To a solution of Example 18 (137 mg, 0.33 mmol) in DMF (3 mL) was added NaH, 60% dispersion in mineral oil (16 mg, 0.40 mmol). After 30 minutes MeI (0.03 mL, 0.40 mmol) was then added. After several hours the reaction was diluted with water and then extracted with EtOAc. The combined organic layers were washed with water, dried over $Na_2SO_4$, filtered and concentrated in vacuo. Purification on a Prep Agilent system with a XBridge C18 OBD 50×100 mm column eluting with 5 to 99% 0.05% $NH_4OH$ in $H_2O$/ACN over 17 min to afforded the title compound as a white solid (61.2 mg, 43%). MS (ESI) mass calcd. $C_{19}H_{15}ClF_3N_5O$, 421.09; m/z found 422.1 $[M+H]^+$. $^1H$ NMR (500 MHz, $CDCl_3$): 9.09-8.92 (m, 1H), 7.82-7.75 (m, 1H), 7.58-7.42 (m, 3H), 7.06-7.01 (m, 1H), 5.19-4.92 (m, 1H), 4.58-4.38 (m, 1H), 4.22-3.94 (m, 4H), 3.57-3.22 (m, 3H).

Example 20

7-[(2,4-Dichloro-3-fluorophenyl)carbonyl]-4-(1H-pyrazol-5-yl)-5,6,7,8-tetrahydropyrido[3,4-d]pyrimidine

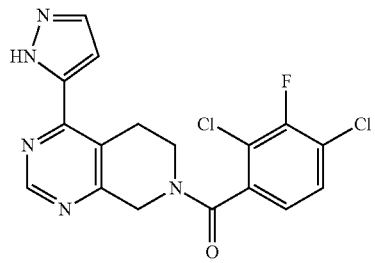 [SMILES: O=C(c1ccc(Cl)c(F)c1Cl)N1CCc2c(ncnc2-c2ccn[nH]2)C1]

Example 20, Step a: 4-(1-(Tetrahydro-2H-pyran-2-yl)-1H-pyrazol-5-yl)-5,6,7,8-tetrahydropyrido[3,4-d]pyrimidine The title compound was prepared in a manner analogous to Example 4, step a, substituting Intermediate 6 for Intermediate 2 and 1-(tetrahydropyran-2-yl)-1H-pyrazole-5-boronic acid pinacol ester for 4-(4,4,5,5-tetramethyl-1,3,2-dioxaborolan-2-yl)-1H-pyrazole. MS (ESI) mass calcd. $C_{15}H_{19}N_5O$, 285.156; m/z found 286.2 $[M+H]^+$. $^1H$ NMR (500 MHz, $CDCl_3$): 9.09-9.03 (m, 1H), 7.70-7.63 (m, 1H), 6.56-6.50 (m, 1H), 5.84-5.75 (m, 1H), 4.27-4.00 (m, 2H), 3.96-3.88 (m, 1H), 3.50-3.39 (m, 1H), 3.32-3.25 (m, 1H), 3.12-3.03 (m, 1H), 2.99-2.90 (m, 1H), 2.86-2.77 (m, 1H), 2.53-2.42 (m, 1H), 2.15-2.03 (m, 2H), 1.74-1.48 (m, 3H).

Example 20, Step b: 7-[(2,4-Dichloro-3-fluorophenyl)carbonyl]-4-[1-(tetrahydro-2H-pyran-2-yl)-1H-pyrazol-5-yl]-5,6,7,8-tetrahydropyrido[3,4-d]pyrimidine The title compound was prepared in a manner analogous to Example 1 substituting the product of Example 20, step a for Intermediate 1 and 2,4-dichloro-3-fluorobenzoic acid for 2-chloro-3-(trifluoromethyl)benzoic acid. MS (ESI) mass calcd. $C_{22}H_{20}Cl_2FN_5O_2$, 475.10; m/z found 476.1 $[M+H]^+$. $^1H$ NMR (500 MHz, $CDCl_3$): 9.18-9.03 (m, 1H), 7.70-7.62 (m, 1H), 7.47-7.39 (m, 1H), 7.14-7.07 (m, 1H), 6.58-6.45 (m, 1H), 5.92-5.80 (m, 1H), 5.36-4.78 (m, 1H), 4.64-4.39 (m, 1H), 3.94-3.31 (m, 4H), 3.17-2.75 (m, 2H), 2.53-2.39 (m, 1H), 2.18-2.06 (m, 2H), 1.73-1.60 (m, 2H), 1.55-1.48 (m, 1H).

Example 20, Step c: 7-[(2,4-Dichloro-3-fluorophenyl)carbonyl]-4-(1H-pyrazol-5-yl)-5,6,7,8-tetrahydropyrido[3,4-d]pyrimidine TFA (0.97 mL, 0.24 mmol) was added to a solution of the product of Example 20, step b (116 mg, 0.24 mmol) in DCM (1 mL) containing triethylsilane (0.1 mL, 0.61 mmol). The reaction was stirred for 30 min. The reaction was concentrated in vacuo and then azeotroped 2× with toluene. The residue was purified on SiO$_2$ eluting with EtOAc/hexane to afford the title compound as a white solid (97 mg, 100%). MS (ESI) mass calcd. C$_{17}$H$_{12}$Cl$_2$FN$_5$O, 391.04; m/z found 392.0 [M+H]$^+$. $^1$H NMR (500 MHz, CDCl$_3$): 9.11-8.93 (m, 1H), 7.77-7.67 (m, 1H), 7.48-7.37 (m, 1H), 7.15-7.07 (m, 1H), 6.99-6.90 (m, 1H), 5.14-4.96 (m, 1H), 4.61-4.40 (m, 1H), 4.17-4.11 (m, 1H), 3.67-3.51 (m, 1H), 3.36-3.08 (m, 2H).

Example 21

7-[(2-chloro-4-fluorophenyl)carbonyl]-4-(1H-pyrazol-5-yl)-5,6,7,8-tetrahydropyrido[3,4-d]pyrimidine

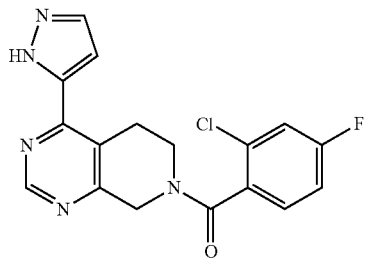 [SMILES: O=C(c1ccc(F)cc1Cl)N1CCc2c(ncnc2-c2ccn[nH]2)C1]

The title compound was prepared in a manner analogous to Example 20 substituting 2-chloro-4-fluorobenzoic acid for 2,4-dichloro-3-fluorobenzoic acid in Example 20, step b. MS (ESI) mass calcd. C$_{17}$H$_{13}$ClFN$_5$O, 357.08; m/z found 358.1 [M+H]$^+$. $^1$H NMR (500 MHz, CDCl$_3$): 9.10-8.92 (m, 1H), 7.78-7.66 (m, 1H), 7.39-7.31 (m, 1H), 7.25-7.04 (m, 2H), 6.98-6.89 (m, 1H), 5.16-4.93 (m, 1H), 4.64-4.40 (m, 1H), 4.18-4.08 (m, 1H), 3.67-3.52 (m, 1H), 3.35-3.05 (m, 2H).

Example 22

7-[(2,3-Dichlorophenyl)carbonyl]-4-(1H-pyrazol-1-yl)-5,6,7,8-tetrahydropyrido[3,4-d]pyrimidine

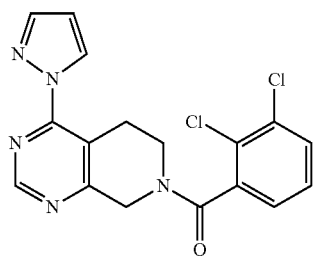 [SMILES: O=C(c1cccc(Cl)c1Cl)N1CCc2c(ncnc2-n2cccn2)C1]

Example 22, Step a: To a suspension of NaH (60% dispersion in mineral oil (25 mg, 0.62 mmol)) in DMF (3 mL) was added pyrazole (39 mg, 0.57 mmol). When gas evolution had ceased and the mixture was homogeneous, Intermediate 2 was added (139 mg, 0.51 mmol). The reaction immediately turned a dark red color and was warm to the touch. After aging overnight, the mixture was diluted with H$_2$O and extracted with EtOAc. The combined organic layers were dried over Na$_2$SO$_4$, filtered and concentrated in vacuo. Chromatography on SiO$_2$ eluting with EtOAc/hexane afforded the desired compound as a viscous colorless oil (81 mg, 52%). MS (ESI) mass calcd. C$_{15}$H$_{19}$N$_5$O$_2$, 301.15; m/z found 302.0 [M+H]$^+$. $^1$H NMR (500 MHz, CDCl$_3$): 8.83 (s, 1H), 8.63-8.56 (m, 1H), 7.82-7.77 (m, 1H), 6.51-6.47 (m, 1H), 4.77-4.65 (m, 2H), 3.72-3.64 (m, J=5.8 Hz, 2H), 3.42-3.32 (m, 2H), 1.50 (s, 9H).

Example 22, Step b: 4-(1H-Pyrazol-1-yl)-5,6,7,8-tetrahydropyrido[3,4-d]pyrimidine To the product of Example 22, step a (78 mg, 0.26 mmol) in DCM (1 mL) was added TFA (0.26 mL). After stirring 3 h the reaction was concentrated in vacuo. The residue was redissolved in DCM and treated with Dowex 550A resin to neutralize the TFA salt. The resin was removed by filtration and concentration afforded a yellow solid (50 mg, 97%). This material was used without subsequent purification. MS (ESI) mass calcd. C$_{10}$H$_{11}$N$_5$, 201.10; m/z found 202.0 [M+H]$^+$.

Example 22, step c: 7-[(2,3-Dichlorophenyl)carbonyl]-4-(1H-pyrazol-1-yl)-5,6,7,8-tetrahydropyrido[3,4-d]pyrimidine The title compound was prepared in a manner analogous to Example 1 substituting the product of Example 22, step b for Intermediate 1 and 2,3-dichlorobenzoic acid for 2-chloro-3-(trifluoromethyl)benzoic acid. MS (ESI) mass calcd. C$_{17}$H$_{13}$Cl$_2$N$_5$O, 373.05; m/z found 374.1 [M+H]$^+$. $^1$H NMR (600 MHz, CDCl$_3$): 8.91-8.76 (m, 1H), 8.66-8.61 (m, 1H), 7.85-7.74 (m, 1H), 7.57-7.51 (m, 1H), 7.35-7.22 (m, 2H), 6.53-6.48 (m, 1H), 5.21-4.94 (m, 1H), 4.60-4.42 (m, 1H), 4.14-4.01 (m, 1H), 3.58-3.49 (m, 2H), 3.47-3.32 (m, 1H).

Example 23

7-[(2,3-Dichlorophenyl)carbonyl]-4-(2H-1,2,3-triazol-2-yl)-5,6,7,8-tetrahydropyrido[3,4-d]pyrimidine

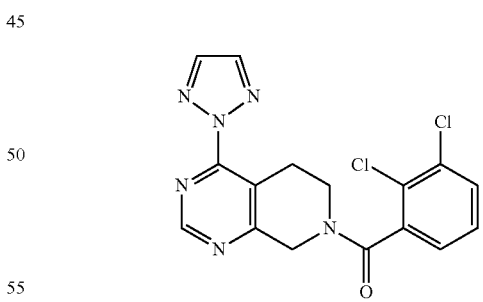

The title compound was prepared in a manner analogous to Example 22 substituting 1H-1,2,3-triazole for pyrazole in Example 22, step a. MS (ESI) mass calcd. C$_{16}$H$_{12}$Cl$_2$N$_6$O, 374.05; m/z found 375.1 [M+H]$^+$. $^1$H NMR (500 MHz, CDCl$_3$): 9.12-8.97 (m, 1H), 8.02-7.95 (m, 2H), 7.58-7.52 (m, 1H), 7.36-7.23 (m, 2H), 5.23-5.04 (m, 1H), 4.67-4.49 (m, 1H), 4.13-4.08 (m, 1H), 3.60-3.42 (m, 2H), 3.36-3.21 (m, 1H).

Example 24

7-{[2-Chloro-3-(trifluoromethyl)phenyl]carbonyl}-4-(2H-1,2,3-triazol-2-yl)-5,6,7,8-tetrahydropyrido[3,4-d]pyrimidine

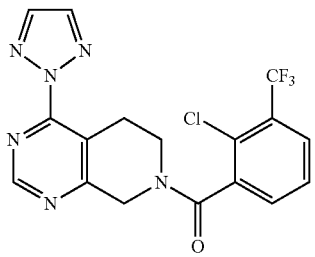 [SMILES: O=C(c1cccc(C(F)(F)F)c1Cl)N1CCc2c(ncnc2-n2nccn2)C1]

The title compound was prepared in a manner analogous to Example 22 substituting 1H-1,2,3-triazole for pyrazole in Example 22, step a and 2-chloro-3-(trifluoromethyl)benzoic acid for 2,4-dichlorobenzoic acid. MS (ESI) mass calcd. $C_{17}H_{12}ClF_3N_6O$, 408.07; m/z found 409.1 [M+H]$^+$. $^1$H NMR (500 MHz, CDCl$_3$): 9.12-8.98 (m, 1H), 8.02-7.96 (m, 2H), 7.83-7.78 (m, 1H), 7.58-7.47 (m, 2H), 5.27-5.03 (m, 1H), 4.66-4.48 (m, 1H), 4.20-4.05 (m, 1H), 3.57-3.43 (m, 2H), 3.36-3.22 (m, 1H).

Intermediate 7: tert-butyl 2-(dimethylamino)-4-hydroxy-5,6-dihydropyrido[3,4-d]pyrimidine-7(8H)-carboxylate

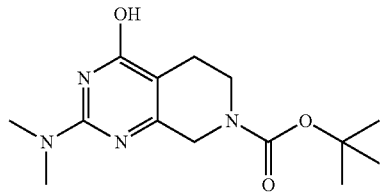 [SMILES: CN(C)c1nc(O)c2c(n1)CN(C(=O)OC(C)(C)C)CC2]

K$_2$CO$_3$ (563 mg, 4.07 mmol) and 1,1-dimethylguanidine sulfate (566 mg, 2.04 mmol) were added to a suspension of ethyl N—BOC-3-oxopiperidine-4-carboxylate in MeOH (2 mL) and H$_2$O (1 mL) in a 40 mL vial. The reaction was heated in an aluminium block at 70° C. for 90 minutes. LCMS analysis showed that the reaction was complete. The mixture was acidified to pH 3 and extracted with DCM (3×). The combined organic extracts were dried over MgSO$_4$, filtered and concentrated to obtain tert-butyl 2-(dimethylamino)-4-hydroxy-5,6-dihydropyrido[3,4-d]pyrimidine-7(8H)-carboxylate as a pale yellow solid which was used without further purification. MS (ESI): mass calcd. for $C_{14}H_{22}N_4O_3$, 294.3; m/z found, 295.3 [M+H]$^+$. $^1$H NMR (400 MHz, MeOD) δ 4.29-4.11 (m, 2H), 3.71-3.46 (m, 2H), 3.09 (s, 6H), 2.42 (t, J=5.8 Hz, 2H), 1.58-1.38 (m, 9H).

Intermediate 8: tert-butyl 4-chloro-2-(dimethylamino)-5,6-dihydropyrido[3,4-d]pyrimidine-7(8H)-carboxylate

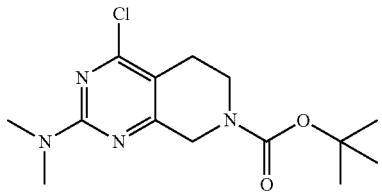

Triphenylphosphine (186 mg, 0.694 mmol) was added to a solution of tert-butyl 4-hydroxy-2-methyl-5,6-dihydropyrido[3,4-d]pyrimidine-7(8H)-carboxylate (92 mg, 0.347 mmol) and CCl$_4$ (160 mg, 1.04 mmol) in DCE (5 mL). The reaction was heated at 70° C. for 2 hours, wherein TLC showed no remaining starting material. The mixture was concentrated mixture under vacuum and purified by sgc, 0-100% hexanes-EtOAc gradient over 12 minutes. Tert-butyl 4-chloro-2-(dimethylamino)-5,6-dihydropyrido[3,4-d]pyrimidine-7(8H)-carboxylate was isolated as a colorless oil (82 mg, 79%). MS (ESI): mass calcd. for $C_{14}H_{21}ClN_4O_2$, 312.8 m/z found, 313.3 [M+H]$^+$. $^1$H NMR (400 MHz, CDCl$_3$) δ 4.37 (s, 2H), 3.73-3.46 (m, 2H), 2.66-2.52 (m, 2H), 1.53-1.34 (m, 9H).

Intermediate 9: N,N-dimethyl-4-phenyl-5,6,7,8-tetrahydropyrido[3,4-d]pyrimidin-2-amine

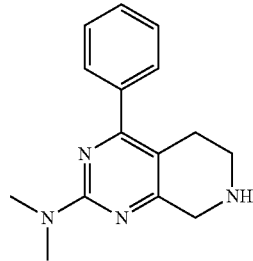 [SMILES: CN(C)c1nc2c(c(-c3ccccc3)n1)CCNC2]

tert-Butyl tert-butyl 4-chloro-2-(dimethylamino)-5,6-dihydropyrido[3,4-d]pyrimidine-7(8H)-carboxylate (82 mg, 0.262 mmol), phenylboronic acid (49 mg, 0.393 mmol), Pd(Ph$_3$P)$_4$ (15 mg, 0.013 mmol), and 1M aqueous Na$_2$CO$_3$ (0.524 mL, 0.524 mmol) were combined in dioxane (4 mL) in a 40 mL vial and heated at 100° C. overnight in an aluminum heating block. The crude mixture was partitioned between EtOAc/H$_2$O and extracted aqueous with EtOAc (2×). The combined organic extracts were dried over MgSO$_4$, filtered and concentrated. The product was purified by sgc 0-100% Hexane-EtOAc gradient over 8 minutes. The purified product was then dissolved in DCM (2 mL) and treated with TFA (0.5 mL), and stirred at room temp for 1 hour. The mixture was neutralized with sat. NaHCO$_3$ solution and extracted with DCM (3×). The combined organic extracts were dried over MgSO$_4$, filtered and concentrated to isolate N,N-dimethyl-4-phenyl-5,6,7,8-tetrahydropyrido[3,4-d]pyrimidin-2-amine (85 mg, 99%). MS (ESI): mass calcd. for $C_{15}H_{18}N_4$, 254.3 m/z found, 255.2 [M+H]$^+$. $^1$H NMR (400 MHz, CDCl₃) δ 7.60-7.54 (m, 2H), 7.48-7.41 (m, 3H), 4.28-4.12 (m, 2H), 3.33-3.24 (m, 2H), 3.19 (s, 6H), 3.08-2.83 (m, 2H).

Example 25

7-[(2,3-Dichlorophenyl)carbonyl]-N,N-dimethyl-4-phenyl-5,6,7,8-tetrahydropyrido[3,4-d]pyrimidin-2-amine

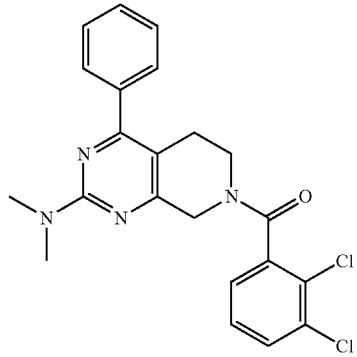 [SMILES: CN(C)c1nc2c(c(-c3ccccc3)n1)CCN(C(=O)c1cccc(Cl)c1Cl)C2]

Intermediate 9 (40 mg, 0.157 mmol), HATU (60 mg, 0.157 mmol), TEA (32 μL, 0.236 mmol) and 2,3-dichlorobenzoic acid (30 mg, 0.157 mmol) were combined and stirred at room temperature for 2 h. The crude mixture was concentrated in vacuo and purified directly using reverse phase prep HPLC on an Agilent system with a XBridge C18 OBD 50×100 mm column eluting with 5 to 99% 0.05% NH₄OH in H₂O/ACN over 17 min to afford the desired product as a yellow solid (30 mg, 45%). MS (ESI): mass calcd. for C₂₂H₂₀Cl₂N₄O, 426.1; m/z found, 427.3 [M+H]⁺. ¹H NMR (500 MHz, CDCl₃) δ 7.64-7.59 (m, 1H), 7.59-7.55 (m, 1H), 7.54-7.49 (m, 1H), 7.49-7.40 (m, 3H), 7.32-7.27 (m, 1H), 7.27-7.24 (m, 1H), 4.85 4.93-4.77 (m, 1H), 4.47-4.16 (m, 1H), 4.03-3.79 (m, 1H), 3.45-3.27 (m, 1H), 3.27-3.10 (m, 6H), 2.86 (t, J=5.7 Hz, 1H), 2.81-2.62 (m, 1H).

Example 26

7-{[2-Chloro-3-(trifluoromethyl)phenyl]carbonyl}-N,N-dimethyl-4-phenyl-5,6,7,8-tetrahydropyrido[3,4-d]pyrimidin-2-amine

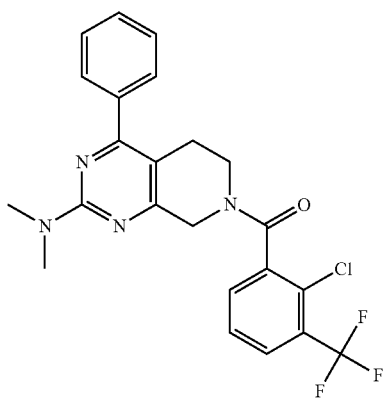 [SMILES: CN(C)c1nc2c(c(-c3ccccc3)n1)CCN(C(=O)c1cccc(C(F)(F)F)c1Cl)C2]

The title compound was prepared in a manner analogous to Example 25 substituting 2-chloro-3-(trifluoromethyl)benzoic acid for 2,3-dichlorobenzoic acid. MS (ESI): mass calcd. for C₂₃H₂₀ClF₃N₄O, 460.9; m/z found, 461.4 [M+H]⁺. ¹H NMR (500 MHz, CDCl₃) δ 7.81-7.73 (m, 1H), 7.64-7.59 (m, 1H), 7.59-7.55 (m, 1H), 7.55-7.51 (m, 1H), 7.51-7.39 (m, 4H), 4.99-4.77 (m, 1H), 4.42-4.19 (m, 1H), 4.05-3.82 (m, 1H), 3.44-3.28 (m, 1H), 3.28-3.18 (s, 3H), 3.19-3.11 (s, 3H), 2.92-2.83 (t, J=5.8 Hz, 1H), 2.80-2.61 (m, 1H).

Intermediate 10: tert-butyl 4-hydroxy-2-methyl-5,6-dihydropyrido[3,4-d]pyrimidine-7(8H)-carboxylate

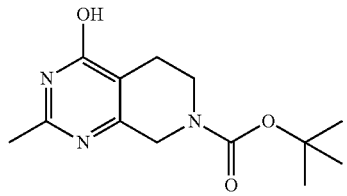 [SMILES: Cc1nc(O)c2c(n1)CN(C(=O)OC(C)(C)C)CC2]

K₂CO₃ (535 mg, 3.87 mmol) and acetamidine hydrochloride (185 mg, 1.93 mmol) were added to a suspension of ethyl N—BOC-3-oxopiperidine-4-carboxylate (525 mg, 1.93 mmol) in MeOH (3 mL) and H₂O (1 mL) in a 40 mL vial. The reaction was heated in an aluminum block at 70° C. for 90 minutes. LCMS analysis indicated complete consumption of the starting material. The reaction mixture was then acidified to pH 3 and extracted with DCM (3×). The combined organic extracts were dried over MgSO₄, filtered and concentrated to obtain tert-butyl 4-hydroxy-2-methyl-5,6-dihydropyrido[3,4-d]pyrimidine-7(8H)-carboxylate as a yellow oil. The product was used without further purification (473 mg, 93%). MS (ESI): mass calcd. for C₁₃H₁₉N₃O₃ 265.1 m/z found, 266.2[M+H]⁺. ¹H NMR (400 MHz, CDCl₃) δ 4.37 (s, 2H), 3.71-3.50 (m, 2H), 2.60 (s, 2H), 2.50-2.38 (m, 3H), 1.52-1.41 (m, 9H).

Intermediate 11: tert-butyl 4-chloro-2-methyl-5,6-dihydropyrido[3,4-d]pyrimidine-7(8H)-carboxylate

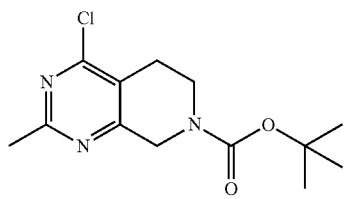 [SMILES: Cc1nc(Cl)c2c(n1)CN(C(=O)OC(C)(C)C)CC2]

Triphenylphosphine (186 mg, 0.694 mmol) was added to a solution Intermediate 10 (92 mg, 0.347 mmol) and CCl₄ (160 mg, 1.04 mmol) in DCE (5 mL). The reaction was heated at 70° C. for 2 hours after which, TLC indicated complete consumption of the starting material. The mixture was concentrated under vacuum and purified by sgc, with a 0-100% hexanes-EtOAc gradient over 12 minutes to provide tert-butyl 4-chloro-2-methyl-5,6-dihydropyrido[3,4-d]pyrimidine-7(8H)-carboxylate was isolated as a pale yellow oil (73 mg, 74%). MS (ESI): mass calcd. for C₁₃H₁₈ClN₃O₂ 283.11 m/z found, 284.2[M+H]⁺. ¹H NMR (500 MHz, CDCl₃) δ 4.59 (s, 2H), 3.72 (t, J=5.9 Hz, 2H), 2.82 (t, J=5.9 Hz, 2H), 2.67 (s, 3H), 1.49 (s, 9H).

Intermediate 12: 2-methyl-4-phenyl-5,6,7,8-tetrahydropyrido[3,4-d]pyrimidine

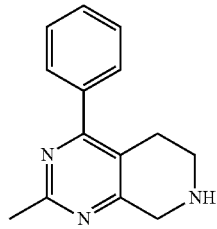

Intermediate 11 (73 mg, 0.293 mmol), phenylboronic acid (55 mg, 0.439 mmol), Pd(Ph₃P)₄ (16 mg, 0.015 mmol), and 1M aqueous Na₂CO₃ (0.586 mL, 0.586 mmol) were combined in dioxane (3 mL) in a microwave vial and heated at 150° C. for 1 h in the microwave. LCMS indicated complete consumption of the starting material. The crude mixture was partitioned between EtOAc/H₂O and the aqueous extracted with EtOAc (2×). The combined organic extracts were dried over MgSO₄, filtered and concentrated. The product was purified by sgc 0-100% hexane-EtOAc gradient over 8 minutes. The purified product was then dissolved in DCM (2 mL) and treated with TFA (0.5 mL), and stirred at room temp for 1 hour. The mixture was neutralized with sat. NaHCO₃ solution and extracted with DCM (3×). The combined organic extracts were dried over MgSO₄ filtered and concentrated to isolate 2-methyl-4-phenyl-5,6,7,8-tetrahydropyrido[3,4-d]pyrimidine as a yellow oil (59 mg, 89%). MS (ESI): mass calcd. for $C_{14}H_{15}N_3$ 225.3 m/z found, 226.2 [M+H]⁺. ¹H NMR (500 MHz, CDCl3) δ 8.08-7.99 (m, 1H), 7.56-7.48 (m, 1H), 7.49-7.34 (m, 3H), 4.23-4.13 (m, 1H), 3.84-3.66 (m, 1H), 3.48 (s, 3H), 3.16 (t, J=5.7 Hz, 1H), 2.83 (t, J=5.6 Hz, 1H), 2.71 (s, 2H).

Example 27

7-[(2,3-Dichlorophenyl)carbonyl]-2-methyl-4-phenyl-5,6,7,8-tetrahydropyrido[3,4-d]pyrimidine

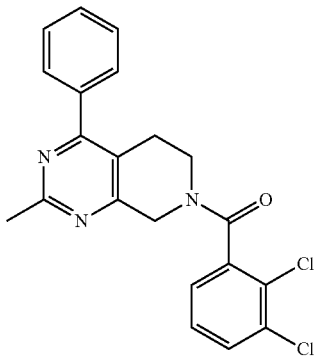

The title compound was prepared in a manner analogous to Example 25 substituting Intermediate 12 for Intermediate 9. MS (ESI): mass calcd. for $C_{21}H_{17}Cl_2N_3O$, 397.1; m/z found, 398.3 [M+H]⁺. ¹H NMR (500 MHz, CDCl₃) δ 7.63-7.57 (m, 1H), 7.56-7.43 (m, 5H), 7.35-7.28 (m, 1H), 7.28-7.22 (m, 1H), 5.02 (s, 1H), 4.63-4.36 (m, 1H), 4.09-3.87 (m, 1H), 3.50-3.33 (m, 1H), 3.05-2.86 (m, 2H), 2.81-2.61 (m, 3H).

Intermediate 13: 4-(4-fluorophenyl)-2-methyl-5,6,7,8-tetrahydropyrido[3,4-d]pyrimidine

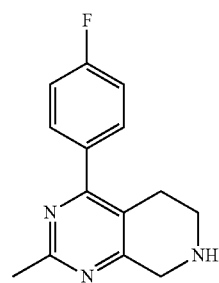 [SMILES: Cc1nc2c(c(-c3ccc(F)cc3)n1)CCNC2]

The title compound was prepared in a manner analogous to Intermediate 9 substituting Intermediate 11 for Intermediate 8 and 4-fluorophenylboronic acid for phenylboronic acid. ¹H NMR (500 MHz, CDCl₃) δ 7.59-7.51 (m, 2H), 7.19-7.11 (m, 2H), 4.19-4.09 (s, 2H), 3.19-3.07 (t, J=5.8 Hz, 2H), 2.87-2.76 (t, J=5.7 Hz, 2H), 2.74-2.67 (s, 3H).

Example 28

7-[(2,3-Dichlorophenyl)carbonyl]-4-(4-fluorophenyl)-2-methyl-5,6,7,8-tetrahydropyrido[3,4-d]pyrimidine

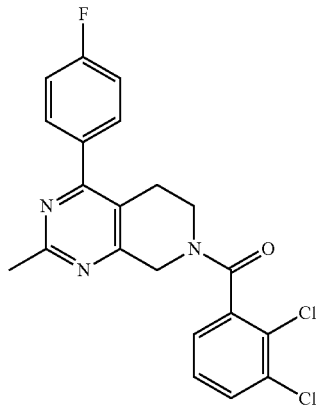 [SMILES: Cc1nc2c(c(-c3ccc(F)cc3)n1)CCN(C(=O)c1cccc(Cl)c1Cl)C2]

The title compound was prepared in a manner analogous to Example 25 substituting Intermediate 13 for Intermediate 9. MS (ESI): mass calcd. for $C_{21}H_{16}Cl_2FN_3O$ 415.1; m/z found, 416.1 [M+H]⁺. ¹H NMR (400 MHz, CDCl₃) δ 7.66-7.49 (m, 3H), 7.36-7.12 (m, 4H), 5.07-4.96 (m, 1H), 4.60-4.35 (m, 1H), 4.03-3.91 (m, 1H), 3.55-3.32 (m, 1H), 3.06-2.85 (m, 2H), 2.78-2.64 (m, 3H).

Intermediate 14: 2-amino-7-benzyl-5,6,7,8-tetrahdrorido[3,4-d]pyrimidin-4-ol

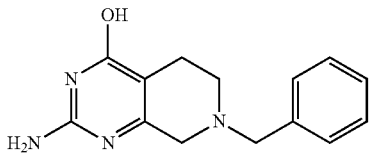

Guanidine carbonate (343 mg, 1.87 mmol) was added to a solution of 1-benzyl-4-ethoxycarbonyl-3-piperidone hydrochloride (488 mg, 1.87 mmol) in tBuOH (18 mL). The reaction was heated to reflux for 2 hours and then was acidified with 1N HCl to pH 5 and stirred for 30 minutes. The mixture was filtered and the solids were dried to obtain 2-amino-7-benzyl-5,6,7,8-tetrahydropyrido[3,4-d]pyrimidin-4-ol as a yellow solid (320 mg, 67%). MS (ESI): mass calcd. for $C_{14}H_{16}N_4O$ 256.3 m/z found, 257.2[M+H]$^+$. $^1$H NMR (500 MHz, MeOD) δ 7.40-7.26 (m, 5H), 3.71 (s, 2H), 3.25 (s, 2H), 2.73 (t, J=5.9 Hz, 2H), 2.46 (t, J=5.9 Hz, 2H).

Intermediate 15: 7-benzyl-4-chloro-5,6,7,8-tetrahydropyrido[3,4-d]pyrimidin-2-amine

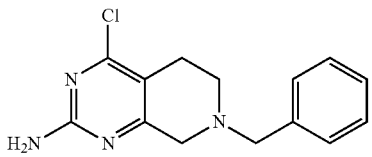 [SMILES: Nc1nc(Cl)c2c(n1)CN(Cc1ccccc1)CC2]

POCl$_3$ (0.580 mL, 6.24 mmol) was added to a suspension of Intermediate 14 (160 mg, 0.624 mmol) and dimethyl aniline (79 μL, 0.624 mmol) in DCE (5 mL). The reaction was heated to reflux overnight. The reaction was then poured over ice and neutralized with solid Na$_2$CO$_3$ and extracted with EtOAc (3×). The combined organic extracts were dried over MgSO$_4$, filtered and concentrated. The crude material was purified by sgc using a 0-100% hexane-EtOAc gradient over 8 minutes. 7-benzyl-4-chloro-5,6,7,8-tetrahydropyrido[3,4-d]pyrimidin-2-amine was isolated as a pale yellow oil. (22 mg, 12%). MS (ESI): mass calcd. for $C_{14}H_{15}ClN_4$ 274.7 m/z found, 275.2 [M+H]$^+$. $^1$H NMR (400 MHz, CDCl$_3$) δ 7.39-7.26 (m, 5H), 4.92 (s, 2H), 3.76-3.60 (m, 2H), 3.44 (d, J=20.4 Hz, 2H), 2.82-2.61 (m, 4H).

Intermediate 16: 7-benzyl-4-phenyl-5,6,7,8-tetrahydropyrido[3,4-d]pyrimidin-2-amine

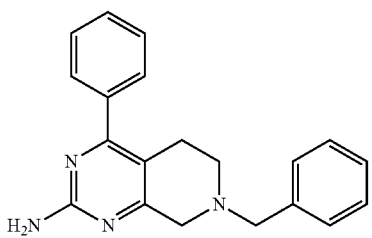 [SMILES: Nc1nc2c(c(-c3ccccc3)n1)CCN(Cc1ccccc1)C2]

The title compound was prepared in a manner analogous to Intermediate 12 substituting Intermediate 15 for Intermediate 11. MS (ESI): mass calcd. for $C_{20}H_{20}N_4$, 316.4; m/z found, 317.3 [M+H]$^+$. $^1$H NMR (400 MHz, CDCl$_3$) δ 7.72-7.62 (m, 3H), 7.49-7.39 (m, 4H), 7.39-7.24 (m, 3H), 5.00 (s, 2H), 3.69 (s, 2H), 3.57 (s, 2H), 2.78-2.58 (m, 4H).

Intermediate 17: 4-phenyl-5,6,7,8-tetrahydropyrido[3,4-d]pyrimidin-2-amine

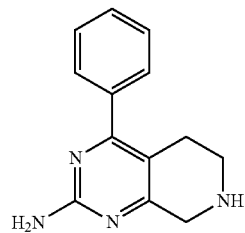

Intermediate 16 (24 mg, 0.0759 mmol), 1-chloroethyl chloroformate (17 μL, 0.152 mmol), and DIEA, (26 μL, 0.152 mmol) were combined in DCM (3 mL) and stirred overnight at room temperature. The reaction was quenched with MeOH (5 mL) and concentrated in vacuo. The resulting residue was dissolved in MeOH (5 mL) and heated at 50° C. for 1 hr. The solution was concentrated in vacuo and the desired product was used without further purification. MS (ESI): mass calcd. for $C_{13}H_{14}N_4$, 226.3; m/z found, 227.2 [M+H]$^+$.

Example 29

7-[(2,3-Dichlorophenyl)carbonyl]-4-phenyl-5,6,7,8-tetrahydropyrido[3,4-d]pyrimidin-2-amine

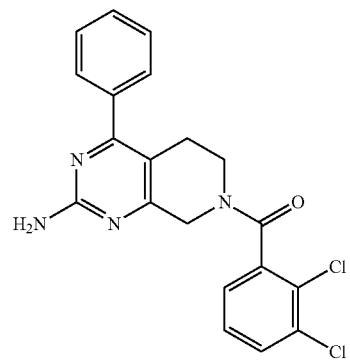 [SMILES: Nc1nc2c(c(-c3ccccc3)n1)CCN(C(=O)c1cccc(Cl)c1Cl)C2]

The title compound was prepared in a manner analogous to Example 25 substituting Intermediate 17 for Intermediate 9. MS (ESI): mass calcd. for $C_{20}H_{16}Cl_2N_4O$, 398.1; m/z found, 399.3 [M+H]$^+$. $^1$H NMR (500 MHz, CDCl$_3$) δ 7.57-7.42 (m, 5H), 7.33-7.27 (m, 1H), 7.26-7.22 (m, 2H), 5.10-4.77 (m, 3H), 4.44-4.20 (m, 1H), 4.07-3.84 (m, 1H), 3.48-3.29 (m, 1H).

Intermediate 18: 2-methyl-4-(pyridin-2-yl)-5,6,7,8-tetrahydropyrido[3,4-d]pyrimidine

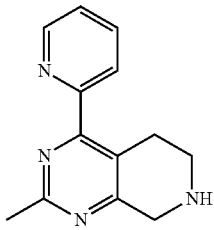 [SMILES: Cc1nc2c(c(-c3ccccn3)n1)CCNC2]

Intermediate 11 (227 mg, 0.800 mmol), 2-tri-n-butylstannylpyridine (519 mg, 1.20 mmol) and Pd(Ph$_3$P)$_4$ (46 mg, 0.04 mmol) were combined in a microwave vial. Dioxane (2 mL) that had been degassed with a stream of N$_2$ (g) was added and the vial was sealed and heated in a microwave reactor at 140° C. for 90 min. The reaction mixture was partitioned between EtOAc and H$_2$O and 2 g of 50% wt KF on celite was added. The resulting mixture was stirred for 30 min and then filtered. The aqueous material was extracted with EtOAc (2×) and the combined organic extracts were dried over MgSO$_4$, filtered and concentrated in vacuo. Chromatography on silica gel eluted with hexanes/EtOAc afforded the desired product as a tan solid. The product was dissolved in DCM (2 mL) and treated with TFA (1 mL). The resulting mixture was stirred at room temperature for 1 h. The reaction was neutralized with sat. aq. NaHCO$_3$ and the aqueous layer was extracted with DCM (2×). The combined organic extracts were dried over MgSO$_4$, filtered and concentrated in vacuo to afford Intermediate 18 as a brown oil. (169 mg, 93%) $^1$H NMR (500 MHz, CDCl$_3$) δ 8.68 (s, 1H), 7.97 (d, J=7.9 Hz, 1H), 7.92-7.80 (m, 1H), 7.45-7.33 (m, 1H), 4.20 (s, 2H), 3.22 (s, 4H), 2.73 (s, 3H).

Example 30

7-{[2-Chloro-3-(trifluoromethyl)phenyl]carbonyl}-2-methyl-4-pyridin-2-yl-5,6,7,8-tetrahydropyrido[3,4-d]pyrimidine

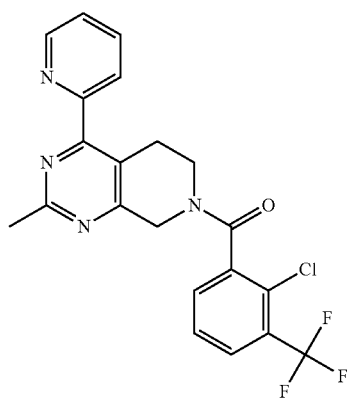 [SMILES: Cc1nc2c(c(-c3ccccn3)n1)CCN(C(=O)c1cccc(C(F)(F)F)c1Cl)C2]

The title compound was prepared in a manner analogous to Example 25 substituting Intermediate 18 for Intermediate 9 and 2-chloro-3-(trifluoromethyl)benzoic acid for 2,3-dichlorobenzoic acid. MS (ESI): mass calcd. for C$_{21}$H$_{16}$ClF$_3$N$_4$O, 432.8; m/z found, 433.1 [M+H]$^+$. $^1$H NMR (500 MHz, CDCl$_3$) δ 8.77-8.61 (m, 1H), 8.11-7.98 (m, 1H), 7.93-7.84 (m, 1H), 7.82-7.72 (m, 1H), 7.62-7.45 (m, 2H), 7.44-7.33 (m, 1H), 5.24-4.87 (m, 1H), 4.64-4.37 (m, 1H), 4.24-3.84 (m, 1H), 3.44-3.15 (m, 3H), 2.80-2.68 (m, 3H).

Example 31

7-[(2,3-Dichlorophenyl)carbonyl]-2-methyl-4-pyridin-2-yl-5,6,7,8-tetrahydropyrido[3,4-d]pyrimidine

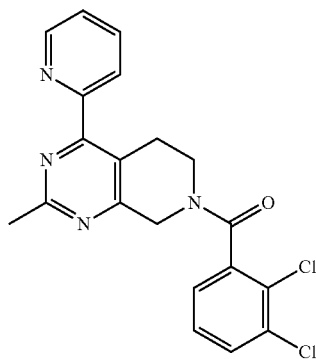 [SMILES: Cc1nc2c(c(-c3ccccn3)n1)CCN(C(=O)c1cccc(Cl)c1Cl)C2]

The title compound was prepared in a manner analogous to Example 25 substituting Intermediate 18 for Intermediate 9. MS (ESI): mass calcd. for C$_{20}$H$_{16}$Cl$_2$N$_4$O, 398.1; m/z found, 399.1 [M+H]$^+$. $^1$H NMR (500 MHz, CDCl$_3$) δ 8.75-8.62 (m, 1H), 8.10-8.00 (m, 1H), 7.92-7.81 (m, 1H), 7.57-7.49 (m, 1H), 7.45-7.34 (m, 1H), 7.32-7.22 (m, 2H), 5.20-4.87 (m, 1H), 4.60-4.35 (m, 1H), 4.26-3.87 (m, 1H), 3.55-3.42 (m, 1H), 3.39-3.16 (m, 2H), 2.80-2.69 (m, 3H).

Example 32

7-{[2-Chloro-3-(trifluoromethyl)phenyl]carbonyl}-2-methyl-4-phenyl-5,6,7,8-tetrahydropyrido[3,4-d]pyrimidine

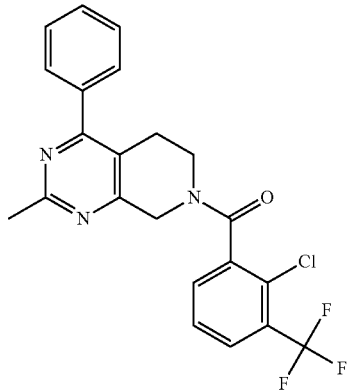

The title compound was prepared in a manner analogous to Example 25 substituting Intermediate 12 for Intermediate 9 and 2-chloro-3-(trifluoromethyl)benzoic acid for 2,3-dichlorobenzoic acid. MS (ESI): mass calcd. for C$_{22}$H$_{17}$ClF$_3$N$_3$O, 431.8; m/z found, 432.1 [M+H]$^+$. $^1$H NMR (500 MHz, MeOD) δ 7.98-7.90 (m, 1H), 7.78-7.71 (m, 1H), 7.71-7.65 (m, 1H), 7.65-7.59 (m, 2H), 7.58-7.49 (m, 3H), 5.17-5.05 (m, 1H), 4.92-4.85 (s, 1H), 4.14-3.95 (m, 1H), 3.54-3.45 (t, J=5.8 Hz, 1H), 3.04-2.98 (t, J=5.9 Hz, 1H), 2.97-2.78 (m, 1H), 2.75-2.59 (m, 3H).

Intermediate 19: tert-butyl 2-methyl-4-(1-(tetrahydro-2H-pyran-2-yl)-1H-pyrazol-5-yl)-5,6-dihydropyrido[3,4-d]pyrimidine-7(8H)-carboxylate

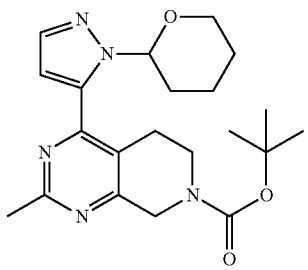 [SMILES: Cc1nc2c(c(-c3ccnn3C3CCCCO3)n1)CCN(C(=O)OC(C)(C)C)C2]

Intermediate 11 (519 mg, 1.83 mmol), 1-(tetrahydropyran-2-yl)-1H-pyrazole-5-boronic acid pinacol ester (589 mg, 2.01 mmol), Pd(Ph₃P)₄ (105 mg, 0.0915 mmol), and 1M aqueous Na₂CO₃ (4.57 mL, 4.57 mmol) were combined in dioxane (8 mL) in a round bottom flask and purged with N₂ (g) for 5 minutes. The reaction was capped and heated at 100° C. overnight in an oil bath. The crude mixture was partitioned between EtOAc/H₂O and extracted with EtOAc (2×). The combined organic extracts were dried over MgSO₄, filtered and concentrated. The product was purified by sgc 0-100% hexane-EtOAc gradient over 8 minutes to afford the desired product (670 mg, 92%). MS (ESI): mass calcd. for $C_{21}H_{29}N_5O_3$, 399.5; m/z found, 400.3 [M+H]⁺.

Intermediate 20: (2-chloro-3-(trifluoromethyl)phenyl)(2-methyl-4-(1-(tetrahydro-2H-pyran-2-yl)-1H-pyrazol-5-yl)-5,6-dihydropyrido[3,4-d]pyrimidin-7(8H)-yl)methanone

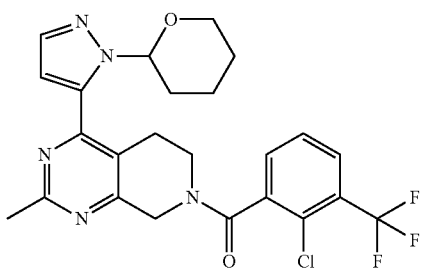 [SMILES: Cc1nc2c(c(-c3ccnn3C3CCCCO3)n1)CCN(C(=O)c1cccc(C(F)(F)F)c1Cl)C2]

Intermediate 19 (1.4 g, 3.50 mmol) was dissolved in DCM (8 mL) and treated with TFA (2 mL), and stirred at room temp for 1 hour. The reaction was concentrated and dried under high vacuum. The residue was then redissolved in DCM (8 mL) and DIEA (9 mL, 52.5 mmol), 2-chloro-3-(trifluoromethyl)benzoic acid (787 mg, 5.50 mmol), and HATU (1.33 g, 3.50 mmol were added. The reaction was stirred at room temperature for 1 h and then concentrated in vacuo and purified directly by sgc using a 0-100% hexane-EtOAc gradient to afford Intermediate 20 (506 mg, 29%). MS (ESI): mass calcd. for $C_{24}H_{23}ClF_3N_5O_2$, 505.9; m/z found, 506.2 [M+H]⁺.

Example 33

7-{[2-Chloro-3-(trifluoromethyl)phenyl]carbonyl}-2-methyl-4-(1H-pyrazol-5-yl)-5,6,7,8-tetrahydropyrido[3,4-d]pyrimidine

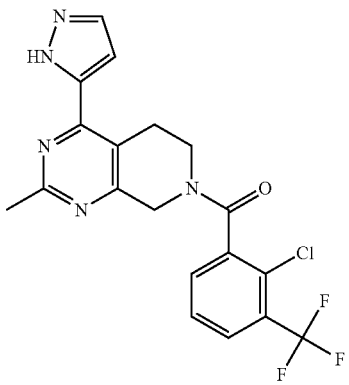 [SMILES: Cc1nc2c(c(-c3ccn[nH]3)n1)CCN(C(=O)c1cccc(C(F)(F)F)c1Cl)C2]

TFA (3 mL) was added to a solution of Intermediate 20 (713 mg, 1.40 mmol) and triethylsilane (566 μL, 3.52 mmol) in DCM (8 mL). The reaction was stirred at room temperature for 30 min and then toluene (15 mL) was added and the solvents were removed in vacuo. Another portion of toluene was added and the mixture was reconcentrated and then purified directly on silica gel eluting with 0-100% hexanes/EtOAc gradient over 12 minutes to obtain the desired product. (506 mg, 85%). (MS (ESI): mass calcd. for $C_{19}H_{15}ClF_3N_5O$, 421.8; m/z found, 422.1 [M+H]⁺. ¹H NMR (400 MHz, CDCl₃) δ 7.83-7.66 (m, 2H), 7.57-7.43 (m, 2H), 6.89 (d, J=22.4 Hz, 1H), 5.15-4.90 (m, 1H), 4.58-4.33 (m, 1H), 4.29-4.13 (m, 1H), 4.13-3.97 (m, 1H), 3.67-3.51 (m, 1H), 3.31-3.22 (m, 1H), 3.23-2.99 (m, 1H), 2.80-2.61 (m, 3H).

Example 34

7-[(2,3-Dichlorophenyl)carbonyl]-2-methyl-4-(1H-pyrazol-5-yl)-5,6,7,8-tetrahydropyrido[3,4-d]pyrimidine

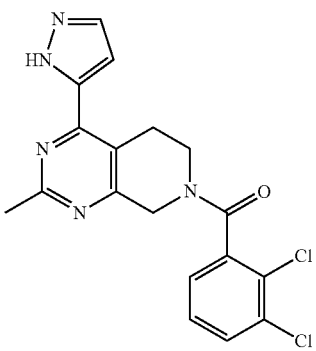 [SMILES: Cc1nc2c(c(-c3ccn[nH]3)n1)CCN(C(=O)c1cccc(Cl)c1Cl)C2]

The title compound was prepared in a manner analogous to Example 33 substituting 2,3-dichlorobenzoic acid for 2-chloro-3-(trifluoromethyl)benzoic acid in the synthesis of Intermediate 20. MS (ESI): mass calcd. for $C_{18}H_{15}Cl_2N_5O$, 387.1; m/z found, 388.1 [M+H]⁺. ¹H NMR (400 MHz, CDCl₃) δ 7.75-7.67 (m, 1H), 7.58-7.50 (m, 1H), 7.36-7.29 (m, 1H), 7.28-7.20 (m, 1H), 6.93-6.83 (m, 1H), 5.12-4.91 (m, 1H), 4.58-4.36 (m, 1H), 4.22-4.02 (m, 1H), 3.64-3.46 (m, 1H), 3.27-2.98 (m, 2H), 2.78-2.63 (m, 3H).

Intermediate 21: tert-butyl 4-(4-fluoro-1H-pyrazol-5-yl)-2-methyl-5,6-dihydropyrido[3,4-d]pyrimidine-7(8H)-carboxylate

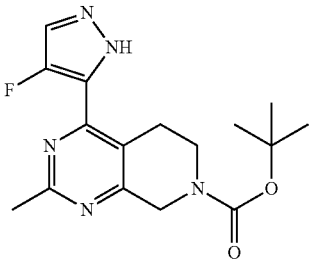 [SMILES: Cc1nc2c(c(-c3[nH]ncc3F)n1)CCN(C(=O)OC(C)(C)C)C2]

The title compound was prepared in a manner analogous to Intermediate 18 substituting 5-tributylstannyl-4-fluoropyrazole for 2-tri-n-butylstannylpyridine and omitting the deprotection. MS (ESI): mass calcd. for $C_{16}H_{20}FN_5O_2$; 333.4; m/z found, 334.2 [M+H]⁺.

Example 35

7-{[2-Chloro-3-(trifluoromethyl)phenyl]carbonyl}-4-(4-fluoro-1H-pyrazol-5-yl)-2-methyl-5,6,7,8-tetrahydropyrido[3,4-d]pyrimidine

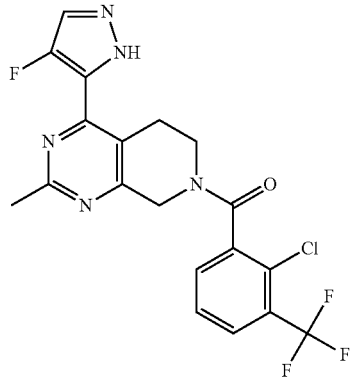 [SMILES: Cc1nc2c(c(-c3[nH]ncc3F)n1)CCN(C(=O)c1cccc(C(F)(F)F)c1Cl)C2]

The title compound was prepared in a manner analogous to Intermediate 20 substituting Intermediate 21 for Intermediate 19. MS (ESI): mass calcd. for $C_{19}H_{14}ClF_4N_5O$, 439.8; m/z found, 440.1 [M+H]⁺. ¹H NMR (500 MHz, DMSO-d₆) δ 8.02-7.93 (m, 2H), 7.86-7.76 (m, 1H), 7.72-7.64 (m, 1H), 4.97-4.72 (m, 1H), 4.42-4.27 (m, 1H), 4.05-3.87 (m, 1H), 3.52-3.37 (m, 2H), 3.14-3.04 (m, 1H), 2.66-2.51 (m, 3H).

Example 36

7-[(2,3-Dichlorophenyl)carbonyl]-4-(4-fluoro-1H-pyrazol-5-yl)-2-methyl-5,6,7,8-tetrahydropyrido[3,4-d]pyrimidine

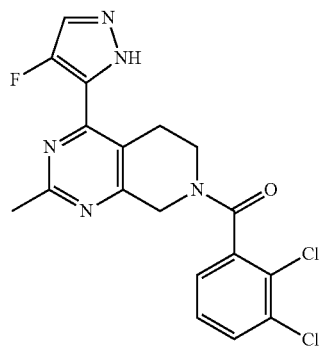 [SMILES: Cc1nc2c(c(-c3[nH]ncc3F)n1)CCN(C(=O)c1cccc(Cl)c1Cl)C2]

The title compound was prepared in a manner analogous to Intermediate 20 substituting Intermediate 21 for Intermediate 19 and 2,3-dichlorobenzoic acid for 2-chloro-3-(trifluoromethyl)benzoic acid. MS (ESI): mass calcd. for $C_{18}H_{14}Cl_2FN_5O$, 405.1; m/z found, 406.1 [M+H]⁺. ¹H NMR (500 MHz, DMSO-d₆) δ 8.01-7.92 (m, 1H), 7.78-7.71 (m, 1H), 7.52-7.41 (m, 2H), 4.95-4.72 (m, 1H), 4.42-4.25 (m, 1H), 4.07-3.81 (m, 1H), 3.17-2.91 (m, 3H), 2.64-2.52 (m, 3H).

Intermediate 22: tert-butyl 4-(thiazol-2-yl)-5,6-dihydropyrido[3,4-d]pyrimidine-7(8H)-carboxylate

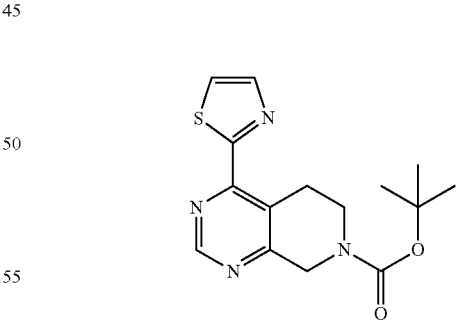

The title compound was prepared in a manner analogous to Intermediate 18 substituting Intermediate 2 for Intermediate 11 and 2-tributylstannylthiazole for 2-tri-n-butylstannylpyridine. MS (ESI): mass calcd. for $C_{15}H_{18}N_4O_2S$, 318.4; m/z found 319.1 [M+H]⁺.

Example 37

7-{[2-Chloro-3-(trifluoromethyl)phenyl]carbonyl}-4-(1,3-thiazol-2-yl)-5,6,7,8-tetrahydropyrido[3,4-d]pyrimidine

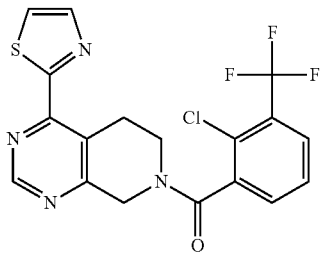 [SMILES: O=C(c1cccc(C(F)(F)F)c1Cl)N1CCc2c(ncnc2-c2nccs2)C1]

The title compound was prepared in a manner analogous to Intermediate 20 substituting Intermediate 22 for Intermediate 19. MS (ESI): mass calcd. for $C_{18}H_{12}ClF_3N_4OS$, 424.8; m/z found, 425.1 [M+H]$^+$. $^1$H NMR (500 MHz, CDCl$_3$) δ 9.11-8.94 (m, 1H), 8.09-7.95 (m, 1H), 7.82-7.73 (m, 1H), 7.61-7.42 (m, 3H), 5.26-4.94 (m, 1H), 4.63-4.40 (m, 1H), 4.24-4.04 (m, 1H), 3.74-3.38 (m, 3H).

Example 38

7-[(2,3-Dichlorophenyl)carbonyl]-4-(1,3-thiazol-2-yl)-5,6,7,8-tetrahydropyrido[3,4-d]pyrimidine

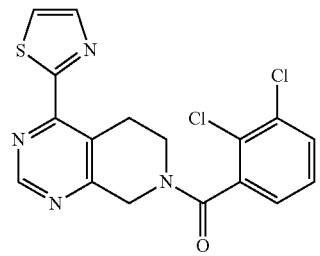 [SMILES: O=C(c1cccc(Cl)c1Cl)N1CCc2c(ncnc2-c2nccs2)C1]

The title compound was prepared in a manner analogous to Intermediate 20 substituting Intermediate 22 for Intermediate 19 and 2,3-dichlorobenzoic acid for 2-chloro-3-(trifluoromethyl)benzoic acid. MS (ESI): mass calcd. for $C_{17}H_{12}Cl_2N_4OS$, 390.0; m/z found, 391.1 [M+H]$^+$. $^1$H NMR (500 MHz, CDCl$_3$) δ 9.08-8.93 (m, 1H), 8.08-7.97 (m, 1H), 7.60-7.50 (m, 2H), 7.35-7.21 (m, 2H), 5.20-4.96 (m, 1H), 4.63-4.43 (m, 1H), 4.16-4.09 (m, 1H), 3.68-3.51 (m, 3H).

Intermediate 23: tert-butyl 2-methyl-4-(4-(trifluoromethyl)-1H-pyrazol-5-yl)-5,6-dihydropyrido[3,4-d]pyrimidine-7(8H)-carboxylate

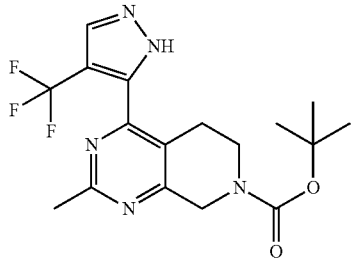 [SMILES: Cc1nc2c(c(-c3[nH]ncc3C(F)(F)F)n1)CCN(C(=O)OC(C)(C)C)C2]

The title compound was prepared in a manner analogous to Intermediate 18 substituting 4-(trifluoromethyl)-5-(tributylstannyl)pyrazole for 2-tri-n-butylstannylpyridine. MS (ESI): mass calcd. for $C_{17}H_{20}F_3N_5O_2$, 383.4; m/z found 384.2[M+H]$^+$.

Example 39

7-{[2-Chloro-3-(trifluoromethyl)phenyl]carbonyl}-2-methyl-4-[4-(trifluoromethyl)-1H-pyrazol-5-yl]-5,6,7,8-tetrahydropyrido[3,4-d]pyrimidine

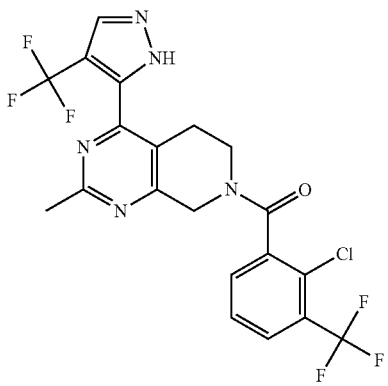 [SMILES: Cc1nc2c(c(-c3[nH]ncc3C(F)(F)F)n1)CCN(C(=O)c1cccc(C(F)(F)F)c1Cl)C2]

The title compound was prepared in a manner analogous to Intermediate 20 substituting Intermediate 23 for Intermediate 19. MS (ESI): mass calcd. for $C_{20}H_{14}ClF_6N_5O$, 489.8; m/z found, 491.1 [M+H]$^+$. $^1$H NMR (400 MHz, CDCl$_3$) δ 8.01-7.95 (m, 1H), 7.81-7.76 (m, 1H), 7.55-7.45 (m, 2H), 5.14-4.91 (m, 1H), 4.60-4.39 (m, 1H), 4.29-4.13 (m, 1H), 4.05-3.89 (m, 1H), 3.56-3.40 (m, 1H), 3.24-3.15 (t, J=5.9 Hz, 1H), 3.07-2.88 (m, 1H), 2.80-2.63 (m, 3H).

Example 40

7-[(2,3-Dichlorophenyl)carbonyl]-2-methyl-4-[4-(trifluoromethyl)-1H-pyrazol-5-yl]-5,6,7,8-tetrahydropyrido[3,4-d]pyrimidine

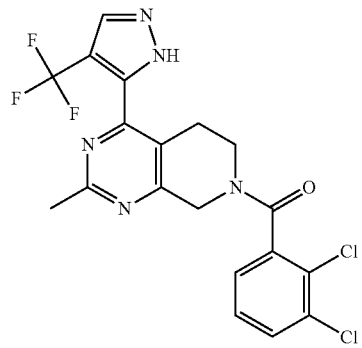 [SMILES: Cc1nc2c(c(-c3[nH]ncc3C(F)(F)F)n1)CCN(C(=O)c1cccc(Cl)c1Cl)C2]

The title compound was prepared in a manner analogous to Intermediate 20 substituting Intermediate 23 for Intermediate 19 and 2,3-dichlorobenzoic acid for 2-chloro-3-(trifluoromethyl)benzoic acid. MS (ESI): mass calcd. for $C_{19}H_{14}Cl_2F_3N_5O$, 455.05; m/z found, 456.1 [M+H]$^+$. $^1$H NMR (400 MHz, CDCl$_3$) δ 8.01-7.95 (m, 1H), 7.56-7.51 (m, 1H), 7.34-7.28 (m, 1H), 7.26-7.21 (m, 1H), 5.14-4.92 (m, 1H), 4.62-4.38 (m, 1H), 4.27-4.07 (m, 1H), 4.06-3.88 (m, 1H), 3.56-3.40 (m, 1H), 3.23-3.13 (t, J=6.0 Hz, 1H), 3.08-2.86 (m, 1H), 2.79-2.59 (m, 3H).

Intermediate 24: tert-butyl 4-(1-(tert-butoxycarbonyl)-1H-pyrrol-2-yl)-5,6-dihydropyrido[3,4-d]pyrimidine-7(8H)-carboxylate

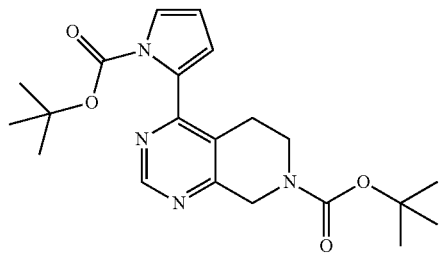 [SMILES: CC(C)(C)OC(=O)N1CCc2c(ncnc2-c2cccn2C(=O)OC(C)(C)C)C1]

The title compound was prepared in a manner analogous to Intermediate 12 substituting Intermediate 2 for Intermediate 11 and 1-(tert-butoxycarbonyl)pyrrole-2-boronic acid for phenylboronic acid. The deprotection was also omitted. MS (ESI): mass calcd. for $C_{21}H_{28}N_4O_4$, 400.5; m/z found, 401.2 [M+H]$^+$.

Example 41

7-[(2,3-Dichlorophenyl)carbonyl]-4-(1H-pyrrol-2-yl)-5,6,7,8-tetrahydropyrido[3,4-d]pyrimidine

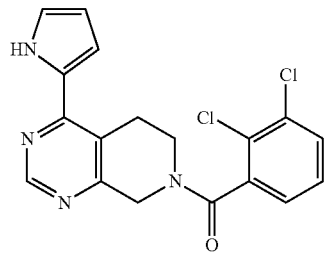 [SMILES: O=C(c1cccc(Cl)c1Cl)N1CCc2c(ncnc2-c2ccc[nH]2)C1]

The title compound was prepared in a manner analogous to Intermediate 20 substituting Intermediate 24 for Intermediate 19 and 2,3-dichlorobenzoic acid for 2-chloro-3-(trifluoromethyl)benzoic acid. MS (ESI): mass calcd. for $C_{18}H_{14}Cl_2N_4O$, 372.1; m/z found, 373.1 [M+H]$^+$. $^1$H NMR (500 MHz, CDCl$_3$) δ 10.19-9.94 (s, 1H), 8.95-8.75 (m, 1H), 7.59-7.48 (m, 1H), 7.37-7.28 (m, 1H), 7.28-7.19 (m, 1H), 7.11-6.99 (m, 1H), 6.89-6.66 (m, 1H), 6.46-6.32 (m, 1H), 5.09-4.90 (m, 1H), 4.54-4.34 (m, 1H), 4.22-4.07 (t, J=6.0 Hz, 1H), 3.65-3.51 (m, 1H), 3.21-3.09 (m, 1H), 3.06-2.87 (m, 1H).

Example 42

7-{[2-Chloro-3-(trifluoromethyl)phenyl]carbonyl}-4-(1H-pyrrol-2-yl)-5,6,7,8-tetrahydropyrido[3,4-d]pyrimidine

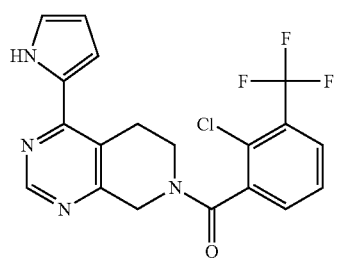 [SMILES: O=C(c1cccc(C(F)(F)F)c1Cl)N1CCc2c(ncnc2-c2ccc[nH]2)C1]

The title compound was prepared in a manner analogous to Intermediate 20 substituting Intermediate 24 for Intermediate 19. MS (ESI): mass calcd. for $C_{19}H_{14}ClF_3N_4O$, 406.8; m/z found, 407.1 [M+H]$^+$. $^1$H NMR (500 MHz, CDCl$_3$) δ 10.15-9.97 (s, 1H), 8.93-8.76 (m, 1H), 7.84-7.71 (m, 1H), 7.58-7.38 (m, 2H), 7.12-7.02 (m, 1H), 6.89-6.68 (m, 1H), 6.48-6.33 (m, 1H), 5.12-4.88 (m, 1H), 4.54-4.32 (m, 1H), 4.30-4.03 (m, 1H), 3.69-3.51 (m, 1H), 3.19-3.10 (m, 1H), 3.09-2.85 (m, 1H).

Intermediate 25: tert-butyl 4-(thiazol-4-yl)-5,6-dihydropyrido[3,4-d]pyrimidine-7(8H)-carboxylate

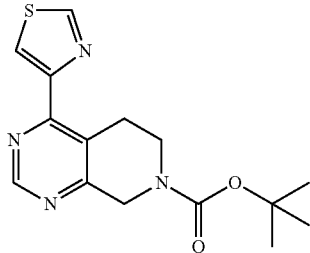 [SMILES: CC(C)(C)OC(=O)N1CCc2c(ncnc2-c2cscn2)C1]

The title compound was prepared in a manner analogous to Intermediate 12 substituting Intermediate 2 for Intermediate 11 and thiazole-4-boronic acid pinacol ester for phenylboronic acid. The deprotection was also omitted. MS (ESI): mass calcd. for $C_{15}H_{18}N_4O_2S$, 318.4; m/z found, 319.1 [M+H]$^+$.

Example 43

7-{[2-Chloro-3-(trifluoromethyl)phenyl]carbonyl}-4-(1,3-thiazol-4-yl)-5,6,7,8-tetrahydropyrido[3,4-d]pyrimidine

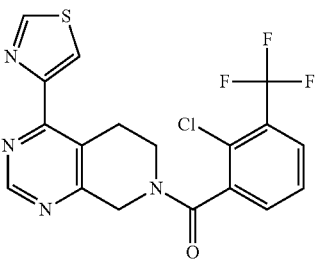 [SMILES: O=C(c1cccc(C(F)(F)F)c1Cl)N1CCc2c(ncnc2-c2cscn2)C1]

The title compound was prepared in a manner analogous to Intermediate 20 substituting Intermediate 25 for Intermediate 19. MS (ESI): mass calcd. for $C_{18}H_{12}ClF_3N_4OS$, 424.8; m/z found, 425.1 [M+H]$^+$. $^1$H NMR (400 MHz, CDCl$_3$) δ 9.09-8.85 (m, 2H), 8.45-8.35 (m, 1H), 7.85-7.73 (m, 1H), 7.59-7.43 (m, 2H), 5.25-4.92 (m, 1H), 4.66-4.38 (m, 1H), 4.24-3.95 (m, 1H), 3.62-3.48 (m, 2H), 3.47-3.24 (m, 1H).

Example 44

7-{[2-Chloro-3-(trifluoromethyl)phenyl]carbonyl}-2-methyl-4-(1,3-thiazol-4-yl)-5,6,7,8-tetrahydropyrido[3,4-d]pyrimidine

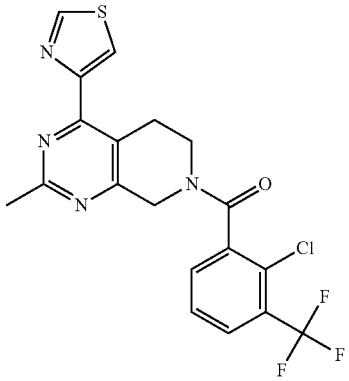 [SMILES: Cc1nc2c(c(-c3cscn3)n1)CCN(C(=O)c1cccc(C(F)(F)F)c1Cl)C2]

The title compound was prepared in a manner analogous to Example 43 substituting intermediate 11 for Intermediate 2 in the synthesis of Intermediate 25. MS (ESI): mass calcd. for $C_{19}H_{14}ClF_3N_4OS$, 438.9; m/z found, 439.1 [M+H]$^+$. $^1$H NMR (500 MHz, MeOD) δ 9.17-9.05 (m, 1H), 8.47-8.39 (m, 1H), 7.95-7.90 (m, 1H), 7.75-7.60 (m, 2H), 5.10-4.87 (m, 1H), 4.46 (s, 1H), 4.20-3.95 (m, 1H), 3.58-3.48 (m, 1H), 3.41 (t, J=5.9 Hz, 1H), 3.29-3.24 (m, 1H), 2.74-2.56 (m, 3H).

Example 45

7-{[2-Chloro-3-(trifluoromethyl)phenyl]carbonyl}-2-methyl-4-(1H-pyrrol-2-yl)-5,6,7,8-tetrahydropyrido[3,4-d]pyrimidine

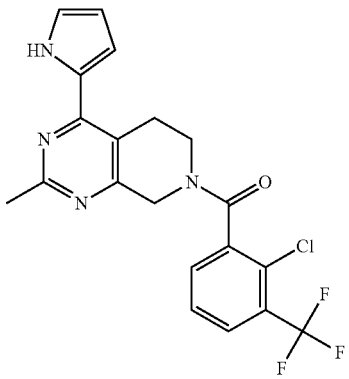 [SMILES: Cc1nc2c(c(-c3ccc[nH]3)n1)CCN(C(=O)c1cccc(C(F)(F)F)c1Cl)C2]

The title compound was prepared in a manner analogous to Example 42 substituting Intermediate 11 for Intermediate 2 in the synthesis of Intermediate 24. MS (ESI): mass calcd. for $C_{20}H_{16}ClF_3N_4O$, 420.8; m/z found, 421.1 [M+H]$^+$. $^1$H NMR (400 MHz, CDCl$_3$) δ 7.84-7.72 (m, 1H), 7.57-7.41 (m, 2H), 7.08-7.00 (m, 1H), 6.85-6.66 (m, 1H), 6.45-6.31 (m, 1H), 5.08-4.84 (m, 1H), 4.51-4.29 (m, 1H), 4.28-3.97 (m, 1H), 3.67-3.48 (m, 1H), 3.17-3.03 (m, 1H), 2.72-2.52 (m, 3H), 2.07-1.93 (m, 1H).

Intermediate 26: tert-butyl 4-(3,5-dimethylisoxazol-4-yl)-2-methyl-5,6-dihydropyrido[3,4-d]pyrimidine-7(8H)-carboxylate

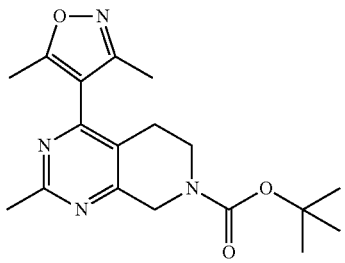 [SMILES: Cc1nc2c(c(-c3c(C)noc3C)n1)CCN(C(=O)OC(C)(C)C)C2]

The title compound was prepared in a manner analogous to Intermediate 12 substituting 3,5-dimethylisoxazole-4-boronic acid for phenylboronic acid and omitting the deprotection step. MS (ESI): mass calcd. for $C_{18}H_{24}N_4O_3$, 344.4; m/z found, 345.2 [M+H]$^+$.

Example 46

7-{[2-Chloro-3-(trifluoromethyl)phenyl]carbonyl}-4-(3,5-dimethylisoxazol-4-yl)-2-methyl-5,6,7,8-tetrahydropyrido[3,4-d]pyrimidine

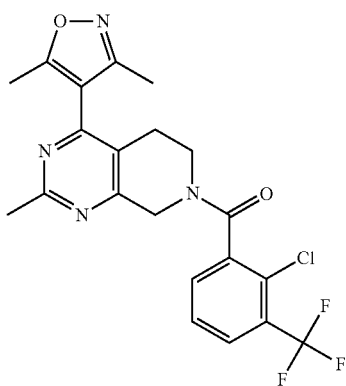 [SMILES: Cc1nc2c(c(-c3c(C)noc3C)n1)CCN(C(=O)c1cccc(C(F)(F)F)c1Cl)C2]

The title compound was prepared in a manner analogous to Intermediate 20 substituting Intermediate 26 for Intermediate 19. MS (ESI): mass calcd. for $C_{21}H_{18}ClF_3N_4O_2$, 450.8; m/z found, 451.2 [M+H]$^+$. $^1$H NMR (500 MHz, CDCl$_3$) δ 7.83-7.75 (m, 1H), 7.57-7.45 (m, 2H), 5.17-4.91 (m, 1H), 4.66-4.34 (m, 1H), 4.10-3.96 (m, 1H), 3.78-3.47 (m, 1H), 3.47-3.09 (m, 1H), 2.79-2.63 (m, 4H), 2.35 (d, J=19.4 Hz, 3H), 2.22 (d, J=16.3 Hz, 3H).

Intermediate 27: (4-((3H-[1,2,3]triazolo[4,5-b]pyridin-3-yl)oxy)-2-methyl-5,6-dihydropyrido[3,4-d]pyrimidin-7(8H)-yl)(2-chloro-3-(trifluoromethyl)phenyl)methanone

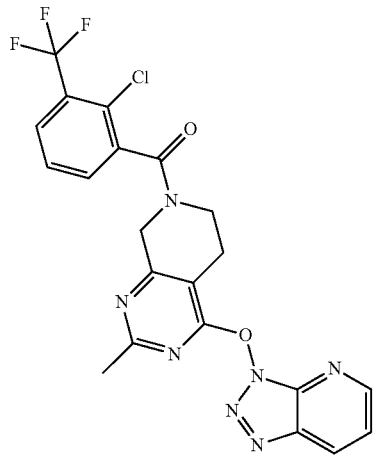 [SMILES: Cc1nc2c(c(On3nnc4cccnc43)n1)CCN(C(=O)c1cccc(C(F)(F)F)c1Cl)C2]

TFA (1.5 mL) was added to a solution of Intermediate 11 (375 mg, 1.32 mmol) in DCM (4 mL). The reaction was stirred at room temperature for 2 h and then neutralized with sat. NaHCO$_3$. The aqueous layer was extracted with DCM (3×) and the combined organic extracts were dried over MgSO$_4$, filtered and concentrated in vacuo. This residue was dissolved in DCM (3 mL) and 2-chloro-3-(trifluoromethyl) benzoic acid (296 mg, 1.32 mmol), TEA (0.367 mL, 2.64 mmol) and HATU (502 mg, 1.32 mmol) were added. The reaction was stirred overnight at room temperature. The crude mixture was purified directly using silica gel chromatography eluted with hexanes/EtOAc to afford the title compound as colorless oil. MS (ESI) mass calcd. $C_{21}H_{15}ClF_3N_7O_2$, 489.8; m/z found 490.1 [M+H]$^+$.

Example 47

7-{[2-Chloro-3-(trifluoromethyl)phenyl]carbonyl}-2-methyl-4-(2H-1,2,3-triazol-2-yl)-5,6,7,8-tetrahydropyrido[3,4-d]pyrimidine

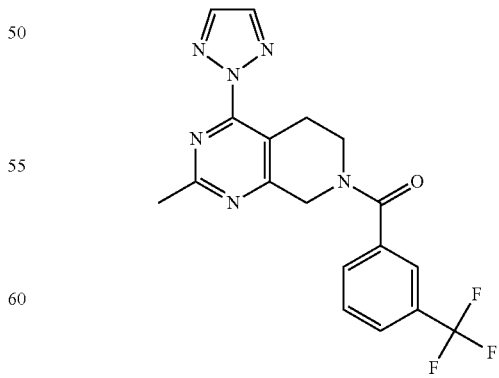

The title compound was prepared in a manner analogous to Example 22 substituting 1H-1,2,3-triazole for pyrazole and Intermediate 27 for Intermediate 2 in Example 22, step a. MS (ESI): mass calcd. for $C_{18}H_{14}ClF_3N_6O$, 422.8; m/z found, 423.1 [M+H]$^+$. $^1$H NMR (500 MHz, MeOD) δ 3.60-3.48 (m, 1H), 3.38-3.32 (m, 1H), 3.25-3.16 (m, 1H), 2.78-2.61 (m, 3H), 4.20-3.98 (m, 1H), 8.16-8.08 (m, 2H), 7.96-7.91 (m, 1H), 7.77-7.69 (m, 1H), 7.68-7.62 (m, 1H), 5.17-4.90 (m, 2H).

Example 48

7-{[2-Chloro-3-(trifluoromethyl)phenyl]carbonyl}-2-methyl-4-(1H-1,2,3-triazol-1-yl)-5,6,7,8-tetrahydropyrido[3,4-d]pyrimidine

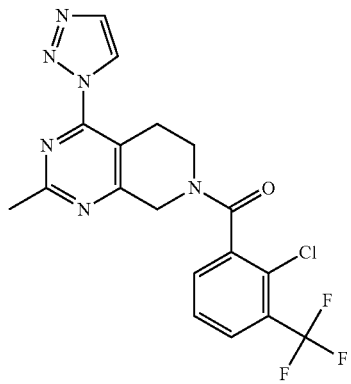 [SMILES: Cc1nc2c(c(-n3ccnn3)n1)CCN(C(=O)c1cccc(C(F)(F)F)c1Cl)C2]

The title compound was prepared in a manner analogous to Example 22 substituting 1H-1,2,3-triazole for pyrazole and Intermediate 27 for Intermediate 2 in Example 22, step a. MS (ESI): mass calcd. for $C_{18}H_{14}ClF_3N_6O$, 422.8; m/z found, 423.1 [M+H]$^+$. $^1$H NMR (500 MHz, MeOD) δ 8.83-8.79 (m, 1H), 7.95-7.90 (m, 2H), 7.77-7.61 (m, 2H), 5.20-4.91 (m, 2H), 4.22-4.00 (m, 1H), 3.63-3.52 (m, 1H), 3.44-3.36 (m, 1H), 3.29-3.19 (m, 1H), 2.77-2.62 (m, 3H).

Example 49

7-{[2-Chloro-3-(trifluoromethyl)phenyl]carbonyl}-4-isoxazol-4-yl-2-methyl-5,6,7,8-tetrahydropyrido[3,4-d]pyrimidine

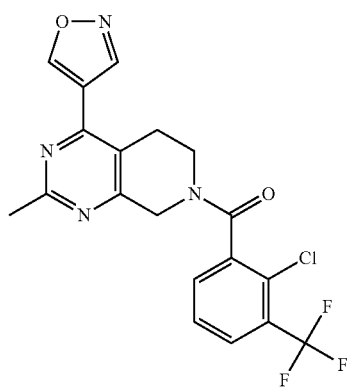 [SMILES: Cc1nc2c(c(-c3cnoc3)n1)CCN(C(=O)c1cccc(C(F)(F)F)c1Cl)C2]

The title compound was prepared in a manner analogous to Example 46 substituting 4-isoxazoleboronic acid pinacol ester for 3,5-dimethylisoxazole-4-boronic acid in the synthesis of Intermediate 26. MS (ESI): mass calcd. for $C_{19}H_{14}ClF_3N_4O_2$, 422.8; m/z found, 423.1 [M+H]$^+$. $^1$H NMR (500 MHz, MeOD) δ 9.43-9.28 (m, 1H), 9.08-9.00 (m, 1H), 7.97-7.90 (m, 1H), 7.77-7.60 (m, 2H), 5.14-5.03 (m, 1H), 4.47-4.39 (s, 1H), 4.29-4.03 (m, 1H), 3.65-3.55 (m, 1H), 3.16-3.04 (m, 1H), 3.03-2.89 (m, 1H), 2.72-2.57 (m, 3H).

Example 50

7-{[2-Chloro-3-(trifluoromethyl)phenyl]carbonyl}-4-(3,5-dimethylisoxazol-4-yl)-5,6,7,8-tetrahydropyrido[3,4-d]pyrimidine

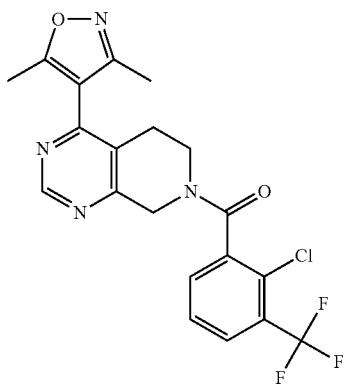 [SMILES: Cc1noc(C)c1-c1ncnc2c1CCN(C(=O)c1cccc(C(F)(F)F)c1Cl)C2]

The title compound was prepared in a manner analogous to Example 43 substituting 3,5-dimethylisoxazole-4-boronic acid for thiazole-4-boronic acid pinacol ester in the synthesis of Intermediate 25. MS (ESI): mass calcd. for $C_{20}H_{16}ClF_3N_4O_2$, 436.8; m/z found, 437.1 [M+H]$^+$. $^1$H NMR (500 MHz, MeOD) δ 9.09-8.96 (m, 1H), 7.96-7.88 (m, 1H), 7.76-7.69 (m, 1H), 7.69-7.61 (m, 1H), 5.16-4.90 (m, 1H), 4.60-4.45 (m, 1H), 4.18-3.96 (m, 1H), 3.65-3.48 (m, 1H), 2.93-2.81 (m, 1H), 2.77-2.66 (m, 1H), 2.41-2.30 (m, 3H), 2.26-2.12 (m, 3H).

Example 51

7-{[2-Fluoro-3-(trifluoromethyl)phenyl]carbonyl}-2-methyl-4-(1H-pyrazol-5-yl)-5,6,7,8-tetrahydropyrido[3,4-d]pyrimidine

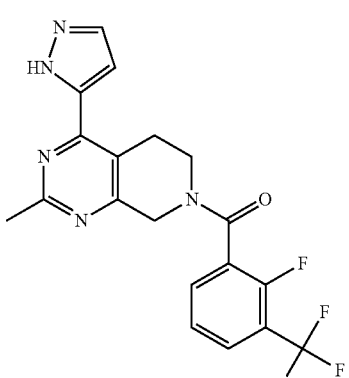

The title compound was prepared in a manner analogous to Example 33 substituting 2-fluoro-3-(trifluoromethyl)benzoic acid for 2-chloro-3-(trifluoromethyl)benzoic acid in the synthesis of Intermediate 20. MS (ESI): mass calcd. for $C_{19}H_{15}F_4N_5O$, 405.4; m/z found, 406.2 [M+H]$^+$. $^1$H NMR (500 MHz, DMSO-d$_6$) δ 7.98-7.80 (m, 3H), 7.59-7.49 (m, 1H), 6.97 (s, 1H), 4.92-4.76 (m, 1H), 4.55-4.41 (m, 1H), 4.06-3.91 (m, 1H), 3.56 (t, J=5.7 Hz, 1H), 3.27-3.09 (m, 2H), 2.67-2.52 (m, 3H).

Example 52

2-Methyl-7-{[2-methyl-3-(trifluoromethyl)phenyl]carbonyl}-4-(1H-pyrazol-5-yl)-5,6,7,8-tetrahydropyrido[3,4-d]pyrimidine

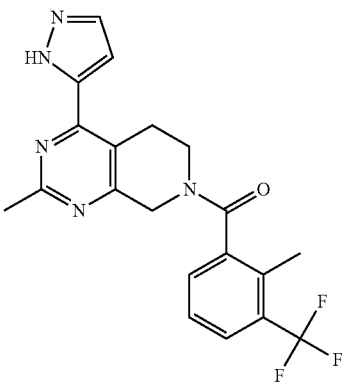 [SMILES: Cc1nc2c(c(-c3ccn[nH]3)n1)CCN(C(=O)c1cccc(C(F)(F)F)c1C)C2]

The title compound was prepared in a manner analogous to Example 33 substituting 2-methyl-3-(trifluoromethyl)benzoic acid for 2-chloro-3-(trifluoromethyl)benzoic acid in the synthesis of Intermediate 20. MS (ESI): mass calcd. for $C_{20}H_{18}F_3N_5O$, 401.4; m/z found, 402.2 [M+H]$^+$. $^1$H NMR (500 MHz, CDCl$_3$) δ 7.75-7.64 (m, 2H), 7.46-7.32 (m, 2H), 6.95-6.84 (m, 1H), 5.20-4.83 (m, 1H), 4.48-4.34 (m, 1H), 4.23-4.05 (m, 1H), 3.62-3.42 (m, 1H), 3.32-3.16 (m, 1H), 3.12-2.98 (m, 1H), 2.70 (d, J=47.3 Hz, 3H), 2.49-2.29 (m, 3H).

Example 53

7-[(2,4-Dichloro-3-fluorophenyl)carbonyl]-2-methyl-4-(1H-pyrazol-5-yl)-5,6,7,8-tetrahydropyrido[3,4-d]pyrimidine

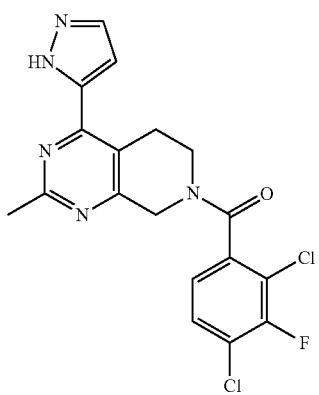 [SMILES: Cc1nc2c(c(-c3ccn[nH]3)n1)CCN(C(=O)c1ccc(Cl)c(F)c1Cl)C2]

The title compound was prepared in a manner analogous to Example 33 substituting 2,4-dichloro-3-fluorobenzoic acid for 2-chloro-3-(trifluoromethyl)benzoic acid in the synthesis of Intermediate 20. MS (ESI): mass calcd. for $C_{18}H_{14}Cl_2FN_5O$, 405.1; m/z found, 406.1 [M+H]$^+$. $^1$H NMR (500 MHz, CDCl$_3$) δ 7.77-7.66 (m, 1H), 7.47-7.35 (m, 1H), 7.16-7.06 (m, 1H), 6.97-6.80 (m, 1H), 5.12-4.90 (m, 1H), 4.59-4.34 (m, 1H), 4.20-4.00 (m, 1H), 3.65-3.47 (m, 1H), 3.35-2.99 (m, 2H), 2.80-2.59 (m, 3H).

Example 54

7-{[2-Chloro-3-(trifluoromethyl)phenyl]carbonyl}-N,N-dimethyl-4-(1H-pyrazol-5-yl)-5,6,7,8-tetrahydropyrido[3,4-d]pyrimidin-2-amine

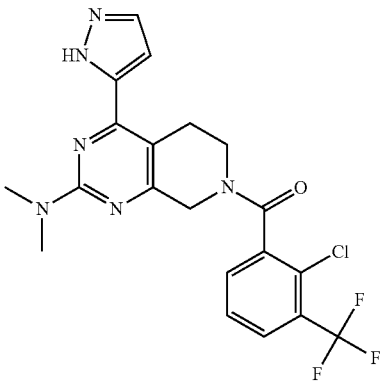 [SMILES: CN(C)c1nc2c(c(-c3ccn[nH]3)n1)CCN(C(=O)c1cccc(C(F)(F)F)c1Cl)C2]

The title compound was prepared in a manner analogous to Example 33 substituting Intermediate 8 for Intermediate 11 in the synthesis of Intermediate 19. MS (ESI): mass calcd. for $C_{20}H_{18}ClF_3N_6O$, 450.8; m/z found, 451.2 [M+H]$^+$. $^1$H NMR (500 MHz, CDCl$_3$) δ 7.97 (d, J=7.8 Hz, 1H), 7.89-7.75 (m, 2H), 7.73-7.60 (m, 1H), 6.95 (s, 1H), 4.85-4.56 (m, 1H), 4.27-4.09 (m, 1H), 4.06-3.79 (m, 1H), 3.50-3.35 (m, 1H), 3.22-2.98 (m, 7H), 2.93-2.70 (m, 1H).

Intermediate 28: 7-benzyl-4-(1-(tetrahydro-2H-pyran-2-yl)-1H-pyrazol-5-yl)-5,6,7,8-tetrahydropyrido[3,4-d]pyrimidin-2-amine

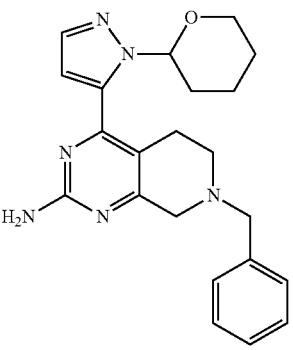 [SMILES: Nc1nc2c(c(-c3ccnn3C3CCCCO3)n1)CCN(Cc1ccccc1)C2]

The title compound was prepared in a manner analogous to Intermediate 16 substituting 1-(tetrahydropyran-2-yl)-1h- pyrazole-5-boronic acid pinacol ester for phenylboronic acid. MS (ESI): mass calcd. for $C_{22}H_{26}N_6O$, 390.5; m/z found, 391.2 $[M+H]^+$.

Intermediate 29: 4-(1-(tetrahydro-2H-pyran-2-yl)-1H-pyrazol-5-yl)-5,6,7,8-tetrahydropyrido[3,4-d]pyrimidin-2-amine

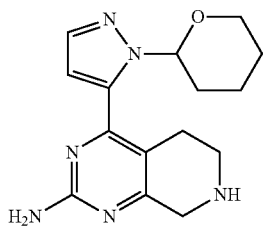 [SMILES: Nc1nc2c(c(-c3ccnn3C3CCCCO3)n1)CCNC2]

The title compound was prepared in a manner analogous to Intermediate 17 substituting Intermediate 28 for Intermediate 16. MS (ESI): mass calcd. for $C_{15}H_{20}N_6O$, 300.4; m/z found, 301.2 $[M+H]^+$.

Intermediate 30: (2-amino-4-(1-(tetrahydro-2H-pyran-2-yl)-1H-pyrazol-5-yl)-5,6-dihydropyrido[3,4-d]pyrimidin-7(8H)-yl)(2-chloro-3-(trifluoromethyl)phenyl)methanone

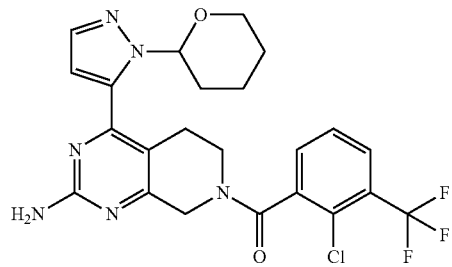 [SMILES: Nc1nc2c(c(-c3ccnn3C3CCCCO3)n1)CCN(C(=O)c1cccc(C(F)(F)F)c1Cl)C2]

The title compound was prepared in a manner analogous to Example 25 substituting Intermediate 29 for Intermediate 9. MS (ESI): mass calcd. for $C_{23}H_{22}ClF_3N_6O_2$, 506.9; m/z found, 507.2 $[M+H]^+$.

Example 55

7-{[2-Chloro-3-(trifluoromethyl)phenyl]carbonyl}-4-(1H-pyrazol-5-yl)-5,6,7,8-tetrahydropyrido[3,4-d]pyrimidin-2-amine

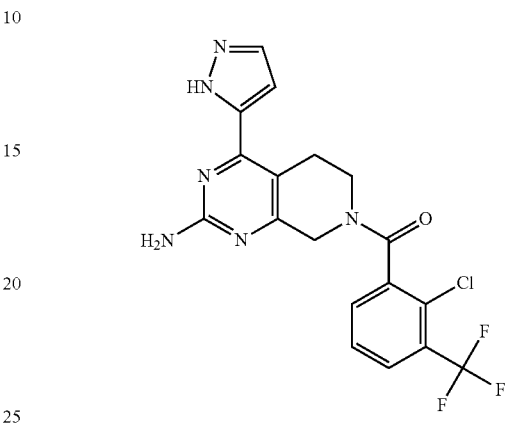

The title compound was prepared in a manner analogous to Example 33 substituting Intermediate 30 for Intermediate 19. MS (ESI): mass calcd. for $C_{18}H_{14}ClF_3N_6O$, 422.8; m/z found, 423.1 $[M+H]^+$. $^1$H NMR (500 MHz, CDCl$_3$) δ 7.86-7.74 (m, 1H), 7.70-7.60 (m, 1H), 7.59-7.43 (m, 2H), 6.83-6.72 (m, 1H), 4.99-4.68 (m, 1H), 4.40-4.18 (m, 1H), 4.16-3.95 (m, 1H), 3.63-3.44 (m, 2H), 3.18-2.86 (m, 2H).

Intermediate 31: ethyl 4-((1-phenylethyl)amino)pentanoate

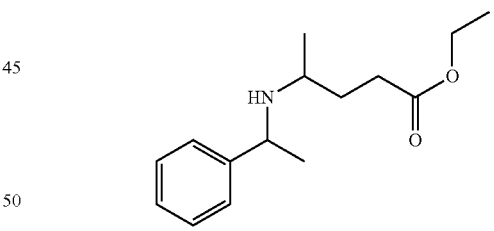

NaBH(OAc)$_3$ (5.97 g, 28.19 mmol) was added to a solution of ethyl levulinate (2 mL, 14.10 mmol) and DL-alpha-methylbenzylamine (1.85 mL, 14.10 mmol) in DCE (25 mL). The reaction was stirred at ambient temperature overnight. The reaction mixture was partitioned between sat. NaHCO$_3$ solution and DCM. The aqueous layer was extracted with DCM (3×) and the combined organic extracts were dried over MgSO$_4$ filtered and concentrated to isolate Intermediate 31 as a pale yellow oil (3.16 g, 90%). MS (ESI): mass calcd. for $C_{15}H_{23}NO_2$, 249.3; m/z found, 250.2 $[M+H]^+$.

Intermediate 32: ethyl 4-((2-ethoxy-2-oxoethyl)(1-phenylethyl)amino)pentanoate

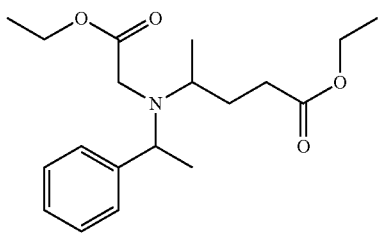 [SMILES: CCOC(=O)CCC(C)N(CC(=O)OCC)C(C)c1ccccc1]

NaBH(OAc)$_3$ (5.37 g, 25.34 mmol) was added to a solution of Intermediate 31 (3.16 g, 12.67 mmol) and glyoxylic acid ethyl ester (2.56 mL, 25.34 mmol) in DCE (25 mL). The reaction was stirred at ambient temperature overnight. The reaction mixture was partitioned between sat. NaHCO$_3$ solution and DCM. The aqueous layer was extracted with DCM (3×) and the combined organic extracts were dried over MgSO$_4$ filtered and concentrated to isolate Intermediate 32 as a pale yellow oil (4.22 g, 99%). MS (ESI): mass calcd. for C$_{19}$H$_{29}$NO$_4$, 335.4; m/z found, 336.2 [M+H]$^+$.

Intermediate 33: ethyl 2-methyl-5-oxo-1-(1-phenylethyl)piperidine-4-carboxylate

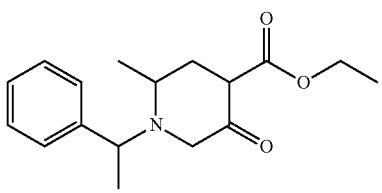 [SMILES: CCOC(=O)C1CC(C)N(C(C)c2ccccc2)CC1=O]

KOtBu (11.26 g, 100 mmol) was added to a solution of Intermediate 32 (20.2 g, 60 mmol) in toluene (100 mL). The reaction was stirred at ambient temperature for 3 hours and then concentrated in vacuo. The crude mixture was partitioned between DCM and sat NH$_4$Cl solution and the aqueous layer was extracted with DCM (3×). The combined organic extracts were washed with sat. NaCl solution and H$_2$O and then dried over MgSO$_4$. Celite was added and the organic extracts were filtered and concentrated in vacuo. The crude material was purified by chromatography on SiO$_2$ and eluted with EtOAc/hexane to afford Intermediate 33 (11.1 g, 64%). MS (ESI): mass calcd. for C$_{17}$H$_{23}$NO$_3$, 289.4; m/z found, 290.2 [M+H]$^+$.

Intermediate 34: 2,6-dimethyl-7-(1-phenylethyl)-5,6,7,8-tetrahydropyrido[3,4-d]pyrimidin-4-ol

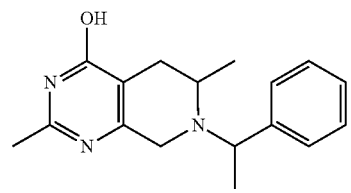 [SMILES: Cc1nc(O)c2c(n1)CN(C(C)c1ccccc1)C(C)C2]

The title compound was prepared in a manner analogous to Intermediate 10 substituting Intermediate 33 for ethyl N—BOC-3-oxopiperidine-4-carboxylate. MS (ESI): mass calcd. for C$_{17}$H$_{21}$N$_3$O 283.4; m/z found, 284.2 [M+H]$^+$.

Intermediate 35: tert-butyl 4-hydroxy-2,6-dimethyl-5,6-dihydropyrido[3,4-d]pyrimidine-7(8H)-carboxylate

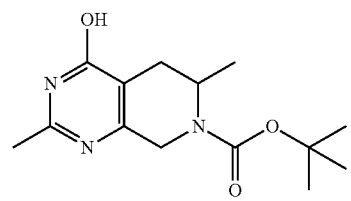 [SMILES: Cc1nc(O)c2c(n1)CN(C(=O)OC(C)(C)C)C(C)C2]

Intermediate 34 (1.1 g, 3.88 mmol) was dissolved in MeOH (15 mL) and THF (15 mL). Ammonium formate (1.24 g, 19.4 mmol), BOC anhydride (1.27 g, 5.82 mmol) and 10% Pd/C (413 mg, 0.388 mmol) were added and the reaction was heated to reflux overnight. The crude reaction was filtered through a pad of celite and the filtrate was concentrated in vacuo. Intermediate 35 was obtained by purification on SiO$_2$ eluting with EtOAc/hexane (890 mg, 82%). MS (ESI): mass calcd. for C$_{14}$H$_{21}$N$_3$O$_3$, 279.3; m/z found, 280.2 [M+H]$^+$.

Intermediate 36: tert-butyl 4-chloro-2,6-dimethyl-5,6-dihydropyrido[3,4-d]pyrimidine-7(8H)-carboxylate

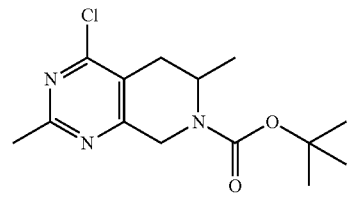 [SMILES: Cc1nc(Cl)c2c(n1)CN(C(=O)OC(C)(C)C)C(C)C2]

The title compound was prepared in a manner analogous to Intermediate 11 substituting Intermediate 35 for Intermediate 10. MS (ESI): mass calcd. for C$_{14}$H$_{20}$ClN$_3$O$_2$ 297.8; m/z found, 298.1 [M+H]$^+$.

Example 56

7-{[2-Chloro-3-(trifluoromethyl)phenyl]carbonyl}-2,6-dimethyl-4-(1H-pyrazol-5-yl)-5,6,7,8-tetrahydropyrido[3,4-d]pyrimidine

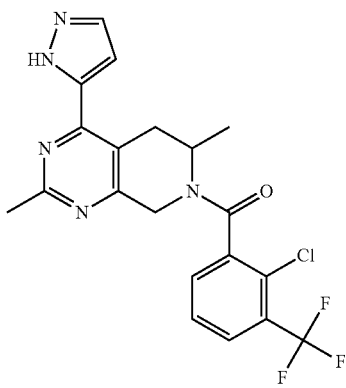 [SMILES: Cc1nc2c(c(-c3ccn[nH]3)n1)CC(C)N(C(=O)c1cccc(C(F)(F)F)c1Cl)C2]

The title compound was prepared in a manner analogous to Example 33 substituting Intermediate 36 for Intermediate 11 in the synthesis of Intermediate 19. MS (ESI): mass calcd. for $C_{20}H_{17}ClF_3N_5O$, 435.8; m/z found, 436.1 [M+H]$^+$. $^1$H NMR (500 MHz, MeOD) δ 7.96-7.90 (m, 1H), 7.79-7.71 (m, 2H), 7.70-7.59 (m, 1H), 7.05-6.95 (s, 1H), 5.53-5.32 (m, 1H), 4.64-4.37 (m, 1H), 4.33-3.97 (m, 1H), 3.50-3.34 (m, 2H), 3.30-3.19 (s, 1H), 2.66-2.56 (m, 2H), 1.35-1.05 (m, 3H).

Intermediate 37: tert-butyl 4-chloro-2-cyclopropyl-5,6-dihydropyrido[3,4-d]pyrimidine-7(8H)-carboxylate

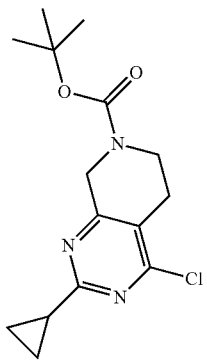 [SMILES: CC(C)(C)OC(=O)N1CCc2c(Cl)nc(C3CC3)nc2C1]

The title compound was prepared in a manner analogous to Intermediate 11 substituting cyclopropylcarbamidine hydrochloride for acetamidine hydrochloride in the synthesis of Intermediate 10. MS (ESI): mass calcd. for $C_{15}H_{20}ClN_3O_2$ 309.8; m/z found, 310.2 [M+H]$^+$. $^1$H NMR (500 MHz, CDCl$_3$) δ 4.54 (s, 2H), 3.69 (t, J=5.7 Hz, 2H), 2.79 (s, 2H), 2.23-2.10 (m, 1H), 1.49 (s, 9H), 1.16-0.99 (m, 4H).

Example 57

7-{[2-Chloro-3-(trifluoromethyl)phenyl]carbonyl}-2-cyclopropyl-4-(1H-pyrazol-5-yl)-5,6,7,8-tetrahydropyrido[3,4-d]pyrimidine

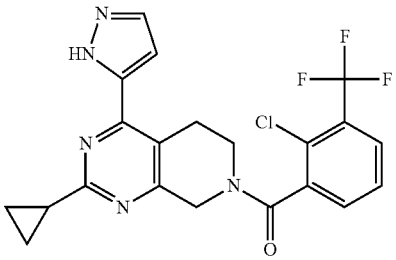 [SMILES: O=C(c1cccc(C(F)(F)F)c1Cl)N1CCc2c(nc(C3CC3)nc2-c2ccn[nH]2)C1]

The title compound was prepared in a manner analogous to Example 33 substituting Intermediate 37 for Intermediate 11 in the synthesis of Intermediate 19. MS (ESI): mass calcd. for $C_{21}H_{17}ClF_3N_5O$, 447.8; m/z found, 448.2 [M+H]$^+$. $^1$H NMR (500 MHz, CDCl$_3$) δ 7.82-7.75 (m, 1H), 7.74-7.65 (m, 1H), 7.56-7.43 (m, 2H), 6.89-6.79 (m, 1H), 5.13-4.84 (m, 1H), 4.54-4.31 (m, 1H), 4.27-3.98 (m, 2H), 3.65-3.45 (m, 1H), 3.26-2.94 (m, 2H), 2.33-2.08 (m, 1H), 1.29-1.00 (m, 4H).

Example 58

(6R*)-7-{[2-Chloro-3-(trifluoromethyl)phenyl]carbonyl}-2,6-dimethyl-4-(1H-pyrazol-5-yl)-5,6,7,8-tetrahydropyrido[3,4-d]pyrimidine

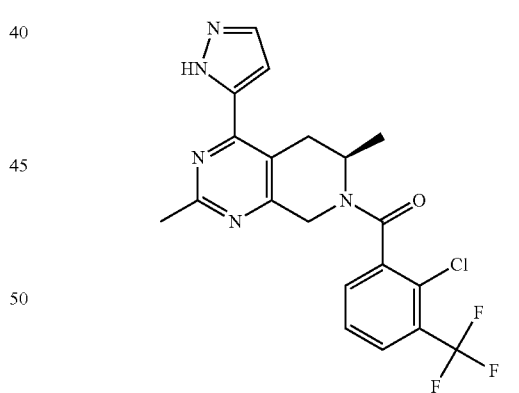

The title compound, absolute configuration unknown, was obtained as a single enantiomer by Chiral SFC purification of Example 56 performed using a CHIRALCEL OD-H (5 μm, 250×20 mm) column and a mobile phase of 70% CO$_2$, 30% MeOH. The enantiomeric purity was confirmed by analytical SFC using a CHIRALCEL OD-H (250×4.6 mm) and a mobile phase of 70% CO$_2$, 25% iPrOH containing 0.3% iPrNH$_2$ over 7 minutes. (100% single enantiomer, 3.66 min retention time). MS (ESI): mass calcd. for $C_{20}H_{17}ClF_3N_5O$, 435.8; m/z found, 436.2 [M+H]$^+$. $^1$H NMR (500 MHz, CDCl$_3$) δ 7.83-7.74 (m, 1H), 7.74-7.66 (m, 1H), 7.56-7.40 (m, 2H), 6.96-6.82 (m, 1H), 5.69-5.46 (m, 1H), 4.68-4.37 (m, 1H), 4.36-4.25 (m, 1H), 3.44-3.25 (m, 1H), 3.24-2.90 (m, 1H), 2.80-2.57 (m, 3H), 1.35-1.09 (m, 3H).

Example 59

(6S*)-7-{[2-Chloro-3-(trifluoromethyl)phenyl]carbonyl}-2,6-dimethyl-4-(1H-pyrazol-5-yl)-5,6,7,8-tetrahydropyrido[3,4-d]pyrimidine

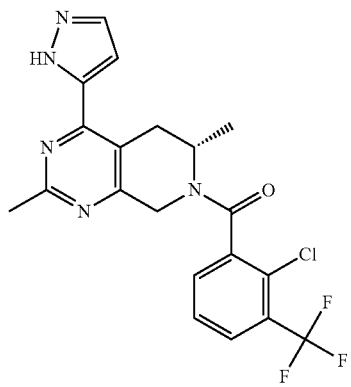 [SMILES: Cc1nc2c(c(-c3ccn[nH]3)n1)C[C@H](C)N(C(=O)c1cccc(C(F)(F)F)c1Cl)C2]

The title compound, absolute configuration unknown, was obtained as a single enantiomer by Chiral SFC purification of Example 56 performed using a CHIRALCEL OD-H (5 μm, 250×20 mm) column and a mobile phase of 70% CO$_2$, 30% MeOH. The enantiomeric purity was confirmed by analytical SFC using a CHIRALCEL OD-H (250×4.6 mm) and a mobile phase of 70% CO$_2$, 25% iPrOH containing 0.3% iPrNH$_2$ over 7 minutes. (99.1% single enantiomer, 4.55 min retention time). MS (ESI): mass calcd. for C$_{20}$H$_{17}$ClF$_3$N$_5$O, 435.1; m/z found, 435.9 [M+H]$^+$. $^1$H NMR (500 MHz, CDCl$_3$) δ 7.84-7.75 (m, 1H), 7.75-7.67 (m, 1H), 7.57-7.41 (m, 2H), 6.95-6.83 (m, 1H), 5.66-5.52 (m, 1H), 4.68-4.36 (m, 1H), 4.36-4.25 (m, 1H), 3.41-3.26 (m, 1H), 3.24-2.96 (m, 1H), 2.79-2.64 (m, 3H), 1.32-1.10 (m, 3H).

Intermediate 38: 7-benzyl-4-(1-(tetrahydro-2H-pyran-2-yl)-1H-pyrazol-5-yl)-2-(trifluoromethyl)-5,6,7,8-tetrahydropyrido[3,4-d]pyrimidine

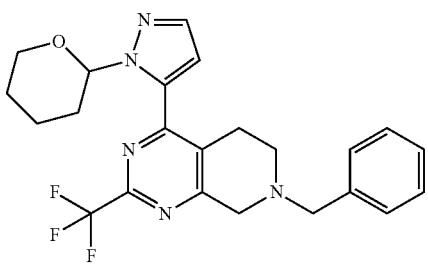 [SMILES: FC(F)(F)c1nc2c(c(-c3ccnn3C3CCCCO3)n1)CCN(Cc1ccccc1)C2]

The title compound was prepared in a manner analogous to Intermediate 12 substituting 7-benzyl-4-chloro-2-(trifluoromethyl)-5,6,7,8-tetrahydropyrido[3,4-d]pyrimidine for Intermediate 11 and 1-(tetrahydropyran-2-yl)-1h-pyrazole-5-boronic acid pinacol ester for phenylboronic acid. MS (ESI): mass calcd. for C$_{23}$H$_{24}$F$_3$N$_5$O, 443.2; m/z found, 444.2 [M+H]$^+$.

Intermediate 39: 4-(1-(tetrahydro-2H-pyran-2-yl)-1H-pyrazol-5-yl)-2-(trifluoromethyl)-5,6,7,8-tetrahydropyrido[3,4-d]pyrimidine

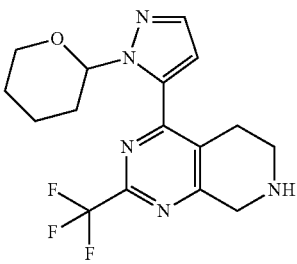 [SMILES: FC(F)(F)c1nc2c(c(-c3ccnn3C3CCCCO3)n1)CCNC2]

The title compound was prepared in a manner analogous to Intermediate 17 substituting Intermediate 38 for Intermediate 16. MS (ESI): mass calcd. for C$_{16}$H$_{18}$F$_3$N$_5$O, 353.3; m/z found, 354.2 [M+H]$^+$.

Intermediate 40: (2-chloro-3-(trifluoromethyl)phenyl)(4-(1-(tetrahydro-2H-pyran-2-yl)-1H-pyrazol-5-yl)-2-(trifluoromethyl)-5,6-dihydropyrido[3,4-d]pyrimidin-7(8H)-yl)methanone

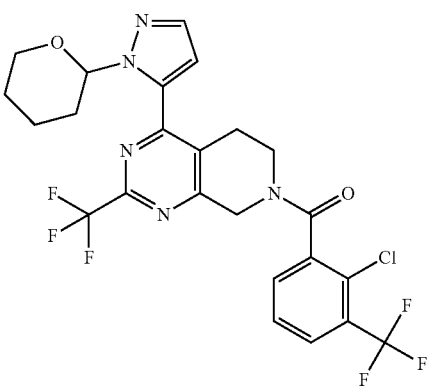 [SMILES: O=C(c1cccc(C(F)(F)F)c1Cl)N1CCc2c(nc(C(F)(F)F)nc2-c2ccnn2C2CCCCO2)C1]

The title compound was prepared in a manner analogous to Example 25 substituting Intermediate 39 for Intermediate 9. MS (ESI): mass calcd. for C$_{24}$H$_{20}$ClF$_6$N$_5$O$_2$, 559.1; m/z found, 476.1 [M-THP]$^+$. $^1$H NMR (500 MHz, CDCl$_3$) δ 7.89-7.77 (m, 1H), 7.74-7.62 (m, 1H), 7.57-7.45 (m, 2H), 6.72-6.53 (m, 1H), 6.09-5.93 (m, 1H), 5.45 (d, J=20.1 Hz, 1H), 4.95-4.83 (m, 1H), 4.76-4.51 (m, 1H), 3.87 (t, J=10.5 Hz, 1H), 3.72-3.51 (m, 1H), 3.51-3.34 (m, 1H), 3.24-3.02 (m, 1H), 3.01-2.87 (m, 1H), 2.51-2.33 (m, 1H), 2.25-2.03 (m, 2H), 1.74-1.48 (m, 3H).

Example 60

(4-(1H-pyrazol-5-yl)-2-(trifluoromethyl)-5,6-dihydropyrido[3,4-d]pyrimidin-7(8H)-yl)(2-chloro-3-(trifluoromethyl)phenyl)methanone

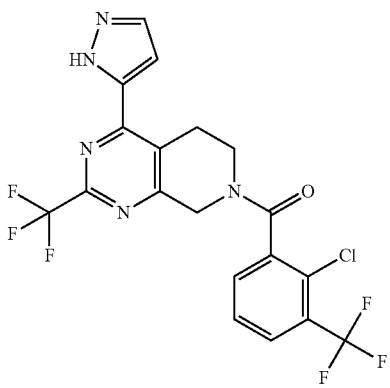 [SMILES: O=C(c1cccc(C(F)(F)F)c1Cl)N1CCc2c(nc(C(F)(F)F)nc2-c2ccn[nH]2)C1]

The title compound was prepared in a manner analogous to Example 33 substituting Intermediate 40 for Intermediate 20. MS (ESI): mass calcd. for $C_{19}H_{12}ClF_6N_5O$, 475.1; m/z found, 476.1 [M+H]$^+$. $^1$H NMR (400 MHz, MeOD) δ 7.96-7.89 (m, 1H), 7.79-7.60 (m, 3H), 7.19-7.12 (m, 1H), 5.23-4.95 (m, 2H), 4.57 (s, 1H), 4.26-4.07 (m, 1H), 3.67-3.54 (m, 2H).

Example 61

3-(2,6-dimethyl-4-(1H-pyrazol-5-yl)-5,6,7,8-tetrahydropyrido[3,4-d]pyrimidine-7-carbonyl)-2-methylbenzonitrile

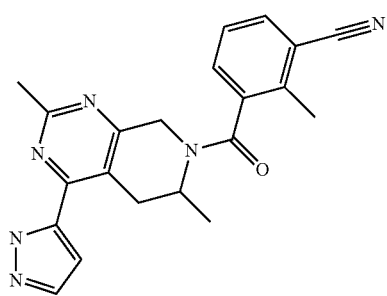 [SMILES: Cc1nc2c(c(-c3ccn[nH]3)n1)CC(C)N(C(=O)c1cccc(C#N)c1C)C2]

The title compound was prepared in a manner analogous to Example 74 substituting 3-cyano-2-methylbenzoic acid for 2-fluoro-3-(trifluoromethyl)benzoic acid in the synthesis of Intermediate 44. MS (ESI) mass calcd. $C_{21}H_{20}N_6O$, 372.2; m/z found 373.2 [M+H]$^+$. $^1$H NMR (400 MHz, CDCl$_3$) δ 11.17 (br s, 1H), 7.79-7.20 (m, 4H), 7.04-6.77 (m, 1H), 5.66-5.46 (m, 1H), 4.58-3.94 (m, 2H), 3.43-2.95 (m, 2H), 2.83-2.09 (m, 6H), 1.45-1.05 (m, 3H).

Example 62

(2-chloro-3-(trifluoromethyl)phenyl)(6-methyl-4-(1H-pyrazol-5-yl)-5,6-dihydropyrido[3,4-d]pyrimidin-7(8H)-yl)methanone

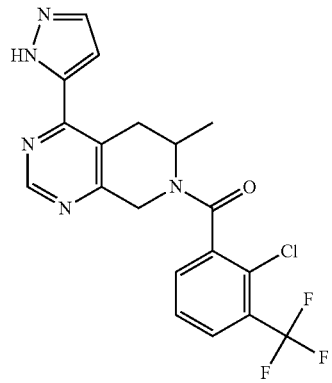 [SMILES: CC1Cc2c(ncnc2-c2ccn[nH]2)CN1C(=O)c1cccc(C(F)(F)F)c1Cl]

The title compound was prepared in a manner analogous to Example 56 substituting imidoformamide acetate for acetamidine hydrochloride in the synthesis of Intermediate 34. MS (ESI): mass calcd. for $C_{19}H_{15}ClF_3N_5O$, 421.1; m/z found, 422.1 [M+H]$^+$. $^1$H NMR (500 MHz, CDCl$_3$) δ 9.12-8.94 (m, 1H), 7.84-7.76 (m, 1H), 7.76-7.67 (m, 1H), 7.61-7.38 (m, 2H), 7.01-6.90 (m, 1H), 5.74-5.51 (m, 1H), 4.72-4.42 (m, 1H), 4.41-4.03 (m, 1H), 3.48-3.06 (m, 2H), 1.35-1.08 (m, 3H).

Example 63

(2-amino-6-methyl-4-(1H-pyrazol-5-yl)-5,6-dihydropyrido[3,4-d]pyrimidin-7(8H)-yl)(2-chloro-3-(trifluoromethyl)phenyl)methanone

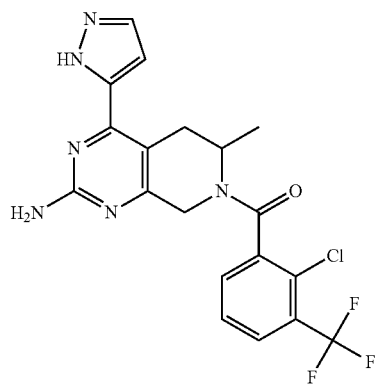 [SMILES: CC1Cc2c(nc(N)nc2-c2ccn[nH]2)CN1C(=O)c1cccc(C(F)(F)F)c1Cl]

The title compound was prepared in a manner analogous to Example 56 substituting guanidine carbonate for acetamidine hydrochloride in the synthesis of Intermediate 34. MS (ESI): mass calcd. for $C_{19}H_{16}ClF_3N_6O$, 436.1; m/z found, 437.1 [M+H]$^+$. $^1$H NMR (500 MHz, CDCl$_3$) δ 7.82-7.74 (m, 1H), 7.72-7.64 (m, 1H), 7.55-7.42 (m, 2H), 6.86-6.71 (m, 1H), 5.13-4.86 (m, 2H), 4.51-4.22 (m, 1H), 4.20-3.97 (m, 1H), 3.30-3.17 (m, 1H), 1.32-1.07 (m, 3H).

Example 64

(2-chloro-4-fluoro-3-(trifluoromethyl)phenyl)(2,6-dimethyl-4-(1H-pyrazol-5-yl)-5,6-dihydropyrido[3,4-d]pyrimidin-7(8H)-yl)methanone

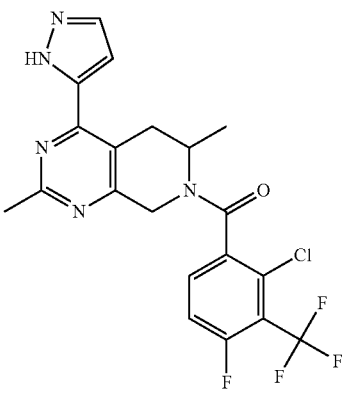

The title compound was prepared in a manner analogous to Example 56 substituting 2-chloro-4-fluoro-3-(trifluoromethyl)benzoic acid for 2-chloro-3-(trifluoromethyl)benzoic acid. MS (ESI): mass calcd. $C_{20}H_{16}ClF_4N_5O$, 453.1; m/z found, 454.1 [M+H]$^+$. $^1$H NMR (500 MHz, MeOD) δ 8.02-7.77 (m, 1H), 7.76-7.64 (m, 1H), 7.55-7.38 (m, 1H), 7.01 (s, 1H), 5.51-5.26 (m, 1H), 4.64-4.36 (m, 1H), 4.32-3.98 (m, 1H), 3.52-3.35 (m, 1H), 3.27-3.17 (m, 1H), 2.74-2.58 (m, 3H), 1.40-1.01 (m, 3H).

Example 65

(S*)-(2-chloro-4-fluoro-3-(trifluoromethyl)phenyl)(2,6-dimethyl-4-(1H-pyrazol-5-yl)-5,6-dihydropyrido[3,4-d]pyrimidin-7(8H)-yl)methanone

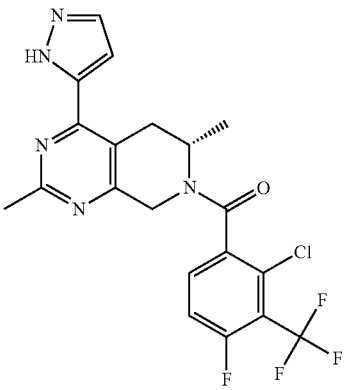 [SMILES: Cc1nc2c(c(-c3ccn[nH]3)n1)C[C@H](C)N(C(=O)c1ccc(F)c(C(F)(F)F)c1Cl)C2]

The title compound, absolute configuration unknown, was obtained as a single enantiomer by Chiral SFC purification of Example 64 performed using an irregular SiOH 15-40 μm, 300 g MERCK column and a mobile phase of 70% CO$_2$, 30% iPrOH. The enantiomeric purity was confirmed by analytical SFC using a CHIRALCEL OD-H (250×4.6 mm) and a mobile phase of 70% CO$_2$, 30% iPrOH containing 0.3% iPrNH$_2$ over 7 minutes. (100% single enantiomer, 3.20 min retention time). MS (ESI): mass calcd. $C_{20}H_{16}ClF_4N_5O$, 453.1; m/z found, 453.7 [M+H]$^+$. $^1$H NMR (400 MHz, CDCl$_3$) δ 7.75-7.67 (m, 1H), 7.55-7.40 (m, 1H), 7.25-7.14 (m, 1H), 6.94-6.82 (m, 1H), 5.68-5.43 (m, 1H), 4.70-4.34 (m, 1H), 4.36-3.99 (m, 1H), 3.43-3.24 (m, 1H), 3.23-2.97 (m, 1H), 2.81-2.60 (m, 3H), 1.32-1.07 (m, 3H).

Example 66

(R*)-(2-chloro-4-fluoro-3-(trifluoromethyl)phenyl)(2,6-dimethyl-4-(1H-pyrazol-5-yl)-5,6-dihydropyrido[3,4-d]pyrimidin-7(8H)-yl)methanone

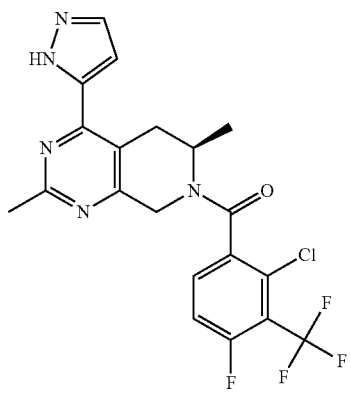 [SMILES: Cc1nc2c(c(-c3ccn[nH]3)n1)C[C@@H](C)N(C(=O)c1ccc(F)c(C(F)(F)F)c1Cl)C2]

The title compound, absolute configuration unknown, was obtained as a single enantiomer by Chiral SFC purification of Example 64 performed using an irregular SiOH 15-40 μm, 300 g MERCK column and a mobile phase of 70% CO$_2$, 30% iPrOH. The enantiomeric purity was confirmed by analytical SFC using a CHIRALCEL OD-H (250×4.6 mm) and a mobile phase of 70% CO$_2$, 30% iPrOH containing 0.3% iPrNH$_2$ over 7 minutes. (100% single enantiomer, 2.42 min retention time). MS (ESI): mass calcd. $C_{20}H_{16}ClF_4N_5O$, 453.1; m/z found, 453.7 [M+H]$^+$. $^1$H NMR (400 MHz, CDCl$_3$) δ 7.78-7.66 (m, 1H), 7.55-7.39 (m, 1H), 7.26-7.16 (m, 1H), 6.94-6.83 (m, 1H), 5.66-5.43 (m, 1H), 4.70-4.35 (m, 1H), 4.34-3.99 (m, 1H), 3.42-3.21 (m, 1H), 3.22-2.96 (m, 1H), 2.83-2.60 (m, 3H), 1.37-1.05 (m, 3H).

Example 67

(2,3-dichlorophenyl)(2,6-dimethyl-4-(1H-pyrazol-5-yl)-5,6-dihydropyrido[3,4-d]pyrimidin-7(8H)-yl)methanone

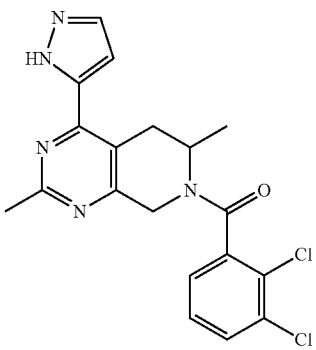 [SMILES: Cc1nc2c(c(-c3ccn[nH]3)n1)CC(C)N(C(=O)c1cccc(Cl)c1Cl)C2]

The title compound was prepared in a manner analogous to Example 56 substituting 2,3-dichlorobenzoic acid for 2-chloro-3-(trifluoromethyl)benzoic acid. MS (ESI): mass calcd. $C_{19}H_{17}Cl_2N_5O$, 401.1; m/z found, 402.1 [M+H]$^+$. $^1$H NMR (500 MHz, MeOD) δ 7.80-7.69 (m, 1H), 7.70-7.64 (m, 1H), 7.51-7.28 (m, 2H), 7.06-6.89 (m, 1H), 5.50-5.28 (m, 1H), 4.62-4.38 (m, 1H), 4.35-4.00 (m, 1H), 3.46-3.35 (m, 1H), 3.29-3.17 (m, 1H), 2.77-2.53 (m, 3H), 1.30-1.03 (m, 3H).

Example 68

(R*)-(2,3-dichlorophenyl)(2,6-dimethyl-4-(1H-pyrazol-5-yl)-5,6-dihydropyrido[3,4-d]pyrimidin-7(8H)-yl)methanone

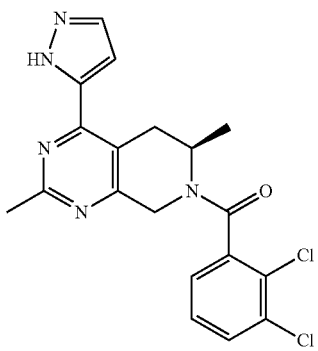

The title compound, absolute configuration unknown, was obtained as a single enantiomer by Chiral SFC purification of Example 67 performed using a CHIRALCEL OD-H (5 μm, 250×20 mm) column and a mobile phase of 70% $CO_2$, 30% iPrOH. The enantiomeric purity was confirmed by analytical SFC using a CHIRALCEL OD-H (250×4.6 mm) and a mobile phase of 70% $CO_2$, 30% iPrOH containing 0.3% iPrNH$_2$ over 7 minutes. (100% single enantiomer, 4.00 min retention time). MS (ESI): mass calcd. $C_{19}H_{17}Cl_2N_5O$, 401.1; m/z found, 401.7 [M+H]$^+$. $^1$H NMR (400 MHz, CDCl$_3$) δ 7.76-7.67 (m, 1H), 7.57-7.48 (m, 1H), 7.37-7.27 (m, 1H), 7.25-7.15 (m, 1H), 6.92-6.80 (m, 1H), 5.71-5.46 (m, 1H), 4.67-4.25 (m, 2H), 4.15-4.02 (m, 1H), 3.42-3.23 (m, 1H), 3.18-2.89 (m, 1H), 2.83-2.61 (m, 3H), 1.35-1.07 (m, 3H).

Example 69

(S*)-(2,3-dichlorophenyl)(2,6-dimethyl-4-(1H-pyrazol-5-yl)-5,6-dihydropyrido[3,4-d]pyrimidin-7(8H)-yl)methanone

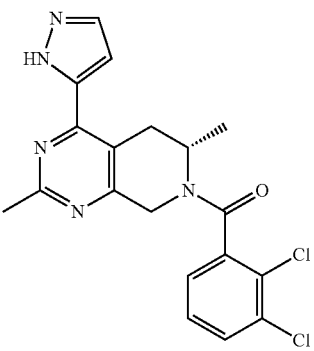 [SMILES: Cc1nc2c(c(-c3ccn[nH]3)n1)C[C@H](C)N(C(=O)c1cccc(Cl)c1Cl)C2]

The title compound, absolute configuration unknown, was obtained as a single enantiomer by Chiral SFC purification of Example 67 performed using a CHIRALCEL OD-H (5 μm, 250×20 mm) column and a mobile phase of 70% $CO_2$, 30% iPrOH. The enantiomeric purity was confirmed by analytical SFC using a CHIRALCEL OD-H (250×4.6 mm) and a mobile phase of 70% $CO_2$, 30% iPrOH containing 0.3% iPrNH$_2$ over 7 minutes. (98.2% single enantiomer, 4.72 min retention time). MS (ESI): mass calcd. $C_{19}H_{17}Cl_2N_5O$, 401.1; m/z found, 401.7 [M+H]$^+$. $^1$H NMR (400 MHz, CDCl$_3$) δ 7.76-7.67 (m, 1H), 7.57-7.48 (m, 1H), 7.37-7.27 (m, 1H), 7.25-7.15 (m, 1H), 6.92-6.80 (m, 1H), 5.71-5.46 (m, 1H), 4.67-4.25 (m, 2H), 4.15-4.02 (m, 1H), 3.42-3.23 (m, 1H), 3.18-2.89 (m, 1H), 2.83-2.61 (m, 3H), 1.35-1.07 (m, 3H).

Example 70

(2,4-dichloro-3-fluorophenyl)(2,6-dimethyl-4-(1H-pyrazol-5-yl)-5,6-dihydropyrido[3,4-d]pyrimidin-7(8H)-yl)methanone

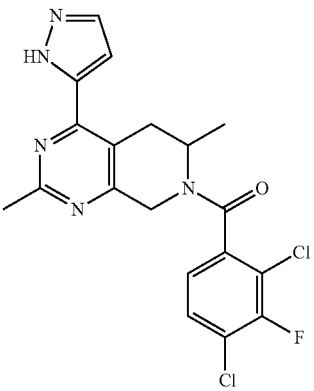 [SMILES: Cc1nc2c(c(-c3ccn[nH]3)n1)CC(C)N(C(=O)c1ccc(Cl)c(F)c1Cl)C2]

The title compound was prepared in a manner analogous to Example 56 substituting 2,4-dichloro-3-fluorobenzoic acid for 2-chloro-3-(trifluoromethyl)benzoic acid. MS (ESI): mass calcd. $C_{19}H_{16}Cl_2FN_5O$, 419.1; m/z found, 420.1 [M+H]$^+$. $^1$H NMR (500 MHz, MeOD) δ 7.74 (d, J=13.5 Hz, 1H), 7.67-7.51 (m, 1H), 7.34-7.18 (m, 1H), 7.00 (s, 1H), 5.53-5.27 (m, 1H), 4.64-4.36 (m, 1H), 4.36-4.00 (m, 1H), 3.43-3.36 (m, 1H), 3.29-3.18 (m, 1H), 2.77-2.49 (m, 3H), 1.36-1.00 (m, 3H).

Example 71

(R)-(2,4-dichloro-3-fluorophenyl)(2,6-dimethyl-4-(1H-pyrazol-5-yl)-5,6-dihydropyrido[3,4-d]pyrimidin-7(8H)-yl)methanone

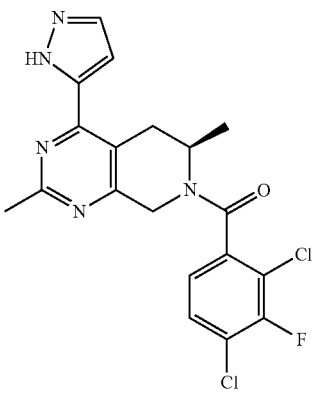

The title compound, absolute configuration unknown, was obtained as a single enantiomer by Chiral SFC purification of Example 70 performed using a CHIRALCEL OD-H (250×20 mm) column and a mobile phase of 70% $CO_2$, 30% iPrOH. The enantiomeric purity was confirmed by analytical SFC using a CHIRALCEL OD-H (250×4.6 mm) and a mobile phase of 70% $CO_2$, 30% iPrOH containing 0.3% $iPrNH_2$ over 7 minutes. (100% single enantiomer, 3.56 min retention time). MS (ESI): mass calcd. $C_{19}H_{16}Cl_2FN_5O$, 419.1; m/z found, 419.8 [M+H]$^+$. $^1$H NMR (500 MHz, CDCl$_3$) δ 7.75-7.67 (m, 1H), 7.47-7.34 (m, 1H), 7.14-7.01 (m, 1H), 6.88 (d, J=25.9 Hz, 1H), 5.65-5.44 (m, 1H), 4.70-4.37 (m, 1H), 4.36-4.03 (m, 1H), 3.42-3.21 (m, 1H), 3.23-2.92 (m, 1H), 2.81-2.61 (m, 3H), 1.35-1.04 (m, 3H).

Example 72

(S)-(2,4-dichloro-3-fluorophenyl)(2,6-dimethyl-4-(1H-pyrazol-5-yl)-5,6-dihydropyrido[3,4-d]pyrimidin-7(8H)-yl)methanone

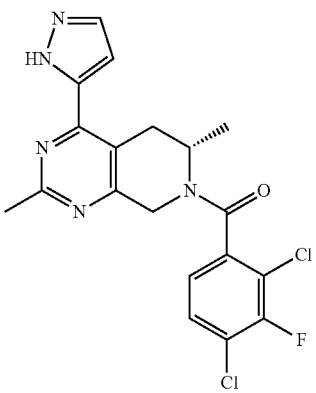 [SMILES: Cc1nc2c(c(-c3ccn[nH]3)n1)C[C@H](C)N(C(=O)c1ccc(Cl)c(F)c1Cl)C2]

The title compound, absolute configuration unknown, was obtained as a single enantiomer by Chiral SFC purification of Example 70 performed using a CHIRALCEL OD-H (5 μm, 250×20 mm) column and a mobile phase of 70% $CO_2$, 30% iPrOH. The enantiomeric purity was confirmed by analytical SFC using a CHIRALCEL OD-H (250×4.6 mm) and a mobile phase of 70% $CO_2$, 30% iPrOH containing 0.3% $iPrNH_2$ over 7 minutes. (99% single enantiomer, 4.26 min retention time). MS (ESI): mass calcd. $C_{19}H_{16}Cl_2FN_5O$, 419.1; m/z found, 419.8 [M+H]$^+$. $^1$H NMR (500 MHz, CDCl$_3$) δ 7.77-7.66 (m, 1H), 7.50-7.32 (m, 1H), 7.16-7.01 (m, 1H), 6.95-6.82 (m, 1H), 5.67-5.46 (m, 1H), 4.71-4.37 (m, 1H), 4.35-4.02 (m, 1H), 3.33 (dd, J=10.7, 5.7 Hz, 1H), 3.25-2.94 (m, 1H), 2.80-2.56 (m, 3H), 1.38-1.04 (m, 3H).

Example 73

(2-chloro-3-(trifluoromethyl)phenyl)(2,6-dimethyl-4-(1-methyl-1H-pyrazol-5-yl)-5,6-dihydropyrido[3,4-d]pyrimidin-7(8H)-yl)methanone

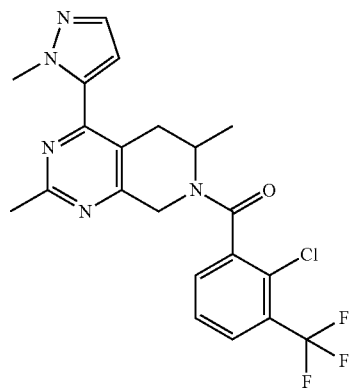 [SMILES: Cc1nc2c(c(-c3ccnn3C)n1)CC(C)N(C(=O)c1cccc(C(F)(F)F)c1Cl)C2]

The title compound was prepared in a manner analogous to Example 56 substituting 1-methyl-1H-pyrazole-5-boronic acid pinacol ester for 1-(tetrahydropyran-2-yl)-1H-pyrazole-5-boronic acid pinacol ester. MS (ESI): mass calcd. for $C_{21}H_{19}ClF_3N_5O$, 449.1; m/z found, 450.2 [M+H]$^+$. $Unable to interpret NMR$ Intermediate 41: 4-chloro-2,6-dimethyl-7-(1-phenylethyl)-5,6,7,8-tetrahydropyrido[3,4-d]pyrimidine

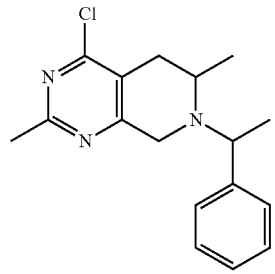 [SMILES: Cc1nc(Cl)c2c(n1)CN(C(C)c1ccccc1)C(C)C2]

The title compound was prepared in a manner analogous to Intermediate 11 substituting Intermediate 34 for Intermediate 10. MS (ESI): mass calcd. for $C_{17}H_{20}ClN_3$ 301.1; m/z found, 302.1 [M+H]$^+$.

Intermediate 42: 2,6-dimethyl-7-(1-phenylethyl)-4-(1-(tetrahydro-2H-pyran-2-yl)-1H-pyrazol-5-yl)-5,6,7,8-tetrahydropyrido[3,4-d]pyrimidine

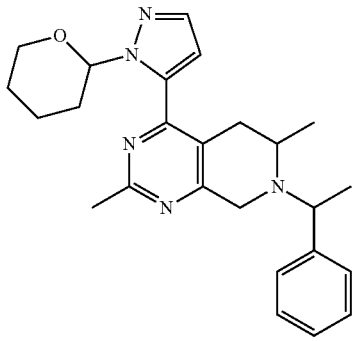 [SMILES: Cc1nc2c(c(-c3ccnn3C3CCCCO3)n1)CC(C)N(C(C)c1ccccc1)C2]

The title compound was prepared in a manner analogous to Intermediate 19 substituting Intermediate 41 for Intermediate 11. MS (ESI): mass calcd. for $C_{25}H_{31}N_5O$ 417.3; m/z found, 418.3 $[M+H]^+$.

Intermediate 43: 2,6-dimethyl-4-(1-(tetrahydro-2H-pyran-2-yl)-1H-pyrazol-5-yl)-5,6,7,8-tetrahydropyrido[3,4-d]pyrimidine

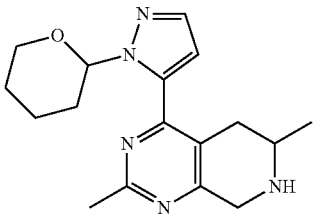 [SMILES: Cc1nc2c(c(-c3ccnn3C3CCCCO3)n1)CC(C)NC2]

Intermediate 42 (3.76 g, 9.00 mmol) was dissolved in MeOH (40 mL) and THF (40 mL). Ammonium formate (2.86 g, 45 mmol) and 10% Pd/C (958 mg, 0.900 mmol) were added and the reaction was heated to reflux overnight. The crude reaction mixture was filtered through a pad of celite and the filtrate was concentrated in vacuo to afford Intermediate 43 (2.98 g, 99%). MS (ESI): mass calcd. for $C_{17}H_{23}N_5O$, 313.2; m/z found, 314.2 $[M+H]^+$.

Intermediate 44: 2-fluoro-3-(trifluoromethyl)benzoyl chloride

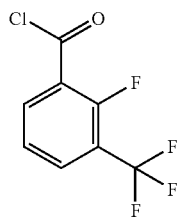 [SMILES: O=C(Cl)c1cccc(C(F)(F)F)c1F]

Oxalyl chloride (0.488 mL, 5.76 mmol) was added to a suspension of 2-fluoro-3-(trifluoromethyl)benzoic acid (1.00 g, 4.81 mmol) in DCM (10 mL) containing catalytic DMF. The reaction was stirred at room temperature for 90 minutes and solvents were removed in vacuo to afford the desired compound (1.08 g, 99%). The product was used without additional purification.

Intermediate 45: 2-chloro-3-(trifluoromethyl)benzoyl chloride

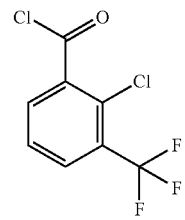

The title compound was prepared in a manner analogous to Intermediate 44 substituting 2-chloro-3-(trifluoromethyl)benzoic acid for 2-fluoro-3-(trifluoromethyl)benzoic acid. The product was used as is without additional purification.

Example 74

(2,6-dimethyl-4-(1H-pyrazol-5-yl)-5,6-dihydropyrido[3,4-d]pyrimidin-7(8H)-yl)(2-fluoro-3-(trifluoromethyl)phenyl)methanone

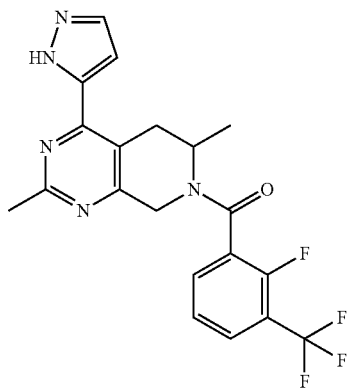 [SMILES: Cc1nc2c(c(-c3ccn[nH]3)n1)CC(C)N(C(=O)c1cccc(C(F)(F)F)c1F)C2]

Intermediate 43 (284 mg, 1.26 mmol) was added to a solution of Intermediate 44 (395 mg, 1.26 mmol) and DIPEA (0.434 mL, 2.52 mmol) in DCM (10 mL). The reaction was stirred at room temperature for one hour. The crude mixture was treated directly with TFA (1.1 mL) and triethylsilane (0.202 mL, 1.26 mmol) and stirred for 30 minutes. The solvents were removed in vacuo and the crude mixture was purified by chromatography on a Prep Agilent system with a XBridge C18 OBD 50×100 mm column eluting with 5 to 99% (0.05% $NH_4OH$ in $H_2O$)/ACN over 17 min to afford the desired product (256 mg, 46%). MS (ESI): mass calcd. for $C_{20}H_{17}F_4N_5O$, 419.1; m/z found, 420.2 $[M+H]^+$. $^1H$ NMR (400 MHz, DMSO-$d_6$) δ7.98-7.80 (m, 3H), 7.61-7.49 (m, 1H), 6.98 (s, 1H), 5.35-5.16 (m, 1H), 4.66-4.34 (m, 1H), 4.33-3.99 (m, 1H), 3.61-3.29 (m, 2H), 2.67-2.53 (m, 3H), 1.23-1.02 (m, 3H).

Example 75

(R*)-(2,6-dimethyl-4-(1H-pyrazol-5-yl)-5,6-dihydro-pyrido[3,4-d]pyrimidin-7(8H)-yl)(2-fluoro-3-(trifluoromethyl)phenyl)methanone

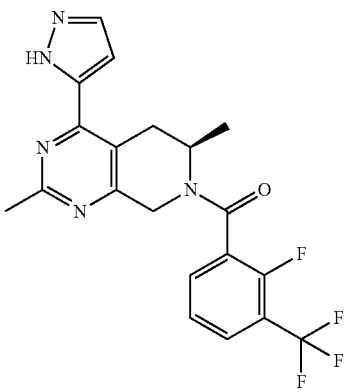 [SMILES: Cc1nc2c(c(-c3ccn[nH]3)n1)C[C@@H](C)N(C(=O)c1cccc(C(F)(F)F)c1F)C2]

The title compound, absolute configuration unknown, was obtained as a single enantiomer by Chiral SFC purification of Example 74 performed using a CHIRALCEL OD-H (5 μm, 250×20 mm) column and a mobile phase of 75% CO$_2$, 25% iPrOH. The enantiomeric purity was confirmed by analytical SFC using a CHIRALCEL OD-H (250×4.6 mm) and a mobile phase of 75% CO$_2$, 25% iPrOH containing 0.3% iPrNH$_2$ over 7 minutes. (100% single enantiomer, 3.34 min retention time). MS (ESI): mass calcd. for C$_{20}$H$_{12}$F$_4$N$_5$O, 419.1; m/z found, 419.8 [M+H]$^+$. $^1$H NMR (400 MHz, DMSO-d$_6$) δ 8.00-7.80 (m, 3H), 7.62-7.47 (m, 1H), 6.99 (s, 1H), 5.25 (d, J=19.3 Hz, 1H), 4.67-4.33 (m, 1H), 4.31-4.01 (m, 1H), 3.52-3.36 (m, 1H), 3.30-3.07 (m, 1H), 2.72-2.52 (m, 3H), 1.27-1.01 (m, 3H).

Example 76

(S*)-(2,6-dimethyl-4-(1H-pyrazol-5-yl)-5,6-dihydro-pyrido[3,4-d]pyrimidin-7(8H)-yl)(2-fluoro-3-(trifluoromethyl)phenyl)methanone

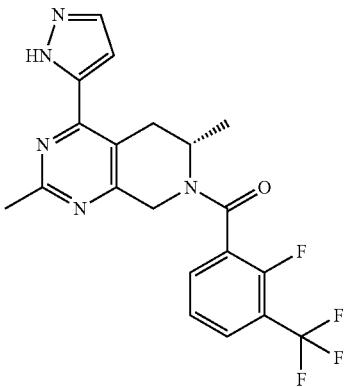

The title compound, absolute configuration unknown, was obtained as a single enantiomer by Chiral SFC purification of Example 74 performed using a CHIRALCEL OD-H (5 μm, 250×20 mm) column and a mobile phase of 75% CO$_2$, 25% iPrOH. The enantiomeric purity was confirmed by analytical SFC using a CHIRALCEL OD-H (250×4.6 mm) and a mobile phase of 75% CO$_2$, 25% iPrOH containing 0.3% iPrNH$_2$ over 7 minutes. (98% single enantiomer, 3.80 min retention time). MS (ESI): mass calcd. for C$_{20}$H$_{17}$F$_4$N$_5$O, 419.1; m/z found, 419.9 [M+H]$^+$. $^1$H NMR (400 MHz, DMSO-d$_6$) δ 7.97-7.84 (m, 3H), 7.62-7.50 (m, 1H), 6.99 (s, 1H), 5.35-5.15 (m, 1H), 4.68-4.39 (m, 1H), 4.37-4.21 (m, 1H), 4.16-3.95 (m, 1H), 3.51-3.36 (m, 1H), 2.75-2.52 (m, 3H), 1.27-0.99 (m, 3H).

Example 77

(2,6-dimethyl-4-(1H-pyrazol-5-yl)-5,6-dihydro-pyrido[3,4-d]pyrimidin-7(8H)-yl)(2-methyl-3-(trifluoromethyl)phenyl)methanone

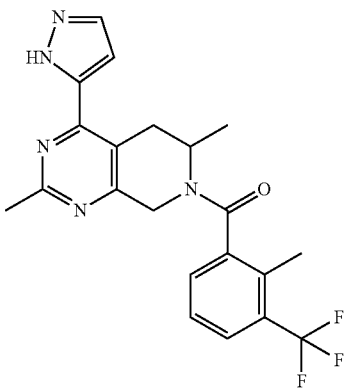

The title compound was prepared in a manner analogous to Example 74 substituting 2-methyl-3(trifluoromethyl)benzoic acid for 2-fluoro-3-(trifluoromethyl)benzoic acid in the synthesis of Intermediate 44. MS (ESI): mass calcd. for C$_{21}$H$_{20}$F$_3$N$_5$O, 415.2; m/z found, 416.1 [M+H]$^+$. $^1$H NMR (400 MHz, DMSO-d$_6$) δ 7.88 (s, 1H), 7.79 (d, J=7.9 Hz, 1H), 7.70-7.59 (m, 1H), 7.60-7.42 (m, 1H), 6.98 (s, 1H), 5.39-5.18 (m, 1H), 4.58-4.27 (m, 1H), 4.17-3.79 (m, 1H), 3.31-3.05 (m, 2H), 2.74-2.52 (m, 3H), 2.46-2.08 (m, 3H), 1.26-0.94 (m, 3H).

Example 78

(R*)-(2,6-dimethyl-4-(1H-pyrazol-5-yl)-5,6-dihydro-pyrido[3,4-d]pyrimidin-7(8H)-yl)(2-methyl-3-(trifluoromethyl)phenyl)methanone

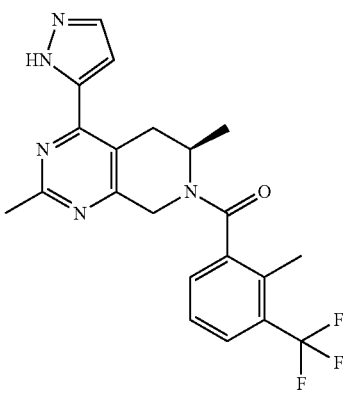 [SMILES: Cc1nc2c(c(-c3ccn[nH]3)n1)C[C@@H](C)N(C(=O)c1cccc(C(F)(F)F)c1C)C2]

The title compound, absolute configuration unknown, was obtained as a single enantiomer by Chiral SFC purification of Example 77 performed using a CHIRALCEL OD-H (5 μm, 250×20 mm) column and a mobile phase of 78% $CO_2$, 22% iPrOH. The enantiomeric purity was confirmed by analytical SFC using a CHIRALCEL OD-H (250×4.6 mm) and a mobile phase of 80% $CO_2$, 20% iPrOH containing 0.3% $iPrNH_2$ over 7 minutes. (100% single enantiomer, 4.81 min retention time). MS (ESI): mass calcd. for $C_{21}H_{20}F_3N_5O$, 415.2; m/z found, 415.9 [M+H]$^+$. $^1$H NMR (400 MHz, CDCl$_3$) δ 7.74-7.64 (m, 2H), 7.46-7.28 (m, 2H), 6.96-6.82 (m, 1H), 5.69-5.53 (m, 1H), 4.47-4.03 (m, 2H), 3.40-3.07 (m, 2H), 2.80-2.73 (s, 1H), 2.72-2.61 (m, 2H), 2.54-2.23 (m, 3H), 1.32-1.11 (m, 3H).

Example 79

(S*)-(2,6-dimethyl-4-(1H-pyrazol-5-yl)-5,6-dihydro-pyrido[3,4-d]pyrimidin-7(8H)-yl)(2-methyl-3-(trifluoromethyl)phenyl)methanone

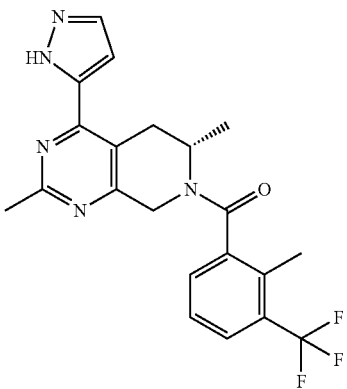 [SMILES: Cc1nc2c(c(-c3ccn[nH]3)n1)C[C@H](C)N(C(=O)c1cccc(C(F)(F)F)c1C)C2]

The title compound, absolute configuration unknown, was obtained as a single enantiomer by Chiral SFC purification of Example 77 performed using a CHIRALCEL OD-H (5 μm, 250×20 mm) column and a mobile phase of 78% $CO_2$, 22% iPrOH. The enantiomeric purity was confirmed by analytical SFC using a CHIRALCEL OD-H (250×4.6 mm) and a mobile phase of 80% $CO_2$, 20% iPrOH containing 0.3% $iPrNH_2$ over 7 minutes. (100% single enantiomer, 6.03 min retention time). MS (ESI): mass calcd. for $C_{21}H_{20}F_3N_5O$, 415.2; m/z found, 415.9 [M+H]$^+$. $^1$H NMR (400 MHz, CDCl$_3$) δ 7.75-7.65 (m, 2H), 7.45-7.29 (m, 2H), 6.93-6.82 (m, 1H), 5.72-5.53 (m, 1H), 4.49-4.36 (m, 1H), 4.34-4.02 (m, 1H), 3.45-3.22 (m, 1H), 3.20-2.97 (m, 1H), 2.80-2.63 (m, 3H), 2.55-2.21 (m, 3H), 1.33-1.10 (m, 3H).

Example 80

(2,3-dichloro-4-fluorophenyl)(2,6-dimethyl-4-(1H-pyrazol-5-yl)-5,6-dihydropyrido[3,4-d]pyrimidin-7(8H)-yl)methanone

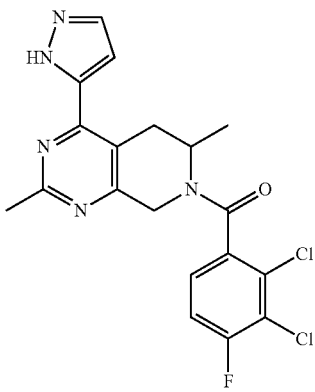 [SMILES: Cc1nc2c(c(-c3ccn[nH]3)n1)CC(C)N(C(=O)c1ccc(F)c(Cl)c1Cl)C2]

The title compound was prepared in a manner analogous to Example 74 substituting 2,3-dichloro-4-fluorobenzoic acid for 2-fluoro-3-(trifluoromethyl)benzoic acid in the synthesis of Intermediate 44. MS (ESI): mass calcd. for $C_{19}H_{16}Cl_2FN_5O$, 419.1; m/z found, 420.1 [M+H]$^+$. $^1$H NMR (400 MHz, DMSO-d$_6$) δ 7.88 (s, 1H), 7.68-7.44 (m, 2H), 6.97 (s, 1H), 5.33-5.15 (m, 1H), 4.55-4.26 (m, 1H), 4.25-3.91 (m, 2H), 3.28-3.18 (m, 1H), 2.73-2.52 (m, 3H), 1.26-0.92 (m, 3H).

Example 81

(R*)-(2,3-dichloro-4-fluorophenyl)(2,6-dimethyl-4-(1H-pyrazol-5-yl)-5,6-dihydropyrido[3,4-d]pyrimidin-7(8H)-yl)methanone

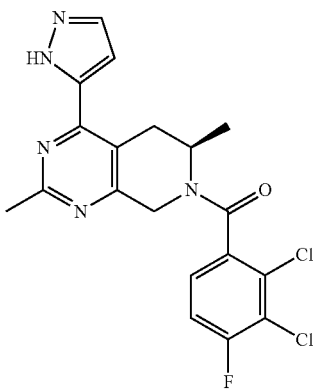 [SMILES: Cc1nc2c(c(-c3ccn[nH]3)n1)C[C@@H](C)N(C(=O)c1ccc(F)c(Cl)c1Cl)C2]

The title compound, absolute configuration unknown, was obtained as a single enantiomer by Chiral SFC purification of Example 80 performed using a CHIRALCEL OD-H (5 µm, 250×20 mm) column and a mobile phase of 70% $CO_2$, 30% iPrOH. The enantiomeric purity was confirmed by analytical SFC using a CHIRALCEL OD-H (250×4.6 mm) and a mobile phase of 70% $CO_2$, 30% iPrOH containing 0.3% $iPrNH_2$ over 7 minutes. (100% single enantiomer, 3.83 min retention time). MS (ESI): mass calcd. for $C_{19}H_{16}Cl_2FN_5O$, 419.1; m/z found, 419.8 [M+H]$^+$. $^1$H NMR (400 MHz, CDCl$_3$) δ 7.75-7.67 (m, 1H), 7.26-7.12 (m, 2H), 6.93-6.82 (m, 1H), 5.68-5.45 (m, 1H), 4.68-4.36 (m, 1H), 4.35-4.01 (m, 1H), 3.46-3.25 (m, 1H), 3.23-2.92 (m, 1H), 2.80-2.61 (m, 3H), 1.36-1.08 (m, 3H).

Example 82

(S*)-(2,3-dichloro-4-fluorophenyl)(2,6-dimethyl-4-(1H-pyrazol-5-yl)-5,6-dihydropyrido[3,4-d]pyrimidin-7(8H)-yl)methanone

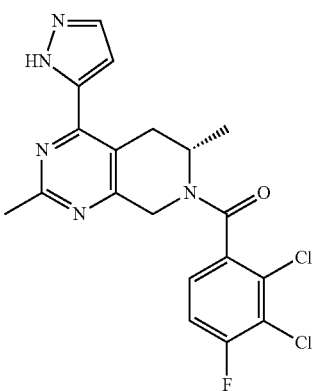 [SMILES: Cc1nc2c(c(-c3ccn[nH]3)n1)C[C@H](C)N(C(=O)c1ccc(F)c(Cl)c1Cl)C2]

The title compound, absolute configuration unknown, was obtained as a single enantiomer by Chiral SFC purification of Example 80 performed using a CHIRALCEL OD-H (5 µm, 250×20 mm) column and a mobile phase of 70% $CO_2$, 30% iPrOH. The enantiomeric purity was confirmed by analytical SFC using a CHIRALCEL OD-H (250×4.6 mm) and a mobile phase of 70% $CO_2$, 30% iPrOH containing 0.3% $iPrNH_2$ over 7 minutes. (100% single enantiomer, 4.92 min retention time). MS (ESI): mass calcd. for $C_{19}H_{16}Cl_2FN_5O$, 419.1; m/z found, 419.8 [M+H]$^+$. $^1$H NMR (400 MHz, CDCl$_3$) δ 7.75-7.67 (m, 1H), 7.24-7.11 (m, 2H), 6.94-6.82 (m, 1H), 5.68-5.46 (m, 1H), 4.68-4.36 (m, 1H), 4.36-4.04 (m, 1H), 3.42-3.25 (m, 1H), 3.16-2.92 (m, 1H), 2.80-2.61 (m, 3H), 1.32-1.08 (m, 3H).

Example 83

(2,4-dichlorophenyl)(2,6-dimethyl-4-(1H-pyrazol-5-yl)-5,6-dihydropyrido[3,4-d]pyrimidin-7(8H)-yl)methanone

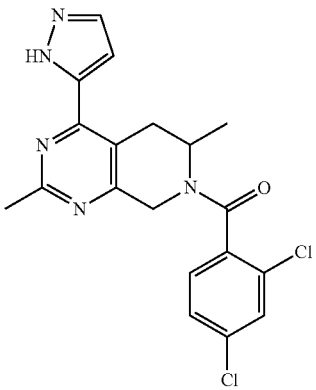 [SMILES: Cc1nc2c(c(-c3ccn[nH]3)n1)CC(C)N(C(=O)c1ccc(Cl)cc1Cl)C2]

The title compound was prepared in a manner analogous to Example 74 substituting 2,4-dichlorobenzoic acid for 2-fluoro-3-(trifluoromethyl)benzoic acid in the synthesis of Intermediate 44. MS (ESI): mass calcd. for $C_{19}H_{17}Cl_2N_5O$, 401.1; m/z found, 402.0 [M+H]$^+$. $^1$H NMR (500 MHz, DMSO-d$_6$) δ 7.91-7.69 (m, 2H), 7.62-7.40 (m, 2H), 6.97 (s, 1H), 5.31-5.17 (m, 1H), 4.55-4.25 (m, 1H), 4.20-3.88 (m, 1H), 3.27-3.08 (m, 2H), 2.66-2.52 (m, 3H), 1.22-0.99 (m, 3H).

Example 84

(R*)-(2,4-dichlorophenyl)(2,6-dimethyl-4-(1H-pyrazol-5-yl)-5,6-dihydropyrido[3,4-d]pyrimidin-7(8H)-yl)methanone

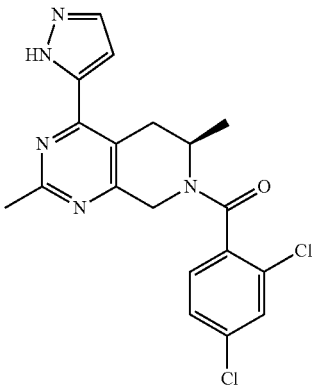 [SMILES: Cc1nc2c(c(-c3ccn[nH]3)n1)C[C@@H](C)N(C(=O)c1ccc(Cl)cc1Cl)C2]

The title compound, absolute configuration unknown, was obtained as a single enantiomer by Chiral SFC purification of Example 83 performed using a CHIRALPAK AD-H (5 µm, 250×20 mm) column and a mobile phase of 70% $CO_2$, 30% iPrOH containing 0.3% $iPrNH_2$. The enantiomeric purity was confirmed by analytical SFC using a CHIRALPAK AD (250×4.6 mm) and a mobile phase of 70% $CO_2$, 30% iPrOH containing 0.3% $iPrNH_2$ over 7 minutes. (100%

Example 85

(S*)-(2,4-dichlorophenyl)(2,6-dimethyl-4-(1H-pyrazol-5-yl)-5,6-dihydropyrido[3,4-d]pyrimidin-7(8H)-yl)methanone

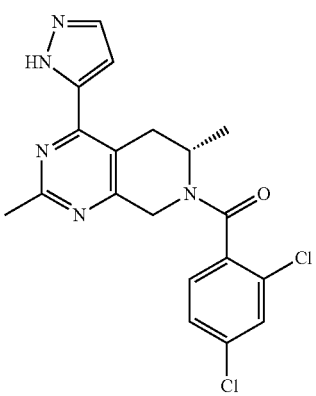 [SMILES: Cc1nc2c(c(-c3ccn[nH]3)n1)C[C@H](C)N(C(=O)c1ccc(Cl)cc1Cl)C2]

The title compound, absolute configuration unknown, was obtained as a single enantiomer by Chiral SFC purification of Example 83 performed using a CHIRALPAK AD-H (5 µm, 250×20 mm) column and a mobile phase of 70% CO$_2$, 30% iPrOH containing 0.3% iPrNH$_2$. The enantiomeric purity was confirmed by analytical SFC using a CHIRALPAK AD (250×4.6 mm) and a mobile phase of 70% CO$_2$, 30% iPrOH containing 0.3% iPrNH$_2$ over 7 minutes. (97% single enantiomer, 3.67 min retention time). MS (ESI): mass calcd. for C$_{19}$H$_{17}$Cl$_2$N$_5$O, 401.1; m/z found, 401.8 [M+H]$^+$.

Example 86

(2,5-dichlorophenyl)(2,6-dimethyl-4-(1H-pyrazol-5-yl)-5,6-dihydropyrido[3,4-d]pyrimidin-7(8H)-yl)methanone

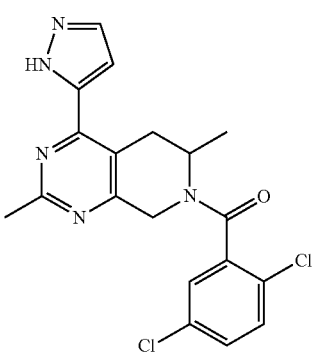 [SMILES: Cc1nc2c(c(-c3ccn[nH]3)n1)CC(C)N(C(=O)c1cc(Cl)ccc1Cl)C2]

The title compound was prepared in a manner analogous to Example 74 substituting 2,5-dichlorobenzoic acid for 2-fluoro-3-(trifluoromethyl)benzoic acid in the synthesis of Intermediate 44. MS (ESI): mass calcd. for C$_{19}$H$_{17}$Cl$_2$N$_5$O, 401.1; m/z found, 402.0 [M+H]$^+$. $^1$H NMR (500 MHz, DMSO) δ 7.91-7.82 (s, 1H), 7.75-7.68 (m, 1H), 7.68-7.61 (m, 1H), 7.60-7.55 (m, 1H), 7.01-6.93 (s, 1H), 5.34-5.17 (m, 1H), 4.58-4.28 (m, 1H), 4.21-3.91 (m, 1H), 3.27-3.14 (m, 2H), 2.68-2.53 (m, 3H), 1.26-1.02 (m, 3H).

Example 87

(4-chloro-2-fluorophenyl)(2,6-dimethyl-4-(1H-pyrazol-5-yl)-5,6-dihydropyrido[3,4-d]pyrimidin-7(8H)-yl)methanone

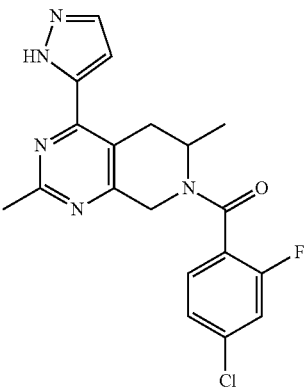 [SMILES: Cc1nc2c(c(-c3ccn[nH]3)n1)CC(C)N(C(=O)c1ccc(Cl)cc1F)C2]

4-chloro-2-fluorobenzoic acid (171 mg, 0.957 mmol) and HATU (364, 0.957 mmol) were added to a solution of Intermediate 43 (300 mg, 0.957 mmol) and DIEA (0.495 mL, 2.87 mmol) in DCM (10 mL). The reaction was stirred at room temperature for one hour. The crude mixture was treated directly with TFA (2.0 mL) and triethylsilane (0.289 mL, 1.80 mmol) and stirred for 30 minutes. The solvents were removed in vacuo and the crude mixture was purified by chromatography on a Prep Agilent system with a XBridge C18 OBD 50×100 mm column eluting with 5 to 99% (0.05% NH$_4$OH in H$_2$O)/ACN over 17 min to afford the desired product (143 mg, 38%). MS (ESI): mass calcd. for C$_{19}$H$_{17}$ClFN$_5$O, 385.1; m/z found, 386.0 [M+H]$^+$. $^1$H NMR (400 MHz, DMSO) δ 7.93-7.84 (s, 1H), 7.67-7.48 (m, 2H), 7.48-7.38 (m, 1H), 7.02-6.93 (s, 1H), 5.31-5.14 (m, 1H), 4.60-4.30 (m, 1H), 4.30-4.05 (m, 1H), 3.32-3.07 (m, 2H), 2.70-2.53 (m, 3H), 1.21-1.01 (m, 3H).

Example 88

(R*)-(4-chloro-2-fluorophenyl)(2,6-dimethyl-4-(1H-pyrazol-5-yl)-5,6-dihydropyrido[3,4-d]pyrimidin-7(8H)-yl)methanone

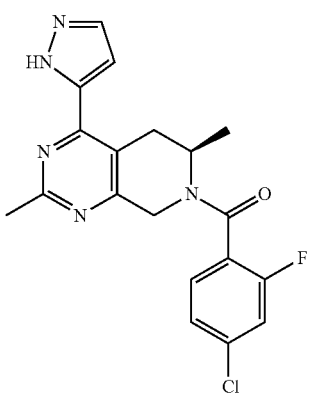 [SMILES: Cc1nc2c(c(-c3ccn[nH]3)n1)C[C@@H](C)N(C(=O)c1ccc(Cl)cc1F)C2]

The title compound, absolute configuration unknown, was obtained as a single enantiomer by Chiral SFC purification of Example 87 performed using a CHIRALPAK AD-H (5 μm, 250×20 mm) column and a mobile phase of 65% $CO_2$, 35% iPrOH. The enantiomeric purity was confirmed by analytical SFC using a CHIRALPAK AD-H (250×4.6 mm) and a mobile phase of 60% $CO_2$, 40% iPrOH containing 0.3% $iPrNH_2$ over 7 minutes. (100% single enantiomer, 2.17 min retention time). MS (ESI): mass calcd. for $C_{19}H_{17}ClFN_5O$, 385.1; m/z found, 385.8 $[M+H]^+$. $^1H$ NMR (400 MHz, $CDCl_3$) δ 7.75-7.67 (m, 1H), 7.42-7.31 (m, 1H), 7.25-7.13 (m, 2H), 6.92-6.80 (m, 1H), 5.60-5.42 (m, 1H), 4.66-4.16 (m, 2H), 3.38-3.25 (m, 1H), 3.12-2.93 (m, 1H), 2.80-2.59 (m, 3H), 1.32-1.11 (m, 3H).

Example 89

(S*)-(4-chloro-2-fluorophenyl)(2,6-dimethyl-4-(1H-pyrazol-5-yl)-5,6-dihydropyrido[3,4-d]pyrimidin-7(8H)-yl)methanone

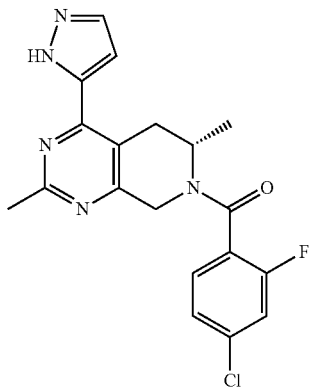

The title compound, absolute configuration unknown, was obtained as a single enantiomer by Chiral SFC purification of Example 87 performed using a CHIRALPAK AD-H (5 μm, 250×20 mm) column and a mobile phase of 65% $CO_2$, 35% iPrOH. The enantiomeric purity was confirmed by analytical SFC using a CHIRALPAK AD-H (250×4.6 mm) and a mobile phase of 60% $CO_2$, 40% iPrOH containing 0.3% $iPrNH_2$ over 7 minutes. (99% single enantiomer, 2.50 min retention time). MS (ESI): mass calcd. for $C_{19}H_{17}ClFN_5O$, 385.1; m/z found, 385.8 $[M+H]^+$. $^1H$ NMR (400 MHz, $CDCl_3$) δ 7.75-7.66 (m, 1H), 7.41-7.31 (m, 1H), 7.25-7.13 (m, 2H), 6.92-6.80 (m, 1H), 5.61-5.41 (m, 1H), 4.66-4.16 (m, 2H), 3.48-3.21 (m, 1H), 3.15-2.94 (m, 1H), 2.79-2.62 (m, 3H), 1.32-1.10 (m, 3H).

Example 90

(2-chloro-4-fluorophenyl)(2,6-dimethyl-4-(1H-pyrazol-5-yl)-5,6-dihydropyrido[3,4-d]pyrimidin-7(8H)-yl)methanone

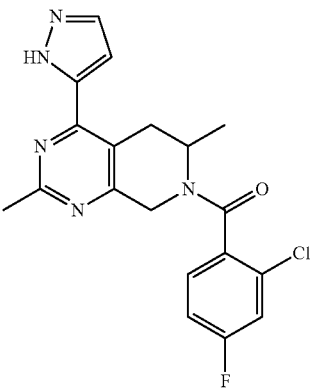 [SMILES: Cc1nc2c(c(-c3ccn[nH]3)n1)CC(C)N(C(=O)c1ccc(F)cc1Cl)C2]

The title compound was prepared in a manner analogous to Example 87 substituting 2-chloro-4-fluorobenzoic acid for 4-chloro-2-fluorobenzoic acid. MS (ESI): mass calcd. for $C_{19}H_{17}ClFN_5O$, 385.1; m/z found, 386.0 $[M+H]^+$. $^1H$ NMR (500 MHz, DMSO-$d_6$) δ 7.86 (s, 1H), 7.67-7.52 (m, 2H), 7.51-7.28 (m, 1H), 6.97 (s, 1H), 5.34-5.14 (m, 1H), 4.56-4.26 (m, 1H), 4.18-3.86 (m, 1H), 3.29-3.11 (m, 2H), 2.71-2.52 (m, 3H), 1.24-0.96 (m, 3H).

Example 91

(R*)-(2-chloro-4-fluorophenyl)(2,6-dimethyl-4-(1H-pyrazol-5-yl)-5,6-dihydropyrido[3,4-d]pyrimidin-7(8H)-yl)methanone

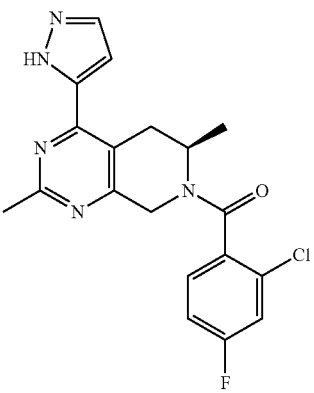 [SMILES: Cc1nc2c(c(-c3ccn[nH]3)n1)C[C@@H](C)N(C(=O)c1ccc(F)cc1Cl)C2]

The title compound, absolute configuration unknown, was obtained as a single enantiomer by Chiral SFC purification of Example 90 performed using a CHIRALCEL OD-H (5 μm, 250×20 mm) column and a mobile phase of 65% $CO_2$, 35% iPrOH containing 0.3% $iPrNH_2$. The enantiomeric purity was confirmed by analytical SFC using a CHIRALCEL OD-H (250×4.6 mm) and a mobile phase of 70% $CO_2$, 30% iPrOH containing 0.3% $iPrNH_2$ over 7 minutes. (100% single enantiomer, 3.11 min retention time). MS (ESI): mass calcd. for $C_{19}H_{17}ClFN_5O$, 385.1; m/z found, 385.8 $[M+H]^+$.

¹H NMR (400 MHz, CDCl₃) δ 7.75-7.67 (m, 1H), 7.39-7.28 (m, 1H), 7.26-7.18 (m, 1H), 7.16-6.99 (m, 1H), 6.92-6.82 (m, 1H), 5.70-5.45 (m, 1H), 4.72-4.36 (m, 1H), 4.37-4.07 (m, 1H), 3.43-3.20 (m, 1H), 3.16-2.92 (m, 1H), 2.78-2.60 (m, 3H), 1.31-1.07 (m, 3H).

Example 92

(S*)-(2-chloro-4-fluorophenyl)(2,6-dimethyl-4-(1H-pyrazol-5-yl)-5,6-dihydropyrido[3,4-d]pyrimidin-7(8H)-yl)methanone

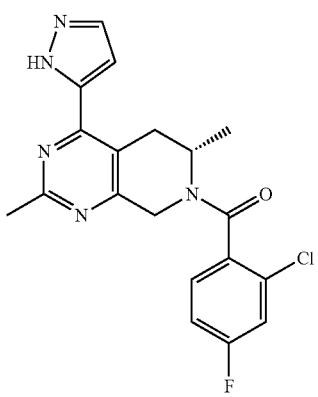

The title compound, absolute configuration unknown, was obtained as a single enantiomer by Chiral SFC purification of Example 90 performed using a CHIRALCEL OD-H (5 μm, 250×20 mm) column and a mobile phase of 65% CO₂, 35% iPrOH containing 0.3% iPrNH₂. The enantiomeric purity was confirmed by analytical SFC using a CHIRALCEL OD-H (250×4.6 mm) and a mobile phase of 70% CO₂, 30% iPrOH containing 0.3% iPrNH₂ over 7 minutes. (99% single enantiomer, 3.80 min retention time). MS (ESI): mass calcd. for C₁₉H₁₇ClFN₅O, 385.1; m/z found, 385.8 [M+H]⁺. ¹H NMR (400 MHz, CDCl₃) δ 7.76-7.66 (m, 1H), 7.40-7.28 (m, 1H), 7.25-7.17 (m, 1H), 7.16-7.00 (m, 1H), 6.93-6.81 (m, 1H), 5.74-5.44 (m, 1H), 4.66-4.37 (m, 1H), 4.36-4.07 (m, 1H), 3.47-3.23 (m, 1H), 3.20-2.90 (m, 1H), 2.82-2.57 (m, 3H), 1.34-1.04 (m, 3H).

Example 93

(2,4-difluorophenyl)(2,6-dimethyl-4-(1H-pyrazol-5-yl)-5,6-dihydropyrido[3,4-d]pyrimidin-7(8H)-yl)methanone

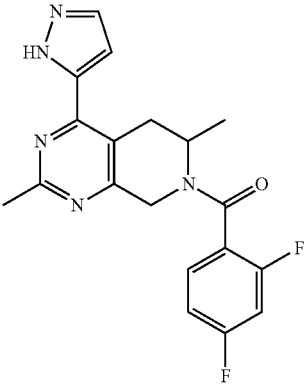

The title compound was prepared in a manner analogous to Example 87 substituting 2,4-difluorobenzoic acid for 4-chloro-2-fluorobenzoic acid. MS (ESI): mass calcd. for C₁₉H₁₇F₂N₅O, 369.1; m/z found, 370.2 [M+H]⁺. ¹H NMR (500 MHz, DMSO-d₆) δ 7.88 (s, 1H), 7.66-7.50 (m, 1H), 7.49-7.33 (m, 1H), 7.23 (s, 1H), 6.98 (s, 1H), 5.34-5.13 (m, 1H), 4.66-4.31 (m, 1H), 4.29-4.01 (m, 1H), 3.52-3.33 (m, 1H), 3.25-3.11 (m, 1H), 2.75-2.54 (m, 3H), 1.22-0.99 (m, 3H).

Example 94

(R*)-(2,4-difluorophenyl)(2,6-dimethyl-4-(1H-pyrazol-5-yl)-5,6-dihydropyrido[3,4-d]pyrimidin-7(8H)-yl)methanone

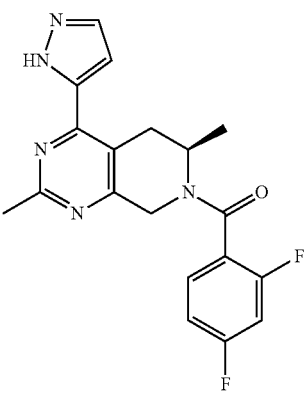

The title compound, absolute configuration unknown, was obtained as a single enantiomer by Chiral SFC purification of Example 93 performed using a CHIRALPAK AD-H (5 μm, 250×20 mm) column and a mobile phase of 75% CO₂, 25% iPrOH. The enantiomeric purity was confirmed by analytical SFC using a CHIRALPAK AD-H (250×4.6 mm) and a mobile phase of 75% CO₂, 25% iPrOH containing 0.3% iPrNH₂ over 7 minutes. (100% single enantiomer, 2.78 min retention time). MS (ESI): mass calcd. for $C_{19}H_{17}F_2N_5O$, 369.1; m/z found, 369.8 [M+H]$^+$. $^1$H NMR (400 MHz, CDCl$_3$) δ 7.76-7.65 (m, 1H), 7.48-7.36 (m, 1H), 7.04-6.81 (m, 3H), 5.63-5.41 (m, 1H), 4.69-4.17 (m, 2H), 3.43-2.94 (m, 2H), 2.79-2.61 (m, 3H), 1.35-1.10 (m, 3H).

Example 95

(S*)-(2,4-difluorophenyl)(2,6-dimethyl-4-(1H-pyrazol-5-yl)-5,6-dihydropyrido[3,4-d]pyrimidin-7(8H)-yl)methanone

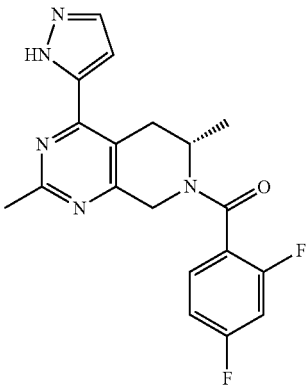 [SMILES: Cc1nc2c(c(-c3ccn[nH]3)n1)C[C@H](C)N(C(=O)c1ccc(F)cc1F)C2]

The title compound, absolute configuration unknown, was obtained as a single enantiomer by Chiral SFC purification of Example 93 performed using a CHIRALPAK AD-H (5 μm, 250×20 mm) column and a mobile phase of 75% CO$_2$, 25% iPrOH. The enantiomeric purity was confirmed by analytical SFC using a CHIRALPAK AD-H (250×4.6 mm) and a mobile phase of 75% CO$_2$, 25% iPrOH containing 0.3% iPrNH$_2$ over 7 minutes. (100% single enantiomer, 3.36 min retention time). MS (ESI): mass calcd. for $C_{19}H_{17}F_2N_5O$, 369.1; m/z found, 369.8 [M+H]$^+$. $^1$H NMR (400 MHz, CDCl$_3$) δ 7.74-7.65 (m, 1H), 7.48-7.36 (m, 1H), 7.03-6.83 (m, 3H), 5.59-5.44 (m, 1H), 4.67-4.19 (m, 2H), 3.43-3.23 (m, 1H), 3.14-2.96 (m, 1H), 2.78-2.63 (m, 3H), 1.32-1.12 (m, 3H).

Example 96

(4-chlorophenyl)(2,6-dimethyl-4-(1H-pyrazol-5-yl)-5,6-dihydropyrido[3,4-d]pyrimidin-7(8H)-yl)methanone

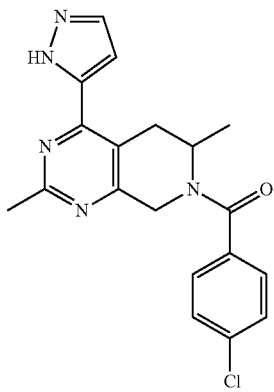 [SMILES: Cc1nc2c(c(-c3ccn[nH]3)n1)CC(C)N(C(=O)c1ccc(Cl)cc1)C2]

The title compound was prepared in a manner analogous to Example 87 substituting 4-chlorobenzoic acid for 4-chloro-2-fluorobenzoic acid. MS (ESI): mass calcd. for $C_{19}H_{18}ClN_5O$, 367.1; m/z found, 368.2 [M+H]$^+$. $^1$H NMR (500 MHz, DMSO) δ 7.88 (s, 1H), 7.58-7.49 (m, 5H), 6.97 (s, 1H), 5.30-4.94 (m, 1H), 4.56-4.13 (m, 2H), 3.39-3.16 (m, 2H), 2.73-2.53 (m, 3H), 1.10 (s, 3H).

Example 97

(2-chlorophenyl)(2,6-dimethyl-4-(1H-pyrazol-5-yl)-5,6-dihydropyrido[3,4-d]pyrimidin-7(8H)-yl)methanone

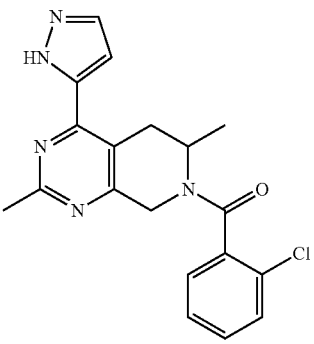 [SMILES: Cc1nc2c(c(-c3ccn[nH]3)n1)CC(C)N(C(=O)c1ccccc1Cl)C2]

The title compound was prepared in a manner analogous to Example 87 substituting 2-chlorobenzoic acid for 4-chloro-2-fluorobenzoic acid. MS (ESI): mass calcd. for $C_{19}H_{18}ClN_5O$, 367.1; m/z found, 368.1 [M+H]$^+$. $^1$H NMR (500 MHz, DMSO) δ 7.92-7.84 (m, 1H), 7.62-7.56 (m, 1H), 7.53-7.35 (m, 3H), 7.01-6.92 (s, 1H), 5.35-5.16 (m, 1H), 4.51-4.27 (m, 1H), 4.18-3.87 (m, 1H), 3.53-3.33 (m, 1H), 3.27-3.10 (m, 2H), 2.70-2.58 (s, 2H), 1.24-0.99 (m, 3H).

Example 98

(2-chloro-3-(trifluoromethyl)phenyl)(2-ethyl-6-methyl-4-(1H-pyrazol-5-yl)-5,6-dihydropyrido[3,4-d]pyrimidin-7(8H)-yl)methanone

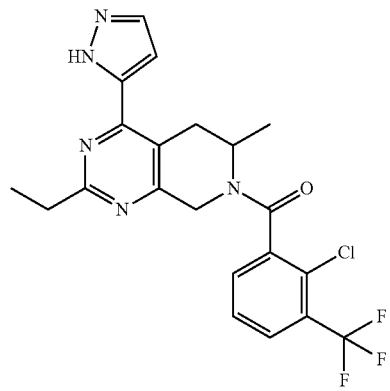 [SMILES: CCc1nc2c(c(-c3ccn[nH]3)n1)CC(C)N(C(=O)c1cccc(C(F)(F)F)c1Cl)C2]

The title compound was prepared in a manner analogous to Example 74 substituting 1-propanimidamide hydrochloride for acetamidine hydrochloride in the synthesis of Intermediate 34 and 2-chloro-3-(trifluoromethyl)benzoic acid for 2-fluoro-3-(trifluoromethyl)benzoic acid in the synthesis of Intermediate 44. MS (ESI): mass calcd. for $C_{21}H_{19}ClF_3N_5O$, 449.1; m/z found, 450.2 [M+H]$^+$. $^1$H NMR (500 MHz, CDCl$_3$) δ 7.83-7.75 (m, 1H), 7.75-7.67 (m, 1H), 7.57-7.41 (m, 2H), 6.93-6.82 (m, 1H), 5.68-5.52 (m, 1H), 4.68-4.39 (m, 1H), 4.37-4.02 (m, 1H), 3.42-3.27 (m, 1H), 3.22-2.98 (m, 2H), 2.96-2.83 (m, 1H), 1.47-1.10 (m, 6H).

Example 99

(R*)-(2-chloro-3-(trifluoromethyl)phenyl)(2-ethyl-6-methyl-4-(1H-pyrazol-5-yl)-5,6-dihydropyrido[3,4-d]pyrimidin-7(8H)-yl)methanone

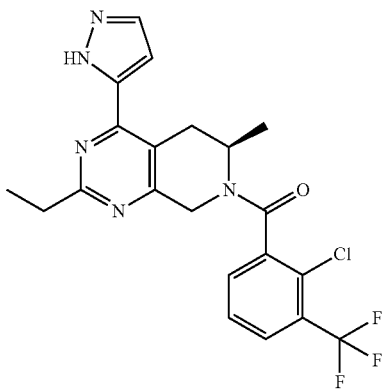 [SMILES: CCc1nc2c(c(-c3ccn[nH]3)n1)C[C@@H](C)N(C(=O)c1cccc(C(F)(F)F)c1Cl)C2]

The title compound, absolute configuration unknown, was obtained as a single enantiomer by Chiral SFC purification of Example 98 performed using a CHIRALCEL OD-H (5 μm, 250×20 mm) column and a mobile phase of 75% CO$_2$, 25% iPrOH. The enantiomeric purity was confirmed by analytical SFC using a CHIRALCEL OD-H (250×4.6 mm) and a mobile phase of 75% CO$_2$, 25% iPrOH containing 0.3% iPrNH$_2$ over 7 minutes. (100% single enantiomer, 3.78 min retention time). MS (ESI): mass calcd. for $C_{21}H_{19}ClF_3N_5O$, 449.1; m/z found, 450.1 [M+H]$^+$. $^1$H NMR (500 MHz, DMSO-d$_6$) δ 7.97 (d, J=8.0 Hz, 1H), 7.92-7.80 (m, 2H), 7.77-7.61 (m, 1H), 7.00 (s, 1H), 5.39-5.19 (m, 1H), 4.56-4.29 (m, 1H), 4.18-3.89 (m, 1H), 3.58-3.33 (m, 1H), 3.27-3.11 (m, 1H), 2.96-2.76 (m, 2H), 1.39-1.01 (m, 6H).

Example 100

(S*)-(2-chloro-3-(trifluoromethyl)phenyl)(2-ethyl-6-methyl-4-(1H-pyrazol-5-yl)-5,6-dihydropyrido[3,4-d]pyrimidin-7(8H)-yl)methanone

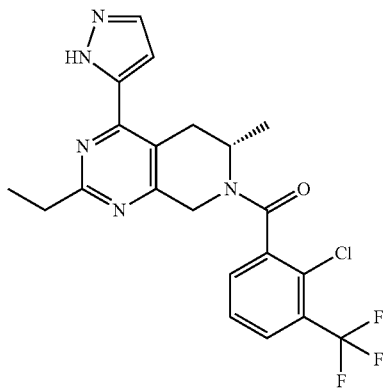 [SMILES: CCc1nc2c(c(-c3ccn[nH]3)n1)C[C@H](C)N(C(=O)c1cccc(C(F)(F)F)c1Cl)C2]

The title compound, absolute configuration unknown, was obtained as a single enantiomer by Chiral SFC purification of Example 98 performed using a CHIRALCEL OD-H (5 μm, 250×20 mm) column and a mobile phase of 75% CO$_2$, 25% iPrOH. The enantiomeric purity was confirmed by analytical SFC using a CHIRALCEL OD-H (250×4.6 mm) and a mobile phase of 75% CO$_2$, 25% iPrOH containing 0.3% iPrNH$_2$ over 7 minutes. (98% single enantiomer, 4.53 min retention time). MS (ESI): mass calcd. for $C_{21}H_{19}ClF_3N_5O$, 449.1; m/z found, 450.0 [M+H]$^+$. $^1$H NMR (500 MHz, DMSO-d$_6$) δ 7.97 (d, J=7.9 Hz, 1H), 7.92-7.82 (m, 2H), 7.76-7.63 (m, 1H), 7.00 (s, 1H), 5.37-5.18 (m, 1H), 4.57-4.29 (m, 1H), 4.20-3.88 (m, 1H), 3.57-3.35 (m, 1H), 3.27-3.13 (m, 1H), 2.96-2.75 (m, 2H), 1.40-1.01 (m, 6H).

Example 101

(2-chloro-3-(trifluoromethyl)phenyl)(2-isopropyl-6-methyl-4-(1H-pyrazol-5-yl)-5,6-dihydropyrido[3,4-d]pyrimidin-7(8H)-yl)methanone

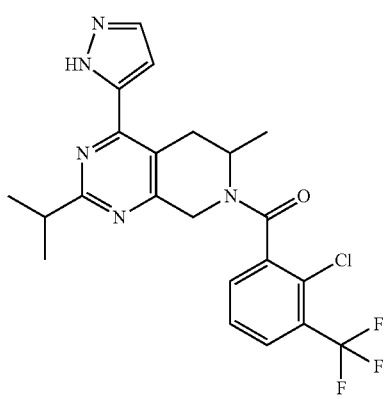 [SMILES: CC(C)c1nc2c(c(-c3ccn[nH]3)n1)CC(C)N(C(=O)c1cccc(C(F)(F)F)c1Cl)C2]

The title compound was prepared in a manner analogous to Example 74 substituting 2-methylpropanimidamide hydrochloride for acetamidine hydrochloride in the synthesis of Intermediate 34 and 2-chloro-3-(trifluoromethyl)benzoic acid for 2-fluoro-3-(trifluoromethyl)benzoic acid in the synthesis of Intermediate 44. MS (ESI): mass calcd. for C$_{22}$H$_{21}$ClF$_3$N$_5$O, 463.1; m/z found, 464.2 [M+H]$^+$. $^1$H NMR (500 MHz, CDCl$_3$) δ 7.83-7.74 (m, 1H), 7.75-7.67 (m, 1H), 7.57-7.42 (m, 2H), 6.92-6.80 (m, 1H), 5.72-5.50 (m, 1H), 4.71-4.38 (m, 1H), 4.37-4.03 (m, 1H), 3.42-3.16 (m, 1H), 3.16-2.91 (m, 2H), 1.46-1.07 (m, 9H).

Example 102

(R*)-(2-chloro-3-(trifluoromethyl)phenyl)(2-isopropyl-6-methyl-4-(1H-pyrazol-5-yl)-5,6-dihydropyrido[3,4-d]pyrimidin-7(8H)-yl)methanone The title compound, absolute configuration unknown, was obtained as a single enantiomer by Chiral SFC purification of Example 101 performed using a CHIRALCEL OD-H (5 µm, 250×20 mm) column and a mobile phase of 75% CO$_2$, 25% iPrOH. The enantiomeric purity was confirmed by analytical SFC using a CHIRALCEL OD-H (250×4.6 mm) and a mobile phase of 75% CO$_2$, 25% iPrOH containing 0.3% iPrNH$_2$ over 7 minutes. (100% single enantiomer, 3.38 min retention time). MS (ESI): mass calcd. for C$_{22}$H$_{21}$ClF$_3$N$_5$O, 463.1; m/z found, 464.1 [M+H]$^+$. $^1$H NMR (500 MHz, DMSO-d$_6$) δ 7.97 (d, J=7.8 Hz, 1H), 7.87 (t, J=13.5 Hz, 2H), 7.77-7.63 (m, 1H), 7.01 (s, 1H), 5.39-5.16 (m, 1H), 4.57-4.28 (m, 1H), 4.18-3.82 (m, 1H), 3.59-3.35 (m, 1H), 3.25-2.96 (m, 2H), 1.40-0.99 (m, 9H).

Example 103

(S*)-(2-chloro-3-(trifluoromethyl)phenyl)(2-isopropyl-6-methyl-4-(1H-pyrazol-5-yl)-5,6-dihydropyrido[3,4-d]pyrimidin-7(8H)-yl)methanone The title compound, absolute configuration unknown, was obtained as a single enantiomer by Chiral SFC purification of Example 101 performed using a CHIRALCEL OD-H (5 µm, 250×20 mm) column and a mobile phase of 75% CO$_2$, 25% iPrOH. The enantiomeric purity was confirmed by analytical SFC using a CHIRALCEL OD-H (250×4.6 mm) and a mobile phase of 75% CO$_2$, 25% iPrOH containing 0.3% iPrNH$_2$ over 7 minutes. (98% single enantiomer, 3.93 min retention time). MS (ESI): mass calcd. for C$_{22}$H$_{21}$ClF$_3$N$_5$O, 463.1; m/z found, 464.1 [M+H]$^+$. $^1$H NMR (500 MHz, DMSO-d$_6$) δ 7.97 (d, J=7.9 Hz, 1H), 7.92-7.82 (m, 2H), 7.77-7.61 (m, 1H), 7.04-6.98 (m, 1H), 5.38-5.18 (m, 1H), 4.60-4.27 (m, 1H), 4.18-3.86 (m, 1H), 3.60-3.33 (m, 1H), 3.26-2.95 (m, 2H), 1.38-0.98 (m, 9H).

Example 104

(2,4-dichloro-3-fluorophenyl)(2-ethyl-6-methyl-4-(1H-pyrazol-5-yl)-5,6-dihydropyrido[3,4-d]pyrimidin-7(8H)-yl)methanone The title compound was prepared in a manner analogous to Example 74 substituting 1-propanimidamide hydrochloride for acetamidine hydrochloride in the synthesis of intermediate 34 and 2,4-dichloro-3-fluorobenzoic acid for 2-fluoro-3-(trifluoromethyl)benzoic acid in the synthesis of Intermediate 44. MS (ESI): mass calcd. for $C_{20}H_{18}Cl_2FN_5O$, 433.1; m/z found, 434.1 [M+H]$^+$. $^1$H NMR (500 MHz, CDCl$_3$) δ 7.75-7.65 (m, 1H), 7.48-7.34 (m, 1H), 7.16-7.02 (m, 1H), 6.94-6.82 (m, 1H), 5.68-5.45 (m, 1H), 4.72-4.25 (m, 1H), 4.19-4.01 (m, 1H), 3.45-3.24 (m, 1H), 3.22-2.82 (m, 3H), 2.13-1.99 (m, 1H), 1.56-1.07 (m, 6H).

Example 105

(4-(1H-pyrazol-1-yl)-5,6-dihydropyrido[3,4-d]pyrimidin-7(8H)-yl)(2,3-dimethylphenyl)methanone

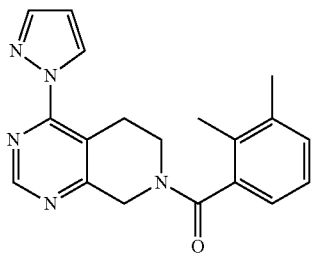 [SMILES: Cc1cccc(C(=O)N2CCc3c(ncnc3-n3cccn3)C2)c1C]

The title compound was prepared in a manner analogous to Example 22 substituting 2,3-dimethylbenzoic acid for 2,3-dichlorobenzoic acid in Example 22, step c. MS (ESI) mass calcd. $C_{19}H_{19}N_5O$, 333.2; m/z found 334.2 [M+H]$^+$. $^1$H NMR (600 MHz, CDCl$_3$): δ 8.90-8.74 (m, 1H), 8.66-8.60 (m, 1H), 7.85-7.74 (m, 1H), 7.23-7.01 (m, 3H), 6.53-6.47 (m, 1H), 5.23-4.95 (m, 1H), 4.53-4.44 (m, 1H), 4.22-3.92 (m, 1H), 3.59-3.44 (m, 2H), 3.37-3.26 (m, 1H), 2.34-2.27 (m, 3H), 2.26-2.13 (m, 3H).

Example 106

(4-(1H-1,2,3-triazol-1-yl)-5,6-dihydropyrido[3,4-d]pyrimidin-7(8H)-yl)(2-chloro-3-(trifluoromethyl)phenyl)methanone

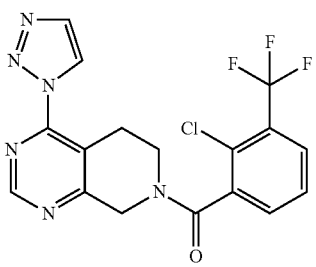 [SMILES: O=C(c1cccc(C(F)(F)F)c1Cl)N1CCc2c(ncnc2-n2ccnn2)C1]

To a suspension of NaH 60% dispersion in mineral oil (21 mg, 0.53 mmol) in DMF (3 mL) was added 1,2,3-triazole (28 L, 0.48 mmol). When gas evolution had ceased the mixture was cooled to 0° C. and Intermediate 4 was added (191 mg, 0.40 mmol). The mixture was allowed to warm to rt overnight and was then diluted with H$_2$O and extracted with EtOAc. The combined organic layers were dried over Na$_2$SO$_4$, filtered and concentrated in vacuo. Chromatography on SiO$_2$ eluting with EtOAc/hexane afforded the desired compound (18 mg, 10%). MS (ESI) mass calcd. $C_{12}H_{12}ClF_3NO$, 408.1; m/z found 409.1 [M+H]$^+$. $^1$H NMR (500 MHz, CDCl$_3$): δ 9.04-8.90 (m, 1H), 8.69-8.65 (m, 1H), 7.89-7.78 (m, 2H), 7.57-7.46 (m, 2H), 5.34-4.98 (m, 1H), 4.67-4.48 (m, 1H), 4.23-4.06 (m, 1H), 3.64-3.35 (m, 3H).

Example 107

7-[(2,3-Dichlorophenyl)carbonyl]-4-(2H-1,2,3-triazol-2-yl)-5,6,7,8-tetrahydropyrido[3,4-d]pyrimidine

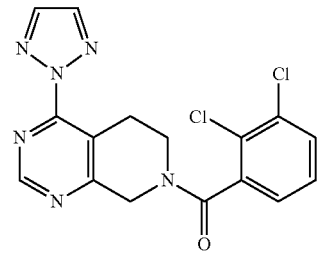

The title compound was prepared in a manner analogous to Example 22 substituting 1H-1,2,3-triazole for pyrazole in Example 22, step a. MS (ESI) mass calcd. $C_{16}H_{12}Cl_2N_6O$, 374.05; m/z found 375.1 [M+H]$^+$. $^1$H NMR (500 MHz, CDCl$_3$): δ 9.12-8.97 (m, 1H), 8.02-7.95 (m, 2H), 7.58-7.52 (m, 1H), 7.36-7.23 (m, 6H), 5.23-5.04 (m, 1H), 4.67-4.49 (m, 1H), 4.13-4.08 (m, 1H), 3.60-3.42 (m, 2H), 3.36-3.21 (m, 1H).

Example 108

7-{[2-Chloro-3-(trifluoromethyl)phenyl]carbonyl}-4-(2H-1,2,3-triazol-2-yl)-5,6,7,8-tetrahydropyrido[3,4-d]pyrimidine

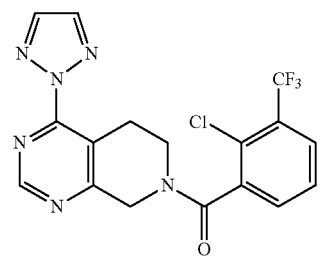

The title compound was prepared in a manner analogous to Example 22 substituting 1H-1,2,3-triazole for pyrazole in Example 22, step a and 2-chloro-3-(trifluoromethyl)benzoic acid for 2,3-dichlorobenzoic acid. MS (ESI) mass calcd. $C_{17}H_{12}ClF_3N_6O$, 408.07; m/z found 409.1 [M+H]$^+$. $^1$H NMR (500 MHz, CDCl$_3$): δ 9.12-8.98 (m, 1H), 8.02-7.96 (m, 2H), 7.83-7.78 (m, 1H), 7.58-7.47 (m, 2H), 5.27-5.03 (m, 1H), 4.66-4.48 (m, 1H), 4.20-4.05 (m, 1H), 3.57-3.43 (m, 2H), 3.36-3.22 (m, 1H).

Example 109

(4-(4H-1,2,4-triazol-4-yl)-5,6-dihydropyrido[3,4-d]pyrimidin-7(8H)-yl)(2-chloro-3-(trifluoromethyl)phenyl)methanone

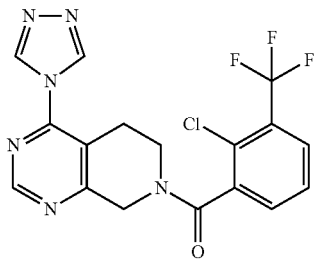 [SMILES: O=C(c1cccc(C(F)(F)F)c1Cl)N1CCc2c(ncnc2-n2cnnc2)C1]

Example 109, Step a: tert-butyl 4-(4H-1,2,4-triazol-4-yl)-5,6-dihydropyrido[3,4-d]pyrimidine-7(8H)-carboxylate To a solution of Intermediate 2 (1.5 g, 5.6 mmol) in ACN (5 mL) was added 1, 2, 4 triazole (0.657 mL, 11.1 mmol) in one portion followed by Hunig's base (1.9 mL, 11.1 mmol). The mixture was stirred at 110° C. overnight. The solvents were removed in vacuo and chromatography on $SiO_2$ eluting with EtOAc/hexane afforded the desired compound (579 mg, 34%). MS (ESI) mass calcd. $C_{14}H_{18}N_6O_2$, 302.1; m/z found 303.2 $[M+H]^+$. $^1$H NMR (500 MHz, $CDCl_3$): δ 9.04 (s, 1H), 7.98 (s, 2H), 4.81-4.75 (m, 2H), 3.75-3.69 (m, 2H), 3.29-3.22 (m, 2H), 1.51 (s, 9H).

Example 109, Step b: 4-(4H-1,2,4-triazol-4-yl)-5,6,7,8-tetrahydropyrido[3,4-d]pyrimidine To the product of Example 109 step a (574 mg, 1.9 mmol) in DCM (9.5 mL) was added TFA (3.8 mL). After stirring 2 h the reaction was concentrated in vacuo. The residue was redissolved in DCM and treated with Dowex 550A resin to neutralize the TFA salt. The resin was removed by filtration and concentration afforded a yellow solid (347 mg, 90%). This material was used without further purification. MS (ESI) mass calcd. $C_9H_{10}N_6$, 202.2; m/z found 203.1 $[M+H]^+$.

Example 109, step c: (4-(4H-1,2,4-triazol-4-yl)-5,6-dihydropyrido[3,4-d]pyrimidin-7(8H)-yl)(2-chloro-3-(trifluoromethyl)phenyl)methanone To the product of Example 109 step b (48 mg, 0.24 mmol) in DCM (3 mL) was added Intermediate 45 (61 mg, 0.25 mmol) and TEA (40 μL, 0.29 mmol). The reaction was stirred at room temperature overnight. The solvents were removed in vacuo and chromatography on $SiO_2$ eluting with EtOAc/hexane afforded the desired compound (93 mg, 94%). MS (ESI) mass calcd. $C_{17}H_{12}ClF_3N_6O$, 408.1; m/z found 409.1 $[M+H]^+$. $^1$H NMR (500 MHz, $CDCl_3$): δ 9.14-8.95 (m, 1H), 8.04-7.95 (m, 2H), 7.83-7.77 (m, 1H), 7.60-7.46 (m, 2H), 5.29-5.01 (m, 1H), 4.68-4.47 (m, 1H), 4.21-4.04 (m, 1H), 3.60-3.22 (m, 3H).

Example 110

(4-(1H-1,2,4-triazol-1-yl)-5,6-dihydropyrido[3,4-d]pyrimidin-7(8H)-yl)(2-chloro-3-(trifluoromethyl)phenyl)methanone

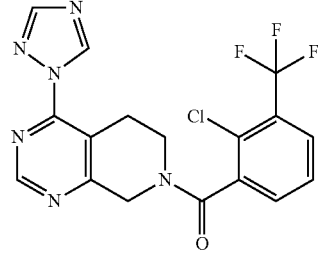 [SMILES: O=C(c1cccc(C(F)(F)F)c1Cl)N1CCc2c(ncnc2-n2cncn2)C1]

Example 110, Step a: tert-butyl 4-(1H-1,2,4-triazol-1-yl)-5,6-dihydropyrido[3,4-d]pyrimidine-7(8H)-carboxylate To a solution of Intermediate 2 (1.5 g, 5.6 mmol) in ACN (5 mL) was added 1, 2, 4 triazole (0.657 mL, 11.1 mmol) in one portion followed by Hunig's base (1.9 mL, 11.1 mmol). The mixture was stirred at 110° C. overnight. The solvents were removed in vacuo and chromatography on $SiO_2$ eluting with EtOAc/hexane afforded the desired compound (855 mg, 50%). MS (ESI) mass calcd. $C_{14}H_{18}N_6O_2$, 302.1; m/z found 303.2 $[M+H]^+$. $^1$H NMR (500 MHz, $CDCl_3$): δ 8.96 (s, 1H), 8.66-8.61 (m, 1H), 7.87-7.84 (m, 1H), 4.78 (s, 2H), 3.76-3.71 (m, 2H), 3.43-3.36 (m, 2H), 1.51 (s, 9H).

Example 110, Step b: 4-(1H-1,2,4-triazol-1-yl)-5,6,7,8-tetrahydropyrido[3,4-d]pyrimidine To the product of Example 110, step a (850 mg, 2.8 mmol) in DCM (14 mL) was added TFA (5 mL). After stirring 2 h, the reaction was concentrated in vacuo. Chromatography on $SiO_2$ eluting with 2 M $NH_3$ in MeOH/DCM afforded the desired product as a pale yellow solid (190 mg, 33%). This material was used without further purification. MS (ESI) mass calcd. $C_9H_{10}N_6$, 202.2; m/z found 203.1 $[M+H]^+$. $^1$H NMR (500 MHz, $CDCl_3$): δ 8.92 (s, 1H), 8.63 (d, J=1.2 Hz, 1H), 7.85 (d, J=1.2 Hz, 1H), 4.23 (s, 2H), 3.36 (t, J=5.7 Hz, 2H), 3.23 (t, J=5.9 Hz, 2H).

Example 110, step c: (4-(4H-1,2,4-triazol-4-yl)-5,6-dihydropyrido[3,4-d]pyrimidin-7(8H)-yl)(2-chloro-3-(trifluoromethyl)phenyl)methanone To the product of Example 110, step b (43 mg, 0.21 mmol) in DCM (2 mL) was added Intermediate 45 (54 mg, 0.22 mmol) and TEA (35 L, 0.26 mmol). The reaction was stirred at room temperature overnight. The solvents were removed in vacuo and chromatography on $SiO_2$ eluting with EtOAc/hexane afforded the desired compound (70 mg, 80%). MS (ESI) mass calcd. $C_{17}H_{12}ClF_3N_6O$, 408.1; m/z found 409.1 $[M+H]^+$. $^1$H NMR (500 MHz, $CDCl_3$): δ 9.06-8.88 (m, 1H), 8.71-8.64 (m, 1H), 7.90-7.76 (m, 2H), 7.59-7.46 (m, 2H), 5.35-4.97 (m, 1H), 4.68-4.47 (m, 1H), 4.24-4.05 (m, 1H), 3.63-3.35 (m, 3H).

Example 111

(4-(1H-pyrazol-5-yl)-5,6-dihydropyrido[3,4-d]pyrimidin-7(8H)-yl)(2-fluoro-3-(trifluoromethyl)phenyl)methanone

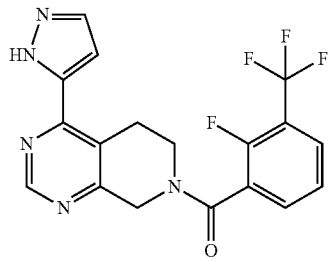 [SMILES: O=C(c1cccc(C(F)(F)F)c1F)N1CCc2c(ncnc2-c2ccn[nH]2)C1]

Example 111, step a: 4-(1-(tetrahydro-2H-pyran-2-yl)-1H-pyrazol-5-yl)-5,6,7,8-tetrahydropyrido[3,4-d]pyrimidine To the microwave vial was added the Intermediate 6 (262 mg, 0.99 mmol) and 1-(tetrahydropyran-2-yl)-1h-pyrazole-5-boronic acid pinacol ester (347 mg, 1.2 mmol) followed by dioxane (5 mL) and 2M $Na_2CO_3$ (1.2 mL). To this mixture was added $Pd(Ph_3P)_4$ (57 mg, 0.049 mmol) and the reaction heated in the microwave for 1 h at 150° C. The reaction was diluted with water and extracted with DCM and EtOAc. The combined organic extracts were dried over $Na_2SO_4$, filtered and concentrated in vacuo. Chromatography on $SiO_2$ eluting with 2 M $NH_3$ in MeOH/DCM afforded the desired product (255 mg, 90%). MS (ESI) mass calcd. $C_{15}H_{19}N_5O$, 285.2; m/z found 286.2 [M+H]+. 1H NMR (500 MHz, CDCl3): δ 9.09-9.03 (m, 1H), 7.70-7.63 (m, 1H), 6.56-6.50 (m, 1H), 5.84-5.75 (m, 1H), 4.27-4.00 (m, 2H), 3.96-3.88 (m, 1H), 3.50-3.39 (m, 1H), 3.32-3.25 (m, 1H), 3.12-3.03 (m, 1H), 2.99-2.90 (m, 1H), 2.86-2.77 (m, 1H), 2.53-2.42 (m, 1H), 2.15-2.03 (m, 2H), 1.74-1.48 (m, 3H).

Example 111, step b: (2-fluoro-3-(trifluoromethyl)phenyl)(4-(1-(tetrahydro-2H-pyran-2-yl)-1H-pyrazol-5-yl)-5,6-dihydropyrido[3,4-d]pyrimidin-7(8H)-yl)methanone The title compound was prepared in a manner analogous to Example 1 substituting the product of Example 111 step a for Intermediate 1 and 2-fluoro-3-(trifluoromethyl)benzoic acid for 2-chloro-3-(trifluoromethyl)benzoic acid. MS (ESI) mass calcd. $C_{23}H_{21}F_4N_5O_2$, 475.4; m/z found 476.2 [M+H]+. 1H NMR (500 MHz, CDCl3): δ 9.19-9.03 (m, 1H), 7.77-7.63 (m, 3H), 7.41-7.35 (m, 1H), 6.59-6.48 (m, 1H), 5.91-5.77 (m, 1H), 5.32-5.23 (m, 1H), 4.93-4.81 (m, 1H), 4.75-4.53 (m, 1H), 3.93-3.86 (m, 1H), 3.71-3.62 (m, 1H), 3.52-3.40 (m, 1H), 3.11-2.82 (m, 2H), 2.53-2.41 (m, 1H), 2.16-2.06 (m, 2H), 1.74-1.59 (m, 2H), 1.57-1.49 (m, 1H).

Example 111, step c: (4-(1H-pyrazol-5-yl)-5,6-dihydropyrido[3,4-d]pyrimidin-7(8H)-yl)(2-fluoro-3-(trifluoromethyl)phenyl)methanone The title compound was prepared in a manner analogous to Example 33 substituting the product of Example 111 step b for Intermediate 20. MS (ESI) mass calcd. $C_{18}H_{13}F_4N_5O$, 391.1; m/z found 392.1 [M+H]+. 1H NMR (500 MHz, CDCl3): δ 11.10 (s, 1H), 9.11-8.93 (m, 1H), 7.79-7.61 (m, 3H), 7.43-7.32 (m, 1H), 7.00-6.91 (m, 1H), 5.06 (s, 1H), 4.72-3.57 (m, 3H), 3.40-3.13 (m, 2H).

Example 112

(2-chloro-3-(trifluoromethyl)phenyl)(8-methyl-4-(1H-pyrazol-5-yl)-5,6-dihydropyrido[3,4-d]pyrimidin-7(8H)-yl)methanone

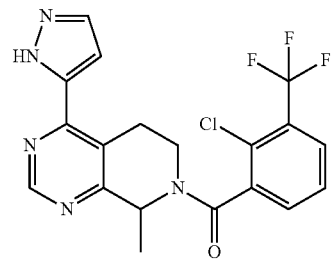 [SMILES: CC1c2ncnc(-c3ccn[nH]3)c2CCN1C(=O)c1cccc(C(F)(F)F)c1Cl]

Example 112, step a: ethyl 2-(benzylamino)propanoate

To a mixture of DL-alanine ethyl ester hydrochloride (913 mg, 5.9 mmol) in DCE (15 mL) was added TEA (1.2 mL, 8.8 mmol) followed by benzaldehyde (0.538 mL, 5.3 mmol) and $Na(OAc)_3BH$ (2.0 g, 9.4 mmol). The mixture was stirred at room temperature overnight and then quenched with saturated aqueous $NaHCO_3$ solution. The layers were separated and the aqueous layer extracted with DCM. The combined organic layers were dried over $Na_2SO_4$, filtered and concentrated in vacuo. Chromatography on $SiO_2$ eluting EtOAc/hexane afforded the desired compound as a colorless liquid (798 mg, 73%). MS (ESI) mass calcd. $C_{12}H_{17}NO_2$, 207.1; m/z found 208.2 [M+H]+. 1H NMR (500 MHz, CDCl3): δ7.39-7.23 (m, 5H), 4.23-4.16 (m, 2H), 3.83-3.65 (m, 2H), 3.37 (q, J=7.0 Hz, 1H), 1.34-1.27 (m, 6H).

Example 112, step b: methyl 4-(benzyl(1-ethoxy-1-oxopropan-2-yl)amino)butanoate

To a solution of the product of Example 112, step a (794 mg, 3.8 mmol) in DCE (10 mL) was added methyl-4-oxobutanoate (0.891 mL, 7.7 mmol) followed by $Na(OAc)_3BH$ (1.6 g, 7.7 mmol). The mixture was stirred at room temperature overnight and then quenched by the addition of saturated aqueous $NaHCO_3$ solution. The layers were separated and the combined organic layers were dried over $Na_2SO_4$, filtered and concentrated in vacuo. Chromatography on $SiO_2$ column eluting with EtOAc/hexane afforded the desired compound as a colorless liquid (1.11 g, 95%). MS (ESI) mass calcd. $C_{17}H_{25}NO_4$, 307.2; m/z found 308.2 [M+H]+. 1H NMR (500 MHz, CDCl3) δ 7.35-7.20 (m, 5H), 4.22-4.12 (m, 2H), 3.86-3.80 (m, 1H), 3.67-3.60 (m, 4H), 3.52-3.45 (m, 1H), 2.69-2.56 (m, 2H), 2.41-2.26 (m, 2H), 1.80-1.71 (m, 2H), 1.33-1.24 (m, 6H).

Example 112, step c: methyl 1-benzyl-2-methyl-3-oxopiperidine-4-carboxylate and ethyl 1-benzyl-2-methyl-3-oxopiperidine-4-carboxylate To a solution of the product of Example 112, step b (1.11 g, 3.62 mmol) in toluene (74 mL) was added KOtBu (731 mg, 6.52 mmol). The mixture was stirred at room temperature overnight and then quenched with saturated aqueous NH$_4$Cl solution. The aqueous layer was extracted with DCM and the combined organic extracts were dried over Na$_2$SO$_4$, filtered and concentrated in vacuo to 790 mg of crude material. Chromatography on SiO$_2$ eluting EtOAc/hexane afforded 576.7 mg of a mixture of methyl 1-benzyl-2-methyl-3-oxopiperidine-4-carboxylate and ethyl 1-benzyl-2-methyl-3-oxopiperidine-4-carboxylate in a ratio of 40:60 as determined by NMR analysis. This mixture was taken on to step d. MS (ESI) mass calcd. C$_{15}$H$_{19}$NO$_3$, 261.1; m/z found 262.2 [M+H]$^+$ and MS (ESI) mass calcd. C$_{16}$H$_{21}$NO$_3$; 275.2 m/z found 276.2 [M+H]$^+$.

Example 112, step d: 7-benzyl-8-methyl-5,6,7,8-tetrahydropyrido[3,4-d]pyrimidin-4-ol To a solution of the mixture of products from Example 112, step c, (575 mg, 2.09 mmol) in EtOH (10 mL) was added formamidine hydrochloride (257 mg, 3.13 mmol) followed by NaOEt (1.95 mL, 5.21 mmol) dropwise. The mixture was then heated to reflux overnight and the reaction was not complete as determined by LC/MS analysis. Additional formamidine hydrochloride (130 mg, 1.57 mmol) and NaOEt (1 mL) was added and heating was continued overnight. The reaction was treated with 1 N HCl until pH 6 and concentrated in vacuo. The residue was then azeotroped with toluene. Chromatography on SiO$_2$ eluting with IPA/EtOAc afforded the desired compound as a pale yellow foam (391 mg, 73%). MS (ESI) mass calcd. C$_{15}$H$_{17}$N$_3$O, 255.1; m/z found 256.2 [M+H]$^+$. $^1$H NMR (500 MHz, CDCl$_3$): δ 12.75 (s, 1H), 8.04 (s, 1H), 7.41-7.23 (m, 5H), 3.87-3.80 (m, 1H), 3.74-3.63 (m, 2H), 3.01-2.91 (m, 1H), 2.74-2.58 (m, 2H), 2.56-2.46 (m, 1H), 1.42 (d, J=6.8, 3H).

Example 112, step e: 7-benzyl-4-chloro-8-methyl-5,6,7,8-tetrahydropyrido[3,4-d]pyrimidine The title compound was prepared in a manner analogous to Intermediate 8 substituting the product of Example 112, step d for Intermediate 7. MS (ESI) mass calcd. C$_{15}$H$_{16}$ClN$_3$, 273.1; m/z found 274.1 [M+H]$^+$. $^1$H NMR (500 MHz, CDCl$_3$): δ 8.76 (s, 1H), 7.39-7.26 (m, 5H), 3.93-3.83 (m, 2H), 3.72-3.66 (m, 1H), 3.07-3.00 (m, 1H), 2.88-2.79 (m, 1H), 2.77-2.69 (m, 2H), 1.48 (d, J=6.8 Hz, 3H).

Example 112, step f: 7-benzyl-8-methyl-4-(1-(tetrahydro-2H-pyran-2-yl)-1H-pyrazol-5-yl)-5,6,7,8-tetrahydropyrido[3,4-d]pyrimidine The title compound was prepared in a manner analogous to Intermediate 19 substituting the product of Example 112 step e for Intermediate 11. MS (ESI) mass calcd. C$_{23}$H$_{27}$N$_5$O, 389.2; m/z found 390.3 [M+H]$^+$.

Example 112, step g, 8-methyl-4-(1-(tetrahydro-2H-pyran-2-yl)-1H-pyrazol-5-yl)-5,6,7,8-tetrahydropyrido[3,4-d]pyrimidine To the product of Example 112, step f (356 mg, 0.91 mmol) in EtOH (9 mL) was added a catalytic amount of 10% Pd/C Degussa type followed by a balloon of hydrogen gas. The mixture was stirred at room temperature overnight. The balloon was refilled with hydrogen gas and an additional spatula tip of 10% Pd/C was added. After an additional 24 h and the reaction was complete. The catalyst was removed by filtration and the liquid was concentrated in vacuo to afford the desired product (268 mg, 98%). MS (ESI) mass calcd. C$_{16}$H$_{21}$N$_5$O, 299.2; m/z found 300.2 [M+H]$^+$.

Example 112, step h: (2-chloro-3-(trifluoromethyl)phenyl)(8-methyl-4-(1H-pyrazol-5-yl)-5,6-dihydropyrido[3,4-d]pyrimidin-7(8H)-yl)methanone The title compound was prepared in a manner analogous to Example 74 substituting the product of Example 112 step g for Intermediate 43 and Intermediate 45 for Intermediate 44. MS (ESI) mass calcd. C$_{19}$H$_{15}$ClF$_3$N$_5$O, 421.1; m/z found 422.1 [M+H]$^+$. $^1$H NMR (400 MHz, CDCl$_3$): δ 9.17-8.94 (m, 1H), 7.86-7.30 (m, 4H), 6.98-6.86 (m, 1H), 5.90-5.76 (m, 1H), 5.17-5.03 (m, 0.5H), 4.67-4.47 (m, 0.5H), 3.68-2.92 (m, 3H), 1.84-1.49 (m, 3H).

Example 113

(R*)-(2-chloro-3-(trifluoromethyl)phenyl)(8-methyl-4-(1H-pyrazol-5-yl)-5,6-dihydropyrido[3,4-d]pyrimidin-7(8H)-yl)methanone

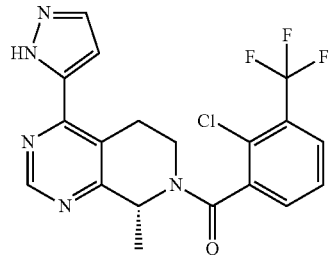 [SMILES: C[C@@H]1c2ncnc(-c3ccn[nH]3)c2CCN1C(=O)c1cccc(C(F)(F)F)c1Cl]

The title compound, absolute configuration unknown, was obtained as a single enantiomer by Chiral SFC purification of Example 112 performed using CHIRALCEL OD-H (5 μm, 250×20 mm) and a mobile phase of 65% CO$_2$, 35% iPrOH. The enantiomeric purity was confirmed by analytical SFC using a CHIRALCEL OD-H (250×4.6 mm) and a mobile phase of 60% CO$_2$, 40% iPrOH containing 0.3% iPrNH$_2$ over 7 minutes. (100% single enantiomer, 1.73 min retention time). MS (ESI) mass calcd. C$_{19}$H$_{15}$ClF$_3$N$_5$O, 421.1; m/z found 421.7 [M+H]$^+$.

Example 114

(S*)-(2-chloro-3-(trifluoromethyl)phenyl)(8-methyl-4-(1H-pyrazol-5-yl)-5,6-dihydropyrido[3,4-d]pyrimidin-7(8H)-yl)methanone

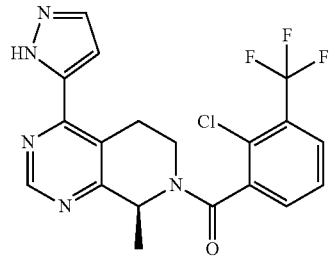 [SMILES: C[C@H]1c2ncnc(-c3ccn[nH]3)c2CCN1C(=O)c1cccc(C(F)(F)F)c1Cl]

The title compound, absolute configuration unknown, was obtained as a single enantiomer by Chiral SFC purification of Example 112 performed using CHIRALCEL OD-H (5 μm, 250×20 mm) and a mobile phase of 65% $CO_2$, 35% iPrOH. The enantiomeric purity was confirmed by analytical SFC using a CHIRALCEL OD-H (250×4.6 mm) and a mobile phase of 60% $CO_2$, 40% iPrOH containing 0.3% $iPrNH_2$ over 7 minutes. (100% single enantiomer, 2.76 min retention time). MS (ESI) mass calcd. $C_{19}H_{15}ClF_3N_5O$, 421.1; m/z found 421.7 [M+H]$^+$.

Example 115

(2-chloro-4-fluoro-3-(trifluoromethyl)phenyl)(8-methyl-4-(1H-pyrazol-5-yl)-5,6-dihydropyrido[3,4-d]pyrimidin-7(8H)-yl)methanone

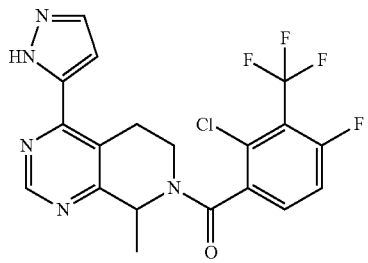 [SMILES: CC1c2ncnc(-c3ccn[nH]3)c2CCN1C(=O)c1ccc(F)c(C(F)(F)F)c1Cl]

To a solution of the product of Example 112, step g (60 mg, 0.20 mmol) in DCM (2 mL) was added 2-chloro-4-fluoro-3-(trifluoromethyl)benzoic acid (49 mg, 0.20 mmol), followed by EDCI (116 mg, 0.607 mmol), HOBt (19 mg, 0.14 mmol) and TEA (2.0 mL, 0.607 mmol). The reaction was stirred at room temperature overnight. The crude mixture was treated directly with TFA (0.8 mL) and triethylsilane (81 L, 0.20 mmol) and stirred for 3 h. The solvents were removed in vacuo and the residue was azeotroped with toluene (1×). Chromatography on $SiO_2$ eluted with EtOAc/hexane afforded the desired product (59 mg, 66%). MS (ESI) mass calcd. $C_{19}H_{14}ClF_4N_5O$, 439.1; m/z found 440.1 [M+H]$^+$. $^1$H NMR (500 MHz, MeOD): δ 9.08-8.87 (m, 1H), 7.92-7.68 (m, 2H), 7.57-7.44 (m, 1H), 7.10-6.92 (m, 1H), 5.71-5.63 (m, 1H), 3.68-3.33 (m, 3H), 3.19-3.08 (m, 1H), 1.77-1.56 (m, 3H).

Example 116

(R*)-(2-chloro-4-fluoro-3-(trifluoromethyl)phenyl)(8-methyl-4-(1H-pyrazol-5-yl)-5,6-dihydropyrido[3,4-d]pyrimidin-7(8H)-yl)methanone

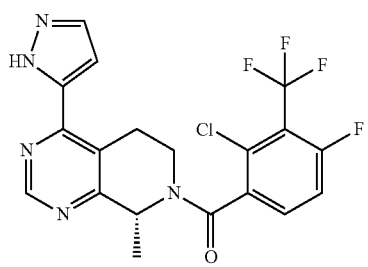 [SMILES: C[C@@H]1c2ncnc(-c3ccn[nH]3)c2CCN1C(=O)c1ccc(F)c(C(F)(F)F)c1Cl]

The title compound, absolute configuration unknown, was obtained as a single enantiomer by Chiral SFC purification of Example 115 performed using CHIRALCEL OD-H (5 μm, 250×20 mm) and a mobile phase of 70% $CO_2$, 30% iPrOH. The enantiomeric purity was confirmed by analytical SFC using a CHIRALCEL OD-H (250×4.6 mm) and a mobile phase of 70% $CO_2$, 30% iPrOH containing 0.3% $iPrNH_2$ over 7 minutes. (100% single enantiomer, 2.47 min retention time). MS (ESI) mass calcd. $C_{19}H_{14}ClF_4N_5O$, 439.1; m/z found 440.0 [M+H]$^+$.

Example 117

(S*)-(2-chloro-4-fluoro-3-(trifluoromethyl)phenyl)(8-methyl-4-(1H-pyrazol-5-yl)-5,6-dihydropyrido[3,4-d]pyrimidin-7(8H)-yl)methanone

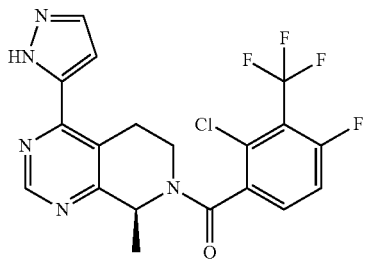 [SMILES: C[C@H]1c2ncnc(-c3ccn[nH]3)c2CCN1C(=O)c1ccc(F)c(C(F)(F)F)c1Cl]

The title compound, absolute configuration unknown, was obtained as a single enantiomer by Chiral SFC purification of Example 115 performed using CHIRALCEL OD-H (5 μm, 250×20 mm) and a mobile phase of 70% $CO_2$, 30% iPrOH. The enantiomeric purity was confirmed by analytical SFC using a CHIRALCEL OD-H (250×4.6 mm) and a mobile phase of 70% $CO_2$, 30% iPrOH containing 0.3% $iPrNH_2$ over 7 minutes. (98% single enantiomer, 4.09 min retention time). MS (ESI) mass calcd. $C_{19}H_{14}ClF_4N_5O$, 439.1; m/z found 440.0 [M+H]$^+$.

Example 118

(2,3-dichloro-4-fluorophenyl)(8-methyl-4-(1H-pyrazol-5-yl)-5,6-dihydropyrido[3,4-d]pyrimidin-7(8H)-yl)methanone

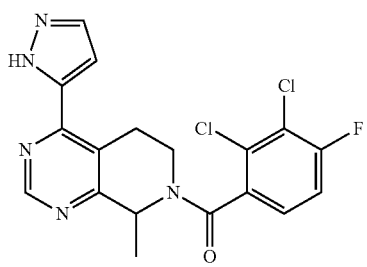

The title compound was prepared in a manner analogous to Example 74 substituting 2,3-dichloro-4-fluorobenzoic acid for 2-fluoro-3-(trifluoromethyl)benzoic acid in the synthesis of Intermediate 44 and the product of Example 112, step g for Intermediate 43. MS (ESI) mass calcd. $C_{18}H_{14}Cl_2FN_5O$, 405.1; m/z found 406.1 [M+H]$^+$. $^1$H NMR (500 MHz, $CD_3OD$) δ 9.04-8.89 (m, 1H), 7.79-7.70 (m, 1H), 7.56-7.28 (m, 2H), 7.07-6.96 (m, 1H), 5.71-5.62 (m, 1H), 3.73-3.32 (m, 3H), 3.29-3.07 (m, 1H), 1.78-1.54 (m, 3H).

Example 119

(R*)-(2,3-dichloro-4-fluorophenyl)(8-methyl-4-(1H-pyrazol-5-yl)-5,6-dihydropyrido[3,4-d]pyrimidin-7(8H)-yl)methanone

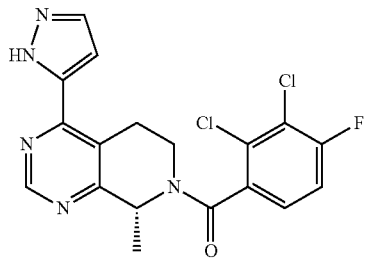 [SMILES: C[C@@H]1c2ncnc(-c3ccn[nH]3)c2CCN1C(=O)c1ccc(F)c(Cl)c1Cl]

The title compound, absolute configuration unknown, was obtained as a single enantiomer by Chiral SFC purification of Example 118 performed using CHIRALCEL OD-H (5 μm, 250×20 mm) and a mobile phase of 60% $CO_2$, 40% iPrOH. The enantiomeric purity was confirmed by analytical SFC using a CHIRALCEL OD-H (250×4.6 mm) and a mobile phase of 60% $CO_2$, 40% iPrOH containing 0.3% iPrNH$_2$ over 7 minutes. (100% single enantiomer, 2.10 min retention time). MS (ESI) mass calcd. $C_{18}H_{14}Cl_2FN_5O$, 405.1; m/z found 406.0 [M+H]$^+$.

Example 120

(S*)-(2,3-dichloro-4-fluorophenyl)(8-methyl-4-(1H-pyrazol-5-yl)-5,6-dihydropyrido[3,4-d]pyrimidin-7(8H)-yl)methanone

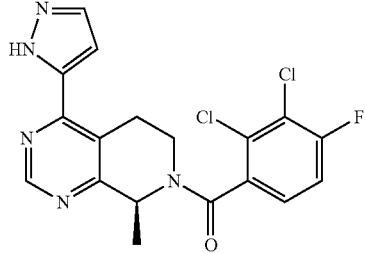

The title compound, absolute configuration unknown, was obtained as a single enantiomer by Chiral SFC purification of Example 118 performed using CHIRALCEL OD-H (5 μm, 250×20 mm) and a mobile phase of 60% $CO_2$, 40% iPrOH. The enantiomeric purity was confirmed by analytical SFC using a CHIRALCEL OD-H (250×4.6 mm) and a mobile phase of 60% $CO_2$, 40% iPrOH containing 0.3% iPrNH$_2$ over 7 minutes. (100% single enantiomer, 2.84 min retention time). MS (ESI) mass calcd. $C_{18}H_{14}Cl_2FN_5O$, 405.1; m/z found 406.0 [M+H]$^+$.

Example 121

((2,4-dichloro-3-fluorophenyl)(8-methyl-4-(1H-pyrazol-5-yl)-5,6-dihydropyrido[3,4-d]pyrimidin-7(8H)-yl)methanone

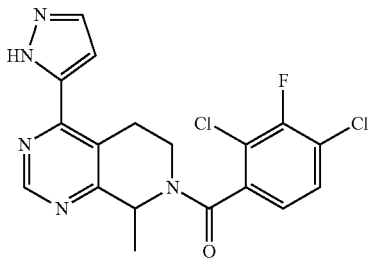 [SMILES: CC1c2ncnc(-c3ccn[nH]3)c2CCN1C(=O)c1ccc(Cl)c(F)c1Cl]

The title compound was prepared in a manner analogous to Example 115 substituting 2,4-dichloro-3-fluorobenzoyl chloride for 2-chloro-4-fluoro-3-(trifluoromethyl)benzoic acid. MS (ESI) mass calcd. $C_{18}H_{14}Cl_2FN_5O$, 405.1; m/z found 406.1 [M+H]$^+$. $^1$H NMR (500 MHz, MeOD): δ 9.05-8.88 (m, 1H), 7.80-7.43 (m, 2H), 7.40-7.21 (m, 1H), 7.08-6.93 (m, 1H), 5.71-5.61 (m, 1H), 4.53-4.46 (m, OH), 3.70-3.33 (m, 3H), 3.28-3.06 (m, 1H), 1.80-1.53 (m, 3H).

Example 122

(R*)-(2,4-dichloro-3-fluorophenyl)(8-methyl-4-(1H-pyrazol-5-yl)-5,6-dihydropyrido[3,4-d]pyrimidin-7(8H)-yl)methanone

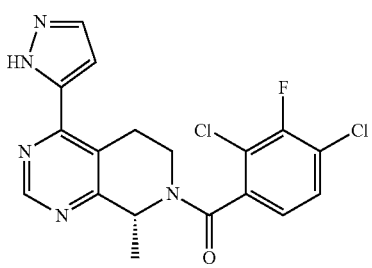 [SMILES: C[C@@H]1c2ncnc(-c3ccn[nH]3)c2CCN1C(=O)c1ccc(Cl)c(F)c1Cl]

The title compound, absolute configuration unknown, was obtained as a single enantiomer by Chiral SFC purification of Example 121 performed using CHIRALCEL OD-H (5 μm, 250×20 mm) and a mobile phase of 60% $CO_2$, 40% iPrOH. The enantiomeric purity was confirmed by analytical SFC using a CHIRALCEL OD-H (250×4.6 mm) and a mobile phase of 60% $CO_2$, 40% iPrOH containing 0.3% iPrNH$_2$ over 7 minutes. (100% single enantiomer, 2.08 min retention time). MS (ESI) mass calcd. $C_{18}H_{14}Cl_2FN_5O$, 405.1; m/z found 406.0 [M+H]$^+$.

Example 123

(S*)-(2,4-dichloro-3-fluorophenyl)(8-methyl-4-(1H-pyrazol-5-yl)-5,6-dihydropyrido[3,4-d]pyrimidin-7(8H)-yl)methanone

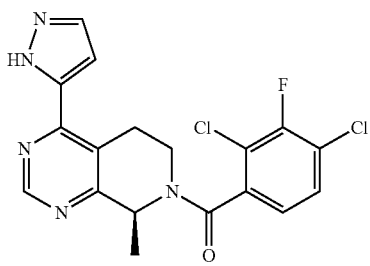 [SMILES: C[C@H]1c2ncnc(-c3ccn[nH]3)c2CCN1C(=O)c1ccc(Cl)c(F)c1Cl]

The title compound, absolute configuration unknown, was obtained as a single enantiomer by Chiral SFC purification of Example 121 performed using CHIRALCEL OD-H (5 μm, 250×20 mm) and a mobile phase of 60% $CO_2$, 40% iPrOH. The enantiomeric purity was confirmed by analytical SFC using a CHIRALCEL OD-H (250×4.6 mm) and a mobile phase of 60% $CO_2$, 40% iPrOH containing 0.3% $iPrNH_2$ over 7 minutes. (99% single enantiomer, 2.78 min retention time). MS (ESI) mass calcd. $C_{18}H_{14}Cl_2FN_5O$, 405.1; m/z found 406.0 [M+H]$^+$.

Example 124

(R*)-(2-chloro-3-(trifluoromethyl)phenyl)(4-(1-(2-fluoroethyl)-1H-pyrazol-3-yl)-2,6-dimethyl-5,6-dihydropyrido[3,4-d]pyrimidin-7(8H)-yl)methanone

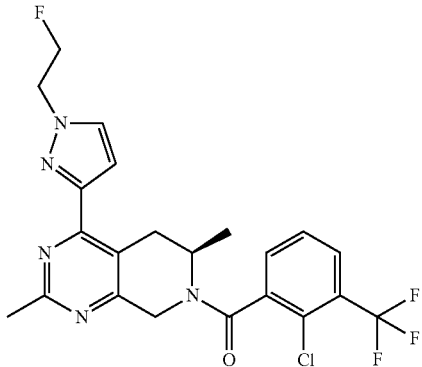 [SMILES: Cc1nc2c(c(-c3ccn(CCF)n3)n1)C[C@@H](C)N(C(=O)c1cccc(C(F)(F)F)c1Cl)C2]

1-bromo-2-fluoroethane (59 mL, 0.688 mmol), $Cs_2CO_3$ (560 mg, 1.72 mmol) and the product from Example 56 (250 mg, 0.574 mmol) were combined in DMF (2 mL) and heated at 120° C. for 10 min under microwave irradiation. The reaction mixture was treated with water and extracted with DCM. The organic layer was separated, dried ($Na_2SO_4$), filtered and concentrated in vacuo. The crude product was purified by chromatography (silica, EtOAc in Heptane 30/70 to 100/0), the desired fractions were collected, the solvent evaporated in vacuo. The racemic product (72 mg, 26%) obtained by trituration with DIPE. The title compound, absolute configuration unknown, was obtained by chiral SFC purification of the racemic product using a CHIRAL-CEL OD-H (5 μm, 250×20 mm) and a mobile phase of 80% $CO_2$, 20% EtOH. The enantiomeric purity was confirmed by analytical SFC using a CHIRALCEL OD-H (250×4.6 mm) and a mobile phase of 80% $CO_2$, 20% EtOH containing 0.3% $iPrNH_2$ over 7 minutes. (100% single enantiomer, 5.15 min retention time). MS (ESI) mass calcd. $C_{22}H_{20}ClF_4N_5O$, 481.1; m/z found 482.1 [M+H]$^+$. $^1$H NMR (400 MHz, $CDCl_3$) δ 7.81-7.73 (m, 1H), 7.70-7.40 (m, 3H), 7.06-7.02 (m, 1H), 5.70-5.51 (m, 0.19H), 5.57-5.44 (m, 0.82H), 4.95-4.69 (m, 2H), 4.66-4.25 (m, 3.6H), 4.07-3.97 (m, 0.42H), 3.46-3.28 (m, 1.6H), 3.25 (d, J=17.1 Hz, 0.19H), 3.08 (dd, J=16.9, 5.8 Hz, 0.19H), 2.76 (s, 1.05H), 2.68 (s, 0.66H), 2.67 (s, 1.29H), 1.28 (d, J=7.2 Hz, 1.05H), 1.26 (d, J=6.9 Hz, 0.72H), 1.25 (d, J=6.9 Hz, 0.66H), 1.10 (d, J=6.7 Hz, 0.57H).

Example 125

(S*)-(2-chloro-3-(trifluoromethyl)phenyl)(4-(1-(2-fluoroethyl)-1H-pyrazol-3-yl)-2,6-dimethyl-5,6-dihydropyrido[3,4-d]pyrimidin-7-(8H)-yl)methanone

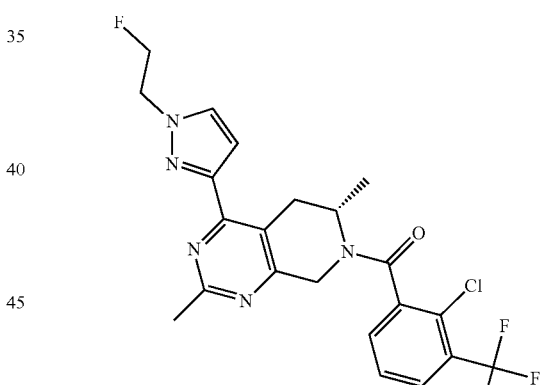

The title compound, absolute configuration unknown, was obtained by chiral SFC purification of the racemic product of Example 124 using a CHIRALCEL OD-H (5 μm, 250×20 mm) and a mobile phase of 80% $CO_2$, 20% EtOH. The enantiomeric purity was confirmed by analytical SFC using a CHIRALCEL OD-H (250×4.6 mm) and a mobile phase of 80% $CO_2$, 20% EtOH containing 0.3% $iPrNH_2$ over 7 minutes. (99% single enantiomer, 5.85 min retention time). MS (ESI) mass calcd. $C_{22}H_{20}ClF_4N_5O$, 481.1; m/z found 482.1 [M+H]$^+$.

Example 126

(2-chloro-3-(trifluoromethyl)phenyl)(4-(1-(2-methoxyethyl)-1H-pyrazol-3-yl)-2,6-dimethyl-5,6-dihydropyrido[3,4-d]pyrimidin-7(8H)-yl)methanone

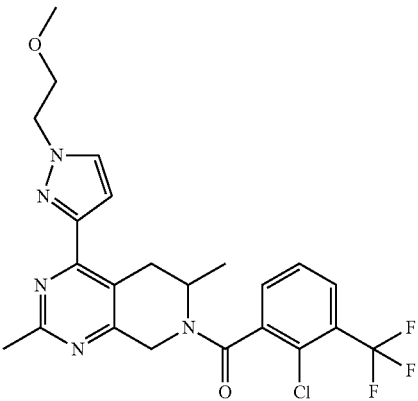 [SMILES: COCCn1ccc(-c2nc(C)nc3c2CC(C)N(C(=O)c2cccc(C(F)(F)F)c2Cl)C3)n1]

The title compound was prepared in a manner analogous to Example 124 substituting 2-bromoethyl methyl ether for 1-bromo-2-fluoroethane. MS (ESI) mass calcd. $C_{23}H_{23}ClF_3N_5O_2$, 493.1; m/z found 494.1 [M+H]$^+$. $^1$H NMR (500 MHz, CDCl$_3$) δ 7.81-7.73 (m, 0.85H), 7.70-7.64 (m, 0.15H), 7.57 (d, J=2.3 Hz, 0.40H), 7.56-7.40 (m, 2.60H), 7.01 (d, J=2.3 Hz, 0.15H), 7.00 (d, J=2.3 Hz, 0.45H), 6.99 (d, J=2.3 Hz, 0.40H), 5.60 (d, J=19.7 Hz, 0.15H), 5.56-5.45 (m, 0.85H), 4.61 (d, J=18.5 Hz, 0.45H), 4.45-4.25 (m, 3.35H), 4.06-3.98 (m, 0.45H), 3.86-3.70 (m, 2H), 3.53-3.21 (m, 4.50H), 3.15-3.05 (m, 0.25H), 2.75 (s, 1.20H), 2.67 (s, 0.45H), 2.66 (s, 1.35H), 1.23-1.30 (m, 2.55H), 1.10 (d, J=6.9 Hz, 0.45H).

Example 127

(S*)-(2-chloro-3-(trifluoromethyl)phenyl)(4-(1-(2-methoxyethyl)-1H-pyrazol-3-yl)-2,6-dimethyl-5,6-dihydropyrido[3,4-d]pyrimidin-7(8H)-yl)methanone

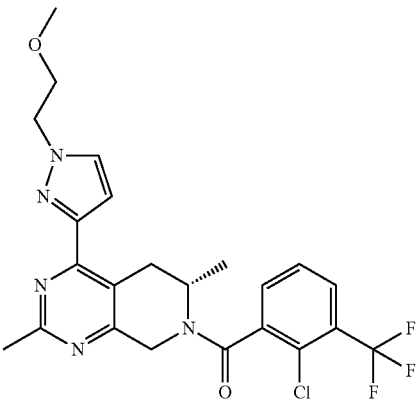 [SMILES: COCCn1ccc(-c2nc(C)nc3c2C[C@H](C)N(C(=O)c2cccc(C(F)(F)F)c2Cl)C3)n1]

The title compound, absolute configuration unknown, was obtained as a single enantiomer by Chiral SFC purification of Example 126 performed using CHIRALCEL OD-H (5 μm, 250×20 mm) and a mobile phase of 80% CO$_2$, 20% EtOH. The enantiomeric purity was confirmed by analytical SFC using a CHIRALCEL OD-H (250×4.6 mm) and a mobile phase of 80% CO$_2$, 20% EtOH containing 0.3% iPrNH$_2$ over 7 minutes. (99% single enantiomer, 4.27 min retention time). MS (ESI) mass calcd. $C_{23}H_{23}ClF_3N_5O_2$, 493.1; m/z found 494.1 [M+H]$^+$. $^1$H NMR (400 MHz, CDCl$_3$) δ 7.81-7.73 (m, 1H), 7.59-7.40 (m, 3H), 7.01 (d, J=2.3 Hz, 0.23H), 7.00 (d, J=2.5 Hz, 0.40H), 6.99 (d, J=2.3 Hz, 0.37H), 5.63-5.44 (m, 1H), 4.61 (d, J=18.5 Hz, 0.40H), 4.46-4.24 (m, 3.24H), 4.07-3.97 (m, 0.40H), 3.87-3.70 (m, 2H), 3.51-3.21 (m, 4.78H), 3.09 (dd, J=17.6, 5.5 Hz, 0.18H), 2.75 (s, 1.11H), 2.67 (s, 0.69H), 2.66 (s, 1.20H), 1.30-1.22 (m, 2.31H), 1.09 (d, J=6.9 Hz, 0.69H).

Example 128

(R*)-(2-chloro-3-(trifluoromethyl)phenyl)(4-(1-(2-methoxyethyl)-1H-pyrazol-3-yl)-2,6-dimethyl-5,6-dihydropyrido[3,4-d]pyrimidin-7(8H)-yl)methanone

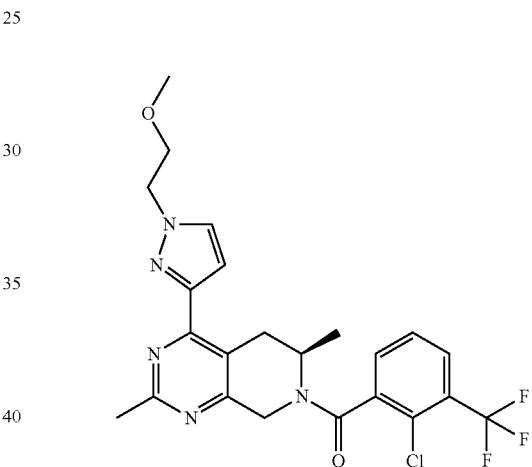

The title compound, absolute configuration unknown, was obtained as a single enantiomer by Chiral SFC purification of Example 126 performed using CHIRALCEL OD-H (5 μm, 250×20 mm) and a mobile phase of 80% CO$_2$, 20% EtOH. The enantiomeric purity was confirmed by analytical SFC using a CHIRALCEL OD-H (250×4.6 mm) and a mobile phase of 80% CO$_2$, 20% EtOH containing 0.3% iPrNH$_2$ over 7 minutes. (100% single enantiomer, 3.49 min retention time). MS (ESI) mass calcd. $C_{23}H_{23}ClF_3N_5O_2$, 493.1; m/z found 494.1 [M+H]$^+$. $^1$H NMR (400 MHz, CDCl$_3$) δ 7.82-7.72 (m, 1H), 7.60-7.40 (m, 3H), 7.01 (d, J=2.5 Hz, 0.23H), 7.00 (d, J=2.3 Hz, 0.40H), 6.99 (d, J=2.3 Hz, 0.37H), 5.65-5.44 (m, 1H), 4.61 (d, J=18.3 Hz, 0.40H), 4.45-4.25 (m, 3.24H), 4.06-3.97 (m, 0.40H), 3.87-3.70 (m, 2H), 3.53-3.20 (m, 4.78H), 3.09 (dd, J=16.9, 5.8 Hz, 0.18H), 2.75 (s, 1.11H), 2.67 (s, 0.69H), 2.66 (s, 1.20H), 1.30-1.22 (m, 2.31H), 1.09 (d, J=6.9 Hz, 0.69H).

Intermediate 46: 2-fluoro-6-(4,4,5,5-tetramethyl-1,3,2-dioxaborolan-2-yl)pyridine

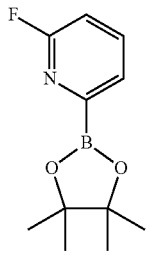

Pd(dppf)$_2$Cl$_2$.HCl (102 mg, 0.14 mmol) was added to a degassed mixture of 2-bromo-6-fluoropyridine (410 mg, 2.33 mmol), bis(pinacolato)diboron (828 mg, 3.26 mmol) and KOAc (685 mg, 6.99 mmol) in dioxane (6 mL) at room temperature. The mixture was heated at 115° C. for 1 h. The solid material was then filtered off the solvent evaporated and the crude compound purified by chromatography (silica, MeOH in DCM 0:100 to 10:90). The desired fractions were collected to obtain the title compound (400 mg, 76%). $^1$H NMR (400 MHz, CDCl$_3$) δ 7.78 (td, J=8.1, 7.2 Hz, 1H), 7.70 (ddd, J=6.9, 2.8, 0.9 Hz, 1H), 6.98 (ddd, J=8.1, 2.7, 0.9 Hz, 1H), 1.38 (s, 12H),

Example 129

(2,3-dichloro-4-fluorophenyl)(4-(6-fluoropyridin-2-yl)-5,6-dihydropyrido[3,4-d]pyrimidin-7(8H)-yl)methanone

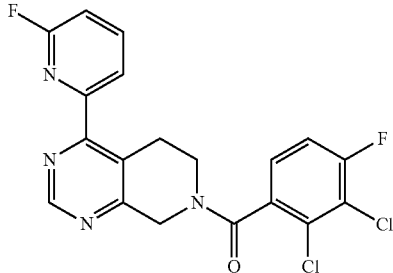 [SMILES: O=C(c1ccc(F)c(Cl)c1Cl)N1CCc2c(ncnc2-c2cccc(F)n2)C1]

The title compound was prepared in a manner analogous to Example 1 substituting Intermediate 46 for phenylboronic acid in the synthesis of Intermediate 1, Step c and 2,3-dichloro-4-fluorobenzoic acid for 2-chloro-3-(trifluoromethyl)benzoic acid. MS (ESI) mass calcd. C$_{19}$H$_{12}$Cl$_2$F$_2$N$_4$O, 420.0; m/z found 421.1 [M+H]$^+$. $^1$H NMR (500 MHz, CDCl$_3$) δ 9.14 (s, 0.55H), 9.03 (s, 0.45H), 8.16 (br d, J=7.2 Hz, 0.55H), 8.11 (br d, J=7.2 Hz, 0.45H), 8.03-7.95 (m, 1H), 7.31-7.16 (m, 2H), 7.08 (dd, J=8.1, 2.6 Hz, 0.45H), 7.04 (dd, J=8.1, 2.3 Hz, 0.55H), 5.20 (d, J=19.4 Hz, 0.55H), 4.95 (d, J=19.4 Hz, 0.55H), 4.59 (d, J=17.9 Hz, 0.45H), 4.46 (d, J=17.9 Hz, 0.45H), 4.17-4.08 (m, 0.55H), 4.05-3.95 (m, 0.45H), 3.59-3.26 (m, 3H).

Example 130

(2-chloro-3-(trifluoromethyl)phenyl)(4-(6-fluoropyridin-2-yl)-5,6-dihydropyrido[3,4-d]pyrimidin-7(8H)-yl)methanone

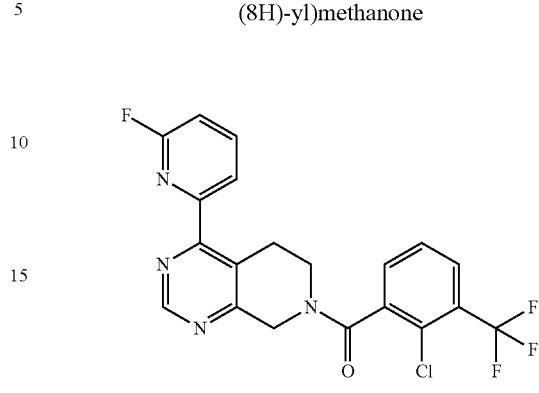

The title compound was prepared in a manner analogous to Example 1 substituting Intermediate 46 for phenylboronic acid in the synthesis of Intermediate 1, Step c. MS (ESI) mass calcd. C$_{20}$H$_{13}$ClF$_4$N$_4$O, 436.1; m/z found 437.1 [M+H]$^+$. $^1$H NMR (500 MHz, CDCl$_3$) δ 9.15 (s, 0.55H), 9.03 (s, 0.45H), 8.16 (d, J=7.2 Hz, 0.55H), 8.11 (d, J=7.2 Hz, 0.45H), 8.05-7.93 (m, 1H), 7.79 (br t, J=8.7, 8.7 Hz, 1H), 7.59-7.44 (m, 2H), 7.08 (dd, J=8.1, 2.3 Hz, 0.45H), 7.04 (dd, J=8.1, 2.3 Hz, 0.55H), 5.27 (d, J=19.7 Hz, 0.55H), 4.93 (d, J=19.7 Hz, 0.55H), 4.60 (d, J=18.2 Hz, 0.45H), 4.46 (d, J=18.2 Hz, 0.45H), 4.23-4.15 (m, 0.45H), 4.02-3.94 (m, 0.45H), 3.60-3.28 (m, 3.1H).

Intermediate 47: 2,6-dimethyl-4-(1H-pyrazol-5-yl)-5,6,7,8-tetrahydropyrido[3,4-d]pyrimidine

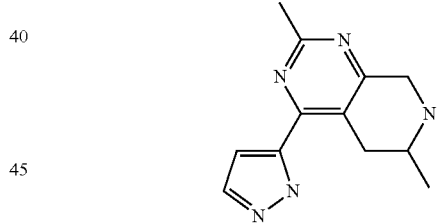

Intermediate 47, Step A: tert-butyl 2,6-dimethyl-4-(1-(tetrahydro-2H-pyran-2-yl)-1H-pyrazol-5-yl)-5,6-dihydropyrido[3,4-d]pyrimidine-7(8H)-carboxylate. The title compound was prepared in a manner analogous to Intermediate 19 substituting Intermediate 36 for Intermediate 11. MS (ESI): mass calcd. for C$_{22}$H$_{31}$N$_5$O$_3$ 413.2; m/z found, 414.3 [M+H]$^+$.

Intermediate 47, Step B: 2,6-dimethyl-4-(1H-pyrazol-5-yl)-5,6,7,8-tetrahydropyrido[3,4-d]pyrimidine TFA (1.2 mL) was added to a solution of the product of Intermediate 47, step A (250 mg, 0.605 mmol) and triethylsilane (0.240 mL, 1.51 mmol) in DCM (5 mL). The reaction was stirred for 3 hours at room temperature. The mixture was quenched with sat. NaHCO3 and the aqueous layer was extracted with DCM (3×). The combined organic extracts were dried over MgSO4, filtered and concentrated. The crude material was purified by Prep Agilent system with a XBridge C18 OBD 30×100 mm column eluting with 5 to 99% (0.05% NH$_4$OH in H$_2$O)/ACN over 17 min (138 mg, 99%). MS (ESI) mass calcd. C$_{12}$H$_{15}$N$_5$, 229.1; m/z found 230.1 [M+H]$^+$.

Intermediate 48: 2,4-dimethylbenzoyl chloride

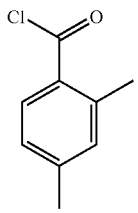

The title compound was prepared in a manner analogous to Intermediate 44 substituting 2,4-dimethylbenzoic acid for 2-fluoro-3-(trifluoromethyl)benzoic acid. The product was used as is without additional purification.

Intermediate 49: 2,3-dimethylbenzoyl chloride

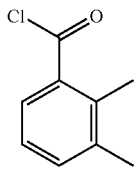

The title compound was prepared in a manner analogous to Intermediate 44 substituting 2,3-dimethylbenzoic acid for 2-fluoro-3-(trifluoromethyl)benzoic acid. The product was used as is without additional purification.

Example 131

(2,6-dimethyl-4-(1H-pyrazol-5-yl)-5,6-dihydropyrido[3,4-d]pyrimidin-7(8H)-yl)(2,4-dimethylphenyl)methanone

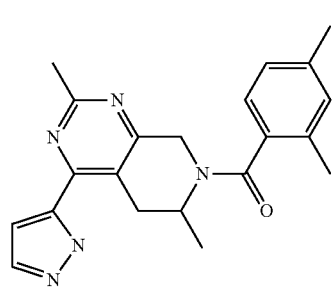 [SMILES: Cc1ccc(C(=O)N2Cc3nc(C)nc(-c4ccn[nH]4)c3CC2C)c(C)c1]

Intermediate 48 (115 mg, 0.686 mmol) was added to a solution of Intermediate 47 (157 mg, 0.686 mmol) and DIEA (0.355 mL, 2.05 mmol) in DCM (2 mL). The reaction was stirred at room temperature for one hour. The solvents were removed in vacuo and the crude mixture was purified by chromatography on a Prep Agilent system with a XBridge C18 OBD 30×100 mm column eluting with 5 to 99% (0.05% NH$_4$OH in H$_2$O)/ACN over 17 min to afford the desired product (10 mg, 4%). MS (ESI) mass calcd. C$_{21}$H$_{23}$N$_5$O, 361.2; m/z found 362.2 [M+H]$^+$. $^1$H NMR (400 MHz, CDCl$_3$) δ 11.28 (br s, 1H), 7.78-7.60 (m, 1H), 7.18-6.70 (m, 4H), 5.75-5.44 (m, 1H), 4.59-4.08 (m, 2H), 3.44-2.86 (m, 2H), 2.83-2.54 (m, 3H), 2.46-2.03 (m, 6H), 1.38-0.97 (m, 3H).

Example 132

(2,6-dimethyl-4-(1H-pyrazol-5-yl)-5,6-dihydropyrido[3,4-d]pyrimidin-7(8H)-yl)(2,3-dimethylphenyl)methanone

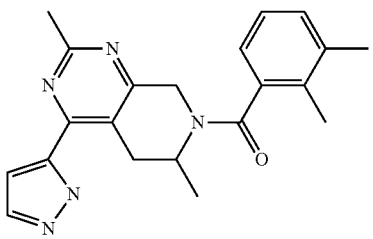

The title compound was prepared in a manner analogous to Example 131 substituting Intermediate 49 for Intermediate 48. MS (ESI) mass calcd. C$_{21}$H$_{23}$N$_5$O, 361.2; m/z found 362.2 [M+H]$^+$. $^1$H NMR (400 MHz, CDCl$_3$) δ 11.12 (br s, 1H), 7.84-7.61 (m, 1H), 7.24-6.76 (m, 4H), 5.78-5.50 (m, 1H), 4.56-4.12 (m, 2H), 3.39-2.83 (m, 2H), 2.83-2.60 (m, 3H), 2.42-2.02 (m, 6H), 1.31-1.09 (m, 3H).

Example 133

(2,6-dimethyl-4-(1H-pyrazol-5-yl)-5,6-dihydropyrido[3,4-d]pyrimidin-7(8H)-yl)(4-fluoro-2-methylphenyl)methanone

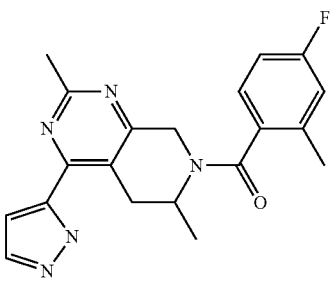 [SMILES: Cc1nc2c(c(-c3ccn[nH]3)n1)CC(C)N(C(=O)c1ccc(F)cc1C)C2]

The title compound was prepared in a manner analogous to Example 74 substituting 4-fluoro-2-methylbenzoic acid for 2-fluoro-3-(trifluoromethyl)benzoic acid in the synthesis of Intermediate 44. MS (ESI) mass calcd. C$_{20}$H$_{20}$FN$_5$O, 365.2; m/z found 366.2 [M+H]$^+$. $^1$H NMR (400 MHz, CDCl$_3$) δ 11.18 (br s, 1H), 7.81-7.61 (m, 1H), 7.24-7.08 (m, 1H), 7.05-6.77 (m, 3H), 5.73-5.49 (m, 1H), 4.56-4.08 (m, 2H), 3.46-2.86 (m, 2H), 2.81-2.58 (m, 3H), 2.49-2.08 (m, 3H), 1.42-1.02 (m, 3H).

Example 134

(2,6-dimethyl-4-(1H-pyrazol-5-yl)-5,6-dihydro-pyrido[3,4-d]pyrimidin-7(8H)-yl)(3-fluoro-2-methylphenyl)methanone

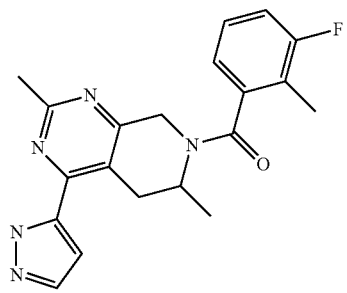 [SMILES: Cc1nc2c(c(-c3ccn[nH]3)n1)CC(C)N(C(=O)c1cccc(F)c1C)C2]

The title compound was prepared in a manner analogous to Example 74 substituting 3-fluoro-2-methylbenzoic acid for 2-fluoro-3-(trifluoromethyl)benzoic acid in the synthesis of Intermediate 44. MS (ESI) mass calcd. $C_{20}H_{20}FN_5O$, 365.2; m/z found 366.2[M+H]$^+$. $^1$H NMR (400 MHz, CDCl$_3$) δ (br s, 1H), 7.77-7.63 (m, 1H), 7.25-6.79 (m, 4H), 5.72-5.47 (m, 1H), 4.57-3.96 (m, 2H), 3.41-2.87 (m, 2H), 2.83-2.58 (m, 3H), 2.39-1.94 (m, 3H), 1.36-1.05 (m, 3H).

Example 135

(2,6-dimethyl-4-(1H-pyrazol-5-yl)-5,6-dihydro-pyrido[3,4-d]pyrimidin-7(8H)-yl)(2-fluoro-3-methylphenyl)methanone

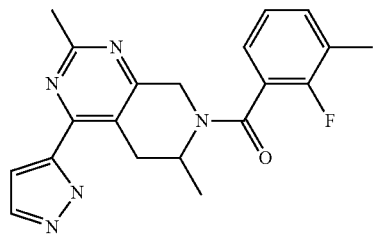 [SMILES: Cc1nc2c(c(-c3ccn[nH]3)n1)CC(C)N(C(=O)c1cccc(C)c1F)C2]

The title compound was prepared in a manner analogous to Example 74 substituting 2-fluoro-3-methylbenzoic acid for 2-fluoro-3-(trifluoromethyl)benzoic acid in the synthesis of Intermediate 44. MS (ESI) mass calcd. $C_{20}H_{20}FN_5O$, 365.2; m/z found 366.2 [M+H]$^+$. $^1$H NMR (400 MHz, CDCl$_3$) δ 11.3-11.0 (br s., 1H), 7.84-7.54 (m, 1H), 7.38-7.00 (m, 3H), 6.95-6.67 (m, 1H), 5.77-5.33 (m, 1H), 4.86-4.10 (m, 2H), 3.45-2.91 (m, 2H), 2.85-2.52 (m, 3H), 2.50-2.07 (m, 3H), 1.47-0.95 (m, 3H).

The following examples (P136-P138) are prophetic examples:

Example P136

(R)-(2,4-dichloro-3-fluorophenyl)(2,6-dimethyl-4-(1H-pyrazol-5-yl)-5,6-dihydropyrido[3,4-d]pyrimidin-7(8H)-yl)methanone

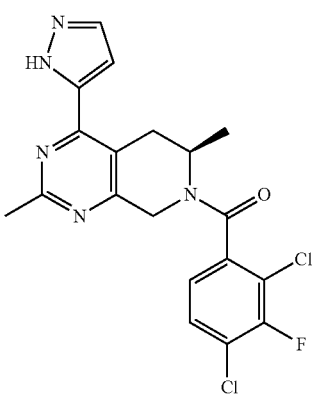 [SMILES: Cc1nc2c(c(-c3ccn[nH]3)n1)C[C@@H](C)N(C(=O)c1ccc(Cl)c(F)c1Cl)C2]

Example P137

(R)-(2,6-dimethyl-4-(1H-pyrazol-5-yl)-5,6-dihydro-pyrido[3,4-d]pyrimidin-7(8H)-yl)(phenyl)methanone

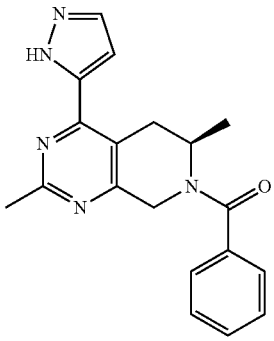 [SMILES: Cc1nc2c(c(-c3ccn[nH]3)n1)C[C@@H](C)N(C(=O)c1ccccc1)C2]

Example P138

(2,4-dichlorophenyl)((6R,8S)-2,6,8-trimethyl-4-(1H-pyrazol-5-yl)-5,6-dihydropyrido[3,4-d]pyrimidin-7(8H)-yl)methanone

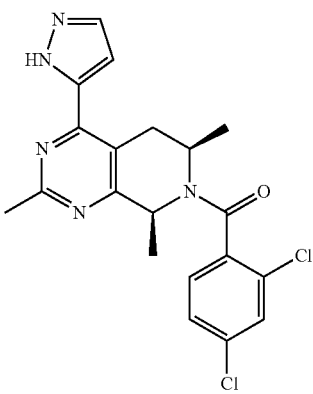 [SMILES: Cc1nc(-c2ccn[nH]2)c2c(n1)[C@H](C)N(C(=O)c1ccc(Cl)cc1Cl)[C@H](C)C2]

Example 139

(2,6-dimethyl-4-(1H-pyrazol-5-yl)-5,6-dihydropyrido[3,4-d]pyrimidin-7(8H)-yl)(2-fluoro-3-(trifluoromethoxy)phenyl)methanone

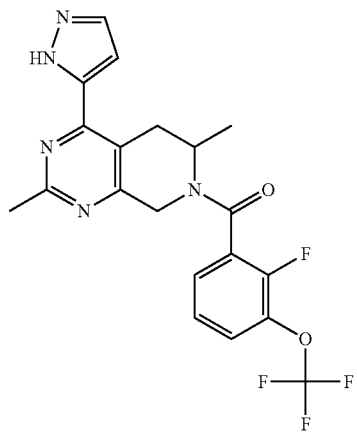 [SMILES: Cc1nc2c(c(-c3ccn[nH]3)n1)CC(C)N(C(=O)c1cccc(OC(F)(F)F)c1F)C2]

The title compound was prepared in a manner analogous to Example 87 substituting -fluoro-3-(trifluoromethoxy)benzoic acid for 4-chloro-2-fluorobenzoic acid. MS (ESI) mass calcd. $C_{20}H_{17}F_4N_5O_2$, 435.13; m/z found 435.90 [M+H]$^+$. $^1$H NMR (400 MHz, CDCl$_3$) δ 11.41-10.89 (m, 1H), 7.81-7.63 (m, 1H), 7.57-7.16 (m, 3H), 6.96-6.81 (m, 1H), 5.82-5.38 (m, 1H), 4.75-4.00 (m, 2H), 3.49-2.95 (m, 2H), 2.86-2.55 (m, 3H), 1.45-0.98 (m, 3H).

Example 140

(2,6-dimethyl-4-(1H-pyrazol-5-yl)-5,6-dihydropyrido[3,4-d]pyrimidin-7(8H)-yl)(3-(trifluoromethoxy)phenyl)methanone

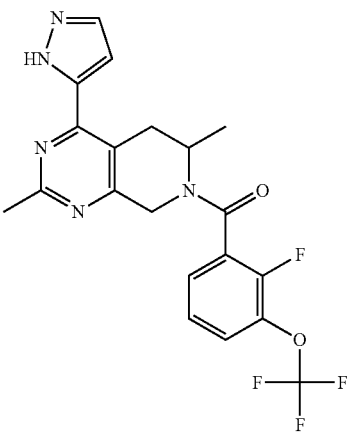 [SMILES: Cc1nc2c(c(-c3ccn[nH]3)n1)CC(C)N(C(=O)c1cccc(OC(F)(F)F)c1F)C2]

The title compound was prepared in a manner analogous to Example 74 substituting 3-(trifluoromethoxy)benzoic acid for 2-methyl-3(trifluoromethyl)benzoic acid in the synthesis of Intermediate 44. Purification of the title compound was accomplished using chromatography on SiO$_2$ eluting with EtOAc/hexanes followed by trituration in hot acetonitrile (55° C.) for 2 minutes and then trituration in acetonitrile at room temperature. After 2 hours, the precipitates were collected and washed with Et$_2$O to afford desired material. MS (ESI): mass calcd. for $C_{20}H_{18}F_3N_5O_2$, 417.14; m/z found, 417.95 [M+H]$^+$. $^1$H NMR (400 MHz, CDCl3) δ 11.69-11.02 (m, 1H), 7.75-7.65 (m, 1H), 7.53-7.46 (m, 1H), 7.40-7.36 (m, 1H), 7.35-7.30 (m, 2H), 6.98-6.76 (m, 1H), 5.67-5.25 (m, 1H), 4.87-4.25 (m, 2H), 3.43-2.90 (m, 2H), 2.71 (s, 3H), 1.24 (s, 3H).

Example 141

(R*)-(2,6-dimethyl-4-(1H-pyrazol-5-yl)-5,6-dihydropyrido[3,4-d]pyrimidin-7(8H)-yl)(3-(trifluoromethoxy)phenyl)methanone

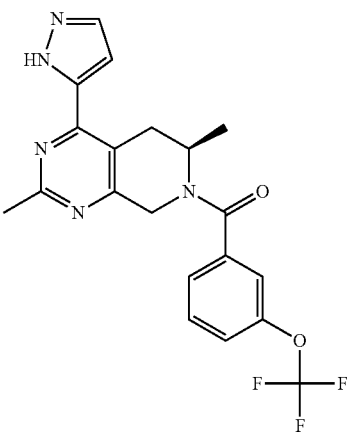 [SMILES: Cc1nc2c(c(-c3ccn[nH]3)n1)C[C@@H](C)N(C(=O)c1cccc(OC(F)(F)F)c1)C2]

The title compound, absolute configuration unknown, was obtained as a single enantiomer by Chiral SFC purification of Example 140 performed using a CHIRALCEL OJ-H (5 μm, 250×20 mm) column and a mobile phase of 90% $CO_2$, 10% iPrOH containing 0.3% $iPrNH_2$. The enantiomeric purity was confirmed by analytical SFC using a CHIRALCEL OJ-H (250×4.6 mm) and a mobile phase of 90% $CO_2$, 10% iPrOH containing 0.3% $iPrNH_2$ over 15 minutes. (100% single enantiomer, 7.78 min retention time). MS (ESI): mass calcd. $C_{20}H_{18}F_3N_5O_2$, 417.14; m/z found, 417.95 $[M+H]^+$. $^1$H NMR (500 MHz, CDCl3) δ 11.47-10.68 (m, 1H) 7.71 (d, J=2.2 Hz, 1H), 7.54-7.45 (m, 1H), 7.41-7.35 (m, 1H), 7.34-7.29 (m, 2H), 6.87 (d, J=2.1 Hz, 1H), 5.65-5.39 (m, 1H), 4.75-4.22 (m, 2H), 3.41-3.18 (m, 1H), 3.11-2.98 (m, 1H), 2.71 (s, 3H), 1.35-1.16 (m, 3H).

Example 142

(S*)-(2,6-dimethyl-4-(1H-pyrazol-5-yl)-5,6-dihydropyrido[3,4-d]pyrimidin-7(8H)-yl)(3-(trifluoromethoxy)phenyl)methanone

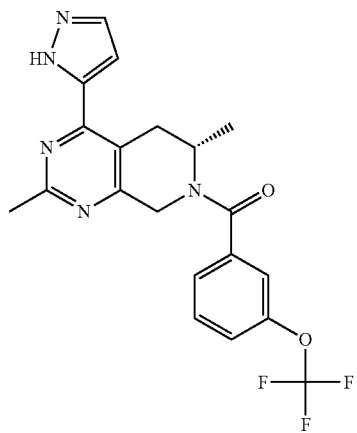 [SMILES: Cc1nc2c(c(-c3ccn[nH]3)n1)C[C@H](C)N(C(=O)c1cccc(OC(F)(F)F)c1)C2]

The title compound, absolute configuration unknown, was obtained as a single enantiomer by Chiral SFC purification of Example 140 performed using a CHIRALCEL OJ-H (5 μm, 250×20 mm) column and a mobile phase of 90% $CO_2$, 10% iPrOH containing 0.3% $iPrNH_2$. The enantiomeric purity was confirmed by analytical SFC using a CHIRALCEL OJ-H (250×4.6 mm) and a mobile phase of 90% $CO_2$, 10% iPrOH containing 0.3% $iPrNH_2$ over 15 minutes. (98.2% single enantiomer, 9.29 min retention time). MS (ESI): mass calcd. $C_{20}H_{18}F_3N_5O_2$, 417.14; m/z found, 417.90 $[M+H]^+$. $^1$H NMR (500 MHz, CDCl3) δ 11.47-10.68 (m, 1H) 7.71 (d, J=2.2 Hz, 1H), 7.54-7.45 (m, 1H), 7.41-7.35 (m, 1H), 7.34-7.29 (m, 2H), 6.87 (d, J=2.1 Hz, 1H), 5.65-5.39 (m, 1H), 4.75-4.22 (m, 2H), 3.41-3.18 (m, 1H), 3.11-2.98 (m, 1H), 2.71 (s, 3H), 1.35-1.16 (m, 3H).

Example 143

(2-chloro-3-fluorophenyl)(2,6-dimethyl-4-(1H-pyrazol-5-yl)-5,6-dihydropyrido[3,4-d]pyrimidin-7(8H)-yl)methanone

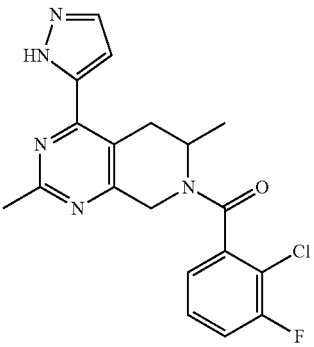 [SMILES: Cc1nc2c(c(-c3ccn[nH]3)n1)CC(C)N(C(=O)c1cccc(F)c1Cl)C2]

The title compound was prepared in a manner analogous to Example 74 2-chloro-3-fluorobenzoic acid for substituting 2-methyl-3(trifluoromethyl)benzoic acid in the synthesis of Intermediate 44. Purification of title compound was done by chromatography on $SiO_2$ eluting with EtOAc/hexanes. MS (ESI): mass calcd. for $C_{19}H_{17}Cl\ F\ N_5O$, 385.11; m/z found, 386.10 $[M+H]^+$. $^1$H NMR (400 MHz, CDCl3) δ 11.36-10.95 (m, 1H), 7.79-7.57 (m, 1H), 7.40-7.05 (m, 3H), 6.94-6.81 (m, 1H), 5.73-5.46 (m, 1H), 4.74-4.03 (m, 2H), 3.45-2.89 (m, 2H), 2.82-2.58 (m, 3H), 1.36-1.07 (m, 3H).

Example 144

(R*)-(2-chloro-3-fluorophenyl)(2,6-dimethyl-4-(1H-pyrazol-5-yl)-5,6-dihydropyrido[3,4-d]pyrimidin-7(8H)-yl)methanone

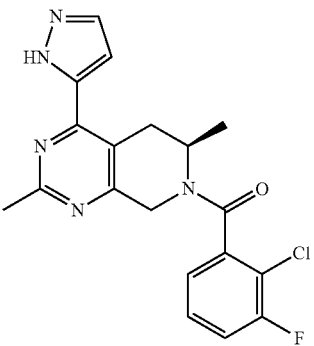 [SMILES: Cc1nc2c(c(-c3ccn[nH]3)n1)C[C@@H](C)N(C(=O)c1cccc(F)c1Cl)C2]

The title compound, absolute configuration unknown, was obtained as a single enantiomer by Chiral SFC purification of Example C performed using a CHIRALCEL OJ-H (5 μm, 250×20 mm) column and a mobile phase of 75% $CO_2$, 25% iPrOH containing 0.3% $iPrNH_2$. The enantiomeric purity was confirmed by analytical SFC using a CHIRALCEL OJ-H (250×4.6 mm) and a mobile phase of 75% $CO_2$, 25% iPrOH containing 0.3% $iPrNH_2$ over 7 minutes. (100% single enantiomer, 3.38 min retention time). MS (ESI): mass calcd. $C_{19}H_{17}Cl\ F\ N_5O$, 385.11; m/z found, 386.10 $[M+H]^+$. $^1$H NMR (400 MHz, CDCl3) δ 11.60-10.80 (m, 1H), 7.79-

7.57 (m, 1H), 7.40-7.05 (m, 3H), 6.94-6.81 (m, 1H), 5.73-5.46 (m, 1H), 4.74-4.03 (m, 2H), 3.45-2.91 (m, 2H), 2.82-2.58 (m, 3H), 1.36-1.07 (m, 3H).

Example 145

(S*)-(2-chloro-3-fluorophenyl)(2,6-dimethyl-4-(1H-pyrazol-5-yl)-5,6-dihydropyrido[3,4-d]pyrimidin-7(8H)-yl)methanone

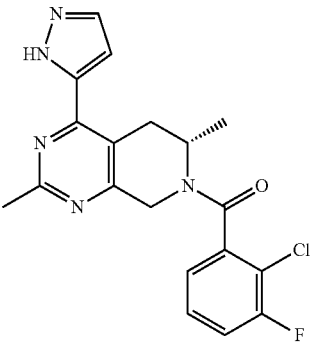 [SMILES: Cc1nc2c(c(-c3ccn[nH]3)n1)C[C@H](C)N(C(=O)c1cccc(F)c1Cl)C2]

The title compound, absolute configuration unknown, was obtained as a single enantiomer by Chiral SFC purification of Example C performed using a CHIRALCEL OJ-H (5 μm, 250×20 mm) column and a mobile phase of 75% CO$_2$, 25% iPrOH containing 0.3% iPrNH$_2$. The enantiomeric purity was confirmed by analytical SFC using a CHIRALCEL OJ-H (250×4.6 mm) and a mobile phase of 75% CO$_2$, 25% iPrOH containing 0.3% iPrNH$_2$ over 7 minutes. (100% single enantiomer, 5.23 min retention time). MS (ESI): mass calcd. C$_{19}$H$_{12}$Cl F N$_5$O, 385.11; m/z found, 386.10 [M+H]$^+$. $^1$H NMR (400 MHz, CDCl3) δ 11.35-10.86 (m, 1H), 7.79-7.57 (m, 1H), 7.40-7.05 (m, 3H), 6.94-6.81 (m, 1H), 5.73-5.46 (m, 1H), 4.74-4.03 (m, 2H), 3.45-2.91 (m, 2H), 2.82-2.58 (m, 3H), 1.36-1.07 (m, 3H).

Example 146

(2,6-dimethyl-4-(1H-pyrazol-5-yl)-5,6-dihydropyrido[3,4-d]pyrimidin-7(8H)-yl)(3-methoxy-2-methylphenyl)methanone

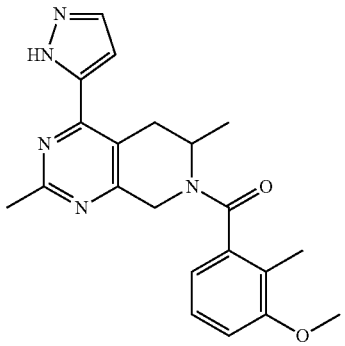

The title compound was prepared in a manner analogous to Example 74 substituting 3-methoxy-2-methylbenzoic acid for 2-methyl-3(trifluoromethyl)benzoic acid in the synthesis of Intermediate 44. MS (ESI): mass calcd. for C$_{21}$H$_{23}$N$_5$O$_2$, 377.19; m/z found, 378.20 [M+H]$^+$. $^1$H NMR (400 MHz, CDCl3) δ 11.85-10.83 (m, 1H), 7.76-7.66 (m, 1H), 7.26-7.14 (m, 1H), 6.93-6.70 (m, 3H), 5.69-5.53 (m, 1H), 4.49-4.13 (m, 2H), 3.90-3.77 (m, 3H), 3.36-2.81 (m, 2H), 2.79-2.60 (m, 3H), 2.27-1.94 (m, 3H), 1.31-1.07 (m, 3H).

Example 147

(2,6-dimethyl-4-(1H-pyrazol-5-yl)-5,6-dihydropyrido[3,4-d]pyrimidin-7(8H)-yl)(5-methoxypyridin-3-yl)methanone

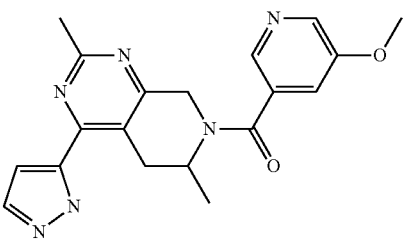 [SMILES: COc1cncc(C(=O)N2Cc3nc(C)nc(-c4ccn[nH]4)c3CC2C)c1]

The title compound was prepared in a manner analogous to Example 74 substituting 5-methoxynicotinic acid hydrochloride for 2-methyl-3(trifluoromethyl)benzoic acid in the synthesis of Intermediate 44. MS (ESI): mass calcd. for C$_{19}$H$_{20}$N$_6$O$_2$, 364.16; m/z found, 365.20 [M+H]$^+$.

Pharmacological Examples

The in vitro affinity of the compounds of the invention for the rat and human P2X7 receptor was determined using a human peripheral blood mononuclear cells (PBMCs), a human whole blood assay, a Ca$^{2+}$ flux and radioligand binding assay in recombinant human P2X7 cells and recombinant rat P2X7 cells. In Tables 2 and 3, when the data cell has been left blank, it is intended to mean that the compound was not tested in that assay. The data represented in Tables 2 and 3 may represent a value from a single determination or when the experiment was run more than once, the data represent averages from between 2-12 runs.

P2X7 Antagonism in Human Peripheral Blood Mononuclear Cells (PBMCs) and Human Whole Blood.

Human blood was collected using a blood donor program. PBMCs were isolated from blood using a Ficoll density gradient technique. Briefly, blood was laid on Ficoll solution and centrifuged at RT for 20 minutes at 2000 rpm. The buffy layer (between red blood cells and plasma) was carefully collected by aspiration, washed with PBS and centrifuged again at 1500 rpm for 15 minutes. The resulting cell pellet was washed and plated on 96 well-plates for experiments. For the Human Whole Blood experiments, 150 μl of human blood was platted on 96 well-plates. Lipopolysaccharide (LPS) (30 ng/ml) was added to each well and incubated for 1 hour. Test compounds were then added and incubated for 30 minutes. The P2X7 agonist, 2'(3')-O-(4-benzoylbenzoyl) adenosine 5'-triphosphate (Bz-ATP) was then added at a final concentration of 0.5 mM (PBMC) or 1 mM (blood). Cells were incubated for an additional 1.5 hours. At that point, supernatant was collected and stored for IL-1β assay using manufacturer's protocol for enzyme-linked immunosorbent assay (ELISA). Data was expressed as percent control, where control is defined as the difference in IL-1β release in LPS+Bz-ATP samples and LPS only samples. Data was plotted as response (% control) versus concentration to generate $IC_{50}$ values. In Tables 2 and 3, this data is represented by PBMC 1 µM (% control) and PBMC 10 µM (% control) and human whole blood $IC_{50}$ (µM). Data are analyzed and graphed on Graphpad Prism 5. For analysis, each concentration point is averaged from triplicate values and the averaged values are plotted on Graphpad Prism. The $IC_{50}$ for each compound is then uploaded into 3DX.

P2X7 Antagonism in Recombinant Human P2X7 Cells or Recombinant Rat P2X7 Cells: (a) $Ca^{2+}$ Flux and (b) Radioligand Binding (a) $Ca^{2+}$ flux: 1321N1 cells expressing the recombinant human or rat P2X7 channel was cultured in HyQ DME/ (HyClone/Dulbecco's Modified Eagle Medium) high glucose supplemented with 10% Fetal Bovine Serum (FBS) and appropriate selection marker. Cells were seeded at a density of 25000 cells/well (96-well clear bottom black walled plates) in 100 µl volume/well. On the day of the experiment, cell plates were washed with assay buffer, containing (in mM): 130 NaCl, 2 KCl, 1 $CaCl_2$, 1 $MgCl_2$, 10 HEPES, 5 glucose; pH 7.40 and 300 mOs. After the wash, cells were loaded with the Calcium-4 dye (Molecular Device) and incubated in the dark for 60 minutes. Test compounds were prepared at 250× the test concentration in neat DMSO. Intermediate 96-well compound plates were prepared by transferring 1.2 µL of the compound into 300 µL of assay buffer. A further 3× dilution occurred when transferring 50 µL/well of the compound plate to 100 µL/well in the cell plate. Cells were incubated with test compounds and dye for 30 minutes. Calcium dye fluorescence was monitored in FLIPR as the cells were challenged by adding 50 µL/well of BzATP (final concentration is 250 µM BzATP (human and rat)). The fluorescence change was measured 180 seconds after adding the agonist. Peak fluorescence was plotted as a function of BzATP concentration using Origin 7 software and the resultant $IC_{50}$ is shown in Tables 2 and 3 under the column headings FLIPR (human) $IC_{50}$ (µM) and FLIPR (rat) $IC_{50}$ (µM).

(b) Radioligand binding: human or rat P2X7-1321N1 cells were collected and frozen @ −80° C. On the day of the experiment, cell membrane preparations were made according to standard published methods. The total assay volume was 100 µl:10 µl compound (10×)+(b) 40 µl tracer (2.5×)+50 µl membrane (2×). The tracer used for the assay was tritiated A-804598. The compound can be prepared as described in the literature. (Donnelly-Roberts, D. *Neuropharmacology* 2008, 56 (1), 223-229.) Compounds, tracer and membranes were incubated for 1 hour @ 4° C. The assay was terminated by filtration (GF/B filters pre-soaked with 0.3% PEI) and washed with washing buffer (Tris-HCl 50 mM). The $IC_{50}$ generated in the binding assay was corrected for tracer concentration and affinity of the tracer to derive at the affinity (K) of the test compounds. The data are presented in Tables 2 and 3 under the headings: P2X7 human $K_i$ (µM) and P2X7 rat $K_i$ (µM). Data are analyzed and graphed on Graphpad Prism 5. For analysis, each concentration point is averaged from triplicate values and the averaged values are plotted on Graphpad Prism.

TABLE 2

P2X7 activity of the compounds of Formula (I) and selected compounds in a panel of in-vitro assays

| Example # | PBMC 1 µm (% control) | PBMC 10 µM (% control) | P2X7 human $K_i$ (µM) | P2X7 rat $K_i$ (µM) | FLIPR (human) $IC_{50}$ (µM) | FLIPR (rat) $IC_{50}$ (µM) | Human whole blood $IC_{50}$ (µM) |
|---|---|---|---|---|---|---|---|
| 1 | 6.6 | | 0.2239 | | 0.0299 | 1.2706 | |
| 2 | 19.4 | | 0.0955 | 0.2512 | 0.0365 | 3.2359 | |
| 3 | | 2.5 | | | 0.7980 | 4.2462 | |
| 4 | 50.2 | | | | 0.3882 | 12.4738 | |
| 5 | 72.0 | | | | 12.7644 | >10 | |
| 6 | 100.0 | 49.5 | | | | | |
| 7 | 14.2 | | 0.0154 | 0.0145 | 0.0207 | 0.4894 | 0.56 |
| 8 | 27.5 | | | | 0.2438 | >10 | |
| 9 | 96.3 | 9.8 | | | | | |
| 10 | 21.5 | | 0.0309 | 0.0219 | 0.0461 | 1.0116 | 2.00 |
| 11 | 45.8 | | 0.0372 | 0.0617 | 0.4159 | >10 | |
| 12 | 26.9 | | 0.0589 | 0.0575 | 0.0281 | 5.9704 | 2.00 |
| 13 | 86.7 | 13.4 | | | | | |
| 14 | 9.8 | | 0.0631 | 0.0316 | 0.0251 | 3.1623 | |
| 15 | 30.0 | | 0.0794 | 0.0501 | 0.0316 | 6.3096 | |
| 16 | 96.6 | 20.4 | | | 13.1826 | >10 | |
| 17 | 101.1 | 9.9 | | | | | |
| 18 | −0.5 | | 0.0200 | 0.0050 | 0.0103 | 0.0762 | |
| 19 | | 13.8 | 0.0251 | | 0.0261 | 0.0099 | 0.63 |
| 20 | | −0.2 | 0.0251 | 0.0035 | 0.0059 | 0.3381 | 1.23 |
| 21 | | −15.5 | 0.0398 | | 0.2799 | 3.2137 | |
| 22 | 15.5 | | | | 0.1977 | 28.0543 | |
| 23 | 71.8 | | 0.0095 | 0.0240 | 0.0045 | 2.4831 | 1.12 |
| 24 | 70.3 | | 0.0266 | 0.0079 | 0.0119 | 0.0679 | |
| 25 | 99.7 | 10.8 | | | | | |
| 26 | 91.0 | 16.1 | | | | | |
| 27 | 48.8 | | 0.4266 | | 0.1170 | 4.5499 | |
| 28 | 98.8 | 12.4 | | | 0.4519 | 8.5704 | |
| 29 | 63.6 | | | | 0.7962 | 1.9679 | |
| 30 | 80.8 | 21.0 | | | | | |
| 31 | 95.4 | 9.2 | | | | | |
| 32 | 66.5 | | | | 0.2652 | 4.0504 | |
| 33 | 18.5 | | 0.0164 | 0.0120 | 0.0080 | 1.1066 | 1.12 |

TABLE 2-continued

P2X7 activity of the compounds of Formula (I) and selected compounds in a panel of in-vitro assays

| Example # | PBMC 1 μm (% control) | PBMC 10 μM (% control) | P2X7 human $K_i$ (μM) | P2X7 rat $K_i$ (μM) | FLIPR (human) $IC_{50}$ (μM) | FLIPR (rat) $IC_{50}$ (μM) | Human whole blood $IC_{50}$ (μM) |
|---|---|---|---|---|---|---|---|
| 34 | 7.9 | | 0.0631 | 0.0200 | 0.0861 | 2.0160 | |
| 35 | 36.3 | | 0.0398 | 0.0126 | 0.0483 | 0.2692 | |
| 36 | 58.8 | | 0.0794 | 0.0316 | | | |
| 37 | 22.0 | | 0.0501 | 0.0251 | 0.0121 | 0.6486 | |
| 38 | 47.8 | | 0.0776 | 0.0457 | 0.0634 | 1.3772 | |
| 39 | 15.1 | | 0.0501 | 0.0178 | 0.1000 | 0.0251 | |
| 40 | 81.0 | 12.9 | | | | | |
| 41 | 52.2 | | | | | | |
| 42 | 34.4 | | 0.0794 | | 0.0200 | 2.5119 | |
| 43 | 36.2 | | 0.0501 | 0.0100 | 0.0158 | 0.1585 | |
| 44 | 44.6 | | 0.0631 | | 0.0348 | 0.1560 | |
| 45 | 80.3 | 7.1 | | | | | |
| 46 | 104.3 | 100.0 | | | | | |
| 47 | 56.7 | | 0.0398 | | 0.0158 | 0.0079 | >10 |
| 48 | 92.4 | | 1.9953 | | 5.0119 | 10.0000 | |
| 49 | 84.9 | 16.3 | | | | | |
| 50 | 100.4 | 83.5 | | | | | |
| 51 | 87.5 | 17.3 | | | | | |
| 52 | 76.9 | 9.3 | | | | | |
| 53 | 52.9 | | 0.0631 | | 0.0834 | 1.8880 | |
| 54 | | 5.0 | 0.1000 | | 0.0210 | 0.5559 | |
| 55 | | −2.1 | 0.0178 | | 0.0459 | 0.1172 | |
| 56 | | 10.2 | 0.0372 | | 0.0143 | 0.0124 | |
| 57 | | −9.6 | 0.0631 | | 0.0165 | 0.1611 | |
| 58 | | 5.0 | 0.0158 | 0.0028 | 0.0111 | 0.0103 | 0.16 |
| 59 | | 2.8 | | | 1.7458 | 0.8610 | |
| 60 | | 10.8 | 0.0794 | | 0.0655 | 0.2679 | |
| 61 | | −1.2 | | | 0.4477 | 3.1117 | |
| 62 | | 44.7 | 0.0251 | | 0.0078 | 0.0056 | |
| 63 | | −4.1 | 0.0224 | | 0.3162 | 0.0025 | |
| 64 | | −2.1 | 0.0794 | | 0.0164 | 0.0133 | |
| 65 | | 3.9 | | | 2.8184 | 1.2246 | |
| 66 | | −6.1 | 0.0501 | | 0.0100 | 0.0100 | |
| 67 | | −1.3 | 0.0126 | | 0.0135 | 0.0145 | |
| 68 | | −0.5 | 0.0158 | | 0.0127 | 0.0088 | |
| 69 | | −6.2 | | | 1.7865 | 0.9376 | |
| 70 | | −2.7 | 0.0398 | | 0.0187 | 0.0124 | |
| 71 | | −4.1 | 0.0126 | | 0.0029 | 0.0024 | |
| 72 | | −2.6 | | | 1.4521 | 1.1803 | |
| 73 | | 2.2 | 0.1259 | | 0.0966 | 0.0178 | |
| 74 | | 22.5 | 0.0251 | | 0.0100 | 0.0100 | |
| 75 | | 2.4 | 0.0063 | | 0.0127 | 0.0077 | |
| 76 | | 14.3 | | | 0.4064 | 0.1262 | |
| 77 | | 20.9 | 0.0316 | | 0.0631 | 0.0200 | |
| 78 | | 1.4 | 0.0079 | | 0.0136 | 0.0129 | |
| 79 | | 2.6 | | | 3.2359 | 0.9886 | |
| 80 | | 18.4 | 0.0251 | | 0.0251 | 0.0200 | |
| 81 | | 21.0 | 0.0079 | | 0.0105 | 0.0153 | |
| 82 | | −1.0 | | | 1.3152 | 0.8670 | |
| 83 | | 2.7 | 0.0316 | | 0.0017 | 0.0149 | |
| 84 | | 7.5 | 0.0100 | 0.0019 | 0.0110 | 0.0131 | |
| 85 | | −0.8 | 0.4571 | | 0.8204 | 0.5861 | |
| 86 | | 92.2 | | | | | |
| 87 | | 0.4 | 0.0316 | | 0.0336 | 0.0152 | |
| 88 | | 49.4 | | | 11.0408 | 8.7700 | |
| 89 | | −16.4 | 0.0115 | 0.0010 | 0.0172 | 0.0159 | |
| 90 | | | | | | | |
| 91 | | −8.8 | 0.0251 | | 0.0587 | 0.1318 | |
| 92 | | 9.4 | | | 1.5922 | 5.9566 | |
| 93 | | −1.7 | 0.1995 | | 0.0285 | 0.3846 | |
| 94 | | 71.8 | | | >10 | >10 | |
| 95 | | −19.2 | 0.0316 | | 0.0647 | 0.1014 | |
| 96 | | 3.8 | 0.6310 | | 0.0500 | 1.8450 | |
| 97 | | −3.1 | 0.1995 | | 0.1663 | 13.9959 | |
| 98 | | 13.2 | 0.0550 | | 0.0255 | 0.0149 | |
| 99 | | 16.4 | 0.0174 | | 0.0139 | 0.0126 | |
| 100 | | 4.0 | | | 1.1940 | 0.2056 | |
| 101 | | 13.6 | 0.1000 | | 0.0824 | 0.0230 | |
| 102 | | 11.7 | 0.0200 | | 0.0273 | 0.0130 | |
| 103 | | 6.3 | | | 1.0328 | 0.4140 | |
| 104 | | −1.3 | 0.0398 | | 0.0191 | 0.0237 | |

TABLE 2-continued

P2X7 activity of the compounds of Formula (I) and selected compounds in a panel of in-vitro assays

| Example # | PBMC 1 μm (% control) | PBMC 10 μM (% control) | P2X7 human $K_i$ (μM) | P2X7 rat $K_i$ (μM) | FLIPR (human) $IC_{50}$ (μM) | FLIPR (rat) $IC_{50}$ (μM) | Human whole blood $IC_{50}$ (μM) |
|---|---|---|---|---|---|---|---|
| 105 | 94.4 | | | | | | |
| 106 | 100.4 | | | | | | |
| 107 | 71.8 | | 0.0095 | 0.0240 | 0.0045 | 2.4831 | 1.12 |
| 108 | 70.3 | | 0.0266 | 0.0079 | 0.0119 | 0.0679 | |
| 109 | | 2.2 | 0.0126 | | 0.0121 | 0.4853 | |
| 110 | | 20.1 | | | >10 | >10 | |
| 111 | | 0.6 | 0.0501 | | 0.3532 | 0.8072 | |
| 112 | | −1.8 | 0.0251 | | 0.0129 | 0.0160 | |
| 113 | | −2.1 | 0.0079 | | 0.0028 | 0.0091 | |
| 114 | | −0.5 | 0.6310 | | 0.1337 | 0.1660 | |
| 115 | | −3.1 | 0.0316 | | 0.0139 | 0.0142 | |
| 116 | | −4.4 | 0.0316 | | 0.0059 | 0.0086 | |
| 117 | | 0.1 | | | 0.9683 | 1.2274 | |
| 118 | | −0.6 | 0.0126 | | 0.0057 | 0.0210 | |
| 119 | | −1.5 | 0.0126 | | 0.0100 | 0.0284 | |
| 120 | | 2.9 | | | 0.6561 | 1.5101 | |
| 121 | | 0.7 | 0.0200 | | 0.0106 | 0.1279 | |
| 122 | | 4.1 | 0.0200 | | 0.0058 | 0.1279 | |
| 123 | | 13.3 | 0.5012 | | 0.1524 | 1.0046 | |
| 124 | | 18.6 | 0.0251 | 0.0035 | 0.0310 | 0.0129 | |
| 125 | | 64.7 | | | | | |
| 126 | | | | | | | |
| 127 | | 38.2 | | | >10 | >10 | |
| 128 | | 7.3 | 0.0316 | 0.0030 | 0.0296 | 0.0097 | |
| 129 | | 2.5 | 0.0398 | | 0.1062 | 1.0641 | |
| 130 | | 12.9 | 0.0631 | | 0.0174 | 1.0940 | |
| 131 | | 7.3 | | | 11.4025 | >10 | |
| 132 | | −0.1 | | | 0.5321 | 7.1614 | |
| 133 | | 0.1 | | | 0.9183 | 2.2182 | |
| 134 | | 0.4 | | | 0.3311 | 1.2735 | |
| 135 | | −1.0 | | | 0.4920 | 1.8707 | |

The following compounds were tested in additional runs for the assays described above and the data is provided in Table 3.

TABLE 3

P2X7 activity of the compounds of Formula (I) and selected compounds in a panel of in-vitro assays

| Example # | PBMC 1 μM (% control) | PBMC 10 μM (% control) | P2X7 human $K_i$ (μM) | P2X7 rat $K_i$ (μM) | FLIPR (human) $IC_{50}$ (μM) | FLIPR (rat) $IC_{50}$ (μM) | Human whole blood $IC_{50}$ (μM) |
|---|---|---|---|---|---|---|---|
| 1 | 6.6 | | 0.2239 | | 0.0299 | 1.2706 | |
| 2 | 19.4 | | 0.0955 | 0.2512 | 0.0365 | 3.2359 | |
| 3 | | 2.5 | | | 0.7980 | 4.2462 | |
| 4 | 50.2 | | | | 0.3882 | 12.4738 | |
| 5 | 72.0 | | | | 12.7644 | >10 | |
| 6 | 100.0 | 49.5 | | | | | |
| 7 | 14.2 | | 0.0154 | 0.0145 | 0.0207 | 0.4894 | 0.562 |
| 8 | 27.5 | | | | 0.2438 | >10 | |
| 9 | 96.3 | 9.8 | | | | | |
| 10 | 21.5 | | 0.0309 | 0.0219 | 0.0461 | 1.0116 | 1.995 |
| 11 | 45.8 | | 0.0372 | 0.0617 | 0.4159 | >10 | |
| 12 | 26.9 | | 0.0589 | 0.0575 | 0.0281 | 5.9704 | 1.995 |
| 13 | 86.7 | 13.4 | | | | | |
| 14 | 9.8 | | 0.0631 | 0.0316 | 0.0251 | 3.1623 | |
| 15 | 30.0 | | 0.0794 | 0.0501 | 0.0316 | 6.3096 | |
| 16 | 96.6 | 20.4 | | | 13.1826 | >10 | |
| 17 | 101.1 | 9.9 | | | | | |
| 18 | −0.5 | | 0.0200 | 0.0050 | 0.0103 | 0.0762 | |
| 19 | | 13.8 | 0.0251 | | 0.0261 | 0.0099 | 0.631 |
| 20 | | −0.2 | 0.0251 | 0.0035 | 0.0059 | 0.3381 | 1.230 |
| 21 | | −15.5 | 0.0398 | | 0.2799 | 3.2137 | |

TABLE 3-continued

P2X7 activity of the compounds of Formula (I) and selected compounds in a panel of in-vitro assays

| Example # | PBMC 1 μM (% control) | PBMC 10 μM (% control) | P2X7 human $K_i$ (μM) | P2X7 rat $K_i$ (μM) | FLIPR (human) $IC_{50}$ (μM) | FLIPR (rat) $IC_{50}$ (μM) | Human whole blood $IC_{50}$ (μM) |
|---|---|---|---|---|---|---|---|
| 22 | 15.5 | | | | 0.1977 | 28.0543 | |
| 23 | 71.8 | | 0.0095 | 0.0240 | 0.0045 | 2.4831 | 1.122 |
| 24 | 70.3 | | 0.0266 | 0.0079 | 0.0119 | 0.0679 | |
| 25 | 99.7 | 10.8 | | | | | |
| 26 | 91.0 | 16.1 | | | | | |
| 27 | 48.8 | | 0.4266 | | 0.1170 | 4.5499 | |
| 28 | 98.8 | 12.4 | | | 0.4519 | 8.5704 | |
| 29 | 63.6 | | | | 0.7962 | 1.9679 | |
| 30 | 80.8 | 21.0 | | | | | |
| 31 | 95.4 | 9.2 | | | | | |
| 32 | 66.5 | | | | 0.2652 | 4.0504 | |
| 33 | 18.5 | | 0.0164 | 0.0120 | 0.0080 | 1.1066 | 1.122 |
| 34 | 7.9 | | 0.0631 | 0.0200 | 0.0861 | 2.0160 | |
| 35 | 36.3 | | 0.0398 | 0.0126 | 0.0483 | 0.2692 | |
| 36 | 58.8 | | 0.0794 | 0.0316 | | | |
| 37 | 22.0 | | 0.0501 | 0.0251 | 0.0121 | 0.6486 | |
| 38 | 47.8 | | 0.0776 | 0.0457 | 0.0634 | 1.3772 | |
| 39 | 15.1 | | 0.0501 | 0.0178 | 0.1000 | 0.0251 | |
| 40 | 81.0 | 12.9 | | | | | |
| 41 | 52.2 | | | | | | |
| 42 | 34.4 | | 0.0794 | | 0.0200 | 2.5119 | |
| 43 | 36.2 | | 0.0501 | 0.0100 | 0.0158 | 0.1585 | |
| 44 | 44.6 | | 0.0631 | | 0.0348 | 0.1560 | |
| 45 | 80.3 | 7.1 | | | | | |
| 46 | 104.3 | 100.0 | | | | | |
| 47 | 56.7 | | 0.0398 | | 0.0158 | 0.0079 | >10 |
| 48 | 92.4 | | 1.9953 | | 5.0119 | 10.0000 | |
| 49 | 84.9 | 16.3 | | | | | |
| 50 | 100.4 | 83.5 | | | | | |
| 51 | 87.5 | 17.3 | | | | | |
| 52 | 76.9 | 9.3 | | | | | |
| 53 | 52.9 | | 0.0631 | | 0.0834 | 1.8880 | |
| 54 | | 5.0 | 0.1000 | | 0.0210 | 0.5559 | |
| 55 | | −2.1 | 0.0178 | | 0.0459 | 0.1172 | |
| 56 | | 10.2 | 0.0372 | | 0.0143 | 0.0124 | |
| 57 | | −9.6 | 0.0631 | | 0.0165 | 0.1611 | |
| 58 | | 5.0 | 0.0158 | 0.0028 | 0.0111 | 0.0103 | 0.158 |
| 59 | | 2.8 | | | 1.7458 | 0.8610 | |
| 60 | | 10.8 | 0.0794 | | 0.0655 | 0.2679 | |
| 61 | | −1.2 | | | 0.4477 | 3.1117 | |
| 62 | | 44.7 | 0.0251 | | 0.0078 | 0.0056 | |
| 63 | | −4.1 | 0.0224 | | 0.3162 | 0.0025 | |
| 64 | | −2.1 | 0.0794 | | 0.0164 | 0.0133 | |
| 65 | | 3.9 | | | 2.8184 | 1.2246 | |
| 66 | | −6.1 | 0.0501 | | 0.0100 | 0.0100 | |
| 67 | | −1.3 | 0.0126 | | 0.0135 | 0.0145 | |
| 68 | | −0.5 | 0.0158 | | 0.0127 | 0.0088 | |
| 69 | | −6.2 | | | 1.7865 | 0.9376 | |
| 70 | | −2.7 | 0.0398 | | 0.0187 | 0.0124 | |
| 71 | | −4.1 | 0.0126 | | 0.0029 | 0.0024 | |
| 72 | | −2.6 | | | 1.4521 | 1.1803 | |
| 73 | | 2.2 | 0.1259 | | 0.0966 | 0.0178 | |
| 74 | | 22.5 | 0.0251 | | 0.0100 | 0.0100 | |
| 75 | | 2.4 | 0.0063 | | 0.0127 | 0.0077 | |
| 76 | | 14.3 | | | 0.4064 | 0.1262 | |
| 77 | | 20.9 | 0.0316 | | 0.0631 | 0.0200 | |
| 78 | | 1.4 | 0.0079 | | 0.0136 | 0.0129 | |
| 79 | | 2.6 | | | 3.2359 | 0.9886 | |
| 80 | | 18.4 | 0.0251 | | 0.0251 | 0.0200 | |
| 81 | | 21.0 | 0.0079 | | 0.0105 | 0.0153 | |
| 82 | | −1.0 | | | 1.3152 | 0.8670 | |
| 83 | | 2.7 | 0.0316 | | 0.0017 | 0.0149 | |
| 84 | | 7.5 | 0.0100 | 0.0019 | 0.0110 | 0.0131 | |
| 85 | | −0.8 | 0.4571 | | 0.8204 | 0.5861 | |
| 86 | | 92.2 | | | | | |
| 87 | | 0.4 | 0.0316 | | 0.0336 | 0.0152 | |
| 88 | | 49.4 | | | 11.0408 | 8.7700 | |
| 89 | | −16.4 | 0.0077 | 0.0012 | 0.0172 | 0.0159 | |
| 90 | | | | | | | |
| 91 | | −8.8 | 0.0251 | | 0.0587 | 0.1318 | |
| 92 | | 9.4 | | | 1.5922 | 5.9566 | |

TABLE 3-continued

P2X7 activity of the compounds of Formula (I) and selected compounds in a panel of in-vitro assays

| Example # | PBMC 1 μM (% control) | PBMC 10 μM (% control) | P2X7 human $K_i$ (μM) | P2X7 rat $K_i$ (μM) | FLIPR (human) $IC_{50}$ (μM) | FLIPR (rat) $IC_{50}$ (μM) | Human whole blood $IC_{50}$ (μM) |
|---|---|---|---|---|---|---|---|
| 93 | | −1.7 | 0.1995 | | 0.0285 | 0.3846 | |
| 94 | | 71.8 | | | >10 | >10 | |
| 95 | | −19.2 | 0.0316 | | 0.0647 | 0.1014 | |
| 96 | | 3.8 | 0.6310 | | 0.0500 | 1.8450 | |
| 97 | | −3.1 | 0.1995 | | 0.1663 | 13.9959 | |
| 98 | | 13.2 | 0.0550 | | 0.0255 | 0.0149 | |
| 99 | | 16.4 | 0.0174 | | 0.0139 | 0.0126 | |
| 100 | | 4.0 | | | 1.1940 | 0.2056 | |
| 101 | | 13.6 | 0.1000 | | 0.0824 | 0.0230 | |
| 102 | | 11.7 | 0.0200 | | 0.0273 | 0.0130 | |
| 103 | | 6.3 | | | 1.0328 | 0.4140 | |
| 104 | | −1.3 | 0.0398 | | 0.0191 | 0.0237 | |
| 105 | 94.4 | | | | | | |
| 106 | 100.4 | | | | | | |
| 107 | 71.8 | | 0.0095 | 0.0240 | 0.0045 | 2.4831 | 1.122 |
| 108 | 70.3 | | 0.0266 | 0.0079 | 0.0119 | 0.0679 | |
| 109 | | 2.2 | 0.0126 | | 0.0121 | 0.4853 | |
| 110 | | 20.1 | | | >10 | >10 | |
| 111 | | 0.6 | 0.0501 | | 0.3532 | 0.8072 | |
| 112 | | −1.8 | 0.0251 | | 0.0129 | 0.0160 | |
| 113 | | −2.1 | 0.0079 | | 0.0028 | 0.0091 | |
| 114 | | −0.5 | 0.6310 | | 0.1337 | 0.1660 | |
| 115 | | −3.1 | 0.0316 | | 0.0139 | 0.0142 | |
| 116 | | −4.4 | 0.0316 | | 0.0059 | 0.0086 | |
| 117 | | 0.1 | | | 0.9683 | 1.2274 | |
| 118 | | −0.6 | 0.0126 | | 0.0057 | 0.0210 | |
| 119 | | −1.5 | 0.0126 | | 0.0100 | 0.0284 | |
| 120 | | 2.9 | | | 0.6561 | 1.5101 | |
| 121 | | 0.7 | 0.0200 | | 0.0106 | 0.1279 | |
| 122 | | 4.1 | 0.0200 | | 0.0058 | 0.1279 | |
| 123 | | 13.3 | 0.5012 | | 0.1524 | 1.0046 | |
| 124 | | 18.6 | 0.0251 | 0.0035 | 0.0310 | 0.0129 | |
| 125 | | 64.7 | | | | | |
| 126 | | | | | | | |
| 127 | | 38.2 | | | >10 | >10 | |
| 128 | | 7.3 | 0.0316 | 0.0030 | 0.0296 | 0.0097 | |
| 129 | | 2.5 | 0.0398 | | 0.1062 | 1.0641 | |
| 130 | | 12.9 | 0.0631 | | 0.0174 | 1.0940 | |
| 131 | | 7.3 | | | 11.4025 | >10 | |
| 132 | | −0.1 | | | 0.5321 | 7.1614 | |
| 133 | | 0.1 | | | 0.9183 | 2.2182 | |
| 134 | | 0.4 | | | 0.3311 | 1.2735 | |
| 135 | | −1.0 | | | 0.4920 | 1.8707 | |
| 139 | | 2.0 | | | 1.1561 | 1.4555 | |
| 140 | | 52.5 | | | >10 | 47.3151 | |
| 141 | | −0.6 | | | 8.9950 | 12.3595 | |
| 142 | | 73.9 | | | | | |
| 143 | | 11.9 | 0.1000 | | 0.0196 | 0.0522 | |
| 144 | | −18.9 | 0.0074 | | 0.0667 | 0.2004 | |
| 145 | | 67.4 | | | | | |
| 146 | | −0.8 | | | 1.0568 | >10 | |
| 147 | | 110.5 | | | | | |

The invention claimed is:
1. A compound of Formula (I):

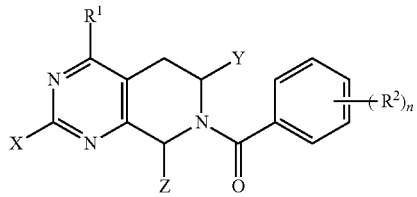

Formula (I)

wherein:
  each $R^2$ is independently selected from the group consisting of H, halo, CN, $C_1$-$C_3$ alkyl, perhaloalkyl, $C_1$-$C_3$ alkoxy and perhaloalkoxy;
  n is an integer from 0-3;
  X is independently selected from the group consisting of H, $C_1$-$C_3$ alkyl, $C_3$ cycloalkyl, perfluoroalkyl, —$NH_2$, and —$N(CH_3)_2$;
  Y and Z are independently H or $CH_3$;
  $R^1$ is independently selected from the group consisting of:

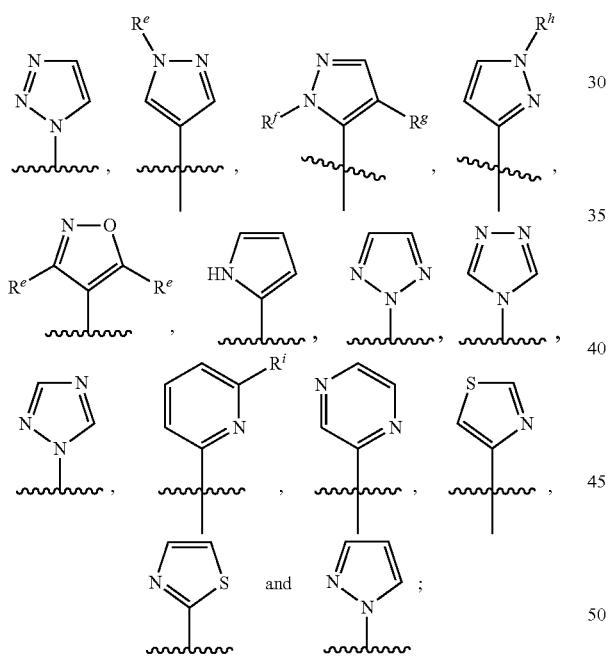

$R^e$ and $R^f$ are H or $C_1$-$C_3$ alkyl;
  $R^g$ is H, F, or perfluoroalkyl;
  $R^h$ is H, $C_1$-$C_3$ alkyl, —$CH_2CH_2OCH_3$ or perfluoroalkyl; and
  $R^i$ is H or halo; or
pharmaceutically acceptable salts of compounds thereof.

2. A compound as defined in claim 1, wherein n is 2.
3. A compound as defined in claim 1, wherein one $R^2$ substituent is in the ortho position.
4. A compound as defined in claim 1, wherein one $R^2$ substituent is in the meta position.
5. A compound as defined in claim 1, wherein n is 2, one $R^2$ substituent is in the ortho position and the other $R^2$ substituent is in the meta position.
6. A compound as defined in claim 1, wherein n is 2, one $R^2$ substituent is in the ortho position and the other $R^2$ substituent is in the para position.
7. A compound as defined in claim 1, wherein n is 2, one $R^2$ substituent is Cl and is in the ortho position and the other $R^2$ substituent is $CF_3$ and is in the meta position.
8. A compound as defined in claim 1, wherein n is 2, one $R^2$ substituent is Cl and is in the ortho position and the other $R^2$ substituent is Cl and is in the meta position.
9. A compound as defined in claim 1, wherein n is 2, one $R^2$ substituent is Cl and is in the ortho position and the other $R^2$ substituent is Cl and is in the para position.
10. A compound as in defined claim 1, wherein n is 2, one $R^2$ substituent is F and is in the ortho position and the other $R^2$ substituent is Cl and is in the para position.
11. A compound as in defined claim 1 wherein $R^1$ is selected from the group consisting of:

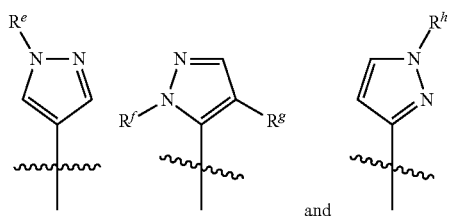

and

12. A compound as defined in claim 1 wherein $R^1$ is selected from the group consisting of:

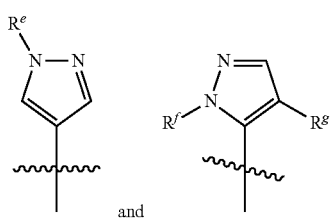

and

13. A compound as defined in claim 1 wherein $R^1$ is:

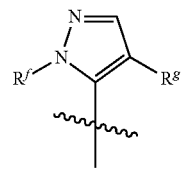

14. A compound as defined in claim 1 wherein $R^f$ and $R^g$ are H and $R^1$ is

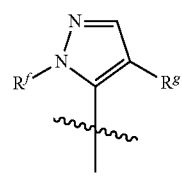

15. A compound as defined in claim 1 wherein X, Y, Z, $R^f$ and $R^g$ are H, n is 2, one $R^2$ substituent is Cl and is in the ortho position, the other $R^2$ substituent is Cl and is in the meta position and $R^1$ is

16. A compound as defined in claim 1 wherein Y, Z, $R^f$ and $R^g$ are H, X is $CH_3$, n is 2, one $R^2$ substituent is Cl and is in the ortho position, the other $R^2$ substituent is $CF_3$ and is in the meta position and $R^1$ is

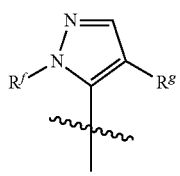

17. A compound as defined in claim 1 wherein Z, $R^f$ and $R^g$ are H, X and Y are $CH_3$, n is 2, one $R^2$ substituent is Cl and is in the ortho position, the other $R^2$ substituent is $CF_3$ and is in the meta position and $R^1$ is

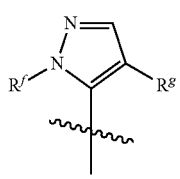

18. A compound as defined in claim 1 wherein Z, $R^f$ and $R^g$ are H, X and Y are $CH_3$, n is 2, one $R^2$ substituent is Cl and is in the ortho position, the other $R^2$ substituent is Cl and is in the para position and $R^1$ is

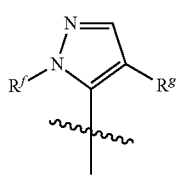

19. A compound as defined in claim 1 wherein Z, $R^f$ and $R^g$ are H, X and Y are $CH_3$, n is 2, one $R^2$ substituent is F and is in the ortho position, the other $R^2$ substituent is Cl and is in the para position and $R^1$ is

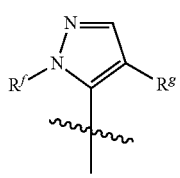

20. A compound selected from the group consisting of:
4-(2,6-dimethyl-4-(1H-pyrazol-5-yl)-5,6,7,8-tetrahydro-pyrido[3,4-d]pyrimidine-7-carbonyl)-3-methylbenzo-nitrile;
7-[(2,3-Dichlorophenyl)carbonyl]-4-(1H-pyrazol-4-yl)-5,6,7,8-tetrahydropyrido[3,4-d]pyrimidine;
7-[(2,3-Dichlorophenyl)carbonyl]-4-(1-methyl-1H-pyrazol-4-yl)-5,6,7,8-tetrahydropyrido[3,4-d]pyrimidine;
7-[(2-Chloro-3-methylphenyl)carbonyl]-4-(1-methyl-1H-pyrazol-4-yl)-5,6,7,8-tetrahydropyrido[3,4-d]pyrimidine;
7-[(2,3-Dichlorophenyl)carbonyl]-4-(1H-pyrazol-5-yl)-5,6,7,8-tetrahydropyrido[3,4-d]pyrimidine;
7-[(2-Chloro-3-methylphenyl)carbonyl]-4-(1H-pyrazol-5-yl)-5,6,7,8-tetrahydropyrido[3,4-d]pyrimidine;
7-[(2,3-Dimethylphenyl)carbonyl]-4-(1H-pyrazol-5-yl)-5,6,7,8-tetrahydropyrido[3,4-d]pyrimidine;
7-{[2-Methyl-3-(trifluoromethyl)phenyl]carbonyl}-4-(1H-pyrazol-5-yl)-5,6,7,8-tetrahydropyrido[3,4-d]pyrimidine;
7-[(2,3-Dichlorophenyl)carbonyl]-4-pyridin-2-yl-5,6,7,8-tetrahydropyrido[3,4-d]pyrimidine;
7-{[2-Chloro-3-(trifluoromethyl)phenyl]carbonyl}-4-pyridin-2-yl-5,6,7,8-tetrahydropyrido[3,4-d]pyrimidine;
7-[(2-Chloro-3-methylphenyl)carbonyl]-4-pyridin-2-yl-5,6,7,8-tetrahydropyrido[3,4-d]pyrimidine;
7-[(2,3-Dichlorophenyl)carbonyl]-4-pyrazin-2-yl-5,6,7,8-tetrahydropyrido[3,4-d]pyrimidine;
7-{[2-Methyl-3-(trifluoromethyl)phenyl]carbonyl}-4-pyrazin-2-yl-5,6,7,8-tetrahydropyrido[3,4-d]pyrimidine;
7-[(2-Chloro-4,5-difluorophenyl)carbonyl]-4-pyrazin-2-yl-5,6,7,8-tetrahydropyrido[3,4-d]pyrimidine;
(4-(1H-pyrazol-5-yl)-5,6-dihydropyrido[3,4-d]pyrimidin-7(8H)-yl)(2-chloro-3-(trifluoromethyl)phenyl)methanone;
7-{[2-Chloro-3-(trifluoromethyl)phenyl]carbonyl}-4-(1-methyl-1H-pyrazol-3-yl)-5,6,7,8-tetrahydropyrido[3,4-d]pyrimidine;
7-[(2,4-Dichloro-3-fluorophenyl)carbonyl]-4-(1H-pyrazol-5-yl)-5,6,7,8-tetrahydropyrido[3,4-d]pyrimidine;
7-[(2-chloro-4-fluorophenyl)carbonyl]-4-(1H-pyrazol-5-yl)-5,6,7,8-tetrahydropyrido[3,4-d]pyrimidine;
7-[(2,3-Dichlorophenyl)carbonyl]-4-(1H-pyrazol-1-yl)-5,6,7,8-tetrahydropyrido[3,4-d]pyrimidine;
7-[(2,3-Dichlorophenyl)carbonyl]-4-(2H-1,2,3-triazol-2-yl)-5,6,7,8-tetrahydropyrido[3,4-d]pyrimidine;
7-{[2-Chloro-3-(trifluoromethyl)phenyl]carbonyl}-2-methyl-4-pyridin-2-yl-5,6,7,8-tetrahydropyrido[3,4-d]pyrimidine;
7-[(2,3-Dichlorophenyl)carbonyl]-2-methyl-4-pyridin-2-yl-5,6,7,8-tetrahydropyrido[3,4-d]pyrimidine;
7-{[2-Chloro-3-(trifluoromethyl)phenyl]carbonyl}-2-methyl-4-(1H-pyrazol-5-yl)-5,6,7,8-tetrahydropyrido[3,4-d]pyrimidine;
7-[(2,3-Dichlorophenyl)carbonyl]-2-methyl-4-(1H-pyrazol-5-yl)-5,6,7,8-tetrahydropyrido[3,4-d]pyrimidine;
7-{[2-Chloro-3-(trifluoromethyl)phenyl]carbonyl}-4-(4-fluoro-1H-pyrazol-5-yl)-2-methyl-5,6,7,8-tetrahydropyrido[3,4-d]pyrimidine;
7-[(2,3-Dichlorophenyl)carbonyl]-4-(4-fluoro-1H-pyrazol-5-yl)-2-methyl-5,6,7,8-tetrahydropyrido[3,4-d]pyrimidine;
7-{[2-Chloro-3-(trifluoromethyl)phenyl]carbonyl}-4-(1,3-thiazol-2-yl)-5,6,7,8-tetrahydropyrido[3,4-d]pyrimidine;

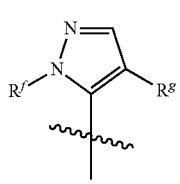

7-[(2,3-Dichlorophenyl)carbonyl]-4-(1,3-thiazol-2-yl)-5,6,7,8-tetrahydropyrido[3,4-d]pyrimidine;

7-{[2-Chloro-3-(trifluoromethyl)phenyl]carbonyl}-2-methyl-4-[4-(trifluoromethyl)-1H-pyrazol-5-yl]-5,6,7,8-tetrahydropyrido[3,4-d]pyrimidine;

7-[(2,3-Dichlorophenyl)carbonyl]-2-methyl-4-[4-(trifluoromethyl)-1H-pyrazol-5-yl]-5,6,7,8-tetrahydropyrido[3,4-d]pyrimidine;

7-[(2,3-Dichlorophenyl)carbonyl]-4-(1H-pyrrol-2-yl)-5,6,7,8-tetrahydropyrido[3,4-d]pyrimidine;

7-{[2-Chloro-3-(trifluoromethyl)phenyl]carbonyl}-4-(1H-pyrrol-2-yl)-5,6,7,8-tetrahydropyrido[3,4-d]pyrimidine;

7-{[2-Chloro-3-(trifluoromethyl)phenyl]carbonyl}-thiazol-4-yl)-5,6,7,8-tetrahydropyrido[3,4-d]pyrimidine;

7-{[2-Chloro-3-(trifluoromethyl)phenyl]carbonyl}-2-methyl-4-(1,3-thiazol-4-yl)-5,6,7,8-tetrahydropyrido[3,4-d]pyrimidine;

7-{[2-Chloro-3-(trifluoromethyl)phenyl]carbonyl}-2-methyl-4-(1H-pyrrol-2-yl)-5,6,7,8-tetrahydropyrido[3,4-d]pyrimidine;

7-{[2-Chloro-3-(trifluoromethyl)phenyl]carbonyl}-4-(3,5-dimethylisoxazol-4-yl)-2-methyl-5,6,7,8-tetrahydropyrido[3,4-d]pyrimidine;

7-{[2-Chloro-3-(trifluoromethyl)phenyl]carbonyl}-2-methyl-4-(2H-1,2,3-triazol-2-yl)-5,6,7,8-tetrahydropyrido[3,4-d]pyrimidine;

7-{[2-Chloro-3-(trifluoromethyl)phenyl]carbonyl}-2-methyl-4-(1H-1,2,3-triazol-1-yl)-5,6,7,8-tetrahydropyrido[3,4-d]pyrimidine;

7-{[2-Chloro-3-(trifluoromethyl)phenyl]carbonyl}-4-isoxazol-4-yl-2-methyl-5,6,7,8-tetrahydropyrido[3,4-d]pyrimidine;

7-{[2-Chloro-3-(trifluoromethyl)phenyl]carbonyl}-4-(3,5-dimethylisoxazol-4-yl)-5,6,7,8-tetrahydropyrido[3,4-d]pyrimidine;

7-{[2-Fluoro-3-(trifluoromethyl)phenyl]carbonyl}-2-methyl-4-(1H-pyrazol-5-yl)-5,6,7,8-tetrahydropyrido[3,4-d]pyrimidine;

2-Methyl-7-{[2-methyl-3-(trifluoromethyl)phenyl]carbonyl}-4-(1H-pyrazol-5-yl)-5,6,7,8-tetrahydropyrido[3,4-d]pyrimidine;

7-[(2,4-Dichloro-3-fluorophenyl)carbonyl]-2-methyl-4-(1H-pyrazol-5-yl)-5,6,7,8-tetrahydropyrido[3,4-d]pyrimidine;

7-{[2-Chloro-3-(trifluoromethyl)phenyl]carbonyl}-N,N-dimethyl-4-(1H-pyrazol-5-yl)-5,6,7,8-tetrahydropyrido[3,4-d]pyrimidin-2-amine;

7-{[2-Chloro-3-(trifluoromethyl)phenyl]carbonyl}-4-(1H-pyrazol-5-yl)-5,6,7,8-tetrahydropyrido[3,4-d]pyrimidin-2-amine;

7-{[2-Chloro-3-(trifluoromethyl)phenyl]carbonyl}-2,6-dimethyl-4-(1H-pyrazol-5-yl)-5,6,7,8-tetrahydropyrido[3,4-d]pyrimidine;

7-{[2-Chloro-3-(trifluoromethyl)phenyl]carbonyl}-2-cyclopropyl-4-(1H-pyrazol-5-yl)-5,6,7,8-tetrahydropyrido[3,4-d]pyrimidine;

(6R)-7-{[2-Chloro-3-(trifluoromethyl)phenyl]carbonyl}-2,6-dimethyl-4-(1H-pyrazol-5-yl)-5,6,7,8-tetrahydropyrido[3,4-d]pyrimidine;

(6S)-7-{[2-Chloro-3-(trifluoromethyl)phenyl]carbonyl}-2, 6-dimethyl-4-(1H-pyrazol-5-yl)-5,6,7,8-tetrahydropyrido[3,4-d]pyrimidine;

(4-(1H-pyrazol-5-yl)-2-(trifluoromethyl)-5,6-dihydropyrido[3,4-d]pyrimidin-7(8H)-yl)(2-chloro-3-(trifluoromethyl)phenyl)methanone;

3-(2,6-dimethyl-4-(1H-pyrazol-5-yl)-5,6,7,8-tetrahydropyrido[3,4-d]pyrimidine-7-carbonyl)-2-methylbenzonitrile;

(2-chloro-3-(trifluoromethyl)phenyl)(6-methyl-4-(1H-pyrazol-5-yl)-5,6-dihydropyrido[3,4-d]pyrimidin-7(8H)-yl)methanone;

(2-amino-6-methyl-4-(1H-pyrazol-5-yl)-5,6-dihydropyrido[3,4-d]pyrimidin-7(8H)-yl)(2-chloro-3-(trifluoromethyl)phenyl)methanone;

(2-chloro-4-fluoro-3-(trifluoromethyl)phenyl)(2, 6-dimethyl-4-(1H-pyrazol-5-yl)-5,6-dihydropyrido[3,4-d]pyrimidin-7(8H)-yl)methanone;

(S)-(2-chloro-4-fluoro-3-(trifluoromethyl)phenyl)(2, 6-dimethyl-4-(1H-pyrazol-5-yl)-5,6-dihydropyrido[3,4-d]pyrimidin-7(8H)-yl)methanone;

(R)-(2-chloro-4-fluoro-3-(trifluoromethyl)phenyl)(2,6-dimethyl-4-(1H-pyrazol-5-yl)-5,6-dihydropyrido[3,4-d]pyrimidin-7(8H)-yl)methanone;

(2,3-dichlorophenyl)(2,6-dimethyl-4-(1H-pyrazol-5-yl)-5,6-dihydropyrido[3,4-d]pyrimidin-7(8H)-yl)methanone;

(R)-(2,3-dichlorophenyl)(2,6-dimethyl-4-(1H-pyrazol-5-yl)-5,6-dihydropyrido[3,4-d]pyrimidin-7(8H)-yl)methanone;

(S)-(2,3-dichlorophenyl)(2,6-dimethyl-4-(1H-pyrazol-5-yl)-5,6-dihydropyrido[3,4-d]pyrimidin-7(8H)-yl)methanone;

(2,4-dichloro-3-fluorophenyl)(2,6-dimethyl-4-(1H-pyrazol-5-yl)-5,6-dihydropyrido[3,4-d]pyrimidin-7(8H)-yl)methanone;

(R)-(2,4-dichloro-3-fluorophenyl)(2,6-dimethyl-4-(1H-pyrazol-5-yl)-5,6-dihydropyrido[3,4-d]pyrimidin-7(8H)-yl)methanone;

(S)-(2,4-dichloro-3-fluorophenyl)(2,6-dimethyl-4-(1H-pyrazol-5-yl)-5,6-dihydropyrido[3,4-d]pyrimidin-7(8H)-yl)methanone;

(2-chloro-3-(trifluoromethyl)phenyl)(2,6-dimethyl-4-(1-methyl-1H-pyrazol-5-yl)-5,6-dihydropyrido[3,4-d]pyrimidin-7(8H)-yl)methanone;

(2,6-dimethyl-4-(1H-pyrazol-5-yl)-5,6-dihydropyrido[3,4-d]pyrimidin-7(8H)-yl)(2-fluoro-3-(trifluoromethyl)phenyl)methanone;

(R)-(2,6-dimethyl-4-(1H-pyrazol-5-yl)-5,6-dihydropyrido[3,4-d]pyrimidin-7(8H)-yl)(2-fluoro-3-(trifluoromethyl)phenyl)methanone;

(S)-(2,6-dimethyl-4-(1H-pyrazol-5-yl)-5,6-dihydropyrido[3,4-d]pyrimidin-7(8H)-yl)(2-fluoro-3-(trifluoromethyl)phenyl)methanone;

(2,6-dimethyl-4-(1H-pyrazol-5-yl)-5,6-dihydropyrido[3,4-d]pyrimidin-7(8H)-yl)(2-methyl-3-(trifluoromethyl)phenyl)methanone;

(R)-(2,6-dimethyl-4-(1H-pyrazol-5-yl)-5,6-dihydropyrido[3,4-d]pyrimidin-7(8H)-yl)(2-methyl-3-(trifluoromethyl)phenyl)methanone;

(S)-(2,6-dimethyl-4-(1H-pyrazol-5-yl)-5,6-dihydropyrido[3,4-d]pyrimidin-7(8H)-yl)(2-methyl-3-(trifluoromethyl)phenyl)methanone;

(2,3-dichloro-4-fluorophenyl)(2,6-dimethyl-4-(1H-pyrazol-5-yl)-5,6-dihydropyrido[3,4-d]pyrimidin-7(8H)-yl)methanone;

(R)-(2,3-dichloro-4-fluorophenyl)(2,6-dimethyl-4-(1H-pyrazol-5-yl)-5,6-dihydropyrido[3,4-d]pyrimidin-7(8H)-yl)methanone;

(S)-(2,3-dichloro-4-fluorophenyl)(2,6-dimethyl-4-(1H-pyrazol-5-yl)-5,6-dihydropyrido[3,4-d]pyrimidin-7(8H)-yl)methanone;

(2,4-dichlorophenyl)(2,6-dimethyl-4-(1H-pyrazol-5-yl)-5,6-dihydropyrido[3,4-d]pyrimidin-7(8H)-yl)methanone;

(R)-(2,4-dichlorophenyl)(2,6-dimethyl-4-(1H-pyrazol-5-yl)-5,6-dihydropyrido[3,4-d]pyrimidin-7(8H)-yl)methanone;

(S)-(2,4-dichlorophenyl)(2,6-dimethyl-4-(1H-pyrazol-5-yl)-5,6-dihydropyrido[3,4-d]pyrimidin-7(8H)-yl)methanone;

(2,5-dichlorophenyl)(2,6-dimethyl-4-(1H-pyrazol-5-yl)-5,6-dihydropyrido[3,4-d]pyrimidin-7(8H)-yl)methanone;

(4-chloro-2-fluorophenyl)(2,6-dimethyl-4-(1H-pyrazol-5-yl)-5,6-dihydropyrido[3,4-d]pyrimidin-7(8H)-yl)methanone;

(R)-(4-chloro-2-fluorophenyl)(2,6-dimethyl-4-(1H-pyrazol-5-yl)-5,6-dihydropyrido[3,4-d]pyrimidin-7(8H)-yl)methanone;

(S)-(4-chloro-2-fluorophenyl)(2,6-dimethyl-4-(1H-pyrazol-5-yl)-5,6-dihydropyrido[3,4-d]pyrimidin-7(8H)-yl)methanone;

(2-chloro-4-fluorophenyl)(2,6-dimethyl-4-(1H-pyrazol-5-yl)-5,6-dihydropyrido[3,4-d]pyrimidin-7(8H)-yl)methanone;

(R)-(2-chloro-4-fluorophenyl)(2,6-dimethyl-4-(1H-pyrazol-5-yl)-5,6-dihydropyrido[3,4-d]pyrimidin-7(8H)-yl)methanone;

(S)-(2-chloro-4-fluorophenyl)(2,6-dimethyl-4-(1H-pyrazol-5-yl)-5,6-dihydropyrido[3,4-d]pyrimidin-7(8H)-yl)methanone;

(2,4-difluorophenyl)(2,6-dimethyl-4-(1H-pyrazol-5-yl)-5,6-dihydropyrido[3,4-d]pyrimidin-7(8H)-yl)methanone;

(R)-(2,4-difluorophenyl)(2,6-dimethyl-4-(1H-pyrazol-5-yl)-5,6-dihydropyrido[3,4-d]pyrimidin-7(8H)-yl)methanone;

(S)-(2,4-difluorophenyl)(2,6-dimethyl-4-(1H-pyrazol-5-yl)-5,6-dihydropyrido[3,4-d]pyrimidin-7(8H)-yl)methanone;

(4-chlorophenyl)(2,6-dimethyl-4-(1H-pyrazol-5-yl)-5,6-dihydropyrido[3,4-d]pyrimidin-7(8H)-yl)methanone;

(2-chlorophenyl)(2,6-dimethyl-4-(1H-pyrazol-5-yl)-5,6-dihydropyrido[3,4-d]pyrimidin-7(8H)-yl)methanone;

(2-chloro-3-(trifluoromethyl)phenyl)(2-ethyl-6-methyl-4-(1H-pyrazol-5-yl)-5,6-dihydropyrido[3,4-d]pyrimidin-7(8H)-yl)methanone;

((R)-(2-chloro-3-(trifluoromethyl)phenyl)(2-ethyl-6-methyl-4-(1H-pyrazol-5-yl)-5,6-dihydropyrido[3,4-d]pyrimidin-7(8H)-yl)methanone;

(S)-(2-chloro-3-(trifluoromethyl)phenyl)(2-ethyl-6-methyl-4-(1H-pyrazol-5-yl)-5,6-dihydropyrido[3,4-d]pyrimidin-7(8H)-yl)methanone;

(2-chloro-3-(trifluoromethyl)phenyl)(2-isopropyl-6-methyl-4-(1H-pyrazol-5-yl)-5,6-dihydropyrido[3,4-d]pyrimidin-7(8H)-yl)methanone;

(R)-(2-chloro-3-(trifluoromethyl)phenyl)(2-isopropyl-6-methyl-4-(1H-pyrazol-5-yl)-5,6-dihydropyrido[3,4-d]pyrimidin-7(8H)-yl)methanone;

(S)-(2-chloro-3-(trifluoromethyl)phenyl)(2-isopropyl-6-methyl-4-(1H-pyrazol-5-yl)-5,6-dihydropyrido[3,4-d]pyrimidin-7(8H)-yl)methanone;

(2,4-dichloro-3-fluorophenyl)(2-ethyl-6-methyl-4-(1H-pyrazol-5-yl)-5,6-dihydropyrido[3,4-d]pyrimidin-7(8H)-yl)methanone;

(4-(1H-pyrazol-1-yl)-5,6-dihydropyrido[3,4-d]pyrimidin-7(8H)-yl)(2,3-dimethylphenyl)methanone;

(4-(1H-1,2,3-triazol-1-yl)-5,6-dihydropyrido[3,4-d]pyrimidin-7(8H)-yl)(2-chloro-3-(trifluoromethyl)phenyl)methanone;

(4-(4H-1,2,4-triazol-4-yl)-5,6-dihydropyrido[3,4-d]pyrimidin-7(8H)-yl)(2-chloro-3-(trifluoromethyl)phenyl)methanone;

(4-(1H-1,2,4-triazol-1-yl)-5,6-dihydropyrido[3,4-d]pyrimidin-7(8H)-yl)(2-chloro-3-(trifluoromethyl)phenyl)methanone;

(4-(1H-pyrazol-5-yl)-5,6-dihydropyrido[3,4-d]pyrimidin-7(8H)-yl)(2-fluoro-3-(trifluoromethyl)phenyl)methanone;

(2-chloro-3-(trifluoromethyl)phenyl)(8-methyl-4-(1H-pyrazol-5-yl)-5,6-dihydropyrido[3,4-d]pyrimidin-7(8H)-yl)methanone;

(R)-(2-chloro-3-(trifluoromethyl)phenyl)(8-methyl-4-(1H-pyrazol-5-yl)-5,6-dihydropyrido[3,4-d]pyrimidin-7(8H)-yl)methanone;

(S)-(2-chloro-3-(trifluoromethyl)phenyl)(8-methyl-4-(1H-pyrazol-5-yl)-5,6-dihydropyrido[3,4-d]pyrimidin-7(8H)-yl)methanone;

(2-chloro-4-fluoro-3-(trifluoromethyl)phenyl)(8-methyl-4-(1H-pyrazol-5-yl)-5,6-dihydropyrido[3,4-d]pyrimidin-7(8H)-yl)methanone;

(R)-(2-chloro-4-fluoro-3-(trifluoromethyl)phenyl)(8-methyl-4-(1H-pyrazol-5-yl)-5,6-dihydropyrido[3,4-d]pyrimidin-7(8H)-yl)methanone;

(2-chloro-4-fluoro-3-(trifluoromethyl)phenyl)(8-methyl-4-(1H-pyrazol-5-yl)-5,6-dihydropyrido[3,4-d]pyrimidin-7(8H)-yl)methanone;

(2,3-dichloro-4-fluorophenyl)(8-methyl-4-(1H-pyrazol-5-yl)-5,6-dihydropyrido[3,4-d]pyrimidin-7(8H)-yl)methanone;

(R)-(2,3-dichloro-4-fluorophenyl)(8-methyl-4-(1H-pyrazol-5-yl)-5,6-dihydropyrido[3,4-d]pyrimidin-7(8H)-yl)methanone;

(S)-(2,3-dichloro-4-fluorophenyl)(8-methyl-4-(1H-pyrazol-5-yl)-5,6-dihydropyrido[3,4-d]pyrimidin-7(8H)-yl)methanone;

((2,4-dichloro-3-fluorophenyl)(8-methyl-4-(1H-pyrazol-5-yl)-5,6-dihydropyrido[3,4-d]pyrimidin-7(8H)-yl)methanone;

(R)-(2,4-dichloro-3-fluorophenyl)(8-methyl-4-(1H-pyrazol-5-yl)-5,6-dihydropyrido[3,4-d]pyrimidin-7(8H)-yl)methanone;

(S)-(2,4-dichloro-3-fluorophenyl)(8-methyl-4-(1H-pyrazol-5-yl)-5,6-dihydropyrido[3,4-d]pyrimidin-7(8H)-yl)methanone;

(R)-(2-chloro-3-(trifluoromethyl)phenyl)(4-(1-(2-fluoroethyl)-1H-pyrazol-3-yl)-2,6-dimethyl-5,6-dihydropyrido[3,4-d]pyrimidin-7(8H)-yl)methanone;

(S)-(2-chloro-3-(trifluoromethyl)phenyl)(4-(1-(2-fluoroethyl)-1H-pyrazol-3-yl)-2,6-dimethyl-5,6-dihydropyrido[3,4-d]pyrimidin-7(8H)-yl)methanone;

(2-chloro-3-(trifluoromethyl)phenyl)(4-(1-(2-methoxyethyl)-1H-pyrazol-3-yl)-2,6-dimethyl-5,6-dihydropyrido[3,4-d]pyrimidin-7(8H)-yl)methanone;

(S)-(2-chloro-3-(trifluoromethyl)phenyl)(4-(1-(2-methoxyethyl)-1H-pyrazol-3-yl)-2,6-dimethyl-5,6-dihydropyrido[3,4-d]pyrimidin-7(8H)-yl)methanone;

(R)-(2-chloro-3-(trifluoromethyl)phenyl)(4-(1-(2-methoxyethyl)-1H-pyrazol-3-yl)-2,6-dimethyl-5,6-dihydropyrido[3,4-d]pyrimidin-7(8H)-yl)methanone;

(2,3-dichloro-4-fluorophenyl)(4-(6-fluoropyridin-2-yl)-5,6-dihydropyrido[3,4-d]pyrimidin-7(8H)-yl)methanone;

(2-chloro-3-(trifluoromethyl)phenyl)(4-(6-fluoropyridin-2-yl)-5,6-dihydropyrido[3,4-d]pyrimidin-7(8H)-yl)methanone;

(2,6-dimethyl-4-(1H-pyrazol-5-yl)-5,6-dihydropyrido[3,4-d]pyrimidin-7(8H)-yl)(2,4-dimethylphenyl)methanone;

(2,6-dimethyl-4-(1H-pyrazol-5-yl)-5,6-dihydropyrido[3,4-d]pyrimidin-7(8H)-yl)(2,3-dimethylphenyl)methanone;

(2,6-dimethyl-4-(1H-pyrazol-5-yl)-5,6-dihydropyrido[3,4-d]pyrimidin-7(8H)-yl)(4-fluoro-2-methylphenyl)methanone;

(2,6-dimethyl-4-(1H-pyrazol-5-yl)-5,6-dihydropyrido[3,4-d]pyrimidin-7(8H)-yl)(3-fluoro-2-methylphenyl)methanone;

(2,6-dimethyl-4-(1H-pyrazol-5-yl)-5,6-dihydropyrido[3,4-d]pyrimidin-7(8H)-yl)(2-fluoro-3-methylphenyl)methanone;

(R)-(2,4-dichloro-3-fluorophenyl)(2,6-dimethyl-4-(1H-pyrazol-5-yl)-5,6-dihydropyrido[3,4-d]pyrimidin-7(8H)-yl)methanone;

(R)-(2,6-dimethyl-4-(1H-pyrazol-5-yl)-5,6-dihydropyrido[3,4-d]pyrimidin-7(8H)-yl)(phenyl)methanone;

(2,4-dichlorophenyl)((6R,8S)-2,6,8-trimethyl-4-(1H-pyrazol-5-yl)-5,6-dihydropyrido[3,4-d]pyrimidin-7(8H)-yl)methanone;

(2,6-dimethyl-4-(1H-pyrazol-5-yl)-5,6-dihydropyrido[3,4-d]pyrimidin-7(8H)-yl)(2-fluoro-3-(trifluoromethoxy)phenyl)methanone;

(2,6-dimethyl-4-(1H-pyrazol-5-yl)-5,6-dihydropyrido[3,4-d]pyrimidin-7(8H)-yl)(3-(trifluoromethoxy)phenyl)methanone;

(R*)-(2,6-dimethyl-4-(1H-pyrazol-5-yl)-5,6-dihydropyrido[3,4-d]pyrimidin-7(8H)-yl)(3-(trifluoromethoxy)phenyl)methanone;

(S*)-(2,6-dimethyl-4-(1H-pyrazol-5-yl)-5,6-dihydropyrido[3,4-d]pyrimidin-7(8H)-yl)(3-(trifluoromethoxy)phenyl)methanone;

(2-chloro-3-fluorophenyl)(2,6-dimethyl-4-(1H-pyrazol-5-yl)-5,6-dihydropyrido[3,4-d]pyrimidin-7(8H)-yl)methanone;

(R*)-(2-chloro-3-fluorophenyl)(2,6-dimethyl-4-(1H-pyrazol-5-yl)-5,6-dihydropyrido[3,4-d]pyrimidin-7(8H)-yl)methanone;

(S*)-(2-chloro-3-fluorophenyl)(2,6-dimethyl-4-(1H-pyrazol-5-yl)-5,6-dihydropyrido[3,4-d]pyrimidin-7(8H)-yl)methanone; and (2,6-dimethyl-4-(1H-pyrazol-5-yl)-5,6-dihydropyrido[3,4-d]pyrimidin-7(8H)-yl)(3-methoxy-2-methylphenyl)methanone.

21. A pharmaceutical composition, comprising:

(a) a therapeutically effective amount of a compound of Formula (I):

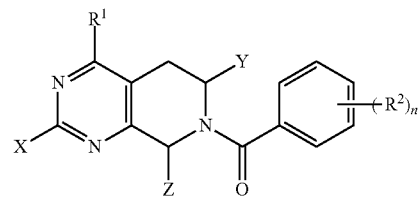

Formula (I)

wherein:
each $R^2$ is independently selected from the group consisting of H, halo, CN, $C_1$-$C_3$ alkyl, perhaloalkyl, $C_1$-$C_3$ alkoxy and perhaloalkoxy;
n is an integer from 0-3;
X is independently selected from the group consisting of H, $C_1$-$C_3$ alkyl, $C_3$ cycloalkyl, perfluoroalkyl, —$NH_2$, and —$N(CH_3)_2$;
Y and Z are independently H or $CH_3$;
$R^1$ is independently selected from the group consisting of:

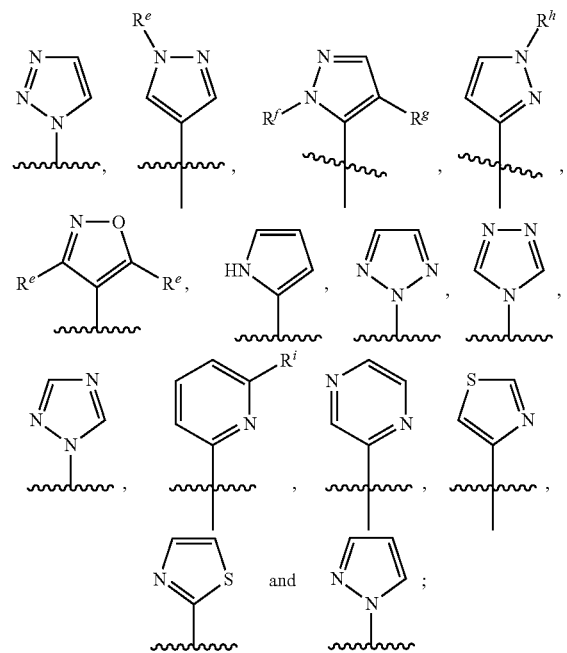

$R^e$ and $R^f$ are H or $C_1$-$C_3$ alkyl;
$R^g$ is H, F, or perfluoroalkyl;
$R^h$ is H, $C_1$-$C_3$ alkyl, —$CH_2CH_2OCH_3$ or perfluoroalkyl; and
$R^i$ is H or halo; or
pharmaceutically acceptable salts thereof; and
(b) at least one pharmaceutically acceptable excipient.

22. A pharmaceutical composition comprising a therapeutically effective amount of at least one compound of claim 20 and at least one pharmaceutically acceptable excipient.

* * * * *